US012545958B2

(12) United States Patent
Zhou et al.

(10) Patent No.: US 12,545,958 B2
(45) Date of Patent: Feb. 10, 2026

(54) METHODS OF ENRICHING TARGETED NUCLEIC ACID, IDENTIFYING OFF-TARGET AND EVALUATING GENE EDITING EFFICIENCY

(71) Applicant: GenEditBio Limited, Hong Kong (CN)

(72) Inventors: Wenjing Zhou, Hong Kong (CN); Bang Wang, Hong Kong (CN); Zongli Zheng, Hong Kong (CN)

(73) Assignee: GenEditBio Limited, Hong Kong (CN)

( * ) Notice: Subject to any disclaimer, the term of this patent is extended or adjusted under 35 U.S.C. 154(b) by 0 days.

(21) Appl. No.: 18/510,106

(22) Filed: Nov. 15, 2023

(65) Prior Publication Data

US 2024/0191295 A1 Jun. 13, 2024

Related U.S. Application Data

(63) Continuation of application No. PCT/IB2022/000278, filed on May 16, 2022.

(60) Provisional application No. 63/277,782, filed on Nov. 10, 2021, provisional application No. 63/201,861, filed on May 16, 2021.

(51) Int. Cl.
*C12Q 1/6876* (2018.01)
*C12Q 1/6811* (2018.01)
*C12Q 1/6855* (2018.01)
*C12Q 1/6874* (2018.01)

(52) U.S. Cl.
CPC ......... *C12Q 1/6876* (2013.01); *C12Q 1/6855* (2013.01); *C12Q 1/6874* (2013.01); *C12Q 1/6811* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 2012/0058468 | A1 | 3/2012 | McKeown |
| 2012/0258867 | A1 | 10/2012 | Cao et al. |
| 2013/0303461 | A1 | 11/2013 | Iafrate et al. |
| 2015/0284712 | A1 | 10/2015 | Kurihara et al. |
| 2019/0078148 | A1 | 3/2019 | Zheng |
| 2019/0136305 | A1 | 5/2019 | Ward |
| 2019/0153515 | A1 | 5/2019 | Chen et al. |
| 2019/0367909 | A1 | 12/2019 | Comstock |
| 2020/0048692 | A1 | 2/2020 | Zheng et al. |
| 2021/0130849 | A1 | 5/2021 | Mitalipov et al. |

FOREIGN PATENT DOCUMENTS

| | | | |
|---|---|---|---|
| WO | WO-2009076238 | A2 | 6/2009 |
| WO | WO-2013169339 | A1 | 11/2013 |
| WO | WO-2014028778 | A1 | 2/2014 |
| WO | WO-2019067092 | A1 | 4/2019 |
| WO | WO-2019213776 | A1 | 11/2019 |

OTHER PUBLICATIONS

Bao, XR et al., "Tools for experimental and computational analyses of off-target editing by programmable nucleases," pp. 10-26, Nature Protocol., vol. 16, No. 1, Jan. 16, 2021, p. 6, 11, 28.
Doench et al., "Optimized sgRNA design to maximize activity and minimize off-target effects of CRISPR-Cas9," Nat Biotechnol. 34:184-191 (2016).
International Search Report and Written Opinion mailed on Dec. 28, 2022, for International Application No. PCT/IB2022/000278, 14 pages.
Jilani, M et al., "Computational Methods for Detecting Large-Scale Structural Rearrangements in Chromosomes," Bioinformatics, Chapter 3, Mar. 2021, p. 5-6.
Naert, T et al., "Maximizing CRISPR/Cas9 phenotype penetrance applying predictive modeling of editing outcomes in Xenopus and zebrafish embryos," Sci Rep. Sep. 4, 2020;10(1), 12 pages.
Ashoub et al., "A Primer-Based Approach to Genome Walking" Plant Molecular Biology Reporter, Jun. 2006, 24, pp. 237-243.
Atkins et al. "Off-Target Analysis in Gene Editing and Applications for Clinical Translation of CRISPR/Cas9 in HIV-1 Therapy" Frontiers in Genome Editing, Aug. 17, 2021, vol. 3, Article 673022, 26 pages.
Boone et al., "Capturing the 'ome': the expanding molecular toolbox for RNA and DNA library construction" Nucleic Acids Research, Mar. 5, 2018, vol. 46, No. 6, pp. 2701-2721.
Craxton, "Linear amplification sequencing, a powerful method for sequencing DNA" Methods, Aug. 1991, vol. 33, Issue 1, pp. 20-26.
Extended European Search Report mailed on Mar. 18, 2025, for European Patent Application No. 22804125.7, 11 pages.
Gansauge et al., "Single-stranded DNA library preparation from highly degraded DNA using T4 DNA ligase" Nucleic Acids Research, 2017, vol. 45, No. 10, 10 pages.
Hrdlickova et al., "RNA-Seq methods for transcriptome analysis" Wiley Interdisciplinary Reviews RNA, Jan. 2017, 8(1), 24 pages.
Murray, "Improved double-stranded DNA sequencing using the linear polymerase chain reaction" Nucleic Acids Research, 1989, vol. 17, No. 21, 1 page.
Office action mailed on Dec. 6, 2024, in Japanese Application No. 2023-571688, 5 pages, 5 page English translation.
Office action mailed on May 21, 2025, in Japanese Application No. 2023-571688, 5 pages 4 page English translation.

*Primary Examiner* — G. Steven Vanni
(74) *Attorney, Agent, or Firm* — COOLEY LLP

(57) ABSTRACT

The present disclosure relates to enriching nucleic acid from a sample. In some embodiments, the present disclosure provides methods for enriching at least one targeted nucleic acid, identifying genome-wide gene editing off-targets, and evaluating gene editing efficiency from a sample comprising a plurality of single-strand nucleic acid fragments. Others example embodiments are also described herein.

19 Claims, 42 Drawing Sheets

Specification includes a Sequence Listing.

220

230

240

330

421

422

METHODS OF ENRICHING TARGETED NUCLEIC ACID, IDENTIFYING OFF-TARGET AND EVALUATING GENE EDITING EFFICIENCY

CROSS-REFERENCE

This application is a continuation of International Application No. PCT/IB2022/000278, filed on May 16, 2022, which claims the benefit of U.S. Provisional Application No. 63/201,861, filed on May 16, 2021 and 63/277,782, filed on Nov. 10, 2021, each of which applications is incorporated herein by reference in its entirety for all purposes.

DESCRIPTION OF THE TEXT FILE SUBMITTED ELECTRONICALLY

The contents of the electronic sequence listing (GEBL_001_02US_SeqList_ST26.xml; Size: 1,479,069 bytes; and Date of Creation: Nov. 14, 2023) are herein incorporated by reference in its entirety.

FIELD

The present disclosure generally relates to enriching nucleic acid, identifying genome-wide gene editing off-targets, and evaluating gene editing efficiency.

BACKGROUND

Genome-targeting, programmable nucleases such as ZFNs, TALENs and CRISPR are profoundly revolutionizing the community of genetic engineering and precise gene therapy. However, unwanted edits within genome (i.e., off-target effect) may cause unpredictable confounding results in research and severe side-effects in gene therapy. Detecting off-target, therefore, represents a necessary checkpoint for ensuring the precision of genome editing. Current off-target profiling methods have various disadvantages, such as being incompatible with in vivo editing, requiring high amounts of sample input, and being time-consuming if a validation is to be conducted. In addition, sensitivity and specificity of the current methods may fluctuate uncontrollably in outcome.

Some current methods employ a multiplex target enrichment using forward and reverse primers. The drawback of these methods is that unknown sequences contiguous to the target sequences cannot be enriched. The forward and reverse primer generated data has identical start and end positions, posing significant challenge in the data analysis of counting molecular complexing, controlling sequencing error, and calculating copy numbers and efficiency.

SUMMARY

In one aspect, provided herein is a method of enriching at least one target nucleic acid from a sample comprising a plurality of single-strand nucleic acid fragments, the method comprising: (a) contacting a universal oligonucleotide adaptor with the sample to produce a ligation product, wherein the universal oligonucleotide adaptor is configured for ligating to a 5' end of the single-strand nucleic acid fragments; (b) amplifying the ligation product by a first PCR with a first target-specific primer and optionally a first universal oligonucleotide adaptor primer to form a first PCR product; and (c) amplifying the first PCR product by a second PCR with a second target-specific primer and a second universal oligonucleotide adaptor primer to form a second PCR product, wherein the second target-specific primer is nested relative to the first target-specific primer.

In some embodiments, prior to (a), the method further comprises at least one of: blocking a 3' end of the single-strand nucleic acid fragments; phosphorylating a 5' end of the single-strand nucleic acid fragments; or adenylating the nucleic acid to produce a 3'-adenosine overhang on the single-strand nucleic acid fragments.

In some embodiments, the first PCR is a linear amplification of the ligation product with the first target-specific primer to obtain a nascent primer extension duplex. In some embodiments, the first PCR is an exponential amplification of the targeted nucleic acid with the first target-specific primer and the first universal oligonucleotide adaptor primer. In some embodiments, the first universal oligonucleotide adaptor primer and the second universal oligonucleotide adaptor primer are the same. In other embodiments, the first universal oligonucleotide adaptor primer and the second universal oligonucleotide adaptor primer are different.

In some embodiments, the universal oligonucleotide adaptor comprises: a 3' recessive end, the 3' recessive end configured for ligating to the 5' end of the single-strand nucleic acid fragments; and/or a 5' protrude end comprising three to twenty bases of random or degenerate nucleotides. In some embodiments, a duplex portion of the universal oligonucleotide adaptor is of sufficient length to remain in duplex form in (a). In some embodiments, the universal oligonucleotide adaptor comprises a hairpin loop connecting a portion of the duplex form. In some embodiments, the universal oligonucleotide adaptor comprises a single strand segment comprising three to twenty random nucleotides as a unique molecular index (UMI) for tracing individual original molecules.

In some embodiments, (c) further comprises forming a sequencing library with a sequencing specific adaptor pair. In some specific embodiments, after (c), further comprises sequencing the sequencing library using a sequencing primer pair, wherein the sequencing primer pair is at least partially complementary to opposite strands of the second PCR product, respectively.

In some embodiments, the sample comprises a plurality of DNA fragments prepared from high molecular weight DNA. In some embodiments, the plurality of single-strand nucleic acid fragments are prepared from denaturation of double-strand DNA fragments. In some embodiments, the sample comprises single-strand cDNA fragments prepared from reverse transcription of RNA fragments. In some embodiments, the method further comprises of analyzing the plurality of nucleic acids fragments. In some embodiments, the first PCR and/or second PCR are multiplexing PCR.

In some embodiments, the sample is from a mammal, and wherein optionally the sample is from human. In some specific embodiments, the human is an individual known to have or suspected of having a disease, and wherein optionally the disease is a cancer or a genetic disorder. In some embodiments, one or more of the target nucleic acids comprise one or more markers for the cancer. In some embodiments, the human is a fetus. In some embodiments, the sample is from a blood sample. In some embodiments, the sample comprises cell-free nucleic acids extracted from a blood sample. In some embodiments, the sample comprises nucleic acids extracted from circulating tumor cells. In some embodiments, the sample comprises nucleic acids extracted from lymphocytes in a blood sample for T-cell and B-cell receptor profiling. In some embodiments, the sample is a CRISPR gene edited sample. In some specific embodiments, the sample is meganucleases edited, zinc finger nucleases (ZFNs) edited, or transcription activator-like effector nucleases (TALENs) edited. In some embodiments, the sample is from CAR-T, CAR-NK, TCR-T, immortalized cell lines (e.g., engineered neural stem cell line CTX) or hematopoietic stem cells for therapeutics. In some embodiments, the sample is from genetically engineered cells (ex-vivo or in vivo), wherein the cells include but are not limited to fibroblasts, chondrocytes, keratinocytes, hepatocytes, pancreatic islet cells, stem cells (e.g., haematopoietic stem cells, mesenchymal stem cells, or skin stem cells), and immune cells (e.g., tumor infiltrating lymphocytes, viral reconstitution T cells, dendritic cells, γδT cells, regulatory T cells (Treg) and macrophages).

In another aspect, provided herein is a method of enriching at least one target nucleic acid from a sample comprising a plurality of single-strand nucleic acid fragments, the method comprising: (a) ligating a universal oligonucleotide adaptor to a 5' end of the single-strand nucleic acid fragments; (b) annealing a first target-specific primer to the single-strand nucleic acid fragments in the vicinity of a target sequence; (c) extending the first target-specific primer over the single-strand nucleic acid fragments using a DNA polymerase; (d) obtaining a nascent primer extension duplex; (e) dissociating the nascent primer extension duplex into single strands; and (f) amplifying a portion of the single stands of the nascent primer extension duplex with a second target-specific primer and a universal oligonucleotide adaptor primer.

In some embodiments, prior to (a), the method further comprises at least one of: blocking a 3' end of the single-strand nucleic acid fragments; phosphorylating a 5' end of the single-strand nucleic acid fragments; or adenylating the nucleic acid to produce a 3-adenosine overhang on the single-strand nucleic acid fragments.

In some embodiments, the universal oligonucleotide adaptor comprises: a 3' recessive end, the 3' recessive end configured for ligating to the 5' end of the single-strand nucleic acid fragments; and/or a 5' protrude end comprising three to twenty bases of random or degenerate nucleotides; wherein a duplex portion of the universal oligonucleotide adaptor is of sufficient length to remain in duplex form in (a). In some embodiments, the universal oligonucleotide adaptor comprises a hairpin loop connecting a portion of the duplex form. In some embodiments, (f) further comprises forming a sequencing library with a sequencing specific adaptor pair. In some embodiments, the method, after (f), further comprises sequencing the sequencing library using a sequencing primer pair, wherein the sequencing primer pair is at least partially complementary to opposite strands of the second PCR product, respectively. In some embodiments, the method further comprises repeating (b)-(f) for one or more cycles.

In some embodiments, the sample comprises a plurality of DNA fragments prepared from high molecular weight DNA. In some embodiments, the plurality of single-strand nucleic acid fragments are prepared from denaturation of double-strand DNA fragments. In some embodiments, the sample comprises single-strand cDNA fragments prepared from reverse transcription of RNA fragments. In some embodiments, the universal oligonucleotide adaptor comprises a single strand segment comprising three to twenty random nucleotides as a unique molecular index (UMI) for tracing individual original molecules. In some embodiments, the method further comprises analyzing the plurality of nucleic acids fragments.

In some embodiments, the sample is from a mammal, and wherein optionally the mammal is a human. In some embodiments, the human is an individual known to have or suspected of having a disease, and wherein optionally the disease is a cancer or a genetic disorder. In some embodiments, the human is a fetus.

In some embodiments, the sample is from a blood sample. In other embodiments, the sample comprises cell-free nucleic acids extracted from a blood sample. In other embodiments, the sample comprises nucleic acids extracted from circulating tumor cells. In other embodiments, the sample comprises nucleic acids extracted from lymphocytes in a blood sample for T-cell and B-cell receptor profiling. In other embodiments, the sample is a CRISPR gene edited sample. In some specific embodiments, the sample is meganucleases edited, zinc finger nucleases (ZFNs) edited, or transcription activator-like effector nucleases (TALENs) edited. In some embodiments, the sample is from CAR-T, CAR-NK, TCR-T, immortalized cell lines (e.g., engineered neural stem cell line CTX) or hematopoietic stem cells for therapeutics. In some embodiments, the sample is from genetically engineered cells (ex-vivo or in vivo), wherein the cells include but are not limited to fibroblasts, chondrocytes, keratinocytes, hepatocytes, pancreatic islet cells, stem cells (e.g., haematopoietic stem cells, mesenchymal stem cells, or skin stem cells), and immune cells (e.g., tumor infiltrating lymphocytes, viral reconstitution T cells, dendritic cells, γδT cells, regulatory T cells (Treg) and macrophages).

In another aspect, provided herein is a method of identifying genome-wide gene editing off-target sites from a sample comprising a plurality of single-strand nucleic acid fragments, comprising: (a) contacting a universal oligonucleotide adaptor with the sample to produce a ligation product, wherein the universal oligonucleotide adaptor is configured for ligating to a 5' end of the single-strand nucleic acid fragments; (b) amplifying the ligation product by performing a first PCR with a first target-specific primer to form a first PCR product; (c) amplifying the first PCR product by a second PCR with a sequencing specific adaptor primer and a second target-specific primer nested relative to the first target-specific primer, to form a sequencing library; (d) quantifying and reading the sequencing library to obtain sequencing results; and (e) mapping the sequencing results to a reference genome.

In another aspect, provided herein is a method of evaluating gene editing efficiency from a sample comprising a plurality of single-strand nucleic acid fragments, comprising: (a) contacting a universal oligonucleotide adaptor with the sample to produce a ligation product, wherein the universal oligonucleotide adaptor is configured for ligating to a 5' end of the single-strand nucleic acid fragments; (b) amplifying the ligation product by performing a first PCR with a first target-specific primer to form a first PCR product, wherein the first target-specific primer is configured for annealing to the single-strand nucleic acid fragments at an on-target site, a predicted off-target site, or a known off-target sites; (c) amplifying the first PCR product by a second PCR with a sequencing specific adaptor primer and a second target-specific primer nested relative to the first target-specific primer, to form a sequencing library; (d) quantifying and reading the sequencing library to form sequencing results; and (e) mapping the sequencing results to a reference genome and evaluating gene editing efficiency.

In some embodiments, the predicted off-target site is predicted in silico based on softwares comprising E-CRISP, Cas-OFFinder, and/or CRISPRscan. In some embodiments, the E-CRISP has a cutoff of mismatch <=10, 9, 8, 7, or 6; the Cas-OFFinder has a mismatch <=6, 5, 4, 3, or 2 and a bulge <=3, 2, or 1; and the CRISPRscan has no threshold. In some embodiments, (e) further comprises: detecting translocation by obtaining a split read and a discordant read or determining an insertion and deletion (indel) frequency. In some specific embodiments, the split read and the discordant read are obtained by: identifying potential candidate translocations and estimating protospacer similarity to an on-target spacer and a cutting frequency determinant (CFD). In some specific embodiments, the indel frequency is obtained by: (a) aligning the mapped results by GATK-realigner to form aligned results; (b) filtering the aligned results not spanning a corresponding spacer region; (c) predicting an insertion and deletion occurring around 5-bp upstream or downstream of a cleavage site; and (d) determining the reliable indel frequency by an indel value of the sample with an elimination by a corresponding value of a negative control.

In another aspect, provided herein is a method of identifying genome-wide gene editing off-target sites from a sample comprising a plurality of single-strand nucleic acid fragments, comprising: (a) contacting a universal oligonucleotide adaptor with the sample to produce a ligation product, wherein the universal oligonucleotide adaptor is configured for ligating to a 5' end of the single-strand nucleic acid fragments; (b) amplifying the ligation product by a first PCR with a first set of target-specific primers, wherein the target-specific primers in the first set are configured for annealing to the single-strand nucleic acid fragments 5' of an on-target site and one or more predicted and/or known off-target sites; (c) amplifying the first PCR product by a second PCR with a second set of target-specific primers and a universal oligonucleotide adaptor primer to form a sequencing library, wherein each member of the second set of target-specific primers is nested relative to a corresponding primer of the first set of target-specific primers; and (d) sequencing the sequencing library to identify off-target sites.

In some embodiments, the predicted off-target sites in (b) are computationally predicted off-target sites. In some embodiments, the computationally predicted off-target sites are top 100, 90, 80, 70, 60, 50, 40, 30, 20, or 10 off-target sites predicted based on software comprising E-CRISP, Cas-OFFinder, or CRISPRscan. In some specific embodiments, the E-CRISP has a cutoff of mismatch <=10, 9, 8, 7, or 6; the Cas-OFFinder has a mismatch <=6, 5, 4, 3, or 2 and a bulge <=3, 2, or 1; and the CRISPRscan has no threshold.

In some embodiments, method further comprises: detecting translocation by obtaining a split read and a discordant read or determining an insertion and deletion (indel) frequency. In some specific embodiments, the split read and the discordant read are obtained by: identifying potential candidate translocations and estimating protospacer similarity to an on-target spacer and a cutting frequency determinant (CFD). In some specific embodiments, the indel frequency is obtained by: aligning the mapped results by GATK-realigner to form aligned results; filtering the aligned results not spanning a corresponding spacer region; predicting an insertion and deletion occurring around 5-bp upstream or downstream of a cleavage site; and determining the reliable indel frequency by an indel value of the sample with an elimination by a corresponding value of a negative control.

In some embodiments, prior to (a), the method further comprises at least one of: blocking a 3' end of the single-strand nucleic acid fragments; phosphorylating a 5' end of the single-strand nucleic acid fragments; or adenylating the nucleic acid to produce a 3'-adenosine overhang on the single-strand nucleic acid fragments.

In some embodiments, the universal oligonucleotide adaptor comprises: a 3' recessive end, the 3' recessive end configured for ligating to the 5' end of the single-strand nucleic acid fragments; and/or a 5' protrude end comprising three to twenty bases of random or degenerate nucleotides. In some embodiments, a duplex portion of the universal oligonucleotide adaptor is of sufficient length to remain in duplex form in (a). In some specific embodiments, the universal oligonucleotide adaptor comprises a hairpin loop connecting a portion of the duplex form. In some embodiments, the universal oligonucleotide adaptor comprises a single strand segment comprising three to twenty random nucleotides as a unique molecular index (UMI) for tracing individual original molecules. In some embodiments, (c) further comprises forming the sequencing library with a sequencing specific adaptor pair. In some embodiments, after (c), further comprises: sequencing the sequencing library using a sequencing primer pair, wherein the sequencing primer pair is at least partially complementary to opposite strands of the second PCR product, respectively. In some embodiments, the sample comprises a plurality of DNA fragments prepared from high molecular weight DNA. In some embodiments, the plurality of single-strand nucleic acid fragments are prepared from denaturation of double-strand DNA fragments.

In some embodiments, the sample comprises single-strand cDNA fragments prepared from reverse transcription of RNA fragments.

In some embodiments, the method further comprises analyzing the plurality of nucleic acids fragments.

In some embodiments, the sample is from a mammal, and wherein optionally the mammal is a human. In some specific embodiments, the human is an individual known to have or suspected of having a disease, and wherein optionally the disease is a cancer or a genetic disorder. In some embodiments, one or more of the target nucleic acids comprise one or more markers for the cancer. In some specific embodiments, the human is a fetus. In some embodiments, the sample is from a blood sample. In some embodiments, the sample comprises cell-free nucleic acids extracted from a blood sample. In some embodiments, the sample comprises nucleic acids extracted from circulating tumor cells. In some embodiments, the sample comprises nucleic acids extracted from lymphocytes in a blood sample for T-cell and B-cell receptor profiling. In some embodiments, the sample is a CRISPR gene edited sample. In some specific embodiments, the sample is meganucleases edited, zinc finger nucleases (ZFNs) edited, or transcription activator-like effector nucleases (TALENs) edited. In some embodiments, the sample is from CAR-T, CAR-NK, TCR-T, immortalized cell lines (e.g., engineered neural stem cell line CTX) or hematopoietic stem cells for therapeutics. In some embodiments, the sample is from genetically engineered cells (ex-vivo or in vivo), wherein the cells include but are not limited to fibroblasts, chondrocytes, keratinocytes, hepatocytes, pancreatic islet cells, stem cells (e.g., haematopoietic stem cells, mesenchymal stem cells, or skin stem cells), and immune cells (e.g., tumor infiltrating lymphocytes, viral reconstitution T cells, dendritic cells, γδT cells, regulatory T cells (Treg) and macrophages).

BRIEF DESCRIPTION OF FIGURES

FIG. 3AA is a cricos plot illustrating the translocation events detected by 17 off-target sites predicted in-silicon in CRISPR-Cas9 targeting VEGFA_2 locus. FIG. 3AB is a cricos plot illustrating the translocation events detected by 18 off-target sites predicted in-silicon in CRISPR-Cas9 targeting VEGFA_2 locus. FIG. 3AC is a cricos plot illustrating the translocation events detected by 19 off-target sites predicted in-silicon in CRISPR-Cas9 targeting VEGFA_2 locus. FIG. 3AD is a cricos plot illustrating the translocation events detected by 20 off-target sites predicted in-silicon in CRISPR-Cas9 targeting VEGFA_2 locus.

Figure 1A:
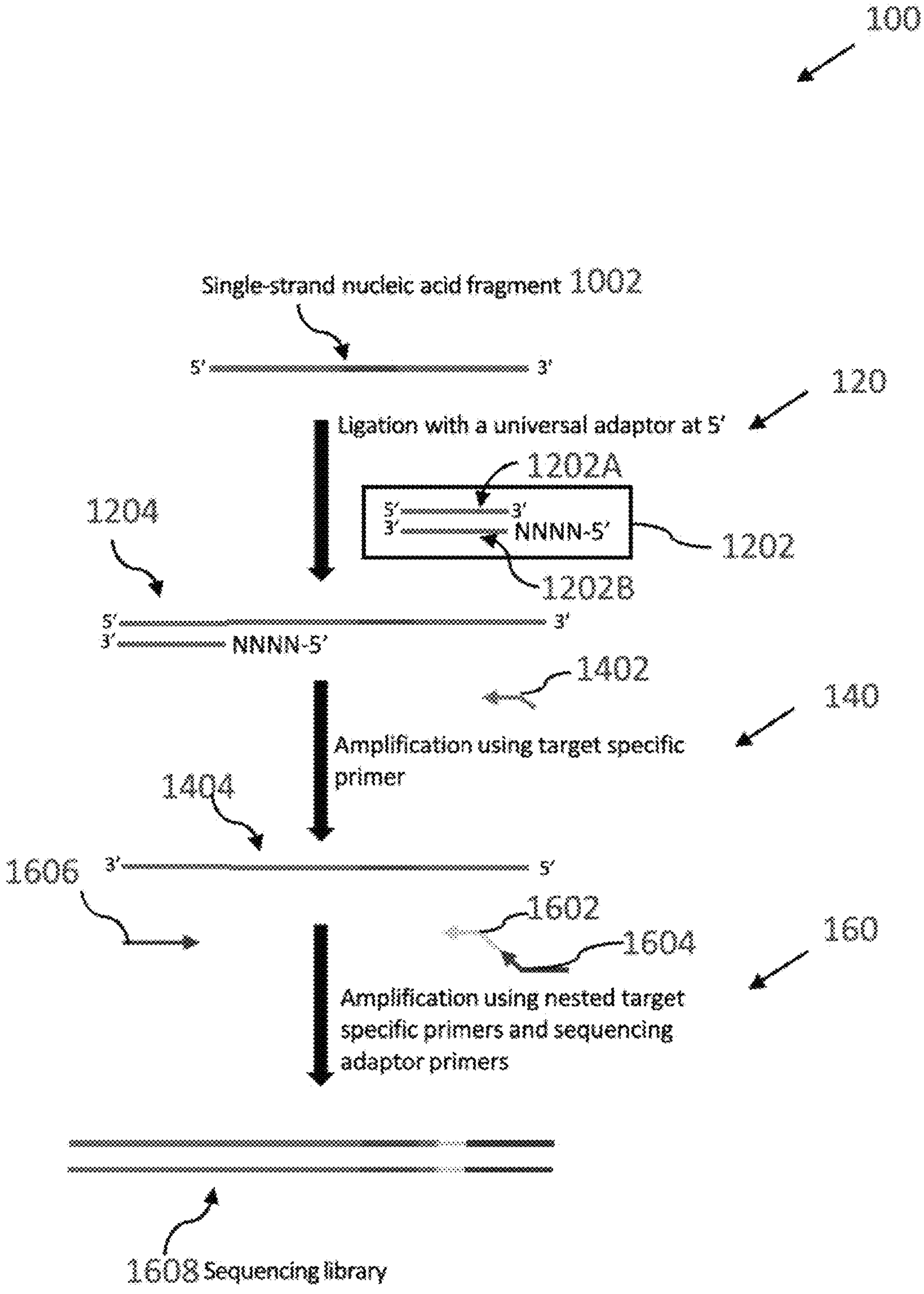
FIG. 1A is a schematic diagram which illustrates an example embodiment of a workflow for amplifying targeted nucleic acid from a sample.

The sequences in FIGS. 2A, 2B, 4C, 4D, 5B, and 5C are shown in Table 1 below.

TABLE 1

Sequences in FIGS. 2A, 2B, 4C, 4D, 5B, and 5C

| SEQ ID NO: | Sequence |
|---|---|
| 961 | GACCCCCTCCACCCCGCCTCCGG |
| 962 | CTACCCCTCCACCCCGCCTCCGG |
| 963 | ATTCCCCCCCACCCCGCCTCAGG |
| 964 | GGGCCCCTCCACCCCGCCTCTGG |
| 965 | GACCCCCTTCACCCCACCTATGG |
| 966 | TACCCCCCACACCCCGCCTCTGG |
| 967 | GCCCCCACCCACCCCGCCTCTGG |
| 968 | TGCCCCCCCCACCCCACCTCTGG |
| 969 | ACACCCCCCCACCCCGCCTCAGG |
| 970 | CTCCCCCCCCTCCCCGCCTCGGG |
| 971 | TGCCCCTCCCACCCCGCCTCTGG |
| 972 | CGCCCTCCCCACCCCGCCTCCGG |
| 973 | AGCCCCCCCCACCCCGACTCAGG |
| 974 | GCCCCCCACCACCCCACCTCGGG |
| 975 | GACACACCCCACCCCACCTCAGG |
| 976 | GGCCCTCTCCACTCCACCTCAGG |
| 977 | CCCCCCCCCCCCCCCGCCTCCGG |
| 978 | TCCCCCCTCAACCCCACCTCAGG |
| 979 | CTGCCCCCCCACCCCGCCACTGG |
| 980 | TGCCCCCCCCACCCCGCCCCCGG |
| 981 | GTCCTCCACCACCCCGCCTCTGG |
| 982 | GCCACCCACCACCCCACCTCAGG |
| 983 | TACCCCCCCCACCCCGCCACAGG |
| 984 | CTCCCCACCCACCCCGCCTCAGG |
| 985 | CAACCCCCCCACCCCGCTTCAGG |
| 986 | GCTTCCCTCCACCCCGCATCCGG |
| 987 | GTCACTCCCCACCCCGCCTCTGG |

TABLE 1-continued

Sequences in FIGS. 2A, 2B, 4C, 4D, 5B, and 5C

| SEQ ID NO: | Sequence |
|---|---|
| 988 | ATCCCCCTCCACCCCACCCCTGG |
| 989 | GACCCCCCCCACCCCGCCCCCGG |
| 990 | GCCACCTTCCACCCCACCTCAGG |
| 991 | CACTCCCCCCACCCCGCCCCAGG |
| 992 | GACCCCTCCCACCCCGACTCCGG |
| 993 | CCCCCCCCCCCCCCCGCCTCAGG |
| 994 | GCCTCTCTGCACCCCGCCTCAGG |
| 995 | CCCCCCCCCCACCCCGCCCCCGG |
| 996 | CTCTCCCCCCACCCCGCCTCTGG |
| 997 | CCCCACCCCCACCCCGCCTCAGG |
| 998 | GACCCCCCCCACCCCACCCCAGG |
| 999 | CCACCCCCCCACCCCGCCCCAGG |
| 1000 | AGGCCCCCCCGCCCCGCCTCAGG |
| 1001 | CCCCCCCCCCCCCCCACCCCCAG |
| 1002 | GATCGACTCCACCCCGCCTCTGG |
| 1003 | AGCCAACCCCACCCCGCCTCTGG |
| 1004 | TCCACCCCCCACCCCGCCCCGGG |
| 1005 | CACCCCCCGCACCCCGCCCCAGG |
| 1006 | CCTCCCCCACACCCCGCATCCGG |
| 1007 | GGCAGCCTCCACCACGCCTCCGG |
| 1008 | CATCCCCCCCACCCCACCCCGGG |
| 1009 | CCACCCCCCCACCCCGCCCCTGG |
| 1010 | AGGCCCCCACACCCCGCCTCAGG |
| 1011 | GTACCCCACCACCCCGCCCCAGG |
| 1012 | CATACCCCCCACCCCGCCCCGGG |
| 1013 | CCGCCCCTCCACCCCGCCACTGG |
| 1014 | AGTAGCCCCCACCCCGCCTCGGG |
| 1015 | ACCCCCCCCCCCCCCGCCCCCGG |
| 1016 | GCCCCGCTCCTCCCCGCCTCCGG |
| 1017 | CCACCCCTCCACCCTGCTTCGGG |
| 1018 | CATTTCCCCTACCCCGCCCCTGG |
| 1019 | AACACGCCCCACCCCGCCCCAGG |
| 1020 | GAGCCACTGTGCCCAGCCTAGGG |
| 1021 | CACTCCCCACCCCCCACCCCCAG |
| 1022 | CCCTCCCCCCACCCCACAACAGG |
| 1023 | GTCCCTTTCCACCCTGCCTCTGG |
| 1024 | GAGCTCCCCCACCCCGCCCCGGG |
| 1025 | AACACCCGCCCCCCCACCCCCGG |

TABLE 1-continued

Sequences in FIGS. 2A, 2B, 4C, 4D, 5B, and 5C

| SEQ ID NO: | Sequence |
|---|---|
| 1026 | GATTCCCTGGACCACATCTCTGG |
| 1027 | GAGCCACCAAACCCAGCCTCAGG |
| 1028 | GAATCCCAGGAGCCCGCCTCGAG |
| 1029 | GGCCCCCTTTCCCACATCTCTGG |
| 1030 | CTCCCCCAGCCCCCCACCTCCCG |
| 1031 | CATTCTCGACACCCCGCCCCCGG |
| 1032 | TACTCCTTCACCCCCACCCCAGG |
| 1033 | CACACTCTCAACCTCACTTCTAG |
| 1034 | TCCATCCTCAGCCCCACCTCTCG |
| 1035 | AACCCATTCCACCCTGCCTCAGG |
| 1036 | GCCACCCCCCACCCTGCCTCCGG |
| 1037 | CACCAGGTCTGCCCCGCATCAGG |
| 1038 | AATCCTCTCACCTCAGCCTCCGG |
| 1039 | GTGCCACTCCACCCCACCCTGGG |
| 1040 | CCCCCCGGCCCCCCCACCCCAGG |
| 1041 | CACCCCCCGCCCCCCGCCCCCGG |
| 1042 | CTCACCATAAACTCCGCCTCCCG |
| 1043 | GAGCCACTGCACCCAGCCTCAAG |
| 1044 | GAGCCACCACAACCAGCCTCGAG |
| 1045 | GTTTCCCTTCTTCCCGCCCCAGG |
| 1046 | CCCCCACCCCCCCCCACCCCCAG |
| 1047 | ATCCTCCCACACCCCACATCAGA |
| 1048 | CACCGCGCCCAGCCAGCTTCTGG |
| 1049 | GAGCCACCTCACCCAGCCTAAAG |
| 1050 | GAGCCACCACACCCAGCCTAAAG |
| 1051 | GAGCCACTGCGCCCAGCCCCAGG |
| 1052 | GAACCAGACCTCCCCATCTCCAG |
| 1053 | GAGCCACTGCACCTGGCCTCAGG |
| 1054 | GCACACCACCCCCCCGCCACCGG |
| 1055 | TGTGAAAACTAAGAGAGAGCTCCACCCCTCTGTGCCCTC CTCCTGTCCTGAGTCGGGGTGGGGGGGGCTGGCCTTGGA GGGGGCGTCCCCT |
| 1056 | GGCCACGTCGCCCGTGTATGAGATGGCAGCCTCCACCAC GCCTCCGGCACTTCCTGCCGCCTCCATGCCCAGCAGCAT GTTGGGCAAGTAGTTGAGGGAG |
| 1057 | AVDGTYSIAAEVVGGASGAAEMGLLMNPLYNLS |
| 1058 | CCACCCACCACCCCACCTCAGGCAAATGCCCAGCCCCTG CCTCGCCTCCAGCCTCCTTTCCACAACCCAGCATCCAGT CACTCCAGTC |
| 1059 | GCCCCGGGTTTCAAGTGATTTTCATACTTCAGCCTCCTG AGTAGCT |
| 1060 | AGCCCCAGCAAGAGCACAAGAGG |
| 1061 | ATCACCCCCAAGAGCACAAGGGG |
| 1062 | AGCCCCAGTGAGAGCACAAGAGG |
| 1063 | AGTTCCAGCAACAGCACAAAAGG |
| 1064 | AACTCCAGCGAGAGCACAAGAGG |
| 1065 | AGCCCCAGTAAGAGCACAAGAGG |
| 1066 | AACACAAGCAAGAGCACGAGAGG |
| 1067 | AGCCCCAGCAAGAGCACGAGAGG |
| 1068 | AGCCTAAGAAAGAACACAAGAGG |
| 1069 | AGCCCCAGCTAAAGCAAAAGAGG |
| 1070 | TGCCCCAGCTAAAACACAAGTGG |
| 1071 | AAACCAAACAAGGACACAAGAGA |
| 1072 | AATCCCAGTGAGAGCACAAGAGG |
| 1073 | ACCCCTAGCTACAGCACAAGAGG |
| 1074 | TGCAGCAGCAAGAGCACAGGCGG |
| 1075 | CACAAGAGCAAGAGCACAAGAGG |
| 1076 | GCTCTCAGCAAGACCACAAGTGG |
| 1077 | TGCCCCAAGAACAACAAAAAAAG |
| 1078 | TGCCTCAGTCAAAGCACAGCAGG |
| 1079 | AAAACCAACAACAGTACAAAAGG |
| 1080 | CACTCCAGCCTGGGCAAAAGAGG |
| 1081 | ATTCTGAGGAAGAAAACAAGGGG |
| 1082 | TCCCCCTACCAGAGCACATACAG |
| 1083 | AGGCAAATCAAAACCACAATGAG |
| 1084 | AAAACAAGAAAGAACAAAAGAGA |
| 1085 | CTTGCCCCACAGGGCAGTAACGG |
| 1086 | CTTGGCCTGCAGGGCAGTTATGG |
| 1087 | TCTACCCCACATGGCAGTAATGG |
| 1088 | ACTGAGCCTCAGGGCAGTAATGG |
| 1089 | CCTGCCCCACAGGGCAATTATGG |
| 1090 | CCTCTCCCACAGGGCAGTAAAGG |
| 1091 | GCTGCCCCACAGGGCAGCAAAGG |
| 1092 | CCTCCAATACAGGGCAGTAAAGG |
| 1093 | CCTGTCCCACAGGGCAGGAAGGG |
| 1094 | CTGGCACCACAGAGCAGAAAGGG |
| 1095 | CATGCTCCACAGAGCAGCAAAGG |
| 1096 | GGGCTGCCCCAGGGCAGTAATGG |

TABLE 1-continued

| Sequences in FIGS. 2A, 2B, 4C, 4D, 5B, and 5C | |
|---|---|
| SEQ ID NO: | Sequence |
| 1097 | CTTGCTGCACAGGACAATAAAGG |
| 1098 | CTCGCCCCTCAGGGCAGTAGTGG |
| 1099 | GTTGGCCCTCAGGGCAGAAATGG |
| 1100 | GAGGCGCCACAGGGCAGTAATGG |
| 1101 | GCTGTGTCATAGGGCAGTAACGG |
| 1102 | CTTTCTTCACAGGGTAGTAATGG |
| 1103 | TGCCCCAGACAGGGCAGTAAGGG |
| 1104 | CTTGCACTACAAGTCAGTAATGG |
| 1105 | ATTTCCTCACAGGGCAGAAAAGG |
| 1106 | TCACCCCCACAGGCCAGTAAAGG |
| 1107 | GTCATGTCACAGGGCAGTAGTGG |
| 1108 | GGCCCTGCCCAGGGCAGTAATGG |
| 1109 | CTTAATACACAGGGAAGGAATGG |
| 1110 | CTTCAAGAGCAACAGTGCTGTGG |
| 1111 | GAGAGACAGCAACAGTGCTATGG |
| 1112 | AGCAAGGAGCAACAGTGATGTGG |
| 1113 | AGCAAACATCAACAGTGCTGAGG |
| 1114 | TAGGAAGAGCAACAGGGCTGTGG |
| 1115 | CATGAAGGGCAACAGAGCTGAGG |
| 1116 | CACTCTAAGCAACAGTGCTGGGG |
| 1117 | TGCGAGGAGCAACAGTGCTTGGG |
| 1118 | GTCTCTAGGCAACAGTGCTGAGG |
| 1119 | GGGCAGCAGCTACAGTGCTGAGG |
| 1120 | GGGCGGTGCTACAACTGGGCTGG |
| 1121 | GGGTGGTTCTACAACCAGGCTGG |
| 1122 | GGGCGGTGCTACAACTGGGCTGG |
| 1123 | GGGAGGTGCCACATCAGGGCCGG |
| 1124 | GGGCAGTGATCCAACTGTGCAGG |
| 1125 | AGCTGGGGCTACATCTGGGCTGG |
| 1126 | GCTGGGTGCTACAACAGGGCAGG |
| 1127 | CTGTGGTGCAACAACTGGGCTGG |
| 1128 | GGGAGGAGGTACAACTGGGAGGG |
| 1129 | CAGTGTGGCTACAACTGCGCAGG |
| 1130 | CTGGTCAGCTACAACTGGCCTGG |
| 1131 | GGTGTAAAATCAACACCCTAAGG |
| 1132 | GCTGGAAAAAAAACACCCTAGGG |
| 1133 | GAGGTAAAACCAACACCTTAAGG |
| 1134 | TGGCTGAAATCAACACCCCAGGG |
| 1135 | TGACACCAATCAACACCTTAAGG |
| 1136 | TCTGATCCATCAACACCCTATGG |

DETAILED DESCRIPTION

Overview

Aspects described herein are methods for enriching or identifying at least one target nucleic acid. In some aspects, the method increases sensitivity of enriching or identifying the at least one target nucleic acid. In some aspects, the method increases specificity of enriching or identifying the at least one target nucleic acid. In some aspects, the method comprises ligating at least one adaptor to the at least one target nucleic acid. In some aspects, the method comprises performing at least one PCR to obtain at least one PCR product. In some aspects, the method comprises performing a first PCR to obtain a first PCR product followed by performing a second PCR to obtain a second PCR product, where the at least one adaptor is ligated to the at least one target nucleic acid or to the PCR product.

In some embodiments, the method comprises enriching at least one target nucleic acid from a sample comprising a plurality of single-strand nucleic acid fragments by contacting a universal oligonucleotide adaptor with the sample to produce a ligation product. In some embodiments, the universal oligonucleotide adaptor is configured for ligating to a 5' end of the single-strand nucleic acid fragments. In some embodiments, the method comprises amplifying the ligation product by a first PCR to form a first PCR product. In some embodiments, the method comprises amplifying the first PCR product by a second PCR with a second target-specific primer and a universal oligonucleotide adaptor primer to form a second PCR product. In some embodiments, the second target-specific primer is nested relative to the first target-specific primer. In some embodiments, the method enriches at least one target nucleic acid from a sample comprising a plurality of single-strand nucleic acid fragments by ligating a universal oligonucleotide adaptor to a 5' end of the single-strand nucleic acid fragments; annealing a first target-specific primer to the single-strand nucleic acid fragments in the vicinity of a target sequence; extending the first target-specific primer over the single-strand nucleic acid fragments using a DNA polymerase; obtaining a nascent primer extension duplex; dissociating the nascent primer extension duplex into single strands; and amplifying a portion of the single stands of the nascent primer extension duplex with a second target-specific primer and a universal oligonucleotide adaptor primer.

In some embodiments, the method described herein identifies genome-wide gene editing off-target sites from a sample comprising a plurality of single-strand nucleic acid fragments by contacting a universal oligonucleotide adaptor with the sample to produce a ligation product, wherein the universal oligonucleotide adaptor is configured for ligating to a 5' end of the single-strand nucleic acid fragments; amplifying the ligation product by performing a first PCR with a first target-specific primer to form a first PCR product; amplifying the first PCR product by a second PCR with a sequencing specific adaptor primer and a second target-specific primer nested relative to the first target-specific primer, to form a sequencing library; quantifying and reading the sequencing library to obtain sequencing results; and mapping the sequencing results to a reference genome. In some embodiments, the method described herein can evaluate gene editing efficiency from a sample comprising a plurality of single-strand nucleic acid fragments by contacting a universal oligonucleotide adaptor with the sample to produce a ligation product, wherein the universal oligonucleotide adaptor is configured for ligating to a 5' end of the single-strand nucleic acid fragments; amplifying the first ligation product by performing a first PCR with a first target-specific primer to form a first PCR product; amplifying the first PCR product by a second PCR with a sequencing specific adaptor primer and a second target-specific primer nested relative to the first target-specific primer, to form a sequencing library; quantifying and reading the sequencing library to form sequencing results; and mapping the sequencing results to a reference genome and evaluating gene editing efficiency. In some aspects, the evaluation of gene editing efficiency can be applied to evaluating translocation or indel frequency.

In some aspects, described herein is a method of identifying genome-wide gene editing off-target sites from a sample comprising at least one target nucleic acid by contacting a universal oligonucleotide adaptor with the sample to produce a ligation product, wherein the universal oligonucleotide adaptor is configured for ligating to a 5' end of the single-strand nucleic acid fragments; amplifying the ligation product by a first PCR with a first set of target-specific primers, wherein the target-specific primers in the first set are configured for annealing to the single-strand nucleic acid fragments 5' of an on-target site and one or more predicted and/or known off-target sites; amplifying the first PCR product by a second PCR with a second set of target-specific primers and a universal oligonucleotide adaptor primer to form a sequencing library, wherein each member of the second set of target-specific primers is nested relative to a corresponding primer of the first set of target-specific primers; and sequencing the sequencing library to identify off-target sites. In some embodiments, the method described herein can be combined with computation prediction for identifying off-target sites.

Enrichment

In certain embodiments, provided is a method of enriching at least one targeted nucleic acid from a sample comprising a plurality of single-strand nucleic acid fragments, the method comprising: contacting a universal oligonucleotide adapter with the sample to produce a ligation product, where the universal oligonucleotide adaptor is configured for ligating to a 5' end of the single-strand nucleic acid fragments. In some embodiments, the method comprises amplifying the ligation product by a first PCR with a first target-specific primer to form a first PCR product. In some embodiments, the method comprises amplifying the first PCR product by a second PCR with a second target-specific primer and a universal oligonucleotide adaptor primer to form a second PCR product, where the second target-specific primer is nested relative to the first target-specific primer. In some embodiments, the sample comprises a plurality of DNA fragments prepared from high molecular weight DNA (e.g., genomic DNA). In some embodiments, the plurality of DNA fragments are prepared by enzyme-based treatment. In other embodiments, the plurality of DNA fragments are prepared by being exposed to short-wavelength, high-frequency acoustic energy. In other embodiments, the plurality of DNA fragments are prepared by heating the DNA at 100° C. to 105° C. In other embodiments, the plurality of DNA fragments are prepared by centrifugal shearing. In other embodiments, the plurality of DNA fragments are prepared by hydrodynamic shear forces. In some embodiments, the plurality of DNA fragments are prepared by being exposed to ultrasound sonication. In some specific embodiments, the plurality of DNA fragments are prepared by Bioruptor® Pico or Diagenode One. In other embodiments, the plurality of DNA fragments are prepared by turbulent flow generated by formation of hydropores. In some specific embodiments, the plurality of DNA fragments are prepared by Megaruptor®, Nebulizer®, and/or Covaris®. In some embodiments, the preparation of the plurality of DNA fragments is analyzed and confirmed by agarose gel electrophoresis. In some embodiments, the preparation of the plurality of DNA fragments is analyzed and confirmed by Fragment Analyzer™. In some embodiments, the preparation of the plurality of DNA fragments is analyzed and confirmed by LabChip® GX Touch™ nucleic acid analyzer.

In some embodiments, the plurality of DNA fragments described herein are about 50 bp to about 5000 bp long. In some specific embodiments, the plurality of DNA fragments described herein are about 50 bp to about 200 bp long, about 50 bp to about 300 bp long, about 50 bp to about 400 bp long, about 50 bp to about 500 bp long, about 50 bp to about 600 bp long, about 50 bp to about 700 bp long, about 50 bp to about 800 bp long, about 50 bp to about 900 bp long, about 50 bp to about 500 bp long, about 50 bp to about 2000 bp long, about 50 bp to about 3000 bp long, about 50 bp to about 4000 bp long, or about 50 bp to about 5000 bp long. In some specific embodiments, the plurality of DNA fragments described herein are about 100 bp to about 200 bp long, about 100 bp to about 300 bp long, about 100 bp to about 400 bp long, about 100 bp to about 500 bp long, about 100 bp to about 600 bp long, about 100 bp to about 700 bp long, about 100 bp to about 800 bp long, about 100 bp to about 900 bp long, about 100 bp to about 1000 bp long, about 100 bp to about 2000 bp long, about 100 bp to about 3000 bp long, about 100 bp to about 4000 bp long, or about 100 bp to about 5000 bp long. In other specific embodiments, the plurality of DNA fragments described herein are about 300 bp to about 400 bp long, about 300 bp to about 500 bp long, about 300 bp to about 600 bp long, about 300 bp to about 700 bp long, about 300 bp to about 800 bp long, about 300 bp to about 900 bp long, about 300 bp to about 1000 bp long, about 300 bp to about 2000 bp long, about 300 bp to about 3000 bp long, about 300 bp to about 4000 bp long, or about 300 bp to about 5000 bp long. In other specific embodiments, the plurality of DNA fragments described herein are about 600 bp to about 700 bp long, about 600 bp to about 800 bp long, about 600 bp to about 900 bp long, about 600 bp to about 1000 bp long, about 600 bp to about 2000 bp long, about 600 bp to about 3000 bp long, about 600 bp to about 4000 bp long, or about 600 bp to about 5000 bp long. In other specific embodiments, the plurality of DNA fragments described herein are about 1000 bp to about 2000 bp long, about 1000 bp to about 3000 bp long, about 1000 bp to about 4000 bp long, or about 1000 bp to about 5000 bp long.

In some embodiments, the plurality of single-strand nucleic acid fragments are prepared from denaturation of double-strand DNA fragments. In some specific embodiments, the double-strand DNA fragments are heated at 95° C. for 1, 5, 10, 20, or 30 minutes. In other specific embodiments, the double-strand DNA fragments are heated at 95° C. for 1, 5, 10, 20, or 30 minutes, followed by being placed on ice for 1 minute. In other specific embodiments, the double-strand DNA fragments are disrupted with glass beads (Disruptor Beads™; Scientific Industries, Bohemia, NY, USA) for 1, 5, 10, 20, or 30 minutes at 2,500 rpm with a Disruptor Genie bead-beater (Scientific Industries); followed by centrifuging at 3,000 rpm for 30 seconds to precipitate out the beads. In other specific embodiments, the double-strand DNA fragments are subjected to direct sonication at 10W for 30, 60, 90, 120, 150, 200, 250, or 300 seconds. In other specific embodiments, the double-strand DNA fragments are indirect sonication at 10 W, 22.4 kHz for 1, 5, 10, 20, or 30 minutes. In other specific embodiments, the double-strand DNA fragments are placed in tubes and immerged into the water of the ultrasonic bath at 40 kHz for 1, 5, 10, 20, or 30 minutes. In other specific embodiments, the double-strand DNA fragments are homogenized in 0.01, 0.1, or 1 mol/L NaOH with continuous pipetting and incubated at ambient temperature for 1, 2, 5, 10, 20, or 30 minutes. In other specific embodiments, the double-strand DNA fragments are homogenized gently with pipette in 25% and 50% formamide solution and incubated at room temperature. In other specific embodiments, the double-strand DNA fragments are homogenized gently with pipette in 25%, 50%, and 60% DMSO solution and incubated at room temperature. In some embodiments, the preparation of the plurality of single-strand nucleic acid fragments is confirmed by measuring the absorbance of DNA fragments at 260 nm.

In some embodiments, the method further comprises at least one of: blocking a 3' end of the single-strand nucleic acid fragments; phosphorylating a 5' end of the single-strand nucleic acid fragments; or adenylating the nucleic acid to produce a 3'-adenosine overhang on the single-strand nucleic acid fragments. In some embodiments, the universal oligonucleotide adaptor is single stranded. In some embodiments, the universal oligonucleotide adaptor is double stranded. In some embodiments, the universal oligonucleotide adaptor comprises: a 3' recessive end, the 3' recessive end configured for ligating to the 5' end of the single-strand nucleic acid fragments; and a 5' protrude end comprising three to twenty bases of random or degenerate nucleotides. A duplex portion of the universal oligonucleotide adaptor is of sufficient length to remain in duplex. In some embodiments, the universal oligonucleotide adaptor comprises a hairpin loop connecting a portion of the duplex form. In some embodiments, the universal oligonucleotide adaptor comprises a Y shape. In some embodiments, the universal oligonucleotide adaptor comprises a barcode. In some embodiments, the universal oligonucleotide adaptor comprises a single strand segment comprising three to twenty random nucleotides as a unique molecular index (UMI) for tracing individual original molecules.

In some embodiments, the universal oligonucleotide adaptor is ligated to the 5' end of the single-stranded nucleic acid fragments. In some embodiments, the universal oligonucleotide adaptor is ligated to the 3' end of the single-stranded nucleic acid fragments. In some embodiments, the universal oligonucleotide adaptor is ligated to the 5' and 3' end of the single-stranded nucleic acid fragments. In some embodiments, the universal oligonucleotide adaptor is ligated via a ligase. When the sample described herein is a targeted gene edited sample, the target of the first target-specific primer described herein is predetermined. In some embodiments, the target comprises an on-target site of the CRISPR gene editing. In other embodiments, the target comprises a predicted off-target site of the CRISPR gene editing. In other embodiments, the target comprises a spontaneous double-strand breakpoint.

The predicted off-target site described herein is computationally predicted. In some specific embodiments, the predicted off-target site described herein is predicted by E-CRISP. In other specific embodiments, the predicted off-target site described herein is predicted by Cas-OFFinder. In other specific embodiments, the predicted off-target site described herein is predicted by CRISPRscan. In other specific embodiments, the predicted off-target site described herein is predicted by CRISPRitz. In other specific embodiments, the predicted off-target site described herein is predicted by CRISPOR. In other specific embodiments, the predicted off-target site described herein is predicted by CRISPR Design website (http://crispr.mit.edu). In other specific embodiments, the predicted off-target site described herein is predicted by Ecrisp. In other specific embodiments, the predicted off-target site described herein is predicted by Crispr2vec. In other specific embodiments, the predicted off-target site described herein is predicted by Hsu-Zhang scores. In other specific embodiments, the predicted off-target site described herein is predicted by CHOPCHOP. In other specific embodiments, the predicted off-target site described herein is predicted by CFD. In other specific embodiments, the predicted off-target site described herein is predicted by CRISTA. In other specific embodiments, the predicted off-target site described herein is predicted by Elevation. In other specific embodiments, the predicted off-target site described herein is predicted by DeepCrispr. In other specific embodiments, the predicted off-target site described herein is predicted by DeepSpCas9. In other specific embodiments, the predicted off-target site described herein is predicted by CALITAS. In other specific embodiments, the predicted off-target site described herein is predicted by an algorithm with a deep convolutional neural network or a deep feedforward neural network. In some embodiments, the cutoff to set in one or more of the above-described prediction algorithms is mismatch(es) being less than or equal to 10, 9, 8, 7, 6, 5, 4, 3, 2, or 1 inside and/or outside of seed. In some embodiments, the cutoff to set in one or more of the above-described prediction algorithms is mismatch(es) being less than or equal to 10, 9, 8, 7, 6, 5, 4, 3, 2, or 1 inside and/or outside of protospacer adjacent motif (PAM). In other embodiments, the cutoff in one or more of the above-described prediction algorithms is set bulge(s) (insertion as DNA bulge or deletion as RNA bulge) being less than or equal to 4, 3, 2, or 1 respectively inside and/or outside of seed. In other embodiments, the cutoff in one or more of the above-described prediction algorithms is set bulge(s) (insertion as DNA bulge or deletion as RNA bulge) being less than or equal to 4, 3, 2, or 1 respectively inside and/or outside of PAM.

In some embodiments, the spontaneous double-strand breakpoints described herein are genome fragile sites. In some specific embodiments, the spontaneous double-strand breakpoints described herein comprise Chr 1:89231183, Chr 1:109838221.

The first target-specific primer described herein is designed to be in the vicinity of the target described herein. In some embodiments, the first target-specific primer described herein is reverse complementary to a DNA segment that is in the downstream of the target described herein on either strand. In some specific embodiments, the DNA segment described herein is about 5 bp to about 1000 bp downstream of one of the target described herein. In some specific embodiments, the DNA segment described herein is about 5 bp to about 500 bp downstream of one of the target described herein. In some specific embodiments, the DNA segment described herein is about 5 bp to about 10 bp, about 10 bp to about 30 bp, about 30 bp to about 50 bp, about 50 bp to about 70 bp, about 70 bp to about 90 bp, or about 90 bp to about 100 bp downstream of the target described herein. In other specific embodiments, the DNA segment described herein is about 100 bp to about 120 bp, about 120 bp to about 140 bp, about 140 bp to about 160 bp, about 160 bp to about 180 bp, about 180 bp to about 200 bp, downstream of the target described herein. In other specific embodiments, the DNA segment described herein is about 200 bp to about 220 bp, about 220 bp to about 240 bp, about 240 bp to about 260 bp, about 260 bp to about 280 bp, about 280 bp to about 300 bp downstream of the target described herein. In other specific embodiments, the DNA segment described herein is about 300 bp to about 400 bp, about 400 bp to about 500 bp, about 500 bp to about 600 bp, about 600 bp to about 700 bp, about 700 bp to about 800 bp, about 800 bp to about 900 bp, about 900 bp to about 100 bp downstream of the target described herein. In other specific embodiments, the DNA segment described herein is at least 10, 50, 100, 150, 200, 250, 300, 350, 400, 450, 500, 550, 600, 650, 700, 750, 800, 850, 900, 950, or 1000 bp downstream of the target described herein.

In some embodiments, the second target-specific primer described herein is designed to be in the vicinity of the target described herein. In some embodiments, the second target-specific primer described herein is reverse complementary to a DNA segment that is in the downstream of the target described herein on either strand. In some specific embodiments, the DNA segment described herein is about 3 bp to about 1000 bp downstream of one of the target described herein. In some specific embodiments, the DNA segment described herein is about 3 bp to about 300 bp downstream of one of the target described herein. In some specific embodiments, the DNA segment described herein is about 3 bp to about 10 bp, 10 bp to about 30 bp, about 30 bp to about 50 bp, about 50 bp to about 70 bp, about 70 bp to about 90 bp, or about 90 bp to about 100 bp downstream of the target described herein. In other specific embodiments, the DNA segment described herein is about 100 bp to about 120 bp, about 120 bp to about 140 bp, about 140 bp to about 160 bp, about 160 bp to about 180 bp, about 180 bp to about 200 bp, downstream of the target described herein. In other specific embodiments, the DNA segment described herein is about 200 bp to about 220 bp, about 220 bp to about 240 bp, about 240 bp to about 260 bp, about 260 bp to about 280 bp, about 280 bp to about 300 bp downstream of the target described herein. In other specific embodiments, the DNA segment described herein is about 300 bp to about 400 bp, about 400 bp to about 500 bp, about 500 bp to about 600 bp, about 600 bp to about 700 bp, about 700 bp to about 800 bp, about 800 bp to about 900 bp, about 900 bp to about 100 bp downstream of the target described herein. In other specific embodiments, the DNA segment described herein is at least 10, 50, 100, 150, 200, 250, 300, 350, 400, 450, 500, 550, 600, 650, 700, 750, 800, 850, 900, 950, or 1000 bp downstream of the target described herein.

The second target-specific primer described herein is designed to be in the vicinity of the first target-specific primer described herein. In some embodiments, the second target-specific primer described herein is reverse complementary to a DNA segment that is in the downstream of the first target-specific primer described herein on either strand. In some specific embodiments, the DNA segment described herein is about 3 bp to about 1000 bp downstream of one of the first target-specific primer described herein. In some specific embodiments, the DNA segment described herein is about 3 bp to about 300 bp downstream of the first target-specific primer described herein. In some specific embodiments, the DNA segment described herein is about 10 bp to about 30 bp, about 30 bp to about 50 bp, about 50 bp to about 70 bp, about 70 bp to about 90 bp, or about 90 bp to about 100 bp downstream of the first target-specific primer described herein. In other specific embodiments, the DNA segment described herein is about 100 bp to about 120 bp, about 120 bp to about 140 bp, about 140 bp to about 160 bp, about 160 bp to about 180 bp, about 180 bp to about 200 bp, downstream of the first target-specific primer described herein. In other specific embodiments, the DNA segment described herein is about 200 bp to about 220 bp, about 220 bp to about 240 bp, about 240 bp to about 260 bp, about 260 bp to about 280 bp, about 280 bp to about 300 bp downstream of the first target-specific primer described herein. In other specific embodiments, the DNA segment described herein is about 300 bp to about 400 bp, about 400 bp to about 500 bp, about 500 bp to about 600 bp, about 600 bp to about 700 bp, about 700 bp to about 800 bp, about 800 bp to about 900 bp, about 900 bp to about 100 bp downstream of the first target-specific primer described herein. In other specific embodiments, the DNA segment described herein is at least 10, 50, 100, 150, 200, 250, 300, 350, 400, 450, 500, 550, 600, 650, 700, 750, 800, 850, 900, 950, or 1000 bp downstream of the first target-specific primer described herein.

Primer Design

The first target-specific primer is 16-32 bp in length. In some embodiments, the first target-specific primer is 16 bp in length. In other embodiments, the first target-specific primer is 17 bp in length. In other embodiments, the first target-specific primer is 18 bp in length. In other embodiments, the first target-specific primer is 19 bp in length. In other embodiments, the first target-specific primer is 20 bp in length. In other embodiments, the first target-specific primer is 21 bp in length. In other embodiments, the first target-specific primer is 22 bp in length. In other embodiments, the first target-specific primer is 23 bp in length. In other embodiments, the first target-specific primer is 24 bp in length. In other embodiments, the first target-specific primer is 25 bp in length. In other embodiments, the first target-specific primer is 26 bp in length. In other embodiments, the first target-specific primer is 27 bp in length. In other embodiments, the first target-specific primer is 28 bp in length. In other embodiments, the first target-specific primer is 29 bp in length. In other embodiments, the first target-specific primer is 30 bp in length. In other embodiments, the first target-specific primer is 31 bp in length. In other embodiments, the first target-specific primer is 32 bp in length.

The first target-specific primer has a GC content of about 40% to about 60%. In some embodiments, the first target-specific primer has a GC content of about 40%. In other embodiments, the first target-specific primer has a GC content of about 45%. In other embodiments, the first target-specific primer has a GC content of about 50%. In other embodiments, the first target-specific primer has a GC content of about 55%. In other embodiments, the first target-specific primer has a GC content of about 60%.

The first target-specific primer has a melting temperature of about 55° C. to about 72° C. In some embodiments, the first target-specific primer has a melting temperature of about 55° C. In some embodiments, the first target-specific primer has a melting temperature of about 56° C. In some embodiments, the first target-specific primer has a melting temperature of about 57° C. In some embodiments, the first target-specific primer has a melting temperature of about 58° C. In other embodiments, the first target-specific primer has a melting temperature of about 59° C. In other embodiments, the first target-specific primer has a melting temperature of about 60° C. In other embodiments, the first target-specific primer has a melting temperature of about 65° C. In other embodiments, the first target-specific primer has a melting temperature of about 70° C. In some embodiments, the first target-specific primer has a melting temperature of about 71° C. In some embodiments, the first target-specific primer has a melting temperature of about 72° C.

The sequence of the first target-specific primer is determined such that any secondary structures are minimized. In some embodiments, the first target-specific primer does not form hairpin structures. In other embodiments, the first target-specific primer does not form dimers between two molecules of the first target-specific primer.

The last five bases on the 3' end of the first target-specific primer do not comprise too many G or C bases. In some embodiments, the last five bases on the 3' end of the first target-specific primer comprise no G or C bases. In other embodiments, the last five bases on the 3' end of the first target-specific primer comprise only one G or C base. In other embodiments, the last five bases on the 3' end of the first target-specific primer comprise only two G or/and C bases. In other embodiments, the last five bases on the 3' end of the first target-specific primer comprise only three G or/and C bases.

The sequence of the first target-specific primer comprises limited repeats of one base or dinucleotide repeats. In some embodiments, the sequence of the first target-specific primer comprises no repeats of one base or dinucleotide repeats. In other embodiments, the sequence of the first target-specific primer comprises one or more repeats of one base but no dinucleotide repeats, and wherein the one or more repeats of one base are repeats with the same base appearing only two times, only three times, or only four times. In other embodiments, the sequence of the first target-specific primer comprises no repeats of one base but one or more dinucleotide repeats, and wherein the one or more dinucleotide repeats are repeats with the same dinucleotide appearing only two times, only three times, or only four times. In other embodiments, the sequence of the first target-specific primer comprises one or more repeats of one base and one or more dinucleotide repeats, wherein the one or more repeats of one base are repeats with the same base appearing only two times, only three times, or only four times, and wherein the one or more dinucleotide repeats are repeats with the same dinucleotide appearing only two times, only three times, or only four times.

The sequence of the first target-specific primer is designed so that it is unlikely to generate additional (non-specific) PCR amplicons using Primer-BLAST, including SNP-containing genome databases. In some embodiments, the top non-specific PCR amplicons have at least four mismatches with the first target-specific primer. In other embodiments, the top non-specific PCR amplicons have at least five, at least six, at least seven, at least eight, at least nine, at least ten mismatches with the first target-specific primer The first target-specific primer may be automatically design by available algorithms. In some embodiments, the first target-specific primer is designed by IDT. In other embodiments, the first target-specific primer is designed by Eurofins Genomics. In other embodiments, the first target-specific primer is designed by Primer-Blast. In other embodiments, the first target-specific primer is designed by Primer3. In other embodiments, the first target-specific primer is designed by NetPrimer. In other embodiments, the first target-specific primer is designed by PerlPrimer. In other embodiments, the first target-specific primer is designed by Primer Premier.

In some embodiments, the first PCR is a linear amplification of the ligation product to obtain a nascent primer extension duplex. In some embodiments, the method described herein further comprises performing a nested amplification of the nascent primer extension duplex. In another exemplary embodiments, the first PCR is an exponential amplification of the targeted nucleic acid with the first target-specific primer and a universal oligonucleotide adaptor primer. In some embodiments, the first PCR comprises annealing the first target-specific primer to single-stranded nucleic acid fragments. The annealing temperature is determined by the melting temperature of the first target-specific primer. In some embodiments, the annealing temperature is about 55° C. In other embodiments, the annealing temperature is about 58° C. In other embodiments, the annealing temperature is about 60° C. In other embodiments, the annealing temperature is about 58° C. In other embodiments, the annealing temperature is about 65° C. In other embodiments, the annealing temperature is about 70° C. In other embodiments, the annealing temperature is about 75° C. In other embodiments, the annealing temperature is about 78° C. In some embodiments, the annealing lasts for about 0.5 minute. In other embodiments, the annealing lasts for about 1 minute. In other embodiments, the annealing lasts for about 1.5 minutes. In other embodiments, the annealing lasts for about 2 minutes. In other embodiments, the annealing lasts for about 3 minutes. In other embodiments, the annealing lasts for about 4 minutes. In other embodiments, the annealing lasts for about 5 minutes. In other embodiments, the annealing lasts for about 6 minutes. In other embodiments, the annealing lasts for about 7 minutes. In other embodiments, the annealing lasts for about 8 minutes. In other embodiments, the annealing lasts for about 9 minutes. In other embodiments, the annealing lasts for about 10 minutes. In other embodiments, the annealing lasts for about 11 minutes. In other embodiments, the annealing lasts for about 12 minutes. In other embodiments, the annealing lasts for about 13 minutes. In other embodiments, the annealing lasts for about 14 minutes. In other embodiments, the annealing lasts for about 15 minutes.

In some embodiments, the first PCR comprises an extension. In some specific embodiments, the extension lasts for about 20 seconds. In some specific embodiments, the extension lasts for about 30 seconds. In some specific embodiments, the extension lasts for about 40 seconds. In some specific embodiments, the extension lasts for about 50 seconds. In some specific embodiments, the extension lasts for about 60 seconds. In some specific embodiments, the extension lasts for about 70 seconds. In some specific embodiments, the extension lasts for about 80 seconds. In some specific embodiments, the extension lasts for about 90 seconds. In some specific embodiments, the extension lasts for about 100 seconds. In some specific embodiments, the extension lasts for about 110 seconds. In some specific embodiments, the extension lasts for about 120 seconds. In some specific embodiments, the extension lasts for about 3 minutes. In some specific embodiments, the extension lasts for about 4 minutes. In some specific embodiments, the extension lasts for about 5 minutes. In some specific embodiments, the extension lasts for about 6 minutes. In some specific embodiments, the extension lasts for about 7 minutes. In some specific embodiments, the extension lasts for about 8 minutes. In some specific embodiments, the extension lasts for about 9 minutes. In some specific embodiments, the extension lasts for about 10 minutes. In some specific embodiments, the extension lasts for about 11 minutes. In some specific embodiments, the extension lasts for about 12 minutes. In some specific embodiments, the extension lasts for about 13 minutes. In some specific embodiments, the extension lasts for about 14 minutes. In some specific embodiments, the extension lasts for about 15 minutes.

The first PCR comprises multiple cycles of the above-described PCR steps (annealing, extension, and denature) so that targets can be searched among samples multiple times. In some embodiments, the cycle number is at least 3. In some embodiments, the cycle number is at least 4. In some embodiments, the cycle number is at least 5. In some embodiments, the cycle number is at least 10. In some embodiments, the cycle number is at least 15. In some embodiments, the cycle number is at least 20. In some embodiments, the cycle number is at least 25. In some embodiments, the cycle number is at least 30. In some embodiments, the cycle number is at least 35. In some embodiments, the cycle number is at least 40. In some embodiments, the cycle number is at least 45. In some embodiments, the cycle number is at least 50. In some embodiments, the cycle number is at least 55. In some embodiments, the cycle number is at least 65. In some embodiments, the cycle number is at least 70. In some embodiments, the cycle number is at least 75.

In some embodiments, the method comprises performing a second PCR (e.g., a nested PCR) with at least one second target-specific primer. The second target-specific primer is 16-32 bp in length. In some embodiments, the second target-specific primer is 16 bp in length. In other embodiments, the second target-specific primer is 17 bp in length. In other embodiments, the second target-specific primer is 18 bp in length. In other embodiments, the second target-specific primer is 19 bp in length. In other embodiments, the second target-specific primer is 20 bp in length. In other embodiments, the second target-specific primer is 21 bp in length. In other embodiments, the second target-specific primer is 22 bp in length. In other embodiments, the second target-specific primer is 23 bp in length. In other embodiments, the second target-specific primer is 24 bp in length. In other embodiments, the second target-specific primer is 25 bp in length. In other embodiments, the second target-specific primer is 26 bp in length. In other embodiments, the second target-specific primer is 27 bp in length. In other embodiments, the second target-specific primer is 28 bp in length. In other embodiments, the second target-specific primer is 29 bp in length. In other embodiments, the second target-specific primer is 30 bp in length. In other embodiments, the second target-specific primer is 31 bp in length. In other embodiments, the second target-specific primer is 32 bp in length.

The second target-specific primer has a GC content of about 40% to about 60%. In some embodiments, the second target-specific primer has a GC content of about 40%. In other embodiments, the second target-specific primer has a GC content of about 45%. In other embodiments, the second target-specific primer has a GC content of about 50%. In other embodiments, the second target-specific primer has a GC content of about 55%. In other embodiments, the second target-specific primer has a GC content of about 60%.

The second target-specific primer has a melting temperature of about 55° C. to about 80° C. In some embodiments, the second target-specific primer has a melting temperature of about 55° C. In some embodiments, the second target-specific primer has a melting temperature of about 56° C. In some embodiments, the second target-specific primer has a melting temperature of about 57° C. In some embodiments, the second target-specific primer has a melting temperature of about 58° C. In other embodiments, the second target-specific primer has a melting temperature of about 59° C. In other embodiments, the second target-specific primer has a melting temperature of about 60° C. In other embodiments, the second target-specific primer has a melting temperature of about 65° C. In other embodiments, the second target-specific primer has a melting temperature of about 70° C. In other embodiments, the second target-specific primer has a melting temperature of about 75° C. In other embodiments, the second target-specific primer has a melting temperature of about 76° C. In other embodiments, the second target-specific primer has a melting temperature of about 77° C. In other embodiments, the second target-specific primer has a melting temperature of about 78° C. In other embodiments, the second target-specific primer has a melting temperature of about 79° C. In other embodiments, the second target-specific primer has a melting temperature of about 80° C.

The sequence of the second target-specific primer is determined such that any secondary structures are minimized. In some embodiments, the second target-specific primer does not form hairpin structures. In other embodiments, the second target-specific primer does not form dimers between two molecules of the second target-specific primer.

The last five bases on the 3' end of the second target-specific primer do not comprise too many G or C bases. In some embodiments, the last five bases on the 3' end of the second target-specific primer comprise no G or C bases. In other embodiments, the last five bases on the 3' end of the second target-specific primer comprise only one G or C base. In other embodiments, the last five bases on the 3' end of the second target-specific primer comprise only two G or/and C bases. In other embodiments, the last five bases on the 3' end of the second target-specific primer comprise only three G or/and C bases.

The sequence of the second target-specific primer comprises limited repeats of one base or dinucleotide repeats. In some embodiments, the sequence of the second target-specific primer comprises no repeats of one base or dinucleotide repeats. In other embodiments, the sequence of the second target-specific primer comprises one or more repeats of one base but no dinucleotide repeats, and wherein the one or more repeats of one base are repeats with the same base appearing only two times, only three times, or only four times. In other embodiments, the sequence of the second target-specific primer comprises no repeats of one base but one or more dinucleotide repeats, and wherein the one or more dinucleotide repeats are repeats with the same dinucleotide appearing only two times, only three times, or only four times. In other embodiments, the sequence of the second target-specific primer comprises one or more repeats of one base and one or more dinucleotide repeats, wherein the one or more repeats of one base are repeats with the same base appearing only two times, only three times, or only four times, and wherein the one or more dinucleotide repeats are repeats with the same dinucleotide appearing only two times, only three times, or only four times.

The sequence of the second target-specific primer is designed so that it is unlikely to generate additional (non-specific) PCR amplicons using Primer-BLAST, including SNP-containing genome databases. In some embodiments, the top non-specific PCR amplicons have at least four mismatches with the second target-specific primer. In other embodiments, the top non-specific PCR amplicons have at least five, at least six, at least seven, at least eight, at least nine, at least ten mismatches with the second target-specific primer The second target-specific primer may be automatically design by available algorithms. In some embodiments, the second target-specific primer is designed by IDT. In other embodiments, the second target-specific primer is designed by Eurofins Genomics. In other embodiments, the second target-specific primer is designed by Primer-Blast. In other embodiments, the second target-specific primer is designed by Primer3. In other embodiments, the second target-specific primer is designed by NetPrimer. In other embodiments, the second target-specific primer is designed by PerlPrimer. In other embodiments, the second target-specific primer is designed by Primer Premier.

In some embodiments, the second PCR is a linear amplification of the ligation product to obtain a nascent primer extension duplex. In some embodiments, the method described herein further comprises performing a nested amplification of the nascent primer extension duplex. In another exemplary embodiments, the second PCR is an exponential amplification of the targeted nucleic acid with the second target-specific primer and a universal oligonucleotide adaptor primer. In some embodiments, the second PCR comprises annealing the second target-specific primer to single-stranded nucleic acid fragments. The annealing temperature is determined by the melting temperature of the second target-specific primer. In some embodiments, the annealing temperature is about 55° C. In other embodiments, the annealing temperature is about 58° C. In other embodiments, the annealing temperature is about 60° C. In other embodiments, the annealing temperature is about 58° C. In other embodiments, the annealing temperature is about 65° C. In other embodiments, the annealing temperature is about 70° C. In other embodiments, the annealing temperature is about 75° C. In other embodiments, the annealing temperature is about 78° C. In some embodiments, the annealing lasts for about 0.5 minute. In other embodiments, the annealing lasts for about 1 minute. In other embodiments, the annealing lasts for about 1.5 minutes. In other embodiments, the annealing lasts for about 2 minutes. In other embodiments, the annealing lasts for about 3 minutes. In other embodiments, the annealing lasts for about 4 minutes. In other embodiments, the annealing lasts for about 5 minutes. In other embodiments, the annealing lasts for about 6 minutes. In other embodiments, the annealing lasts for about 7 minutes. In other embodiments, the annealing lasts for about 8 minutes. In other embodiments, the annealing lasts for about 9 minutes. In other embodiments, the annealing lasts for about 10 minutes. In other embodiments, the annealing lasts for about 11 minutes. In other embodiments, the annealing lasts for about 12 minutes. In other embodiments, the annealing lasts for about 13 minutes. In other embodiments, the annealing lasts for about 14 minutes. In other embodiments, the annealing lasts for about 15 minutes.

In some embodiments, the second PCR comprises an extension. In some specific embodiments, the extension lasts for about 20 seconds. In some specific embodiments, the extension lasts for about 30 seconds. In some specific embodiments, the extension lasts for about 40 seconds. In some specific embodiments, the extension lasts for about 50 seconds. In some specific embodiments, the extension lasts for about 60 seconds. In some specific embodiments, the extension lasts for about 70 seconds. In some specific embodiments, the extension lasts for about 80 seconds. In some specific embodiments, the extension lasts for about 90 seconds. In some specific embodiments, the extension lasts for about 100 seconds. In some specific embodiments, the extension lasts for about 110 seconds. In some specific embodiments, the extension lasts for about 120 seconds. In some specific embodiments, the extension lasts for about 3 minutes. In some specific embodiments, the extension lasts for about 4 minutes. In some specific embodiments, the extension lasts for about 5 minutes. In some specific embodiments, the extension lasts for about 6 minutes. In some specific embodiments, the extension lasts for about 7 minutes. In some specific embodiments, the extension lasts for about 8 minutes. In some specific embodiments, the extension lasts for about 9 minutes. In some specific embodiments, the extension lasts for about 10 minutes. In some specific embodiments, the extension lasts for about 11 minutes. In some specific embodiments, the extension lasts for about 12 minutes. In some specific embodiments, the extension lasts for about 13 minutes. In some specific embodiments, the extension lasts for about 14 minutes. In some specific embodiments, the extension lasts for about 15 minutes.

The second PCR comprises multiple cycles of the above-described PCR steps (annealing, extension, and denature) so that targets can be searched among samples multiple times. In some embodiments, the cycle number is at least 3. In some embodiments, the cycle number is at least 4. In some embodiments, the cycle number is at least 5. In some embodiments, the cycle number is at least 10. In some embodiments, the cycle number is at least 15. In some embodiments, the cycle number is at least 20. In some embodiments, the cycle number is at least 25. In some embodiments, the cycle number is at least 30. In some embodiments, the cycle number is at least 35. In some embodiments, the cycle number is at least 40. In some embodiments, the cycle number is at least 45. In some embodiments, the cycle number is at least 50. In some embodiments, the cycle number is at least 55. In some embodiments, the cycle number is at least 65. In some embodiments, the cycle number is at least 70. In some embodiments, the cycle number is at least 75.

In some embodiments, the method comprises forming a sequencing library with the first or the second, or any other additional primer described herein. In some embodiments, the method comprises forming a sequencing library with a sequencing specific adaptor pair. In some embodiments, the method comprises sequencing the sequencing library using a sequencing primer pair, where the sequencing primer pair is at least partially complementary to opposite strands of the second PCR product, respectively. In some embodiments, the sample comprises single-strand cDNA fragments prepared from reverse transcription of RNA fragments. In some embodiments, the method further comprises analyzing the plurality of nucleic acids fragments. In some embodiments, the first PCR and/or second PCR are multiplexing PCR. In some embodiments, the sample is from a mammal, (e.g., a human). In some embodiments, the human is an individual known to have or suspected of having a disease, (e.g. a cancer or a genetic disorder). In some embodiments, one or more of the target sequences comprise one or more markers for the cancer. In another aspect, provided is a method of enriching at least one targeted nucleic acid from a sample comprising a plurality of single-strand nucleic acid fragments, the method comprising ligating a universal oligonucleotide adaptor to a 5' end of the single-strand nucleic acid fragments. In some embodiments, the method comprises annealing a first target-specific primer to the single-strand nucleic acid fragments in the vicinity of a target sequence. In some embodiments, the method comprises extending the first target-specific primer over the single-strand nucleic acid fragments using a DNA polymerase. In some embodiments, the method comprises obtaining a nascent primer extension duplex. In some embodiments, the method comprises dissociating the nascent primer extension duplex into single strands. In some embodiments, the method comprises repeating for one or more cycles In some embodiments, the method comprises amplifying a portion of the single stands of the nascent primer extension duplex with a second target-specific primer and an adaptor primer.

In some embodiments, the method further comprises at least one of: blocking a 3' end of the single-strand nucleic acid fragments; phosphorylating a 5' end of the single-strand nucleic acid fragments; or adenylating the nucleic acid to produce a 3'-adenosine overhang on the single-strand nucleic acid fragments. In some embodiments, the universal oligonucleotide adaptor comprises: a 3' recessive end, the 3' recessive end configured for ligating to the 5' end of the single-strand nucleic acid fragments; and a 5' protrude end comprising three to twenty bases of random or degenerate nucleotides. A duplex portion of the universal oligonucleotide adaptor is of sufficient length to remain in duplex form. In some embodiments, the universal oligonucleotide adaptor comprises a hairpin loop connecting a portion of the duplex form. In some embodiments, the method comprises forming a sequencing library with a sequencing specific adaptor pair. In some embodiments, the method, further comprises sequencing the sequencing library using a sequencing primer pair, wherein the sequencing primer pair is at least partially complementary to opposite strands of the second PCR product, respectively. In some embodiments, the sample comprises a plurality of DNA fragments prepared from high molecular weight DNA (e.g., genomic DNA). In some embodiments, the plurality of single-strand nucleic acid fragments are prepared from denaturation of double-strand DNA fragments. In some embodiments, the sample comprises single-strand cDNA fragments prepared from reverse transcription of RNA fragments. In some embodiments, the universal oligonucleotide adaptor primer is added for exponential amplification of the target sequence. In some embodiments, the universal oligonucleotide adaptor comprises a single strand segment comprising three to twenty random nucleotides as a unique molecular index (UMI) for tracing individual original molecules. In some embodiments, the method further comprises analyzing the plurality of nucleic acids fragments. In some embodiments, the first PCR and/or second PCR are multiplexing PCR.

In some embodiments, the sample is from a mammal, (e.g., a human). In some embodiments, the human is an individual known to have or suspected of having a disease, (e.g. a cancer or a genetic disorder). In some embodiments, one or more of the target sequences comprise one or more markers for the cancer. In some embodiments, the human is a fetus. In some embodiments, the sample is from a blood sample. In some embodiments, the sample is cell-free nucleic acids extracted from a blood sample. In some embodiments, the sample is nucleic acids extracted from circulating tumor cells. In some embodiments, the sample is nucleic acids extracted from lymphocytes in a blood sample for T-cell and B-cell receptor profiling. In some embodiments, the sample is a CRISPR gene edited sample. In some specific embodiments, the sample is meganucleases edited, zinc finger nucleases (ZFNs) edited, or transcription activator-like effector nucleases (TALENs) edited. In some embodiments, the sample is from CAR-T, CAR-NK, TCR-T, immortalized cell lines (e.g., engineered neural stem cell line CTX) or hematopoietic stem cells for therapeutics. In some embodiments, the sample is from genetically engineered cells (ex-vivo or in vivo), wherein the cells include but are not limited to fibroblasts, chondrocytes, keratinocytes, hepatocytes, pancreatic islet cells, stem cells (e.g., haematopoietic stem cells, mesenchymal stem cells, or skin stem cells), and immune cells (e.g., tumor infiltrating lymphocytes, viral reconstitution T cells, dendritic cells, γδT cells, regulatory T cells (Treg) and macrophages).

In another aspect, provided is a method of identifying genome-wide gene editing off-target sites from a sample comprising a plurality of single-strand nucleic acid fragments, comprising ligating a universal oligonucleotide adaptor to the sample to produce a ligation product, where the universal oligonucleotide adaptor is configured for ligating to a 5' end of the single-strand nucleic acid fragments. In some embodiments, the method comprises amplifying the ligation product by performing a first PCR with a first target-specific primer to form a first PCR product. In some embodiments, the method comprises amplifying the first PCR product by a second PCR with a sequencing specific adaptor primer and a second target-specific primer nested relative to the first target-specific primer, to form a sequencing library. In some embodiments, the method comprises quantifying and reading the sequencing library to obtain sequencing results. In some embodiments, the method comprises mapping the sequencing results to a reference genome.

In another aspect, provided is a method of evaluating gene editing efficiency from a sample comprising a plurality of single-strand nucleic acid fragments, comprising ligating a universal oligonucleotide adaptor to the sample to produce a ligation product, wherein the universal oligonucleotide adaptor is configured for ligating to a 5' end of the single-strand nucleic acid fragments. In some embodiments, the method comprises amplifying the first ligation product by performing a first PCR with a first target-specific primer to form a first PCR product. In some embodiments, the method comprises amplifying the first PCR product by a second PCR with a sequencing specific adaptor primer and a second target-specific primer nested relative to the first target-specific primer, to form a sequencing library. In some embodiments, the method comprises quantifying and reading the sequencing library to form sequencing results. In some embodiments, the method comprises mapping the sequencing results to a reference genome. In some embodiments, the method comprises validating computationally predicted off-target sites such that the gene editing efficiencies at the off-target sites are determined. In some embodiments, the predicted off-target sites are predicted in silico based on software (e.g., E-CRISP, Cas-OFFinder, and/or CRISPRscan). In some embodiments, the E-CRISP has a cutoff of mismatch <=10. In some embodiments, the E-CRISP has a cutoff of mismatch <=9. In some embodiments, the E-CRISP has a cutoff of mismatch <=8. In some embodiments, the E-CRISP has a cutoff of mismatch <=7. In some embodiments, the E-CRISP has a cutoff of mismatch <=6. In some embodiments, the E-CRISP has a cutoff of mismatch <=5. In some embodiments, the Cas-OFFinder has a mismatch <=6. In some embodiments, the Cas-OFFinder has a mismatch <=5. In some embodiments, the Cas-OFFinder has a mismatch <=4. In some embodiments, the Cas-OFFinder has a mismatch <=3. In some embodiments, the Cas-OFFinder has a mismatch <=2. In some embodiments, Cas-OFFinder has a bulge <=3. In some embodiments, Cas-OFFinder has a bulge <=2. In some embodiments, Cas-OFFinder has a bulge <=1. In some embodiments, the CRISPRscan has no threshold. In some embodiments, the E-CRISP has a cutoff of mismatch <=7; the Cas-OFFinder has a mismatch <=4 and a bulge <=2; and the CRISPRscan has no threshold. In some embodiments, the method comprises further: detecting translocation by obtaining a split read and a discordant read and/or determining an insertion and deletion (indel) frequency. In some embodiments, the split read and the discordant read are obtained by: identifying potential candidate translocations and estimating protospacer similarity to an on-target spacer and a cutting frequency determinant (CFD). In some embodiments, the indel frequency is obtained by: aligning the mapped results by GATK-realigner to form aligned results; filtering the aligned results not spanning a corresponding spacer region; predicting an insertion and deletion occurring around 5-bp upstream or downstream of a cleavage site; and determining the reliable indel frequency by an indel value of the sample with an elimination by a corresponding value of a negative control.

In some embodiments, the gene editing nucleases comprise the following types but not excluding others: CRISPR-Cas9, CRISPR-Cas12, CRISPR base editors, CRISPR prime editors, transposon-based gene editors and writers, transcription activator-like effector nucleases (TALEN), meganucleases, zinc finger nucleases (ZFN).

Off-Target Identification

In another aspect, provided is a method of identifying genome-wide gene editing off-target sites from a sample comprising a plurality of single-strand nucleic acid fragments, comprising: contacting a universal oligonucleotide adaptor with the sample to produce a ligation product, wherein the universal oligonucleotide adaptor is configured for ligating to a 5' end of the single-strand nucleic acid fragments. In some embodiments, the method comprises amplifying the ligation product by a first PCR with a first set of target-specific primers, wherein the target-specific primers in the first set are configured for annealing to the single-strand nucleic acid fragments 5' of an on-target site and one or more predicted and/or known off-target sites. In some embodiments, the method comprises amplifying the first PCR product by a second PCR with a second set of target-specific primers and a universal oligonucleotide adaptor primer to form a sequencing library, wherein each member of the second set of target-specific primers is nested relative to a corresponding primer of the first set of target-specific primers. In some embodiments, the method comprises sequencing the sequencing library to identify off-target sites. In some embodiments the predicted off-target sites in (b) are computationally predicted off-target sites.

In some embodiments, the computationally predicted off-target sites are top 100, 90, 80, 70, 60, 50, 40, 30, 20, or 10 off-target sites predicted based on software comprising E-CRISP, Cas-OFFinder, or CRISPRscan. In some embodiments, the E-CRISP has a cutoff of mismatch <=10. In some embodiments, the E-CRISP has a cutoff of mismatch <=9. In some embodiments, the E-CRISP has a cutoff of mismatch <=8. In some embodiments, the E-CRISP has a cutoff of mismatch <=7. In some embodiments, the E-CRISP has a cutoff of mismatch <=6. In some embodiments, the E-CRISP has a cutoff of mismatch <=5. In some embodiments, the Cas-OFFinder has a mismatch <=6. In some embodiments, the Cas-OFFinder has a mismatch <=5. In some embodiments, the Cas-OFFinder has a mismatch <=4. In some embodiments, the Cas-OFFinder has a mismatch <=3. In some embodiments, the Cas-OFFinder has a mismatch <=2. In some embodiments, Cas-OFFinder has a bulge <=3. In some embodiments, Cas-OFFinder has a bulge <=2. In some embodiments, Cas-OFFinder has a bulge <=1. In some embodiments, the CRISPRscan has no threshold. In some embodiments the E-CRISP has a cutoff of mismatch <=7; the Cas-OFFinder has a mismatch <=4 and a bulge <=2; and the CRISPRscan has no threshold. In some embodiments, the method comprises detecting translocation by obtaining a split read and a discordant read or determining an insertion and deletion (indel) frequency. In some embodiments, the split read and the discordant read are obtained by: identifying potential candidate translocations and estimating protospacer similarity to an on-target spacer and a cutting frequency determinant (CFD). In some embodiments, the indel frequency is obtained by aligning the mapped results by GATK-realigner to form aligned results. In some embodiments, the indel frequency is obtained by filtering the aligned results not spanning a corresponding spacer region; predicting an insertion and deletion occurring around 5-bp upstream or downstream of a cleavage site. In some embodiments, the indel frequency is obtained by determining the reliable indel frequency by an indel value of the sample with an elimination by a corresponding value of a negative control. In some embodiments, the method comprises blocking a 3' end of the single-strand nucleic acid fragments. In some embodiments, the method comprises phosphorylating a 5' end of the single-strand nucleic acid fragments. In some embodiments, the method comprises adenylating the nucleic acid to produce a 3'-adenosine overhang on the single-strand nucleic acid fragments.

In some embodiments, the universal oligonucleotide adaptor comprises a 3' recessive end, where the 3' recessive end is configured for ligating to the 5' end of the single-strand nucleic acid fragments. In some embodiments, the universal oligonucleotide adaptor comprises a 5' protrude end comprising three to twenty bases of random or degenerate nucleotides, where a duplex portion of the universal oligonucleotide adaptor is of sufficient length to remain in duplex form. In some embodiments, the universal oligonucleotide adaptor comprises a hairpin loop connecting a portion of the duplex form. In some embodiments, the universal oligonucleotide adaptor comprises a single strand segment comprising three to twenty random nucleotides as a unique molecular index (UMI) for tracing individual original molecules. In some embodiments, the method comprises forming a sequencing library with a sequencing specific adaptor pair. In some embodiments, the method comprises sequencing the sequencing library using a sequencing primer pair, where the sequencing primer pair is at least partially complementary to opposite strands of the second PCR product, respectively.

Nucleic Acid Fragment

In some embodiments, the sample comprises a plurality of DNA fragments prepared from high molecular weight DNA (e.g., genomic DNA). In some embodiments, the plurality of DNA fragments are prepared by enzyme-based treatment. In other embodiments, the plurality of DNA fragments are prepared by being exposed to short-wavelength, high-frequency acoustic energy. In other embodiments, the plurality of DNA fragments are prepared by centrifugal shearing. In other embodiments, the plurality of DNA fragments are prepared by heating the DNA at 100° C. to 105° C. In other embodiments, the plurality of DNA fragments are prepared by hydrodynamic shear forces. In some embodiments, the plurality of DNA fragments are prepared by being exposed to ultrasound sonication. In some specific embodiments, the plurality of DNA fragments are prepared by Bioruptor® Pico or Diagenode One. In other embodiments, the plurality of DNA fragments are prepared by turbulent flow generated by formation of hydropores. In some specific embodiments, the plurality of DNA fragments are prepared by Megaruptor®, Nebulizer®, and/or Covaris®. In some embodiments, the preparation of the plurality of DNA fragments is analyzed and confirmed by agarose gel electrophoresis. In some embodiments, the preparation of the plurality of DNA fragments is analyzed and confirmed by Fragment Analyzer™. In some embodiments, the preparation of the plurality of DNA fragments is analyzed and confirmed by LabChip® GX Touch™ nucleic acid analyzer.

In some embodiments, the plurality of DNA fragments described herein are about 50 bp to about 5000 bp long. In some specific embodiments, the plurality of DNA fragments described herein are about 50 bp to about 200 bp long, about 50 bp to about 300 bp long, about 50 bp to about 400 bp long, about 50 bp to about 500 bp long, about 50 bp to about 600 bp long, about 50 bp to about 700 bp long, about 50 bp to about 800 bp long, about 50 bp to about 900 bp long, about 50 bp to about 500 bp long, about 50 bp to about 2000 bp long, about 50 bp to about 3000 bp long, about 50 bp to about 4000 bp long, or about 50 bp to about 5000 bp long. In some specific embodiments, the plurality of DNA fragments described herein are about 100 bp to about 200 bp long, about 100 bp to about 300 bp long, about 100 bp to about 400 bp long, about 100 bp to about 500 bp long, about 100 bp to about 600 bp long, about 100 bp to about 700 bp long, about 100 bp to about 800 bp long, about 100 bp to about 900 bp long, about 100 bp to about 1000 bp long, about 100 bp to about 2000 bp long, about 100 bp to about 3000 bp long, about 100 bp to about 4000 bp long, or about 100 bp to about 5000 bp long. In other specific embodiments, the plurality of DNA fragments described herein are about 300 bp to about 400 bp long, about 300 bp to about 500 bp long, about 300 bp to about 600 bp long, about 300 bp to about 700 bp long, about 300 bp to about 800 bp long, about 300 bp to about 900 bp long, about 300 bp to about 1000 bp long, about 300 bp to about 2000 bp long, about 300 bp to about 3000 bp long, about 300 bp to about 4000 bp long, or about 300 bp to about 5000 bp long. In other specific embodiments, the plurality of DNA fragments described herein are about 600 bp to about 700 bp long, about 600 bp to about 800 bp long, about 600 bp to about 900 bp long, about 600 bp to about 1000 bp long, about 600 bp to about 2000 bp long, about 600 bp to about 3000 bp long, about 600 bp to about 4000 bp long, or about 600 bp to about 5000 bp long. In other specific embodiments, the plurality of DNA fragments described herein are about 1000 bp to about 2000 bp long, about 1000 bp to about 3000 bp long, about 1000 bp to about 4000 bp long, or about 1000 bp to about 5000 bp long.

In some embodiments, the plurality of single-strand nucleic acid fragments are prepared from denaturation of double-strand DNA fragments. In some specific embodiments, the double-strand DNA fragments are heated at 95° C. for 1, 5, 10, 20, or 30 minutes. In other specific embodiments, the double-strand DNA fragments are heated at 95° C. for 1, 5, 10, 20, or 30 minutes, followed by being placed on ice for 1 minute. In other specific embodiments, the double-strand DNA fragments are disrupted with glass beads (Disruptor Beads™; Scientific Industries, Bohemia, NY, USA) for 1, 5, 10, 20, or 30 minutes at 2,500 rpm with a Disruptor Genie bead-beater (Scientific Industries); followed by centrifuging at 3,000 rpm for 30 seconds to precipitate out the beads. In other specific embodiments, the double-strand DNA fragments are subjected to direct sonication at 10W for 30, 60, 90, 120, 150, 200, 250, or 300 seconds. In other specific embodiments, the double-strand DNA fragments are indirect sonication at 10 W, 22.4 kHz for 1, 5, 10, 20, or 30 minutes. In other specific embodiments, the double-strand DNA fragments are placed in tubes and immerged into the water of the ultrasonic bath at 40 kHz for 1, 5, 10, 20, or 30 minutes. In other specific embodiments, the double-strand DNA fragments are homogenized in 0.01, 0.1, or 1 mol/L NaOH with continuous pipetting and incubated at ambient temperature for 1, 2, 5, 10, 20, or 30 minutes. In other specific embodiments, the double-strand DNA fragments are homogenized gently with pipette in 25% and 50% formamide solution and incubated at room temperature. In other specific embodiments, the double-strand DNA fragments are homogenized gently with pipette in 25%, 50%, and 60% DMSO solution and incubated at room temperature. In some embodiments, the preparation of the plurality of single-strand nucleic acid fragments is confirmed by measuring the absorbance of DNA fragments at 260 nm.

In some embodiments, prior to (a), the method further comprises at least one of: (i) blocking a 3' end of the single-strand nucleic acid fragments; (ii) phosphorylating a 5' end of the single-strand nucleic acid fragments; and (iii) adenylating the nucleic acid to produce a 3'-adenosine overhang on the single-strand nucleic acid fragments.

In some embodiments, the universal oligonucleotide adaptor is single stranded. In some embodiments, the universal oligonucleotide adaptor is double stranded. In some embodiments, the universal oligonucleotide adaptor comprises: a 3' recessive end, the 3' recessive end configured for ligating to the 5' end of the single-strand nucleic acid fragments; and a 5' protrude end comprising three to twenty bases of random or degenerate nucleotides. A duplex portion of the universal oligonucleotide adaptor is of sufficient length to remain in duplex form in (a).

In some embodiments, the universal oligonucleotide adaptor comprises a hairpin loop connecting a portion of the duplex form. In some embodiments, the universal oligonucleotide adaptor comprises a Y shape.

In some embodiments, the universal oligonucleotide adaptor comprises a barcode. In some embodiments, the universal oligonucleotide adaptor comprises a single strand segment comprising three to twenty random nucleotides as a unique molecular index (UMI) for tracing individual original molecules.

In some embodiments, the universal oligonucleotide adaptor is ligated to the 5' end of the single-stranded nucleic acid fragments. In some embodiments, the universal oligonucleotide adaptor is ligated to the 3' end of the single-stranded nucleic acid fragments. In some embodiments, the universal oligonucleotide adaptor is ligated to the 5' and 3' end of the single-stranded nucleic acid fragments. In some embodiments, the universal oligonucleotide adaptor is ligated via a ligase.

When the sample described herein is a targeted gene edited sample, the targets of the first set of target-specific primers described herein are predetermined. In some embodiments, the targets comprise an on-target site of the CRISPR gene editing. In other embodiments, the targets comprise one or more predicted off-target sites of the CRISPR gene editing. In other embodiments, the targets comprise one or more spontaneous double-strand breakpoints. In other embodiments, the targets comprise a combination of part or all of the sites described above.

Computation Prediction

The predicted off-target sites described herein are computationally predicted. In some specific embodiments, the predicted off-target sites described herein are predicted by E-CRISP. In other specific embodiments, the predicted off-target sites described herein are predicted by Cas-OFFinder. In other specific embodiments, the predicted off-target sites described herein are predicted by CRISPRscan. In other specific embodiments, the predicted off-target sites described herein are predicted by CRISPRitz. In other specific embodiments, the predicted off-target sites described herein are predicted by CRISPOR. In other specific embodiments, the predicted off-target sites described herein are predicted by CRISPR Design website (http://crispr.mit.edu). In other specific embodiments, the predicted off-target sites described herein are predicted by Ecrisp. In other specific embodiments, the predicted off-target sites described herein are predicted by Crispr2vec. In other specific embodiments, the predicted off-target sites described herein are predicted by Hsu-Zhang scores. In other specific embodiments, the predicted off-target sites described herein are predicted by CHOPCHOP. In other specific embodiments, the predicted off-target sites described herein are predicted by CFD. In other specific embodiments, the predicted off-target sites described herein are predicted by *CRISTA*. In other specific embodiments, the predicted off-target sites described herein are predicted by Elevation. In other specific embodiments, the predicted off-target sites described herein are predicted by DeepCrispr. In other specific embodiments, the predicted off-target sites described herein are predicted by DeepSpCas9. In other specific embodiments, the predicted off-target sites described herein are predicted by CALITAS. In other specific embodiments, the predicted off-target sites described herein are predicted by an algorithm with a deep convolutional neural network or a deep feedforward neural network.

In some embodiments, the cutoff to set in one or more of the above-described prediction algorithms is mismatch(es) being less than or equal to 10, 9, 8, 7, 6, 5, 4, 3, 2, or 1 inside and/or outside of seed. In some embodiments, the cutoff to set in one or more of the above-described prediction algorithms is mismatch(es) being less than or equal to 10, 9, 8, 7, 6, 5, 4, 3, 2, or 1 inside and/or outside of protospacer adjacent motif (PAM). In other embodiments, the cutoff in one or more of the above-described prediction algorithms is set bulge(s) (insertion as DNA bulge or deletion as RNA bulge) being less than or equal to 4, 3, 2, or 1 respectively inside and/or outside of seed. In other embodiments, the cutoff in one or more of the above-described prediction algorithms is set bulge(s) (insertion as DNA bulge or deletion as RNA bulge) being less than or equal to 4, 3, 2, or 1 respectively inside and/or outside of PAM.

After proper cutoff setting in one or more chosen algorithms described herein, in some embodiments, about top 100 predicted off-target sites are selected for designing the first set of target-specific primers. In other embodiments, about top 90 predicted off-target sites are selected for designing the first set of target-specific primers. In other embodiments, about the top 80 predicted off-target sites are selected for designing the first set of target-specific primers. In other embodiments, about the top 70 predicted off-target sites are selected for designing the first set of target-specific primers. In other embodiments, about the top 60 predicted off-target sites are selected for designing the first set of target-specific primers. In other embodiments, about the top 50, 40, 30, 20, or 10 predicted off-target sites are selected for designing the first set of target-specific primers.

In some embodiments, the spontaneous double-strand breakpoints described herein are genome fragile sites. In some specific embodiments, the spontaneous double-strand breakpoints described herein comprise Chr 1:89231183, Chr 1:109838221.

The first set of target-specific primers described herein are designed to be in the vicinity of the targets described herein. In some embodiments, each of the first set of target-specific primers described herein is reverse complementary to a DNA segment that is in the downstream of the one of targets described herein on sense or antisense strand. In some specific embodiments, the DNA segment described herein is about 5 bp to about 1000 bp downstream of one of the targets described herein. In some specific embodiments, the DNA segment described herein is about 5 bp to about 500 bp downstream of one of the targets described herein. In some specific embodiments, the DNA segment described herein is about 5 bp to about 10 bp, about 10 bp to about 30 bp, about 30 bp to about 50 bp, about 50 bp to about 70 bp, about 70 bp to about 90 bp, or about 90 bp to about 100 bp downstream of one of the targets described herein. In other specific embodiments, the DNA segment described herein is about 100 bp to about 120 bp, about 120 bp to about 140 bp, about 140 bp to about 160 bp, about 160 bp to about 180 bp, about 180 bp to about 200 bp, downstream of one of the targets described herein. In other specific embodiments, the DNA segment described herein is about 200 bp to about 220 bp, about 220 bp to about 240 bp, about 240 bp to about 260 bp, about 260 bp to about 280 bp, about 280 bp to about 300 bp downstream of one of the targets described herein. In other specific embodiments, the DNA segment described herein is about 300 bp to about 400 bp, about 400 bp to about 500 bp, about 500 bp to about 600 bp, about 600 bp to about 700 bp, about 700 bp to about 800 bp, about 800 bp to about 900 bp, about 900 bp to about 100 bp downstream of one of the targets described herein. In other specific embodiments, the DNA segment described herein is at least 10, 50, 100, 150, 200, 250, 300, 350, 400, 450, 500, 550, 600, 650, 700, 750, 800, 850, 900, 950, or 1000 bp downstream of one of the targets described herein.

The first set of target-specific primers have relatively uniformed length. In some embodiments, each of the first set of target-specific primers is about 13-16 bp in length. In other embodiments, each of the first set of target-specific primers is about a 16-19 bp in length. In other embodiments, each of the first set of target-specific primers is about 19-22 bp in length. In other embodiments, each of the first set of target-specific primers is about 22-25 bp in length. In other embodiments, each of the first set of target-specific primers is about 25-28 bp in length. In other embodiments, each of the first set of target-specific primers is about 28-31 bp in length. In other embodiments, each of the first set of target-specific primers is about 31-34 bp in length.

The first set of target-specific primers have relatively uniformed GC contents of about 40% to about 60%. In some embodiments, the first set of target-specific primers have relatively uniformed GC contents of about 40%. In other embodiments, the first set of target-specific primers have relatively uniformed GC contents of about 45%. In other embodiments, the first set of target-specific primers have relatively uniformed GC contents of about 50%. In other embodiments, the first set of target-specific primers have relatively uniformed GC contents of about 55%. In other embodiments, the first set of target-specific primers have relatively uniformed GC contents of about 60%.

The first set of target-specific primers have relatively uniformed melting temperatures of about 55° C. to about 80° C. In some embodiments, the first set of target-specific primers have relatively uniformed melting temperatures of about 55° C. In some embodiments, the first set of target-specific primers have relatively uniformed melting temperatures of about 56° C. In some embodiments, the first set of target-specific primers have relatively uniformed melting temperatures of about 57° C. In some embodiments, the first set of target-specific primers have relatively uniformed melting temperatures of about 58° C. In other embodiments, the first set of target-specific primers have relatively uniformed melting temperatures of about 60° C. In other embodiments, the first set of target-specific primers have relatively uniformed melting temperatures of about 65° C. In other embodiments, the first set of target-specific primers have relatively uniformed melting temperatures of about 70° C. In other embodiments, the first set of target-specific primers have relatively uniformed melting temperatures of about 75° C. In other embodiments, the first set of target-specific primers have relatively uniformed melting temperatures of about 78° C. In other embodiments, the first set of target-specific primers have relatively uniformed melting temperatures of about 80° C.

The sequences of the first set of target-specific primers are determined such that secondary structures are minimized. In some embodiments, the first set of target-specific primers do not form hairpin structures. In other embodiments, the first set of target-specific primers do not form dimers between two molecules of the same target-specific primer. In other embodiments, the first set of target-specific primers do not form dimers between different target-specific primers.

The last five bases on the 3' end of the first set of target-specific primers do not comprise too many G or C bases. In some embodiments, the last five bases on the 3' end of the first set of target-specific primers comprise no G or C bases. In other embodiments, the last five bases on the 3' end of the first set of target-specific primers comprise only one G or C base. In other embodiments, the last five bases on the 3' end of the first set of target-specific primers comprise only two G or/and C bases. In other embodiments, the last five bases on the 3' end of the first set of target-specific primers comprise only three G or/and C bases.

The sequences of the first set of target-specific primers comprise limited repeats of one base or dinucleotide repeats. In some embodiments, the sequences of the first set of target-specific primers comprise no repeats of one base or dinucleotide repeats. In other embodiments, the sequences of the first set of target-specific primers comprise one or more repeats of one base but no dinucleotide repeats, and wherein the one or more repeats of one base are repeats with the same base appearing only two times, only three times, or only four times. In other embodiments, the sequences of the first set of target-specific primers comprise no repeats of one base but one or more dinucleotide repeats, and wherein the one or more dinucleotide repeats are repeats with the same dinucleotide appearing only two times, only three times, or only four times. In other embodiments, the sequences of the first set of target-specific primers comprise one or more repeats of one base and one or more dinucleotide repeats, wherein the one or more repeats of one base are repeats with the same base appearing only two times, only three times, or only four times, and wherein the one or more dinucleotide repeats are repeats with the same dinucleotide appearing only two times, only three times, or only four times.

The sequences of the first set of target-specific primers are designed so that it is unlikely to generate additional (non-specific) PCR amplicons using Primer-BLAST, including SNP-containing genome databases. In some embodiments, the top non-specific PCR amplicons have at least four mismatches with the first set of target-specific primers. In other embodiments, the top non-specific PCR amplicons have at least five, at least six, at least seven, at least eight, at least nine, at least ten mismatches with the first set of target-specific primers The first set of target-specific primers may be automatically design by available algorithms. In some embodiments, the first set of target-specific primers are designed by NGS-PrimerPlex. In other embodiments, the first set of target-specific primers are designed by PrimerPlex. In other embodiments, the first set of target-specific primers are designed by MPD. In other embodiments, the first set of target-specific primers are designed by MPprimer. In other embodiments, the first set of target-specific primers are designed by PRIMEval. In other embodiments, the first set of target-specific primers are designed by openPrimeR. In other embodiments, the first set of target-specific primers are designed by Visual OMP. In other embodiments, the first set of target-specific primers are designed by Oli2go.

In some embodiments, the first PCR comprises annealing the first set of target-specific primers to single-stranded nucleic acid fragments. The annealing temperature is determined by the lowest melting temperature among the first set of target-specific primers. In some embodiments, the annealing temperature is about 55° C. In some embodiments, the annealing temperature is about 56° C. In some embodiments, the annealing temperature is about 57° C. In other embodiments, the annealing temperature is about 58° C. In other embodiments, the annealing temperature is about 60° C. In other embodiments, the annealing temperature is about 65° C. In other embodiments, the annealing temperature is about 70° C. In other embodiments, the annealing temperature is about 75° C. In some embodiments, the annealing lasts for about 0.5 minute. In other embodiments, the annealing lasts for about 1 minute. In other embodiments, the annealing lasts for about 1.5 minutes. In other embodiments, the annealing lasts for about 2 minutes. In other embodiments, the annealing lasts for about 3 minutes. In other embodiments, the annealing lasts for about 4 minutes. In other embodiments, the annealing lasts for about 5 minutes. In other embodiments, the annealing lasts for about 6 minutes. In other embodiments, the annealing lasts for about 7 minutes. In other embodiments, the annealing lasts for about 8 minutes. In other embodiments, the annealing lasts for about 9 minutes. In other embodiments, the annealing lasts for about 10 minutes. In other embodiments, the annealing lasts for about 11 minutes. In other embodiments, the annealing lasts for about 12 minutes. In other embodiments, the annealing lasts for about 13 minutes. In other embodiments, the annealing lasts for about 14 minutes. In other embodiments, the annealing lasts for about 15 minutes.

In some embodiments, the first PCR comprises an extension. In some specific embodiments, the extension lasts for about 20 seconds. In some specific embodiments, the extension lasts for about 30 seconds. In some specific embodiments, the extension lasts for about 40 seconds. In some specific embodiments, the extension lasts for about 50 seconds. In some specific embodiments, the extension lasts for about 60 seconds. In some specific embodiments, the extension lasts for about 70 seconds. In some specific embodiments, the extension lasts for about 80 seconds. In some specific embodiments, the extension lasts for about 90 seconds. In some specific embodiments, the extension lasts for about 100 seconds. In some specific embodiments, the extension lasts for about 110 seconds. In some specific embodiments, the extension lasts for about 120 seconds. In some specific embodiments, the extension lasts for about 3 minutes. In some specific embodiments, the extension lasts for about 4 minutes. In some specific embodiments, the extension lasts for about 5 minutes. In some specific embodiments, the extension lasts for about 6 minutes. In some specific embodiments, the extension lasts for about 7 minutes. In some specific embodiments, the extension lasts for about 8 minutes. In some specific embodiments, the extension lasts for about 9 minutes. In some specific embodiments, the extension lasts for about 10 minutes. In some specific embodiments, the extension lasts for about 11 minutes. In some specific embodiments, the extension lasts for about 12 minutes. In some specific embodiments, the extension lasts for about 13 minutes. In some specific embodiments, the extension lasts for about 14 minutes. In some specific embodiments, the extension lasts for about 15 minutes.

The first PCR comprises multiple cycles of the above-described PCR (annealing, extension, and denature) so that targets can be searched among samples multiple times. In some embodiments, the cycle number is at least 3. In some embodiments, the cycle number is at least 4. In some embodiments, the cycle number is at least 5. In some embodiments, the cycle number is at least 10. In some embodiments, the cycle number is at least 15. In some embodiments, the cycle number is at least 20. In some embodiments, the cycle number is at least 25. In some embodiments, the cycle number is at least 30. In some embodiments, the cycle number is at least 35. In some embodiments, the cycle number is at least 40. In some embodiments, the cycle number is at least 45. In some embodiments, the cycle number is at least 50. In some embodiments, the cycle number is at least 55. In some embodiments, the cycle number is at least 65. In some embodiments, the cycle number is at least 70. In some embodiments, the cycle number is at least 75.

In some embodiments, the methods described herein can be used for identifying genome-wide gene editing off-target sites from a sample that is edited by CRISPR-Cas9. In some embodiments, the methods described herein can be used for identifying genome-wide gene editing off-target sites from a sample that is edited by CRISPR-Cas12. In some embodiments, the methods described herein can be used for identifying genome-wide gene editing off-target sites from a sample that is edited by a CRISPR-Cas system other than CRISPR-Cas9 or CRISPR-Cas12. In some embodiments, the methods described herein can be used for identifying genome-wide gene editing off-target sites from a sample that is edited by CRISPR base editors. In some embodiments, the methods described herein can be used for identifying genome-wide gene editing off-target sites from a sample that is edited by CRISPR prime editors. In some embodiments, the methods described herein can be used for identifying genome-wide gene editing off-target sites from a sample that is edited by transposon-based gene editors. In some embodiments, the methods described herein can be used for identifying genome-wide gene editing off-target sites from a sample that is edited by transcription activator-like effector nucleases (TALEN). In some embodiments, the methods described herein can be used for identifying genome-wide gene editing off-target sites from a sample that is edited by zinc finger nucleases (ZFN). In some embodiments, the methods described herein can be used for identifying genome-wide gene editing off-target sites from a sample that is edited by meganucleases.

In some embodiments, the methods described herein can be used to detect the random insertion site of a virus-vector delivery. In some embodiments, the methods described herein can be used to detect the random insertion site of a transposon. In some embodiments, the methods described herein can be used to detect insertion site of a donor DNA. In some embodiments, the methods described herein can be used to detect insertion site of virus, such as hepatitis B virus and human papillomavirus. In some embodiments, the methods described herein can be used to detect the neighboring sequences of any known sequences.

As used herein and in the claims, the terms "comprising" (or any related form such as "comprise" and "comprises"), "including" (or any related forms such as "include" or "includes"), "containing" (or any related forms such as "contain" or "contains"), means including the following elements but not excluding others. It shall be understood that for every embodiment in which the term "comprising" (or any related form such as "comprise" and "comprises"), "including" (or any related forms such as "include" or "includes"), or "containing" (or any related forms such as "contain" or "contains") is used, this disclosure/application also includes alternate embodiments where the term "comprising", "including," or "containing," is replaced with "consisting essentially of" or "consisting of". These alternate embodiments that use "consisting of" or "consisting essentially of" are understood to be narrower embodiments of the "comprising", "including," or "containing," embodiments.

Use of absolute or sequential terms, for example, "will," "will not," "shall," "shall not," "must," "must not," "first," "initially," "next," "subsequently," "before," "after," "lastly," and "finally," are not meant to limit scope of the present embodiments disclosed herein but as exemplary.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, "or" may refer to "and", "or," or "and/or" and may be used both exclusively and inclusively. For example, the term "A or B" may refer to "A or B", "A but not B", "B but not A", and "A and B". In some cases, context may dictate a particular meaning.

Any systems, methods, software, and platforms described herein are modular. Accordingly, terms such as "first" and "second" do not necessarily imply priority, order of importance, or order of acts.

The term "about" when referring to a number or a numerical range means that the number or numerical range referred to is an approximation within experimental variability (or within statistical experimental error), and the number or numerical range may vary from, for example, from 1% to 15% of the stated number or numerical range. In examples, the term "about" refers to ±10% of a stated number or value.

The terms "increased", "increasing", or "increase" are used herein to generally mean an increase by a statically significant amount. In some aspects, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, standard, or control. Other examples of "increase" include an increase of at least 2-fold, at least 5-fold, at least 10-fold, at least 20-fold, at least 50-fold, at least 100-fold, at least 1000-fold or more as compared to a reference level.

The terms "decreased", "decreasing", or "decrease" are used herein generally to mean a decrease by a statistically significant amount. In some aspects, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

For the sake of clarity, "characterized by" or "characterized in" (together with their related forms as described above), does not limit or change the nature of whether the list of terms following it are open or closed. For example, in a claim directed towards "a composition comprising A, B, C, and characterized in D, E, and F", the elements D, E, and F are still open-ended terms and the claim is meant to include other elements due to the use of the word "comprising" earlier in the claim.

As used herein and in the claims, the singular forms "a", "an" and "the" are intended to include the plural forms as well, unless the context clearly indicates otherwise. Where a range is referred in the specification, the range is understood to include each discrete point within the range. For example, 1-7 means 1, 2, 3, 4, 5, 6, and 7.

As used herein and in the claims, the term "about" or "around" is understood as within a range of normal tolerance in the art and not more than ±10% of a stated value. By way of example only, about 50 means from 45 to 55 including all values in between. As used herein, the phrase "about" a specific value also includes the specific value, for example, about 50 includes 50.

As used herein and in the claims, "enriching" means increasing the proportion of molecule target of interest among all molecules from a sample.

As used herein and in the claims, "nucleic acid fragments" means the nucleic acid has been fragmented into shorter pieces. In certain embodiments, the nucleic acid fragmented into typical sizes peaking at around 50 bp to 1000 bp long. In certain embodiments, the nucleic acid fragmented into typical sizes peaking at around 20 to 50 bp, 51 to 100 bp, 101 to 300 bp, 301 to 500, and 501 to 1000 bp.

As used herein and in the claims "high molecular weight DNA" refers to DNA that has not been fragmented into shorter pieces. In certain embodiments, a high molecular weight DNA can be around 300 bp or longer. In certain embodiments, a high molecular weight DNA can be around 500 bp or longer.

As used herein and in the claims, "indel" means an insertion or deletion of bases in the genome of an organism.

As used herein and in the claims, "off-target genome editing" refers to unintended genetic modifications that can arise through the use of engineered nuclease technologies, such as CRISPR-Cas9, CRISPR-Cas12 and other CRISPR-Cas systems, CRISPR base editors, CRISPR prime editors, transposon-based gene editors and writers, transcription activator-like effector nucleases (TALEN), meganucleases, and zinc finger nucleases (ZFN).

As used herein and in the claims, "off-target" or "off-targets" refer to one or more sites in a given genome or set of user-defined sequences that are subjected to genetic modifications by off-target genome editing.

As used herein and in the claims, "on-target genome editing" refers to intended or expected genetic modifications that can arise through the use of engineered nuclease technologies, such as CRISPR-Cas9, CRISPR-Cas12 and other CRISPR-Cas systems, CRISPR base editors, CRISPR prime editors, transposon-based gene editors and writers, transcription activator-like effector nucleases (TALEN), meganucleases, and zinc finger nucleases (ZFN).

As used herein and in the claims, "universal oligonucleotide adaptor" refers to a nucleic acid molecule comprised of two strands (a top strand and a bottom strand) and comprising a first ligatable 5' protrude end and a second un-ligatable end. In some embodiments, the top strand of the universal oligonucleotide adaptor comprises a 5' duplex portion, and the bottom strand comprises an unpaired 5' portion, a 3' duplex portion, and nucleic acid sequences identical to a first and second sequencing primers. The duplex portions of the adaptor may be substantially complementary and the duplex portion is of sufficient length to remain in duplex form at the ligation temperature. In certain embodiments, the top strand and the bottom strand are connected to each other and form a hairpin loop. The term "sufficient" means that the number of bases in the duplex portion is long enough so that the bonding therebetween can keep in duplex form at the ligation temperature.

As used herein and in the claims, "genome editing", or "genome engineering", or "gene editing", is a type of genetic engineering in which DNA is inserted, deleted, modified or replaced in the genome of a living organism. As an example, genome editing targets the insertions to site specific locations.

As used herein and in the claims, "CRISPR (Clustered, Regularly Interspaced, Short Palindromic Repeats) gene editing" is a genetic engineering technique in molecular biology by which the genomes of living organisms may be modified by an engineered Cas (Clustered, Regularly Interspaced, Short Palindromic Repeats-associated protein) nuclease.

As used herein and in the claims, "GUIDE-Seq (Genome-wide, Unbiased Identification of DSBs Enabled by Sequencing)" is a molecular biology technique that allows for the unbiased in vitro and cell-based detection of off-target genome editing events in DNA caused by CRISPR/Cas nucleases as well as other RNA-guided nucleases in living cells.

As used herein and in the claims, "DISCOVER-Seq (Discovery of in situ Cas off-targets and verification by sequencing)" is a molecular biology technique that allows for unbiased CRISPR-Cas off-target identification in cells and tissues.

As used herein and in the claims, "EDITED-Seq (editing events detection by sequencing)" is a molecular biology technique as described in the present disclosure that allows for detection and/or evaluation of off-targets.

As used herein and in the claims, "anchored polymerase chain reaction" or "anchored PCR" refers to PCR performed with at least one anchored primer and extending from at least one end of the nucleic acid fragments. In certain embodiments, anchored PCR can be PCR performed with an anchored primer and extending from a single-end of the nucleic acid fragments. In certain embodiments, anchored PCR can be PCR performed with two anchored primers and extending from both ends of the nucleic acid fragments.

As used herein and in the claims, "a universal oligonucleotide adaptor primer" refers to a primer that can anneal to part of the sequence of the universal oligonucleotide adaptor. In some aspects, the universal oligonucleotide adaptor comprises at least one secondary structure such as a hairpin structure, As used herein, "nested", "nested amplification", or "nested PCR" refers to a polymerase chain reaction for decreases non-specific binding in products due to the amplification of unexpected primer binding sites. Nested PCR comprises at least two sets of primers, used in at least two successive runs of PCR, where a second PCR amplifies a secondary target within the first PCR product. Such arrangement allows amplification for a low number of runs in the first PCR, limiting non-specific products. The second nested primer set can amplify the intended product from the first PCR. The at least one target nucleic acid undergoes the first PCR with a first set of primers. The PCR product from the first PCR can then be amplified with a second PCR with a second set of primers.

As used herein, "unique molecular index" refers to nucleic acid sequences added to the at least one target nucleic acid or any nucleic acid fragment described herein during nucleic acid library preparation for identifying the nucleic acid. The unique molecular index can be added before any round of the PCR described herein (e.g., first round of PCR, second round of PCR, etc) and can be used to decrease errors and quantitative bias introduced by the amplification.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

Provided herein are examples that describe in more detail certain embodiments of the present disclosure. The examples provided herein are merely for illustrative purposes and are not meant to limit the scope of the disclosure in any way.

Example 1—Example Workflow

FIG. 1A shows a workflow of an example method 100 for amplifying targeted nucleic acid from a sample. In this example, the sample contains single-stranded nucleic acid fragment 1002, which contain a target nucleic acid sequence. By way of example, the sample is from a mammal, (e.g., a human). By way of example, the human is a fetus. By way of example, the human is an individual known to have or suspected of having a disease, (e.g. a cancer or a genetic disorder). By way of example, one or more of the target sequences comprise one or more markers for a disease, e.g., a cancer. By way of example, the sample is from a blood sample. By way of example, the sample is cell-free nucleic acids extracted from a blood sample. By way of example, the sample is nucleic acids extracted from circulating tumor cells. By way of example, the single-stranded nucleic acid 1002 in the sample is single-strand DNA fragments prepared from denaturation of double-strand DNA fragments. By way of example, the single-stranded nucleic acid 1002 in the sample is single-strand cDNA fragments prepared from reverse transcription of RNA fragments. By way of example, the sample is nucleic acids extracted from lymphocytes in a blood sample for T-cell and B-cell receptor profiling. By way of example, the sample is a CRISPR gene edited sample. By way of example, the sample is meganucleases edited, zinc finger nucleases (ZFNs) edited, or transcription activator-like effector nucleases (TALENs) edited. By way of example, the sample is from CAR-T, CAR-NK, TCR-T, immortalized cell lines (e.g., engineered neural stem cell line CTX) or hematopoietic stem cells for therapeutics. By way of example, the sample is from genetically engineered cells (ex-vivo or in vivo), wherein the cells include but are not limited to fibroblasts, chondrocytes, keratinocytes, hepatocytes, pancreatic islet cells, stem cells (e.g., haematopoietic stem cells, mesenchymal stem cells, or skin stem cells), and immune cells (e.g., tumor infiltrating lymphocytes, viral reconstitution T cells, dendritic cells, γδT cells, regulatory T cells (Treg) and macrophages).

Still referring to FIG. 1A, in 120, a universal oligonucleotide adaptor (or universal adaptor) 1202 is ligated with the single-stranded nucleic acid fragment 1002 at the 5' end to form a ligation product 1204. In this example, the universal oligonucleotide adaptor 1202 includes a top strand 1202A with a 3' recessive end which is configured for ligating to the 5' end of the single-stranded nucleic acid fragment 1002, and a bottom strand 1202B with a 5' protrude end including multiple number bases of random or degenerate nucleotides, for example, three to twenty. In this example, the number of bases of random nucleotides is four. In some embodiments, the top strand 1202A of the universal oligonucleotide adaptor 1202 comprises a 5' duplex portion, and the bottom strand 1202B comprises a 3' duplex portion. The duplex portions of the adaptor may be substantially complementary and the duplex portion is of sufficient length to remain in duplex form at the ligation temperature. In some embodiments, the universal oligonucleotide adaptor 1202 may further comprise three to twenty random nucleotides incorporated in the duplex portion or in a 5'end of the top strand 1202A as a unique molecular index (UMI) for tracing individual original molecules. In 140, the ligation product 1204 is subsequently amplified by a first PCR with a first target-specific primer 1402 to form a first PCR product 1404. In this example, the first PCR is a linear amplification of the ligation product to obtain a nascent primer extension duplex. By way of example, the first PCR includes (1) annealing a first target-specific primer 1402 to the single-strand nucleic acid fragments 1002 in the vicinity of a target sequence, (2) extending the first target-specific primer 1402 over the single-strand nucleic acid fragments 1002 using a DNA polymerase, (3) obtaining a nascent primer extension duplex and (4) dissociating the nascent primer extension duplex into single strands. By way of example, the first PCR may further repeat the (1)-(4) in one or more cycles. In another example embodiment, the first PCR of the 140 is an exponential amplification of the targeted nucleic acid with the first target-specific primer 1402 and a universal oligonucleotide adaptor primer. By way of example, the first PCR product is optionally cleaned up to remove the first target-specific primer 1402 before the subsequent step(s). In 160, the first PCR product 1404 is amplified by a second PCR with a second target-specific primer 1602 nested relative to the first target-specific primer 1402 and a sequencing adaptor reverse primer 1606 (also referred to as a universal oligonucleotide adaptor primer in some embodiments). The second target-specific primer 1602 and the sequencing adaptor reverse primer 1606 are used in the amplification of the first PCR product 1404 to form a second PCR product 1608. By way of example, the first PCR is a linear PCR. By way of example, the first PCR is a gene-specific primer (GSP) PCR. By way of example, the first PCR and/or second PCR are multiplexing PCR. By way of example, the 160 may further include performing a nested amplification of the nascent primer extension duplex. Optionally, a sequencing adaptor forward primer 1604 is provided so that the second PCR product 1608 can be used as a sequencing library. By way of example, the sequencing adaptor primer 1604 is provided so that a plurality of 1602 can be bridged and sequenced using a same sequencing primer identical to 1604. By ways of example, the sequencing adaptor forward primer 1604 and the sequencing adaptor reverse primer 1606 are Illumina sequencing primers. By way of example, sequencing adaptor forward primer 1604 is not provided. By way of example, the sequencing library may be used for subsequent sequencing with a sequencing primer pair (not shown), which is at least partially complementary to opposite strands of the second PCR product 1608, respectively. In another example embodiment, the second target-specific primer 1602 includes the sequence of sequencing adaptor forward primer 1604.

Figure 1B:
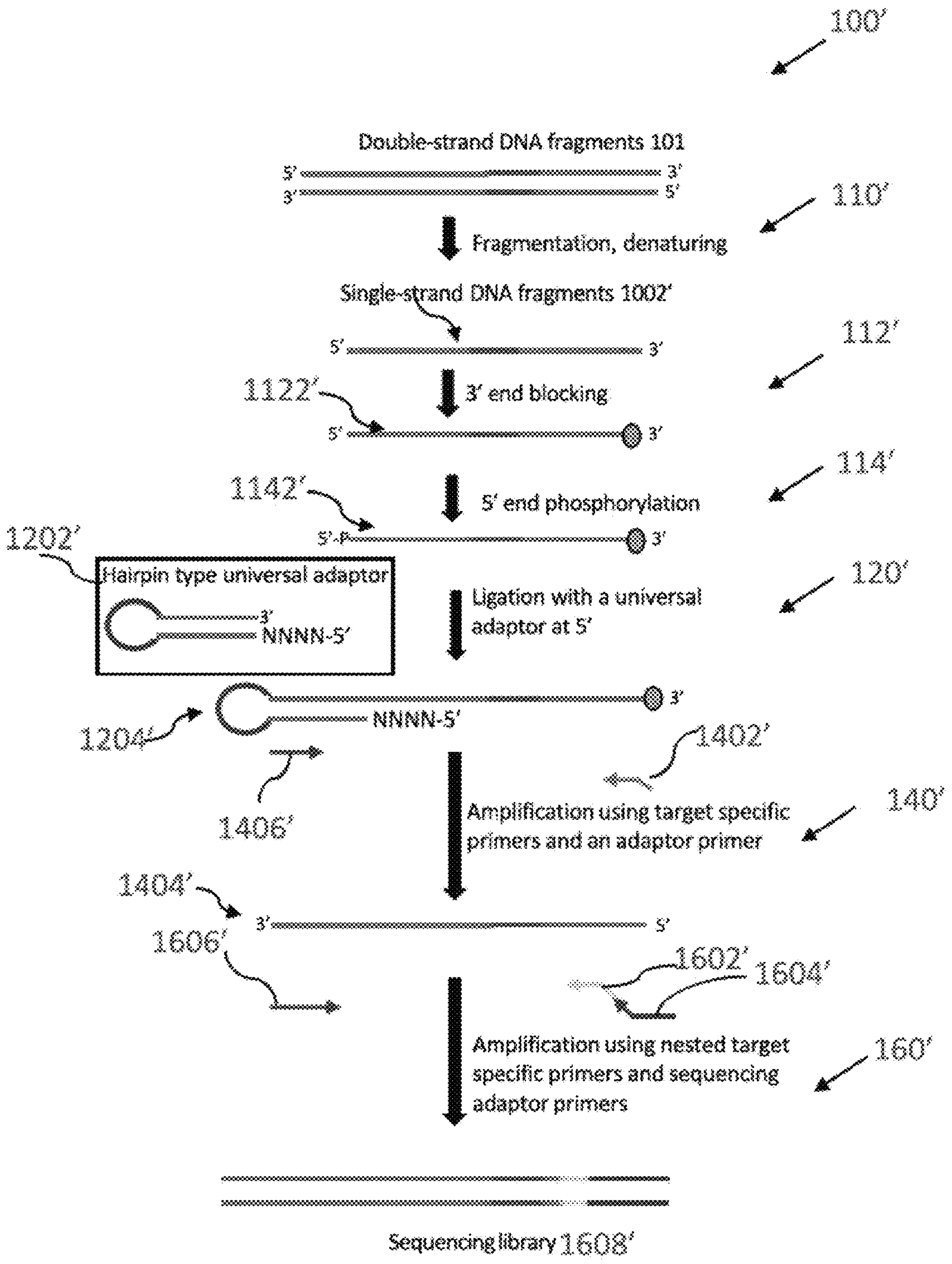
FIG. 1B is a schematic diagram which illustrates another example embodiment of a workflow for amplifying targeted nucleic acid from a sample.

Referring now to FIG. 1B, which shows workflow of alternative example method 100' for amplifying targeted nucleic acid from a sample. For the sake of clarity, any one or more of the additional or alternate steps in this example can be added into or replaced with the corresponding steps in method 100 (FIG. 1A), respectively. In this example, the starting material of the nucleic acid is double-stranded DNA 101 which contains a targeted DNA sequence. By way of example, the sample includes a plurality of DNA fragments prepared from high molecular weight DNA, e.g., genomic DNA. In an additional 110', the double-stranded DNA 101 is fragmented and denatured to form single-stranded DNA fragments 1002'. In an optional 112', the 3' end of the single-stranded DNA fragments 1002' may be optionally blocked to form 3' end blocked single-stranded DNA fragments 1122'. In an optional 114', the 5' end of the single-stranded DNA fragments 1002' or 1122' may be optionally phosphorylated to form 5' end phosphorylated single-stranded DNA fragments 1142'. Then 5' end phosphorylated single-stranded DNA fragments 1142' is ready for the subsequent 120' (or 120). Optionally, the single-stranded nucleic acid fragments as described may be further adenylated to produce a 3'-adenosine overhang on the single-strand nucleic acid fragments prior to ligation 120'. In alternative 120', the universal oligonucleotide adaptor 1202' which contain a hairpin loop connecting a portion of the duplex form (as shown in the box in FIG. 1B) is used to ligate to 5' end phosphorylated single-stranded DNA fragments 1142' at 5' end to form a ligation product 1204'. By way of example, the single-stranded DNA fragments for ligation may be single-stranded DNA fragments 1002' or 3' end blocked single-stranded DNA fragments 1122'. In alternative 140', the ligation product 1204' is subsequently amplified by a first PCR with a first target-specific primer 1402' and a first universal adaptor specific primer 1406' to form a first PCR product 1404'. In 160', the first PCR product 1404' is amplified by a second PCR with a second target-specific primer 1602' and a sequencing adaptor reverse primer 1606' (also referred to as a universal oligonucleotide adaptor primer in some embodiments) to form a sequencing library 1608', which is a double-stranded DNA product containing targeted DNA sequence with sequencing adaptor primer sequence. The second target-specific primer 1602' is nested relative to the first target-specific primer 1402'. Optionally, a sequencing adaptor forward primer 1604' is provided. In another example embodiment, the second target-specific primer 1602' includes the sequence of sequencing adaptor forward primer 1604'.

Example 2. Plasmid Construction

Figure 6:
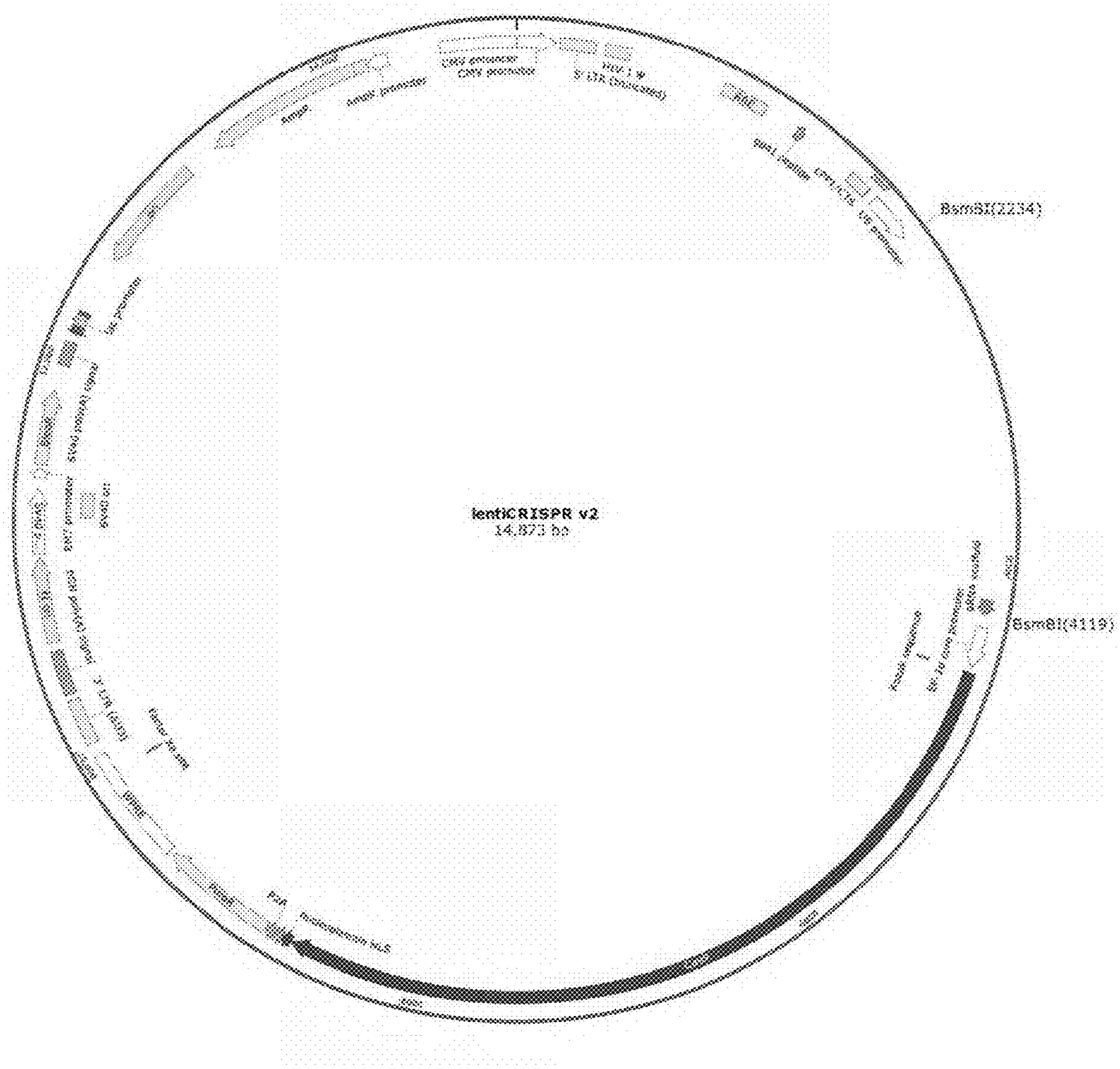
FIG. 6 is a schematic diagram which illustrates the topology of a lentiCRISPR vector.

Paring protospacer oligos were annealed and inserted between two BsmI cleavage sites of the lentiCRISPR vector (Addgene #42230). The topology of the lentiCRISPR vector is shown in FIG. 6. Sequence authenticity of each vector was confirmed by Sanger sequencing. The sequences of paring protospacer oligos are shown in Table 2 below.

TABLE 2

Sequences of paring protospacer oligos

| Primer Name/ID | Sequence | Usage/Remarks | SEQ ID NO: |
|---|---|---|---|
| sgVEGFA4-F | caccgGACCCCCTCCACCCCGCCTC | sgRNA cloning | 1 |
| sgVEGFA4-R | aaacGAGGCGGGGTGGAGGGGGTCc | sgRNA cloning | 2 |
| sgHBB-F | caccgCTTGCCCCACAGGGCAGTAA | sgRNA cloning | 3 |
| sgHBB-R | aaacTTACTGCCCTGTGGGGCAAGc | sgRNA cloning | 4 |

TABLE 2-continued

| Sequences of paring protospacer oligos | | | |
|---|---|---|---|
| Primer Name/ID | Sequence | Usage/Remarks | SEQ ID NO: |
| sgPD1-F | caccgGGGCGGTGCTACAACTGGGC | sgRNA cloning | 5 |
| sgPD1-R | aaacGCCCAGTTGTAGCACCGCCCc | sgRNA cloning | 6 |
| sgTRAC-F | caccgCTTCAAGAGCAACAGTGCTG | sgRNA cloning | 7 |
| sgTRAC-R | aaacCAGCACTGTTGCTCTTGAAGc | sgRNA cloning | 8 |
| sgALB-F | caccgGGTGTAAAATCAACACCCTA | sgRNA cloning | 9 |
| sgALB-R | aaacTAGGGTGTTGATTTTACACCc | sgRNA cloning | 10 |
| sgALB-F | caccgGGTGTAAAATCAACACCCTA | sgRNA cloning | 9 |
| sgALB-R | aaacTAGGGTGTTGATTTTACACCc | sgRNA cloning | 10 |
| sgGAPDH-F | caccgAGCCCCAGCAAGAGCACAAG | sgRNA cloning | 11 |
| sgGAPDH-R | aaacCTTGTGCTCTTGCTGGGGCTc | sgRNA cloning | 12 |
| Illumina.Y.adaptor.primer | AATGATACGGCGACCACCGAGATCTACACNNNNNNNNACACTCTTTCCCTACACGACGCTCTTCCGATCT | Illumina adaptor | 13 |
| Illumina.i7.adaptor.primer | CAAGCAGAAGACGGCATACGAGATNNNNNNNNGTGACTGGAGTTCAGACGTGTGCTCTTCCGATC | Illumina adaptor | 14 |

Example 3. Off-Targets Prediction and Anchored Multiplex Primers Design

Potential off-targets were initially predicted in silico based on three professional tools, E-CRISP, Cas-OFFinder, and CRISPRscan. The following cutoffs were used respectively, mismatch <=7 for E-CRISP, mismatch <=4 and bulge <=2 for Cas-OFFinder, and no threshold for CRISPRsan. To reduce false positive and computational bias, a combinatorial strategy was used that those sites found by at least two methods were applied to further primer design.

Example 4. Cell Culture and Transfection

K562 cells were seeded in a flask containing 15 mL Roswell Park Memorial Institute 1640 medium (RPMI 1640; Thermo Fisher Scientific, Waltham, MA, USA), supplemented with 10% heat-inactivated fetal bovine serum (FBS, Thermo Fisher Scientific), grown at 37° C. within 5% carbon dioxide ($CO_2$). After grown for 20-24 hours to achieve a confluence of 70-90%, cells were harvested for Neon transfection. Neon transfection was conducted using a Neon transfection platform (Thermo Fisher Scientific) according to the manufacturer's instructions. Briefly, $2\times10^6$ cells per test were suspended in the Electrolyte Buffer mixed with 5 μg of lentiCRSIPR-sgRNA plasmids to a final volume of 100 μL. Then cell/DNA mixture was pulsed by the Neon machine under the following parameters: voltage=1600 V; width=10 ms; number=3. Cells were continued typically for 72 hours followed by DNA and mRNA extraction. For GUIDE-Seq, 200 pmol of annealed double-stranded oligonucleotide (dsODN) was mixed with desired plasmid, followed by the same Neon transfection process described above.

HEK293 or NIH 3T3 cells were seeded at a density of $1.5\times10^5$ cells/well in a 12-well plate, grown at 37° C. within 5% $CO_2$ in Dulbecco's modified Eagle's medium (DMEM; Life Technologies), supplemented with 10% FBS, 1% penicillin, and 1% streptomycin. After grown for 24 hours, transfection was carried out with Lipofectmin3000 (Thermo Fisher Scientific) according to the manufacturer's instruction. Briefly, 1 μg of lentiCRSIPR-sgRNA vectors, 2 μL of P3000, and 2.5 μL of Lipofectmin3000 were mixed gently with FBS-free DMEM to a final volume of 100 μL, incubated at room temperature for 15 min, and added to the medium. Cells were harvested after 72 hours post transfection for DNA extraction. For GUIDE-Seq experiment, 10 pmol of annealed dsODN was mixed and co-incubated with Lipofectmin3000, followed by the same protocol above.

Example 5. DNA and Total RNA Extraction

Total DNA and RNA were extracted separately using the AllPrep DNA/RNA Kit (QIAGEN, Hilden, Germany) according to the manufacturer's instructions. Briefly, cells/tissues were lysed by Buffer RLT Plus (350 μL per test of $<10^7$ cells or 30 mg tissues). The lysed mixture was filtered by AllPrep DNA column, followed by washing and elution of the column-bound genomic DNA. The flow-through from the column was used as RNA origin for mRNA extraction through AllPrep RNA column. Extracted DNA/RNA was quantified by the corresponding DNA/RNA Qubit Assay Kit (Thermo Fisher Scientific), and were stored at −80° C. until use.

Example 6. Genome Editing in Primary Cells and iPSC

Figure 4A:
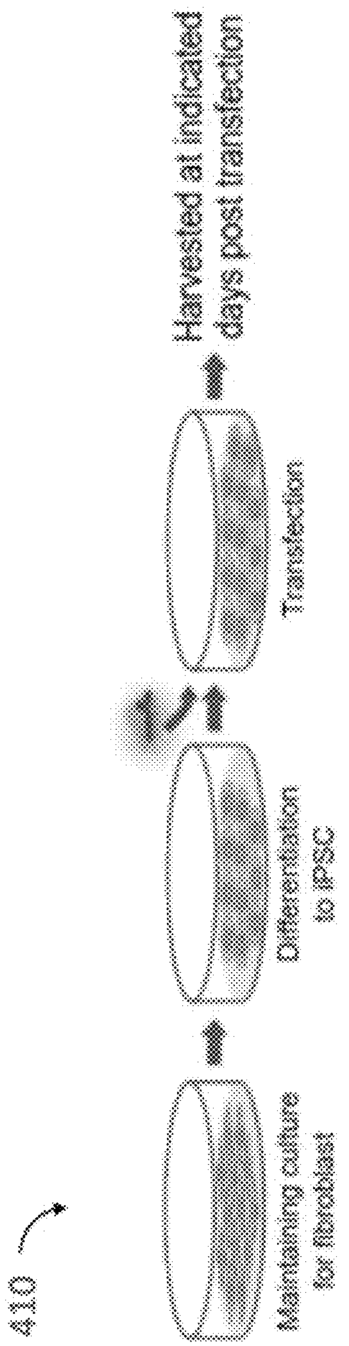
FIG. 4A is a schematic diagram which shows a workflow of iPSC editing by CRISPR-Cas9, according to an example embodiment.

FIG. 4A shows a workflow of an example method 410 of iPSC editing by CRISPR-Cas9, according to an example embodiment. A culture for fibroblast was maintained and the culture was allowed to differentiate to iPSC. iPSCs were then transfected using Amaxa nucleofection (Lonza, Allendale, NJ, USA) according to the manufacturer's instructions.

Briefly, cells were firstly dissociated into single cells using TrypLE. For each transfection, 5×10[6] cells were mixed with 100 μL pre-warmed nucleofection reagents (82 μL solution-1 and 18 μL solution-B); then 10 μg DNA (6 μg Cas9+4 μg sgRNA) was added into the suspension and electroporated. Electroporated iPSCs were cultured on inactivated MEF feeders, with fresh medium changed daily for 4-5 days and then harvested for DNA isolation. The cells were harvested at indicated days post transfection.

Figure 4B:
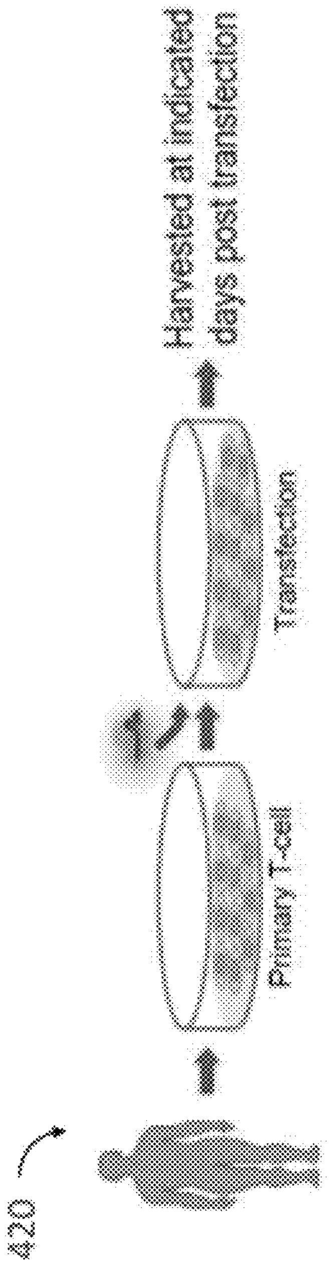
FIG. 4B is a schematic diagram which shows a workflow of primary T-cell editing by CRISPR-Cas9, according to an example embodiment.

FIG. 4B shows a workflow of an example method 420 of T-cell editing by CRISPR-Cas9, according to an example embodiment. In this example embodiment, the T-cells were transfected similarly as previously described for iPSC (FIG. 4A).

Example 7. Genome Editing in Mouse

Figure 5A:
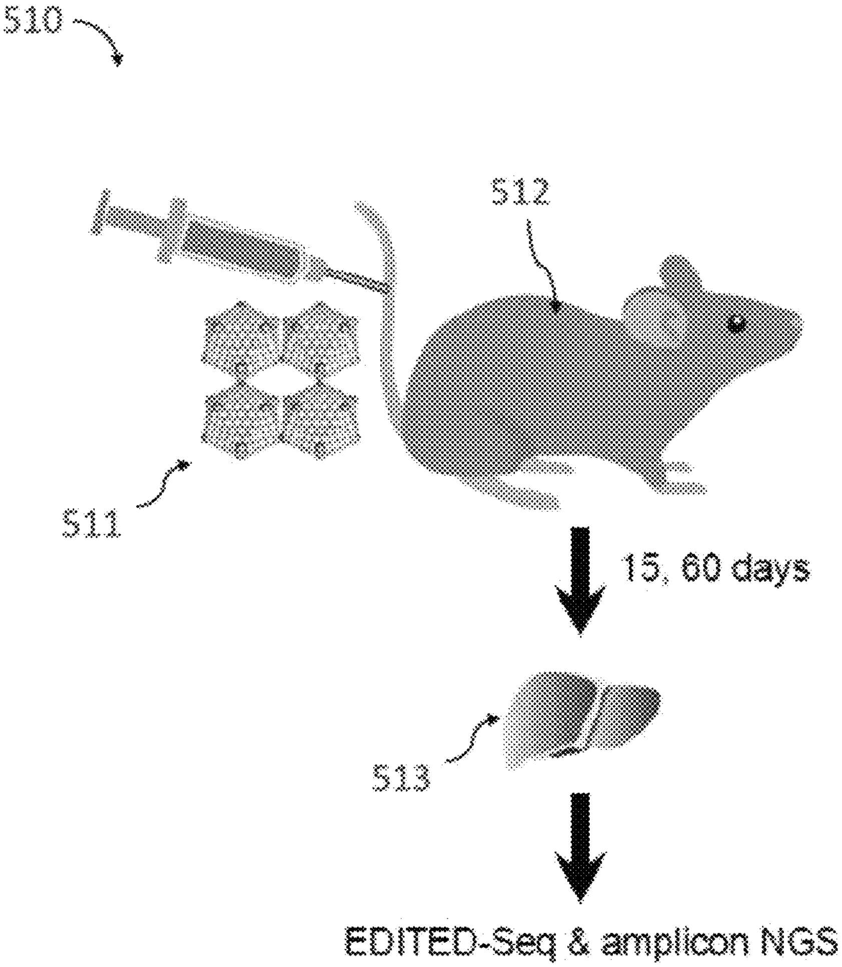
FIG. 5A is a schematic diagram which illustrates a workflow of EDITED-Seq conducted in a mouse, according to an example embodiment.

FIG. 5A shows a workflow of an example method 510 of EDITED-Seq conducted in a mouse, according to an example embodiment. A total of $10^7$-$10^8$ TU AAV8 virus 511 were injected into nine- to eleven-week-old male C57BL/6 mice 512 (weighed before experiment) via tail vein within 5-7 s. Mouse (weighed before sacrifice) was euthanized by cardiac puncture after 15, 30, and 60 days. Blood was collected in EDTA-coated capillary tubes and kept on ice for up to 2 hours before extraction of centrifugation at 10,000 rpm for 20 min at 4° C. The liver organ 513 was dissected, snap-frozen in liquid nitrogen and stored at −80° C. until use. Ground tissues were lysed by Buffer RLT Plus (350 μL per 20 mg tissues) and extracted by AllPrep DNA/RNA Kit (Qiagen) according to manufacturer's instructions. DNA and RNA were stored at −80° C. until subjected to EDITED-Seq, amplicon-NGS and qRT-PCR.

Example 8. EDITED-Seq Pipeline

Genomic DNA and anchored single-end multiplex primers were the inputs to generate EDITED-Seq library via two-round gene-specific primer (GSP) PCR, one anchored PCR and one nested anchored plus indexing PCR, according to the example methods 100 or 100' as described in Example 1. In brief, indicated amount of DNA was fragmented to typical sizes peaking at 300-500 bp, then single-stranded adaptor was used to block the 3-termini of these DNA fragments. Indexed single-stranded adaptor was ligated to the 5-termini after phosphorylation by T4 polynucleotide kinase (T4 PNK; New England Biolabs, Ipswich, MA, USA) so as to improve the ligation efficiency, which was followed by first-round linear GSP PCR to capture all potential off-targets. The second-round nested GSP PCR was conducted after cleaning up the primers from the first round. Final sequencing library was checked by gel electrophoresis and quantified by quantitative PCR (qPCR) using the Illumina sequencing primers, followed by Next-Seq/MiSeq (Illumina, San Diego, CA, USA).

Example 9. Detection of Gene Translocation and Edit of Potential Off-Targets

Qualified reads were mapped to human genome (GRCh38) using Burrows-Wheeler Alignment Tool (BWA mem) (version 0.7.17-r1188). Translocation can be observed when one read is split into different loci (split read) or the mate of one anchored read mapped to a new locus (discordant read). To identify split/discordant reads, Breakmer (version 0.0.7; with parameters: trl_sr_thresh 1, rearr_sr_thresh 1, and discread_only_thresh 1) were used to profile potential candidate translocations, followed by estimate of protospacer similarity to on-target spacer and cutting frequency determinant (CFD). The resulting off-target candidates with CFD above 0.01 were further filtered by the orientations of split/discordant reads at each corresponding locus and the negative control to minimize nonspecific fusion by false amplification and hotspot DSB sites.

For Indel frequency determination, mapped reads were re-aligned by GATK-realigner (version 3.8.0), then subjected to filtering those reads not spanning the corresponding spacer regions. The resulting reads were then estimated the insertion and deletion occurring around 5-bp up/downstream of cleavage site using custom script. Reliable Indel frequency was determined by the Indel value of treatment sample with an elimination by corresponding value of negative control.

Example 10. EDITED-Seq Strategy

In this example embodiment, a method for editing events detection by sequencing (EDITED-Seq) was conducted according to procedures described in Examples 8 and 9 to simultaneously detect new and validate known or in-silico-predicted off-target sites.

In some embodiments, by using on-target as well as highly potential off-targets as seeds, novel CRISPR-edited off-target sites could be extensively hooked via linear amplification using targeted-primers because of fusions between double-strand breaks that are induced by CRISPR editing. Anchored polymerase chain reaction was implemented to capture and also validate all potential edited off-targets, without any preliminary experimental process before starting off-target profiling.

In this example embodiment, EDITED-Seq was initially performed according to Examples 8 and 9 on VEGFA_2 in K562 cells. The sequences of anchored primers for VEGFA_2 used in EDITED-Seq in this example embodiment is shown in Table 3 below.

TABLE 3

Sequences of anchored primers for VEGFA_2

| 1st PCR primer name | Sequence | SEQ ID NO: | 2nd PCR primer name | Sequence | SEQ ID NO: |
|---|---|---|---|---|---|
| ABLIM1_m1 | CCCCTTAGGGATAACAGGGTAATCCAACTGCCATATGCCCTGGGT | 15 | ABLIM1_m2 | GTGACTGGAGTTCAGACGTGTGCTCTTCCGATCTGCCCTGGGTCTCTGAAGAAGCT | 150 |

TABLE 3-continued

| Sequences of anchored primers for VEGFA_2 | | | | | |
|---|---|---|---|---|---|
| 1st PCR primer name | Sequence | SEQ ID NO: | 2nd PCR primer name | Sequence | SEQ ID NO: |
| ABLIM1_p1 | CCCCTTAGGGATA ACAGGGTAATCCG GCGGGTGGGTCAC AAA | 16 | ABLIM1_p2 | GTGACTGGAGTTCA GACGTGTGCTCTTCC GATCTGGCGGGTGG GTCACAAAATAAAAT GT | 151 |
| ACLY_m1 | CCCCTTAGGGATA ACAGGGTAATCCA CAGGACAGGGTC AGCGT | 17 | ACLY_m2 | GTGACTGGAGTTCA GACGTGTGCTCTTCC GATCTACAGGACAGG GTCAGCGTTTAAGA | 152 |
| ACLY_p1 | CCCCTTAGGGATA ACAGGGTAATCGG CCCCTACAATACT ATCTTGACCCT | 18 | ACLY_p2 | GTGACTGGAGTTCA GACGTGTGCTCTTCC GATCTAAGTTTGCTG GCCCTGGTTTAGA | 153 |
| ATL3-NC_m1 | CCCCTTAGGGATA ACAGGGTAATCTG AGAGACAGGGTCT TGCTGTTG | 19 | ATL3-NC_m2 | GTGACTGGAGTTCA GACGTGTGCTCTTCC GATCTTGCAGTACAG TGATGGGACCGT | 154 |
| B4GALNT4_m1 | CCCCTTAGGGATA ACAGGGTAATCCC AACTTGGTGGGGG TAGAGTG | 20 | B4GALNT4_m2 | GTGACTGGAGTTCA GACGTGTGCTCTTCC GATCTCCTTAGGGGG CCAGCAGTG | 155 |
| CALY_m1 | CCCCTTAGGGATA ACAGGGTAATCTC ACGCAGACGCCCC CAT | 21 | CALY_m2 | GTGACTGGAGTTCA GACGTGTGCTCTTCC GATCTGCAGACGCCC CCATCAAGCC | 156 |
| CALY_p1 | CCCCTTAGGGATA ACAGGGTAATCAG CCTGGAGTTAAGG GTGTCTCC | 22 | CALY_p2 | GTGACTGGAGTTCA GACGTGTGCTCTTCC GATCTTGGAGTTAAG GGTGTCTCCGAGGTG | 157 |
| CDC42SE1_m1 | CCCCTTAGGGATA ACAGGGTAATCCC CCAGGAGCGTGG ATGACTAC | 23 | CDC42SE1_m2 | GTGACTGGAGTTCA GACGTGTGCTCTTCC GATCTGCGCGCACCC CTTTCCCA | 158 |
| CDC42SE1_p1 | CCCCTTAGGGATA ACAGGGTAATCGC AGGTGAGGCCGTG CAG | 24 | CDC42SE1_p2 | GTGACTGGAGTTCA GACGTGTGCTCTTCC GATCTGGTGAGGCCG TGCAGTTGGTC | 159 |
| CDKN2C-NC_m1 | CCCCTTAGGGATA ACAGGGTAATCTG AGTTATGTGGTCC CCTCTAGGAA | 25 | CDKN2C-NC_m2 | GTGACTGGAGTTCA GACGTGTGCTCTTCC GATCTAAGCCTCTTG AACATGCCGAAATGT A | 160 |
| CDKN2C-NC_p1 | CCCCTTAGGGATA ACAGGGTAATCAG CGTCGTCTCCTGG AGCTC | 26 | CDKN2C-NC_p2 | GTGACTGGAGTTCA GACGTGTGCTCTTCC GATCTTCGTCTCCTG GAGCTCTGGACAC | 161 |
| Chr4-NC_m1 | CCCCTTAGGGATA ACAGGGTAATCTG ATGGCATCAAAAT GTGTGTCCAGT | 27 | Chr4-NC_m2 | GTGACTGGAGTTCA GACGTGTGCTCTTCC GATCTCCACCTGTGG CTGATAGTGACGTCT | 162 |
| Chr4-NC_p1 | CCCCTTAGGGATA ACAGGGTAATCGG AGGTGGCTTCACT TAGGAGGTC | 28 | Chr4-NC_p2 | GTGACTGGAGTTCA GACGTGTGCTCTTCC GATCTAGGTCTGGGG AGCGGAGTCC | 163 |
| Chr6-NC_m1 | CCCCTTAGGGATA ACAGGGTAATCAG CAAGGCTGACACC AGGTG | 29 | Chr6-NC_m2 | GTGACTGGAGTTCA GACGTGTGCTCTTCC GATCTACCGCCTCCA CCCCCAAGG | 164 |
| Chr6-NC_p1 | CCCCTTAGGGATA ACAGGGTAATCGG | 30 | Chr6-NC_p2 | GTGACTGGAGTTCA GACGTGTGCTCTTCC | 165 |

TABLE 3-continued

| Sequences of anchored primers for VEGFA_2 | | | | | |
|---|---|---|---|---|---|
| 1st PCR primer name | Sequence | SEQ ID NO: | 2nd PCR primer name | Sequence | SEQ ID NO: |
| | CTGGGATCTGGGGAGAGAG | | | GATCTGGATCTGGGGAGAGAGGTGACC | |
| CLYBL_m1 | CCCCTTAGGGATAACAGGGTAATCAATCATCAGGTGCAAGGCAAGACTG | 31 | CLYBL_m2 | GTGACTGGAGTTCAGACGTGTGCTCTTCCGATCTTGTATGTATGCAAAGCCCCGTCACG | 166 |
| CLYBL_p1 | CCCCTTAGGGATAACAGGGTAATCTCTGACTGGAGTTCCCTTCACCA | 32 | CLYBL_p2 | GTGACTGGAGTTCAGACGTGTGCTCTTCCGATCTGACTGGAGTTCCCTTCACCATTTCAA | 167 |
| CRB2_m1 | CCCCTTAGGGATAACAGGGTAATCGAGGAGCCTGGACAGACGAAG | 33 | CRB2_m2 | GTGACTGGAGTTCAGACGTGTGCTCTTCCGATCTCCTGGACAGACGAAGGCAGCA | 168 |
| CRB2_p1 | CCCCTTAGGGATAACAGGGTAATCGCTGCCAGAAGCCTGTAGAGAT | 34 | CRB2_p2 | GTGACTGGAGTTCAGACGTGTGCTCTTCCGATCTGCCTGTAGAGATCAAGGCTGCTC | 169 |
| CXXC5_m1 | CCCCTTAGGGATAACAGGGTAATCAGCTCGGGGGTGATTAGTTGC | 35 | CXXC5_m2 | GTGACTGGAGTTCAGACGTGTGCTCTTCCGATCTTCGGGGGTGATTAGTTGCTTTTTGTT | 170 |
| CXXC5_p1 | CCCCTTAGGGATAACAGGGTAATCGCCGTGGCCCGACACCTA | 36 | CXXC5_p2 | GTGACTGGAGTTCAGACGTGTGCTCTTCCGATCTCCCGACACCTACCGGCTCTCC | 171 |
| DOLK-NC_m1 | CCCCTTAGGGATAACAGGGTAATCTAAGAAGGGCCCCTTGATGAGGTC | 37 | DOLK-NC_m2 | GTGACTGGAGTTCAGACGTGTGCTCTTCCGATCTGGTCCTGGTGCTGTTCAGCCCATCTT | 172 |
| DOLK-NC_p1 | CCCCTTAGGGATAACAGGGTAATCGGGAGAGGTGGGTCAACTTTGG | 38 | DOLK-NC_p2 | GTGACTGGAGTTCAGACGTGTGCTCTTCCGATCTGGTGGGTCAACTTTGGCAGGGT | 173 |
| ELL-NC_m1 | CCCCTTAGGGATAACAGGGTAATCGAGGGTGGGCGTGGCTATGTA | 39 | ELL-NC_m2 | GTGACTGGAGTTCAGACGTGTGCTCTTCCGATCTGGTGGGCGTGGCTATGTAAACGGA | 174 |
| ELL-NC_p1 | CCCCTTAGGGATAACAGGGTAATCATGAAGCTGGACTGCACCATCG | 40 | ELL-NC_p2 | GTGACTGGAGTTCAGACGTGTGCTCTTCCGATCTCTGGACTGCACCATCGCTCAGG | 175 |
| EXD3_m1 | CCCCTTAGGGATAACAGGGTAATCTGGGGAGGGGCGAAGGTC | 41 | EXD3_m2 | GTGACTGGAGTTCAGACGTGTGCTCTTCCGATCTAAGGGAGTCTCAGGCCCGTGAG | 176 |
| EXD3_p1 | CCCCTTAGGGATAACAGGGTAATCCCGGGTCCTGCGTCCCTT | 42 | EXD3_p2 | GTGACTGGAGTTCAGACGTGTGCTCTTCCGATCTGTCCTGCGTCCCTTCCCCTGA | 177 |
| FAM83H_m1 | CCCCTTAGGGATAACAGGGTAATCCCGCAGCCTCCAGATGCA | 43 | FAM83H_m2 | GTGACTGGAGTTCAGACGTGTGCTCTTCCGATCTGCACCGGCAGCCACCTGT | 178 |
| FAM83H_p1 | CCCCTTAGGGATAACAGGGTAATCCTGAGGCTCTTATCAAACAACTGCCA | 44 | FAM83H_p2 | GTGACTGGAGTTCAGACGTGTGCTCTTCCGATCTAACTGCCACTACTCCCGTCCTCAG | 179 |

TABLE 3-continued

Sequences of anchored primers for VEGFA_2

| 1st PCR primer name | Sequence | SEQ ID NO: | 2nd PCR primer name | Sequence | SEQ ID NO: |
|---|---|---|---|---|---|
| FBXO2_m1 | CCCCTTAGGGATA ACAGGGTAATCCG AGTCCCGGCGCTG TCC | 45 | FBXO2_m2 | GTGACTGGAGTTCA GACGTGTGCTCTTCC GATCTTGTCCGCGTC TGTGTCGGT | 180 |
| FBXO2_p1 | CCCCTTAGGGATA ACAGGGTAATCCC TCCTCGGTCCGCT GAG | 46 | FBXO2_p2 | GTGACTGGAGTTCA GACGTGTGCTCTTCC GATCTCCCGGGCCTC GAGCAGAC | 181 |
| FMN1_m1 | CCCCTTAGGGATA ACAGGGTAATCCA ATCTCTGACTTGG ACAGCTGCA | 47 | FMN1_m2 | GTGACTGGAGTTCA GACGTGTGCTCTTCC GATCTCTTGGACAGC TGCAGTACTCCCT | 182 |
| FMN1_p1 | CCCCTTAGGGATA ACAGGGTAATCTC GATGATGGCCTAT GGGTTGAAAA | 48 | FMN1_p2 | GTGACTGGAGTTCA GACGTGTGCTCTTCC GATCTAGTGCGGTGG AGAAAGGCAAG | 183 |
| FSTL4_m1 | CCCCTTAGGGATA ACAGGGTAATCTG TGCTTCTTCCAAG CTGCGT | 49 | FSTL4_m2 | GTGACTGGAGTTCA GACGTGTGCTCTTCC GATCTGCGTCTCTTT GGACCCGTACTTGC | 184 |
| FSTL4_p1 | CCCCTTAGGGATA ACAGGGTAATCTG TGATTTTCCTGGCT TTAGCGCTA | 50 | FSTL4_p2 | GTGACTGGAGTTCA GACGTGTGCTCTTCC GATCTTCCTGGCTTT AGCGCTATACGTTTG A | 185 |
| HDLBP_m1 | CCCCTTAGGGATA ACAGGGTAATCTC TACAACCAAGCCC ATTTGTCCA | 51 | HDLBP_m2 | GTGACTGGAGTTCA GACGTGTGCTCTTCC GATCTCATTTGTCCA GGAACCCCTAGCC | 186 |
| HDLBP_p1 | CCCCTTAGGGATA ACAGGGTAATCAG CCTCTCTACCATTT GTGCTGA | 52 | HDLBP_p2 | GTGACTGGAGTTCA GACGTGTGCTCTTCC GATCTACCATTTGTG CTGATCTGTGGGTAT C | 187 |
| HMX1-NC_m1 | CCCCTTAGGGATA ACAGGGTAATCCC TGCCAGGGTTGCA TGGG | 53 | HMX1-NC_m2 | GTGACTGGAGTTCA GACGTGTGCTCTTCC GATCTCAGGGTTGCA TGGGAACTTCCTCTG | 188 |
| HMX1-NC_p1 | CCCCTTAGGGATA ACAGGGTAATCTT GTCCCCACCCTCG TCACTC | 54 | HMX1-NC_p2 | GTGACTGGAGTTCA GACGTGTGCTCTTCC GATCTCCCACCCTCG TCACTCTCTGACC | 189 |
| IL27RA_m1 | CCCCTTAGGGATA ACAGGGTAATCGG CAGGGACCCGGC GACA | 55 | IL27RA_m2 | GTGACTGGAGTTCA GACGTGTGCTCTTCC GATCTCCGGCGACAC TGGGGAATG | 190 |
| IL27RA_p1 | CCCCTTAGGGATA ACAGGGTAATCGG AAGGGAGGCGCTA GGCA | 56 | IL27RA_p2 | GTGACTGGAGTTCA GACGTGTGCTCTTCC GATCTCCCGGGCTCC GTGCAAAC | 191 |
| INPPL1_m1 | CCCCTTAGGGATA ACAGGGTAATCGC TGGGCCTGCACGC TCA | 57 | INPPL1_m2 | GTGACTGGAGTTCA GACGTGTGCTCTTCC GATCTAGGCCCCCTG GAGCTGCA | 192 |
| INPPL1_p1 | CCCCTTAGGGATA ACAGGGTAATCGA CAGCCACCCTGCT CCAC | 58 | INPPL1_p2 | GTGACTGGAGTTCA GACGTGTGCTCTTCC GATCTCCACCCTGCT CCACACACCT | 193 |

TABLE 3-continued

| Sequences of anchored primers for VEGFA_2 | | | | | |
|---|---|---|---|---|---|
| 1st PCR primer name | Sequence | SEQ ID NO: | 2nd PCR primer name | Sequence | SEQ ID NO: |
| IUQB-NC_m1 | CCCCTTAGGGATA ACAGGGTAATCCC TAGCAACGGCCCT GGCA | 59 | IUQB-NC_m2 | GTGACTGGAGTTCA GACGTGTGCTCTTCC GATCTACGGCCCTGG CACCACCT | 194 |
| IUQB-NC_p1 | CCCCTTAGGGATA ACAGGGTAATCCC CTACCCTGCCGCG CTCCT | 60 | IUQB-NC_p2 | GTGACTGGAGTTCA GACGTGTGCTCTTCC GATCTCTGCCGCGCT CCTCCTTCC | 195 |
| JAKMIP3_m1 | CCCCTTAGGGATA ACAGGGTAATCGG CACCTCATTGGGG ACGT | 61 | JAKMIP3_m2 | GTGACTGGAGTTCA GACGTGTGCTCTTCC GATCTCCTCATTGGG GACGTCTGTTGTGAA A | 196 |
| JAKMIP3_p1 | CCCCTTAGGGATA ACAGGGTAATCTG CTCTGAACCGAGG CCTTG | 62 | JAKMIP3_p2 | GTGACTGGAGTTCA GACGTGTGCTCTTCC GATCTAGTCCCCAGT TACGGAGACAAATCT | 197 |
| KCNQ1_m1 | CCCCTTAGGGATA ACAGGGTAATCGC AGGGCCCCAGAG AGGT | 63 | KCNQ1_m2 | GTGACTGGAGTTCA GACGTGTGCTCTTCC GATCTGGCCCCAGAG AGGTGAGGTCACTAT A | 198 |
| KCNQ1_p1 | CCCCTTAGGGATA ACAGGGTAATCGC AGCGACGCCACTC TTTATCT | 64 | KCNQ1_p2 | GTGACTGGAGTTCA GACGTGTGCTCTTCC GATCTGGTACCCCGT GCCTCAGCT | 199 |
| KLHL23_m1 | CCCCTTAGGGATA ACAGGGTAATCCG CGCTGACAGCTGT TGC | 65 | KLHL23_m2 | GTGACTGGAGTTCA GACGTGTGCTCTTCC GATCTCCAGGTTGTT TATCTGGGCCTCT | 200 |
| KLHL23_p1 | CCCCTTAGGGATA ACAGGGTAATCTG AGTTTCATGCTCA GTCCCTGCA | 66 | KLHL23_p2 | GTGACTGGAGTTCA GACGTGTGCTCTTCC GATCTGCAGGACAC AGCACAGGTAAGGG A | 201 |
| LAMA3_m1 | CCCCTTAGGGATA ACAGGGTAATCAG GGCTCTGGGGTGA CTCC | 67 | LAMA3_m2 | GTGACTGGAGTTCA GACGTGTGCTCTTCC GATCTCTGGGGTGAC TCCAAGGCTTTTCG | 202 |
| LAMA3_p1 | CCCCTTAGGGATA ACAGGGTAATCCT CCCTACTCAACCC CGAGCCCTCCT | 68 | LAMA3_p2 | GTGACTGGAGTTCA GACGTGTGCTCTTCC GATCTCCCCGAGCCC TCCTCTCTTG | 203 |
| LINC00415_m1 | CCCCTTAGGGATA ACAGGGTAATCGC GCCAGACCAGCTC CGA | 69 | LINC00415_m2 | GTGACTGGAGTTCA GACGTGTGCTCTTCC GATCTAGCTCCGACT CCGCTCGCT | 204 |
| LINC00415_p1 | CCCCTTAGGGATA ACAGGGTAATCCT CCTTGCCCGGGGT AGG | 70 | LINC00415_p2 | GTGACTGGAGTTCA GACGTGTGCTCTTCC GATCTTTGCCCGGGG TAGGAAAGTGA | 205 |
| LINC01258_m1 | CCCCTTAGGGATA ACAGGGTAATCCT TCTCATCCTTGTAT CAGCTGCCTT | 71 | LINC01258_m2 | GTGACTGGAGTTCA GACGTGTGCTCTTCC GATCTGTATCAGCTG CCTTCTCATCACAAG A | 206 |
| LINC01258_p1 | CCCCTTAGGGATA ACAGGGTAATCGG GAGAGTGCCATTC TCAGCCTAA | 72 | LINC01258_p2 | GTGACTGGAGTTCA GACGTGTGCTCTTCC GATCTGTGCCATTCT CAGCCTAAAAGGTA GA | 207 |

TABLE 3-continued

Sequences of anchored primers for VEGFA_2

| 1st PCR primer name | Sequence | SEQ ID NO: | 2nd PCR primer name | Sequence | SEQ ID NO: |
|---|---|---|---|---|---|
| LUC7L2_m1 | CCCCTTAGGGATA ACAGGGTAATCGG TGGATCACGCAGT CGGA | 73 | LUC7L2_m2 | GTGACTGGAGTTCA GACGTGTGCTCTTCC GATCTACGCAGTCGG AGGCCATCC | 208 |
| MIR3681-NC_m1 | CCCCTTAGGGATA ACAGGGTAATCCA TGAGCACACCCAC CACCA | 74 | MIR3681-NC_m2 | GTGACTGGAGTTCA GACGTGTGCTCTTCC GATCTAGCACACCCA CCACCACTCCTA | 209 |
| MIR3681-NC_p1 | CCCCTTAGGGATA ACAGGGTAATCGC CTTGTCCCACATC ACAGCA | 75 | MIR3681-NC_p2 | GTGACTGGAGTTCA GACGTGTGCTCTTCC GATCTCTTGTCCCAC ATCACAGCAAACTCT | 210 |
| MIR4647-NC_m1 | CCCCTTAGGGATA ACAGGGTAATCCG CCTGGGACTACTT CTCGTTTGAAA | 76 | MIR4647-NC_m2 | GTGACTGGAGTTCA GACGTGTGCTCTTCC GATCTCGGGGCTGCG GAAGGATCC | 211 |
| MIR4647-NC_p1 | CCCCTTAGGGATA ACAGGGTAATCCC CCCAACGTGGCCT CAG | 77 | MIR4647-NC_p2 | GTGACTGGAGTTCA GACGTGTGCTCTTCC GATCTCAACGTGGCC TCAGCTGCTC | 212 |
| MOB3B_m1 | CCCCTTAGGGATA ACAGGGTAATCCA CAGCTGTCCAAAC GAGGCT | 78 | MOB3B_m2 | GTGACTGGAGTTCA GACGTGTGCTCTTCC GATCTACGAGGCTGG CTCCCCACT | 213 |
| MOB3B_p1 | CCCCTTAGGGATA ACAGGGTAATCGG ATGCAACTGAGGG CTCCTTA | 79 | MOB3B_p2 | GTGACTGGAGTTCA GACGTGTGCTCTTCC GATCTCTCCTTAGAA AGTCATGCCCCAGGA G | 214 |
| MSI2_m1 | CCCCTTAGGGATA ACAGGGTAATCGG AAGGTCGCTGGGA AGCC | 80 | MSI2_m2 | GTGACTGGAGTTCA GACGTGTGCTCTTCC GATCTGGGCTGGGA GGGGATTGGC | 215 |
| MSI2_p1 | CCCCTTAGGGATA ACAGGGTAATCTG CCCAGCCTCCCTG CAG | 81 | MSI2_p2 | GTGACTGGAGTTCA GACGTGTGCTCTTCC GATCTGCCTCCCTGC AGGATGATTGGC | 216 |
| MTMR1_m1 | CCCCTTAGGGATA ACAGGGTAATCAG CTCCTCTGTGTGA CATGCC | 82 | MTMR1_m2 | GTGACTGGAGTTCA GACGTGTGCTCTTCC GATCTATGCCACAGA TGACTATTGCACACC T | 217 |
| MTMR1_p1 | CCCCTTAGGGATA ACAGGGTAATCAC CAACCAGCTAACA CTGCTATGCA | 83 | MTMR1_p2 | GTGACTGGAGTTCA GACGTGTGCTCTTCC GATCTACCTCAGGGG CCGCTGCA | 218 |
| NC-Chr12_m1 | CCCCTTAGGGATA ACAGGGTAATCAC TCAGGTGTGCTGG CACTGAT | 84 | NC-Chr12_m2 | GTGACTGGAGTTCA GACGTGTGCTCTTCC GATCTGCTGGCACTG ATCTGTGGTCCCA | 219 |
| NC-Chr12_p1 | CCCCTTAGGGATA ACAGGGTAATCAC ATACAACCAGTTC ACCCAGTTAC | 85 | NC-Chr12_p2 | GTGACTGGAGTTCA GACGTGTGCTCTTCC GATCTAACCAGTTCA CCCAGTTACAGTAGA C | 220 |
| NFIX_m1 | CCCCTTAGGGATA ACAGGGTAATCGG TGTGTGTTTGCTG TTACCGCTTA | 86 | NFIX_m2 | GTGACTGGAGTTCA GACGTGTGCTCTTCC GATCTACCGCTTAAA TTAACCCTGAGTGAC G | 221 |

TABLE 3-continued

Sequences of anchored primers for VEGFA_2

| 1st PCR primer name | Sequence | SEQ ID NO: | 2nd PCR primer name | Sequence | SEQ ID NO: |
|---|---|---|---|---|---|
| NFIX_p1 | CCCCTTAGGGATAACAGGGTAATCCCTGGAGCGAAGGCCTGGAG | 87 | NFIX_p2 | GTGACTGGAGTTCAGACGTGTGCTCTTCCGATCTTAGCGTGCGGCCCGAGCT | 222 |
| NoName1_m1 | CCCCTTAGGGATAACAGGGTAATCTACTGATGGGGGTGAGCTCCA | 88 | NoName1_m2 | GTGACTGGAGTTCAGACGTGTGCTCTTCCGATCTGGGGGTGAGCTCCAACTCTG | 223 |
| NoName1_p1 | CCCCTTAGGGATAACAGGGTAATCTGTGTCTCTGCTTTCTGTTGGCA | 89 | NoName1_p2 | GTGACTGGAGTTCAGACGTGTGCTCTTCCGATCTATGTATCTGGCATTACAGCTGAGCAG | 224 |
| NoName10_m1 | CCCCTTAGGGATAACAGGGTAATCTCTTCAAGCAGCCCACCTTCTG | 90 | NoName10_m2 | GTGACTGGAGTTCAGACGTGTGCTCTTCCGATCTCAGCCACTGCACCGACTTCA | 225 |
| NoName10_p1 | CCCCTTAGGGATAACAGGGTAATCACTCCCGCCGGTTCCAAG | 91 | NoName10_p2 | GTGACTGGAGTTCAGACGTGTGCTCTTCCGATCTCGGTTCCAAGTTATCGGAGTGAGCCA | 226 |
| NoName11_m1 | CCCCTTAGGGATAACAGGGTAATCCCAAAGCACAGGTGGGGACT | 92 | NoName11_m2 | GTGACTGGAGTTCAGACGTGTGCTCTTCCGATCTGGACTCATAGCCTGGGGGTAAATGTT | 227 |
| NoName11_p1 | CCCCTTAGGGATAACAGGGTAATCCAGCTGCTTGGGCTCCGTTG | 93 | NoName11_p2 | GTGACTGGAGTTCAGACGTGTGCTCTTCCGATCTTGCTTGGGCTCCGTTGCAATCC | 228 |
| NoName12_m1 | CCCCTTAGGGATAACAGGGTAATCCCCCAGGCCACAGGAAACC | 94 | NoName12_m2 | GTGACTGGAGTTCAGACGTGTGCTCTTCCGATCTAAACCAGGGGAGAGGGCCATAGAG | 229 |
| NoName12_p1 | CCCCTTAGGGATAACAGGGTAATCGCTAGGGTGGCTGTGACTCAG | 95 | NoName12_p2 | GTGACTGGAGTTCAGACGTGTGCTCTTCCGATCTGCTGTGACTCAGAGCCATGGC | 230 |
| NoName13_m1 | CCCCTTAGGGATAACAGGGTAATCCCTCTGGCTTCCCATGGGTGAG | 96 | NoName13_m2 | GTGACTGGAGTTCAGACGTGTGCTCTTCCGATCTGGCTTCCCATGGGTGAGTCCTGT | 231 |
| NoName13_p1 | CCCCTTAGGGATAACAGGGTAATCCTCCCTGAGAAGAGCTGAACATAGC | 97 | NoName13_p2 | GTGACTGGAGTTCAGACGTGTGCTCTTCCGATCTGAAGAGCTGAACATAGCCAGGCAATT | 232 |
| NoName14_m1 | CCCCTTAGGGATAACAGGGTAATCTCAACCCTTCCCATGACTGAGGTG | 98 | NoName14_m2 | GTGACTGGAGTTCAGACGTGTGCTCTTCCGATCTTGACTGAGGTGGATGAACCCCTAAGC | 233 |
| NoName14_p1 | CCCCTTAGGGATAACAGGGTAATCCCCAACCCCCTGCAGCTG | 99 | NoName14_p2 | GTGACTGGAGTTCAGACGTGTGCTCTTCCGATCTAACCCCCTGCAGCTGCTCACAA | 234 |
| NoName15_m1 | CCCCTTAGGGATAACAGGGTAATCTCAAAATCCCAAGGGCATTGTTC | 100 | NoName15_m2 | GTGACTGGAGTTCAGACGTGTGCTCTTCCGATCTAAATCCCAAGGGCATTGTTCACATAA | 235 |

TABLE 3-continued

Sequences of anchored primers for VEGFA_2

| 1st PCR primer name | Sequence | SEQ ID NO: | 2nd PCR primer name | Sequence | SEQ ID NO: |
|---|---|---|---|---|---|
| NoName15_p1 | CCCCTTAGGGATA ACAGGGTAATCCA TTGTGTCTTCTTG GTACCCTTTTT | 101 | NoName15_p2 | GTGACTGGAGTTCA GACGTGTGCTCTTCC GATCTACCCTTTTTG AAAATTAGTTGCCCA T | 236 |
| NoName16_m1 | CCCCTTAGGGATA ACAGGGTAATCAG ATCACACGAGGCA GAGGGAA | 102 | NoName16_m2 | GTGACTGGAGTTCA GACGTGTGCTCTTCC GATCTGAGGCAGAG GGAACTACAGGTGC A | 237 |
| NoName16_p1 | CCCCTTAGGGATA ACAGGGTAATCGC AATCTCACCTCCT CCCTCTC | 103 | NoName16_p2 | GTGACTGGAGTTCA GACGTGTGCTCTTCC GATCTCCTCCCTCTC CTACCAACTTCATCC | 238 |
| NoName2_m1 | CCCCTTAGGGATA ACAGGGTAATCAG CCAAACACAGAA AGGCC | 104 | NoName2_m2 | GTGACTGGAGTTCA GACGTGTGCTCTTCC GATCTCCAAACACAG AAAGGCCATTTATTG T | 239 |
| NoName2_p1 | CCCCTTAGGGATA ACAGGGTAATCGT GAGCCATGATCGT GCACTC | 105 | NoName2_p2 | GTGACTGGAGTTCA GACGTGTGCTCTTCC GATCTCCATGATCGT GCACTCTAGCCT | 240 |
| NoName3_p1 | CCCCTTAGGGATA ACAGGGTAATCAC TACATTGGAGGAG TGTGTACC | 106 | NoName3_p2 | GTGACTGGAGTTCA GACGTGTGCTCTTCC GATCTAGGAGTGTGT ACCATTTAAGGATGT G | 241 |
| NoName4_m1 | CCCCTTAGGGATA ACAGGGTAATCCT CTGCTTTCCCCTC CCACCT | 107 | NoName4_m2 | GTGACTGGAGTTCA GACGTGTGCTCTTCC GATCTCCCACCTGGC CCTGCAAGA | 242 |
| NoName4_p1 | CCCCTTAGGGATA ACAGGGTAATCCT GCCCTGTTGGATA ACCCTTCT | 108 | NoName4_p2 | GTGACTGGAGTTCA GACGTGTGCTCTTCC GATCTTCTCTGCCCC TGGACAGATTCTATA G | 243 |
| NoName5_m1 | CCCCTTAGGGATA ACAGGGTAATCCT TGGAAAGGGATGC TCTGAATACCT | 109 | NoName5_m2 | GTGACTGGAGTTCA GACGTGTGCTCTTCC GATCTGGGCCCTGCT GCACTATGATCAA | 244 |
| NoName5_p1 | CCCCTTAGGGATA ACAGGGTAATCAG CTGCACTTTCTCC CGGACAA | 110 | NoName5_p2 | GTGACTGGAGTTCA GACGTGTGCTCTTCC GATCTGGGCCAGCTT CATGACCTGAAACC | 245 |
| NoName6_m1 | CCCCTTAGGGATA ACAGGGTAATCTG TTGTTAAGGCTGT TGGCATCTGT | 111 | NoName6_m2 | GTGACTGGAGTTCA GACGTGTGCTCTTCC GATCTTGCACCTGGC TGCACCAC | 246 |
| NoName6_p1 | CCCCTTAGGGATA ACAGGGTAATCAG GAAAACACGGTTG CATCCTGA | 112 | NoName6_p2 | GTGACTGGAGTTCA GACGTGTGCTCTTCC GATCTCATCCTGAAT GCTCGTTGAGTGGAT G | 247 |
| NoName7_m1 | CCCCTTAGGGATA ACAGGGTAATCGC ACCAGCTCTTCGG CCAAG | 113 | NoName7_m2 | GTGACTGGAGTTCA GACGTGTGCTCTTCC GATCTGGCCAAGCCC ATGTAGTACTGCAG | 248 |
| NoName7_p1 | CCCCTTAGGGATA ACAGGGTAATCTC | 114 | NoName7_p2 | GTGACTGGAGTTCA GACGTGTGCTCTTCC | 249 |

TABLE 3-continued

Sequences of anchored primers for VEGFA_2

| 1st PCR primer name | Sequence | SEQ ID NO: | 2nd PCR primer name | Sequence | SEQ ID NO: |
|---|---|---|---|---|---|
| | CGTGTGTTTGACT CCCTCAAC | | | GATCTCCCTCAACTA CTTGCCCAACATGC | |
| NoName8_m1 | CCCCTTAGGGATA ACAGGGTAATCGG CGGTGTCAGCAAA GCTAGG | 115 | NoName8_m2 | GTGACTGGAGTTCA GACGTGTGCTCTTCC GATCTCGGTGTCAGC AAAGCTAGGTAAGG AG | 250 |
| NoName8_p1 | CCCCTTAGGGATA ACAGGGTAATCAG CACCGATGAGGCA TGGG | 116 | NoName8_p2 | GTGACTGGAGTTCA GACGTGTGCTCTTCC GATCTCCGATGAGGC ATGGGTTATGAAGTA | 251 |
| NoName9_m1 | CCCCTTAGGGATA ACAGGGTAATCGT GCTGCCTCCCCCT CTGGTA | 117 | NoName9_m2 | GTGACTGGAGTTCA GACGTGTGCTCTTCC GATCTCCCCTCTGGT ATGCCCCCTCAT | 252 |
| NoName9_p1 | CCCCTTAGGGATA ACAGGGTAATCGG AGTGACTGGATGC TGGGTT | 118 | NoName9_p2 | GTGACTGGAGTTCA GACGTGTGCTCTTCC GATCTTGACTGGATG CTGGGTTGTGGAAA | 253 |
| nr-HERPUD1_m1 | CCCCTTAGGGATA ACAGGGTAATCGG AGAGGGGCCTGG AAGATTCTC | 119 | nr-HERPUD1_m2 | GTGACTGGAGTTCA GACGTGTGCTCTTCC GATCTTTCTCCCCCG AGGCCTCAGAA | 254 |
| nr-HERPUD1_p1 | CCCCTTAGGGATA ACAGGGTAATCGG GTAGACTTGACAT AAGCACCA | 120 | nr-HERPUD1_p2 | GTGACTGGAGTTCA GACGTGTGCTCTTCC GATCTGACTTGACAT AAGCACCATACTTCG G | 255 |
| PAPD_m1 | CCCCTTAGGGATA ACAGGGTAATCAA GAAAAGGGGCTG CTGGGT | 121 | PAPD7_m2 | GTGACTGGAGTTCA GACGTGTGCTCTTCC GATCTGGGCTGCTGG GTAGGACCTG | 256 |
| PAPD7_p1 | CCCCTTAGGGATA ACAGGGTAATCGA CGTGATTCGAGTT CCTGGCA | 122 | PAPD7_p2 | GTGACTGGAGTTCA GACGTGTGCTCTTCC GATCTCGTGATTCGA GTTCCTGGCAATGCT A | 257 |
| PAX6_m1 | CCCCTTAGGGATA ACAGGGTAATCGG GTCTGGGGTCCTG AAATGAC | 123 | PAX6_m2 | GTGACTGGAGTTCA GACGTGTGCTCTTCC GATCTGGGTCCTGAAA TGACCCCCAAGG | 258 |
| PAX6_p1 | CCCCTTAGGGATA ACAGGGTAATCCC CACTAGATCCTGT CACAATTCCC | 124 | PAX6_p2 | GTGACTGGAGTTCA GACGTGTGCTCTTCC GATCTCGCAGCCTAT TGTCTCCTGGT | 259 |
| PLPPR1-NC_m1 | CCCCTTAGGGATA ACAGGGTAATCTG TGCTCCCGCTCCC ATGAG | 125 | PLPPR1-NC_m2 | GTGACTGGAGTTCA GACGTGTGCTCTTCC GATCTGCACGCCGTG GCCGAACA | 260 |
| PLPPR1-NC_p1 | CCCCTTAGGGATA ACAGGGTAATCTG CACAAGAACCTGC TGTCTAAACTT | 126 | PLPPR1-NC_p2 | GTGACTGGAGTTCA GACGTGTGCTCTTCC GATCTAACTTCCATA CCAGCAGCAGTTCC | 261 |
| PRR19_m1 | CCCCTTAGGGATA ACAGGGTAATCAC GACGGCCGCACA GTGG | 127 | PRR19_m2 | GTGACTGGAGTTCA GACGTGTGCTCTTCC GATCTCCGCTCGGGC CGCTGACT | 262 |

TABLE 3-continued

Sequences of anchored primers for VEGFA_2

| 1st PCR primer name | Sequence | SEQ ID NO: | 2nd PCR primer name | Sequence | SEQ ID NO: |
|---|---|---|---|---|---|
| PRR19_p1 | CCCCTTAGGGATA ACAGGGTAATCCC CGCCCACTCTCGA CTCTT | 128 | PRR19_p2 | GTGACTGGAGTTCA GACGTGTGCTCTTCC GATCTCGCCCACTCT CGACTCTTCAGGTAG | 263 |
| SAMD11_m1 | CCCCTTAGGGATA ACAGGGTAATCCC AGGACTCCCCAGG TGCT | 129 | SAMD11_m2 | GTGACTGGAGTTCA GACGTGTGCTCTTCC GATCTACTCCCCAGG TGCTGAAGAGACG | 264 |
| SAMD11_p1 | CCCCTTAGGGATA ACAGGGTAATCCT CTAGCCCGAAAAG CCAAGCT | 130 | SAMD11_p2 | GTGACTGGAGTTCA GACGTGTGCTCTTCC GATCTGCAGGGGGTC CGAGTGCA | 265 |
| SBF1_m1 | CCCCTTAGGGATA ACAGGGTAATCCT CTGCCAGATGCTG CTCGT | 131 | SBF1_m2 | GTGACTGGAGTTCA GACGTGTGCTCTTCC GATCTTGCTGCTCGT TGCCTGGCA | 266 |
| SBF1_p1 | CCCCTTAGGGATA ACAGGGTAATCGC TGTTGCAGGTCCA GAGGACAC | 132 | SBF1_p2 | GTGACTGGAGTTCA GACGTGTGCTCTTCC GATCTCACTTGAGGT GGACGTCAGTTTCTG G | 267 |
| SLC22A1_m1 | CCCCTTAGGGATA ACAGGGTAATCGA AGACGTGGGTTCT GGCAGA | 133 | SLC22A1_m2 | GTGACTGGAGTTCA GACGTGTGCTCTTCC GATCTGTGGGTTCTG GCAGAAGTTCCTATG T | 268 |
| SLC22A1_p1 | CCCCTTAGGGATA ACAGGGTAATCCC CCCGTCCCCTCTG CCA | 134 | SLC22A1_p2 | GTGACTGGAGTTCA GACGTGTGCTCTTCC GATCTCCCCTCTGCC ACCCCCAT | 269 |
| SPNS3_m1 | CCCCTTAGGGATA ACAGGGTAATCTG CCTGTGTCCGGAG CTGT | 135 | SPNS3_m2 | GTGACTGGAGTTCA GACGTGTGCTCTTCC GATCTCCTGTGTCCG GAGCTGTTTCTGC | 270 |
| SPNS3_p1 | CCCCTTAGGGATA ACAGGGTAATCCC TACCGGGGCAAGA CAGC | 136 | SPNS3_p2 | GTGACTGGAGTTCA GACGTGTGCTCTTCC GATCTCCTGGCTGGA AAGGCAACCC | 271 |
| SRPK2_m1 | CCCCTTAGGGATA ACAGGGTAATCTG GTGACAACTACCA CTCTAGAATTT | 137 | SRPK2_m2 | GTGACTGGAGTTCA GACGTGTGCTCTTCC GATCTACCACTCTAG AATTTGGCAAGATGT | 272 |
| TBATA_m1 | CCCCTTAGGGATA ACAGGGTAATCTG TCCTAAAACCCCT GCTTGGATTT | 138 | TBATA_m2 | GTGACTGGAGTTCA GACGTGTGCTCTTCC GATCTATTTCTCCACC TAGGTGTGCTCTCTC | 273 |
| TBATA_p1 | CCCCTTAGGGATA ACAGGGTAATCTG CGGAACACAGGA GCTAGTCT | 139 | TBATA_p2 | GTGACTGGAGTTCA GACGTGTGCTCTTCC GATCTGAACACAGG AGCTAGTCTGGGAA GA | 274 |
| TRIM42_m1 | CCCCTTAGGGATA ACAGGGTAATCTC AGTAGCTCCCCAA CGTTACTGT | 140 | TRIM42_m2 | GTGACTGGAGTTCA GACGTGTGCTCTTCC GATCTCGTTACTGTG CATTGAAGTCACCTG A | 275 |
| TRIM42_p1 | CCCCTTAGGGATA ACAGGGTAATCCT GTCTCCCAAAATC AGGCCTGT | 141 | TRIM42_p2 | GTGACTGGAGTTCA GACGTGTGCTCTTCC GATCTGCCTGTTCTT GCACCTGGATTCTTA C | 276 |

TABLE 3-continued

Sequences of anchored primers for VEGFA_2

| 1st PCR primer name | Sequence | SEQ ID NO: | 2nd PCR primer name | Sequence | SEQ ID NO: |
|---|---|---|---|---|---|
| TSKU_m1 | CCCCTTAGGGATA ACAGGGTAATCTT TGTGCGCCCTGCC CTT | 142 | TSKU_m2 | GTGACTGGAGTTCA GACGTGTGCTCTTCC GATCTGCGCCCTGCC CTTCGGATAA | 277 |
| TSKU_p1 | CCCCTTAGGGATA ACAGGGTAATCGG GGAGGAGGGTGTT TACGG | 143 | TSKU_p2 | GTGACTGGAGTTCA GACGTGTGCTCTTCC GATCTACGGTTATCTT TGCGACTTAGGCTCA | 278 |
| UTP14A_m1 | CCCCTTAGGGATA ACAGGGTAATCAG GCAGTGCAGGCGT TATAAACT | 144 | UTP14A_m2 | GTGACTGGAGTTCA GACGTGTGCTCTTCC GATCTGCGTTATAAA CTCCCCGAATCTTGG A | 279 |
| UTP14A_p1 | CCCCTTAGGGATA ACAGGGTAATCCA CTTTCCCTGGGGC TTGCTTA | 145 | UTP14A_p2 | GTGACTGGAGTTCA GACGTGTGCTCTTCC GATCTTCCCTGGGGC TTGCTTAGTAAAGTA G | 280 |
| UTP4_m1 | CCCCTTAGGGATA ACAGGGTAATCGG AAGGGGCGTGGG AAGCG | 146 | UTP4_m2 | GTGACTGGAGTTCA GACGTGTGCTCTTCC GATCTAGGTGGCCGG CCCAGGGT | 281 |
| UTP4_p1 | CCCCTTAGGGATA ACAGGGTAATCCC GCAGACAGAGCA AGCGCGTT | 147 | UTP4_p2 | GTGACTGGAGTTCA GACGTGTGCTCTTCC GATCTTCGGGCCGGG GCGTCTGA | 282 |
| VEGFA_m1 | CCCCTTAGGGATA ACAGGGTAATCGC CCCAGCTACCACC TCCTC | 148 | VEGFA_m2 | GTGACTGGAGTTCA GACGTGTGCTCTTCC GATCTCGGCGGCGG ACAGTGGAC | 283 |
| VEGFA_p1 | CCCCTTAGGGATA ACAGGGTAATCCG CGGACCACGGCTC CTC | 149 | VEGFA_p2 | GTGACTGGAGTTCA GACGTGTGCTCTTCC GATCTCCGAAGCGA GAACAGCCCAGAAG TT | 284 |

Figure 2A:
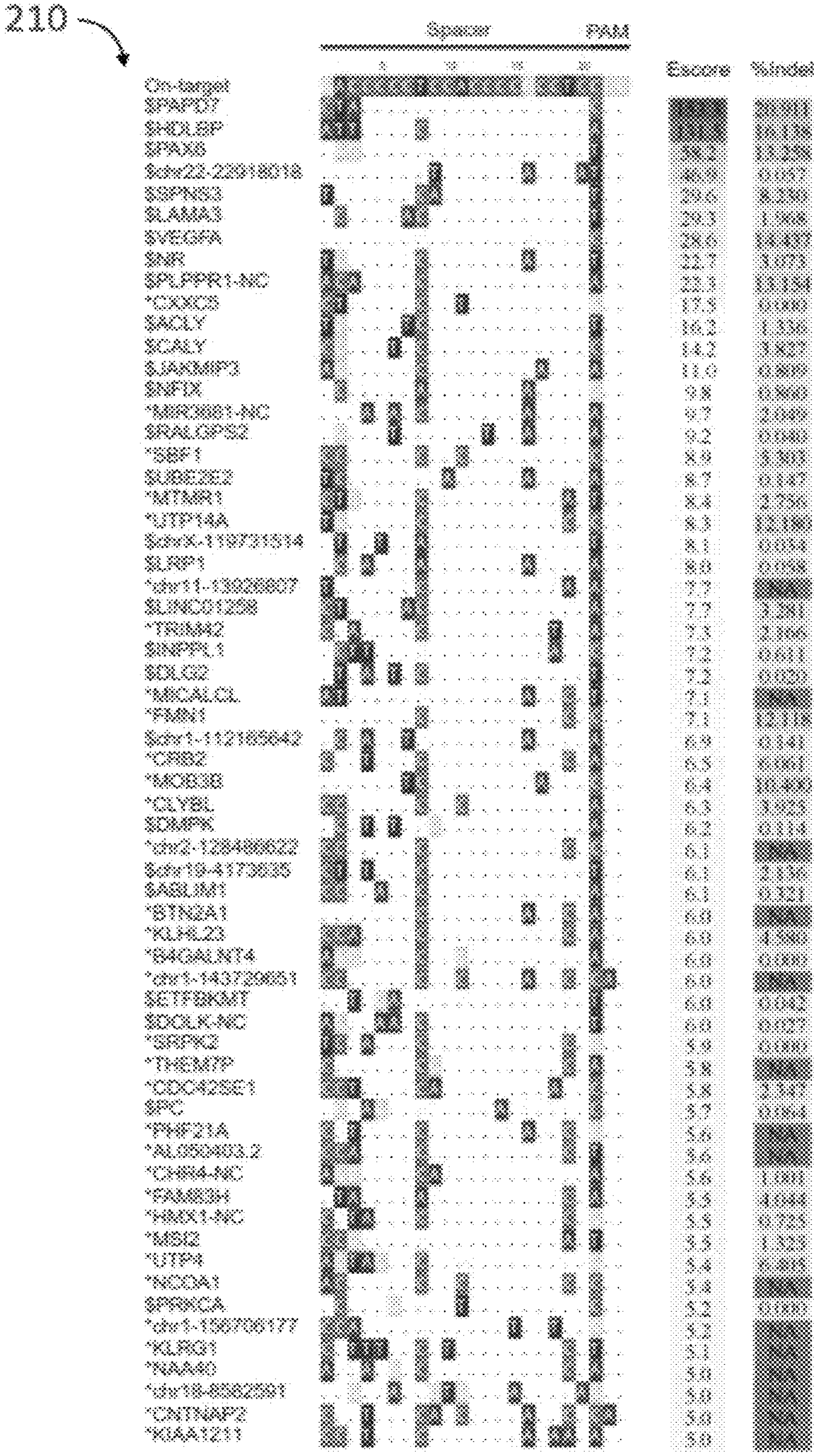
FIG. 2A and FIG. 2B are charts which show the off-target identification and validation (Chart 210, SEQ ID NOs: 961-1022 and Chart 210', SEQ ID NOs: 1023-1054) using an example technique described in the present disclosure, namely EDITED-Seq, at VEGFA_2 locus edited by CRISPR-Cas9, according to an example embodiment.
Figure 2B:
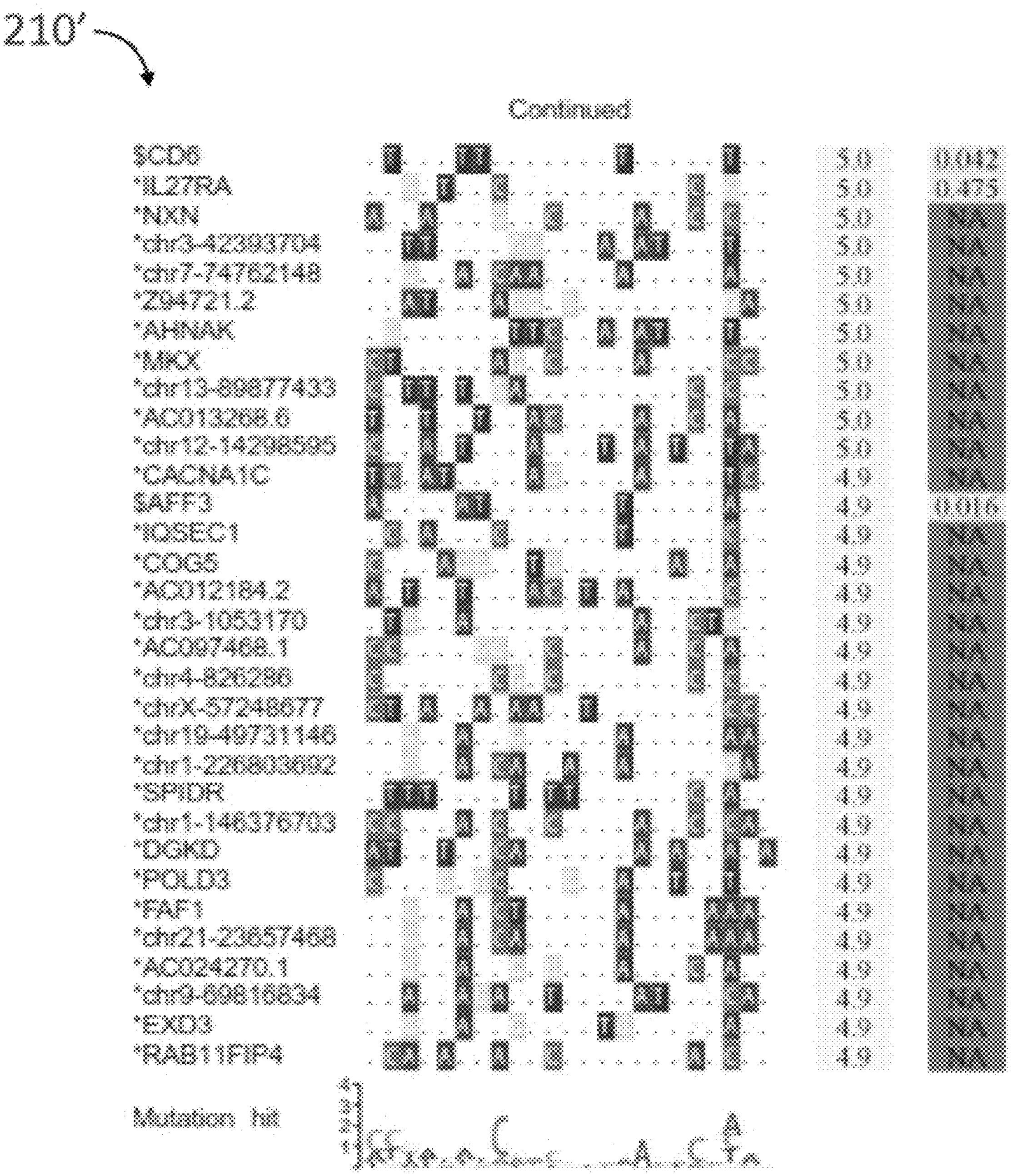

Referring now to FIG. 2A and FIG. 2B, charts 210 and 210' show the off-target identification and validation using EDITED-Seq at VEGFA_2 locus edited by CRISPR-Cas9, respectively. As shown in charts 210 and 210', there were a portion of off-targets (64 out of 94) captured by the in silico-predicted off-targets as revealed by split-fusion detection. Furthermore, the vast majority (92%) of those sites found fusion events were also validated as there were Indels detected by EDITED-Seq.

Figure 2C:
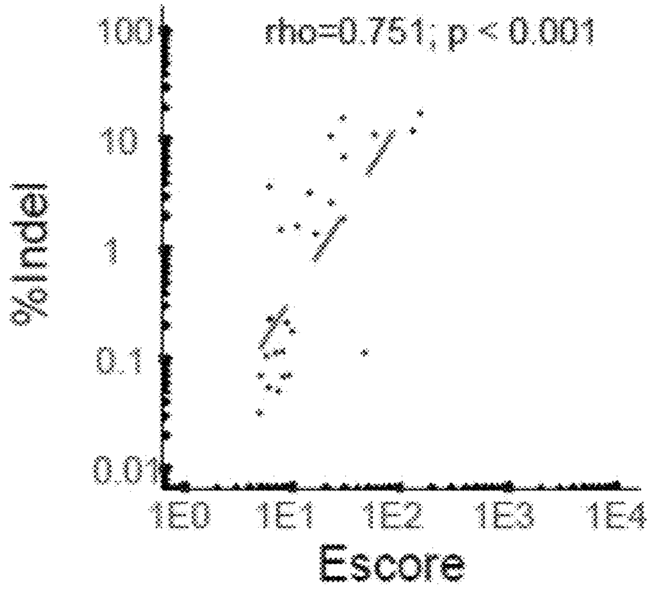
FIG. 2C is a diagram which shows the correlation between EDITED-Seq score (Escore) and Indel frequencies (%), according to the same example embodiment of FIG. 2A and FIG. 2B.
Figure 2D:
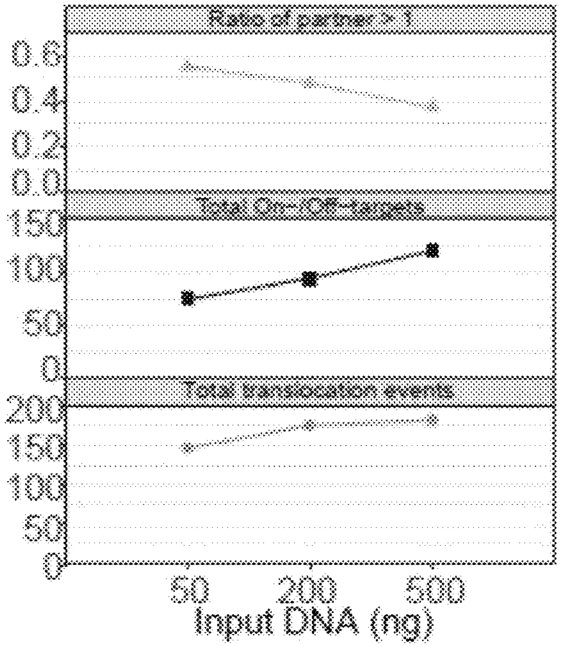
FIG. 2D is a diagram which shows the detection titration of input genomic DNA at VEGFA_2 locus, according to the same example embodiment of FIG. 2A and FIG. 2B.
Figure 2E:
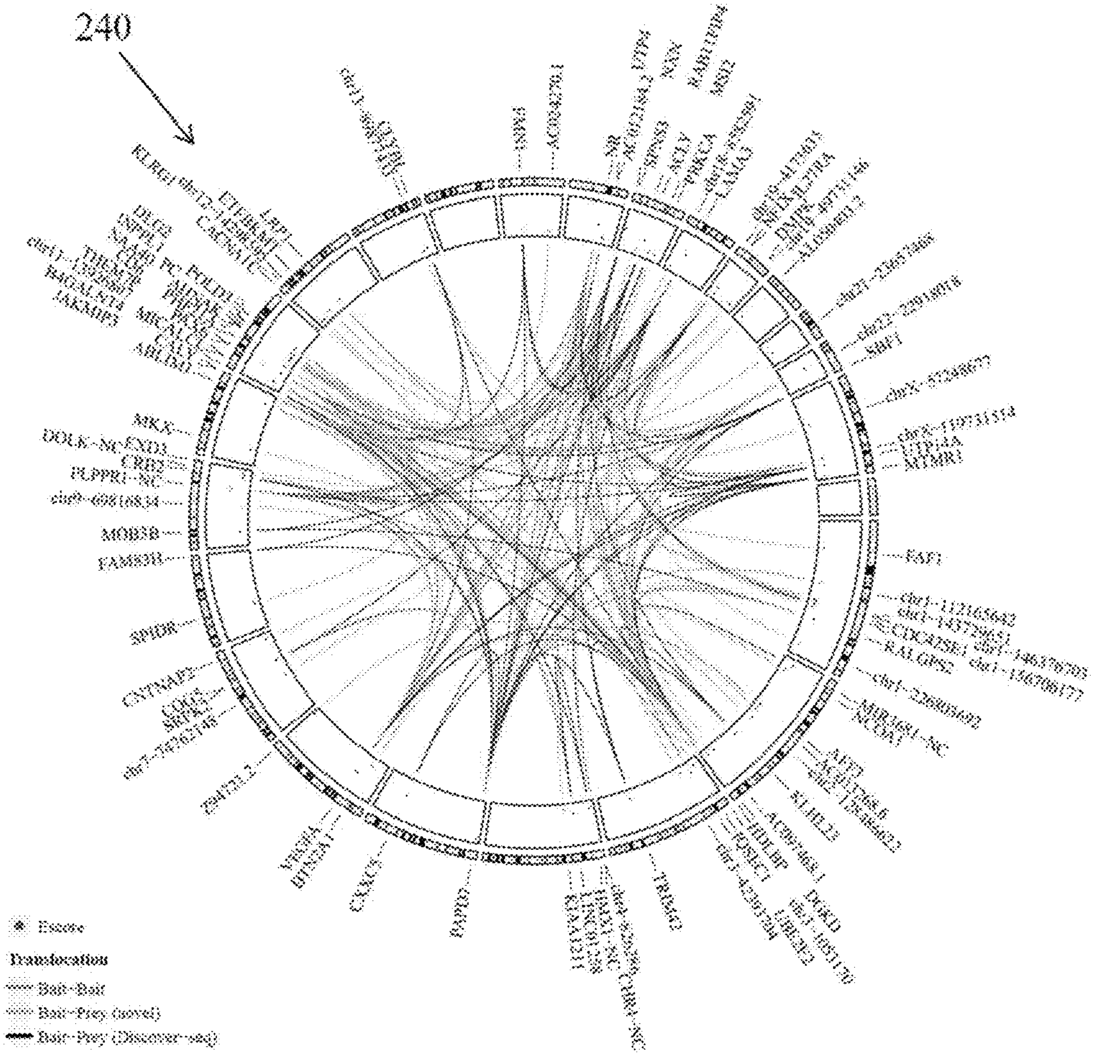
FIG. 2E is a diagram which shows a translocation circus plot of VEGFA_2 within chromosome coordinate, according to the same example embodiment of FIG. 2A and FIG. 2B.

Referring now to FIG. 2C, a diagram 220 shows the correlation between EDITED-Seq score (Escore) and Indel frequencies (%), according to the same example embodiment of FIG. 2A and FIG. 2B. EDITED-Seq score (Escore) showed strong correlation with Indel frequency simultaneously estimated from the same sequencing data. FIG. 2E shows a translocation circus plot 370 of VEGFA_2 within chromosome coordinate, showing that there were around 48% sites connecting to more than one fusion partner. Referring now to FIG. 2D, diagram 230 shows the detection titration of input genomic DNA at VEGFA_2 locus, according to the same example embodiment of FIG. 2A and FIG. 2B. EDITED-Seq required a total input cells of about 30,000-70,000 to saturation of detecting off-target number and total translocation partner. These results show that EDITED-Seq can easily and sensitively detect in situ post-edited off-targets through capturing translocations among Cas-induced DSBs in human genome.

Example 11. Comparison of EDITED-Seq with DISCOVER-Seq and GUIDE-Seq

Figure 3A:
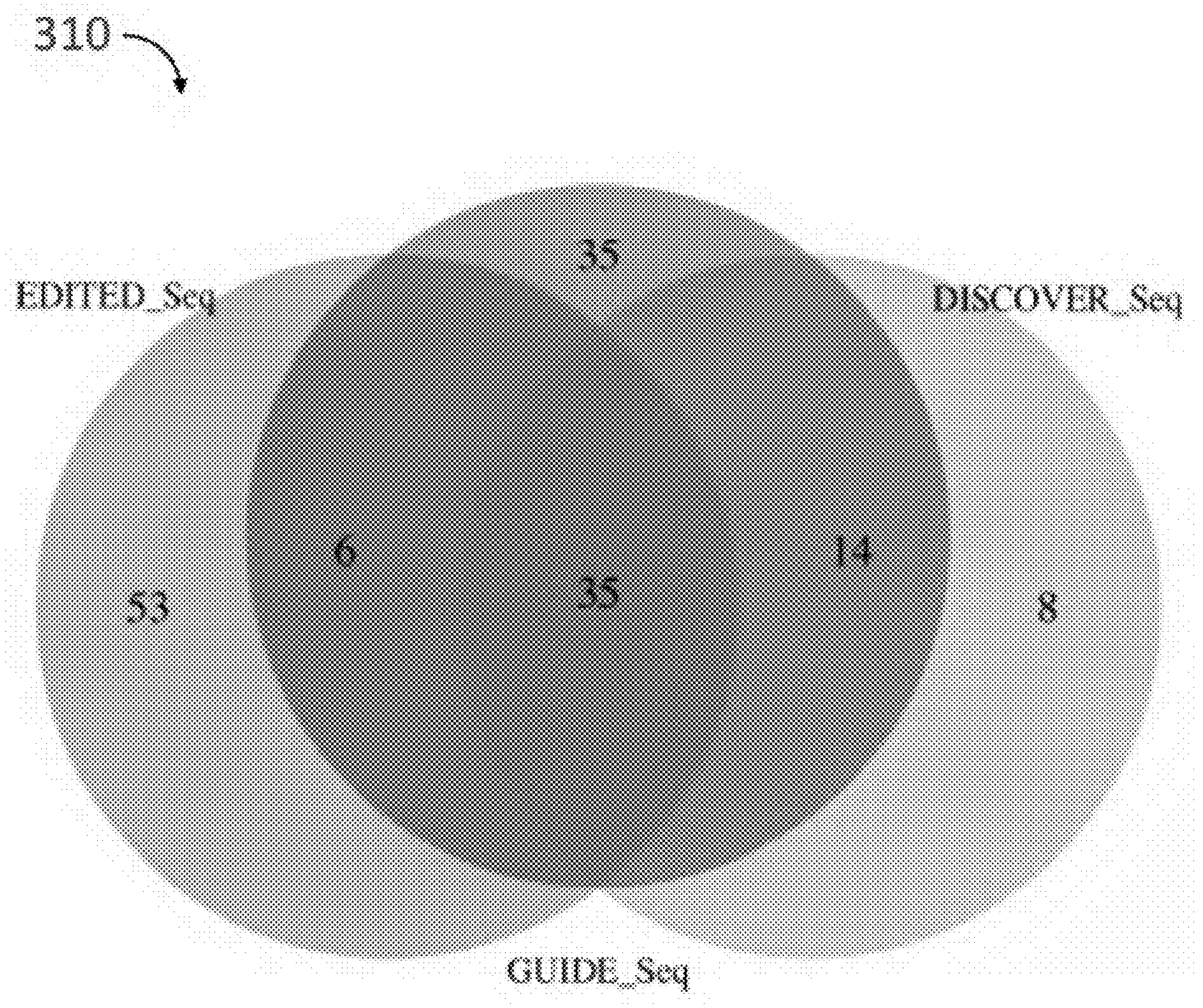
FIG. 3A is a Venn diagram which shows a comparison between EDITED-Seq off-target profile and GUIDE-Seq and DISCOVER-Seq in detection of off-targets at VEGFA_2 locus, according to the example embodiment of FIGS. 2A-2E.

Referring now to FIG. 3A, the performance of EDITED-Seq with that of DISCOVER-Seq and GUIDE-Seq were compared in this example embodiment. As shown in a Venn diagram 310 comparing the three methods (EDITED-Seq, GUIDE-Seq and DISCOVER-Seq) in detection of off-targets at VEFGA_2 locus. It showed that 94, 90 and 57 off-targets were detected at VEFGA_2 locus by EDITED-Seq, DISCOVER-Seq and GUIDE-Seq respectively, indicating that EDITED-Seq can identify more off-targets. There were around 45.6% and 61.4% sites of GUIDE-Seq or DISCOVER-Seq that were identified by EDITED-Seq (FIG. 3A). On the other hand, there were more than a half (around 56.4%) sites of EDITED-Seq that were never identified by GUIDE-Seq nor DISCOVER-Seq, indicated that EDITED-Seq can surprisingly identify most unique off-targets that have never been identified. Therefore, EDITED-Seq showed the most unique off-targets, of which 92.3% were confirmed by NGS amplicon. Those unidentified by EDITED-Seq were most unlikely detected Indel or which Indel frequencies were below 0.001% (FIG. 2A and FIG. 2B).

Figure 3B:
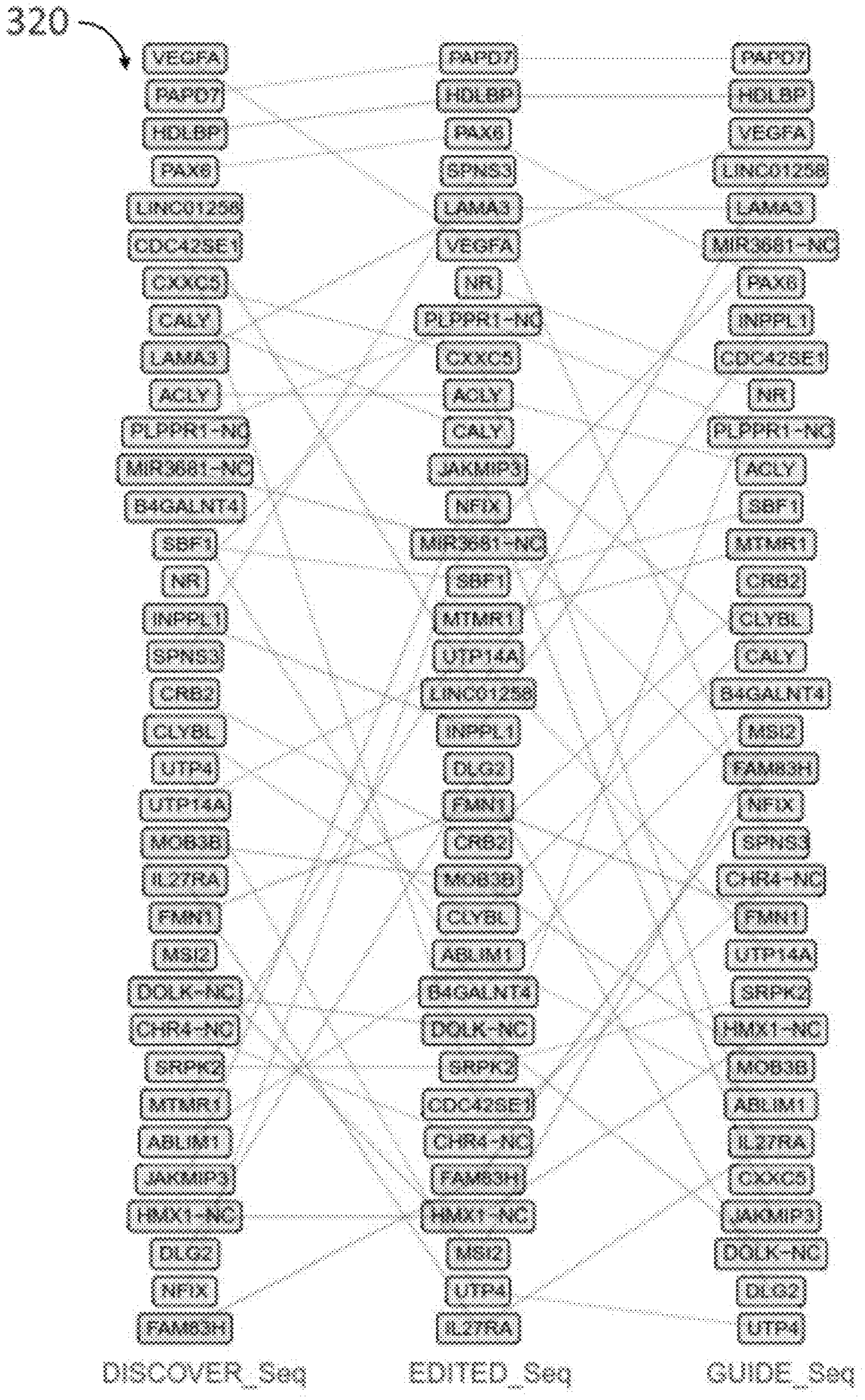
FIG. 3B is a diagram which shows a rank comparison of the commonly identified 35 sites based on the corresponding scoring values, e.g. Escore, GUIDE-Seq count, DISCOVER score, according to the same example embodiment of FIG. 3A.

Referring now to FIG. 3B, a diagram 320 showed a rank comparison of the commonly identified 35 sites based on the corresponding scoring values (e.g. Escore) of EDITED-Seq, GUIDE-Seq, and DISCOVER-Seq, according to the same example embodiment of FIG. 3A. Besides several top-scored sites showing consistent ranks across different methods, most of EDITED-Seq were not at the same level in the dataset of DISCOVER-Seq or GUIDE-Seq, respectively.

Figure 3C:
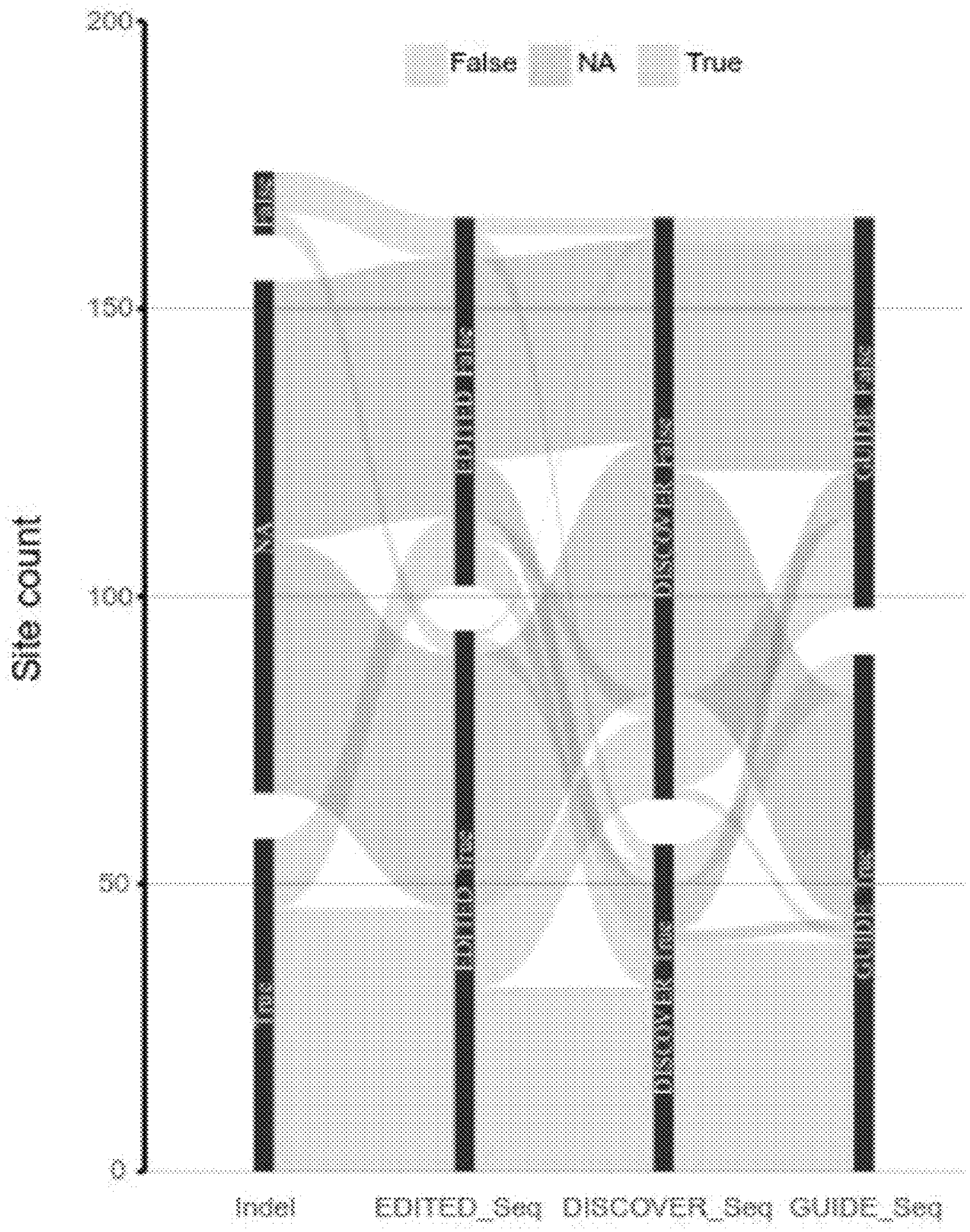
FIG. 3C is a diagram which shows Paranal distributions of identified (true) and missed (false) off-targets of EDITED-Seq, compared to GUIDE-Seq and DISCOVER-Seq, according to the same example embodiment of FIG. 3A.
Figure 3D:
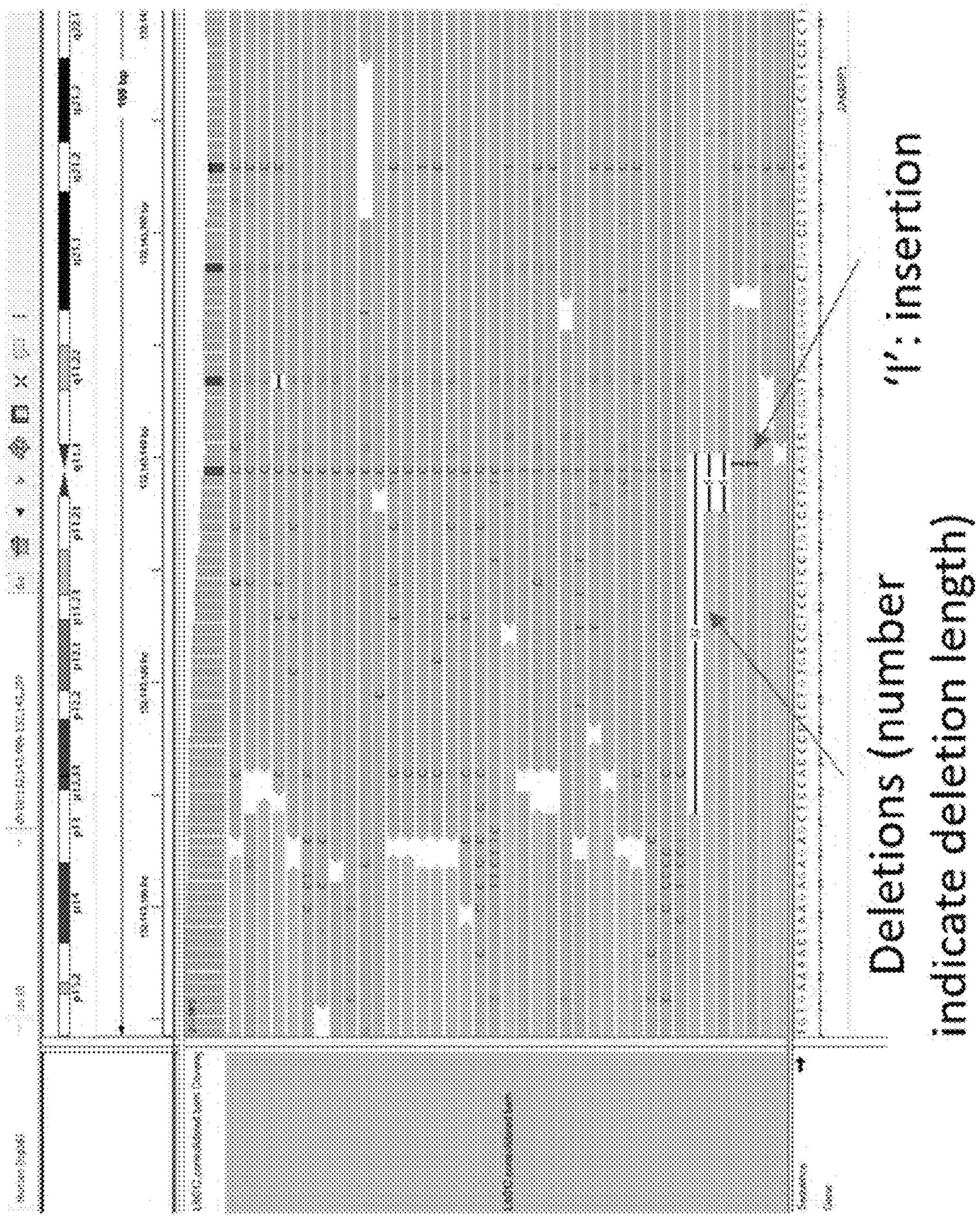
FIG. 3D is an exemplary result of deep amplicon sequencing shown in Integrated Genome Viewer, indicating additional off-target insertions (shown as "I") and deletions in chromosome 10 were detected by EDITED-Seq, but not by DISCOVER-Seq or GUIDE-Seq (reference nucleotide sequence SEQ ID NO: 1055).
Figure 3E:
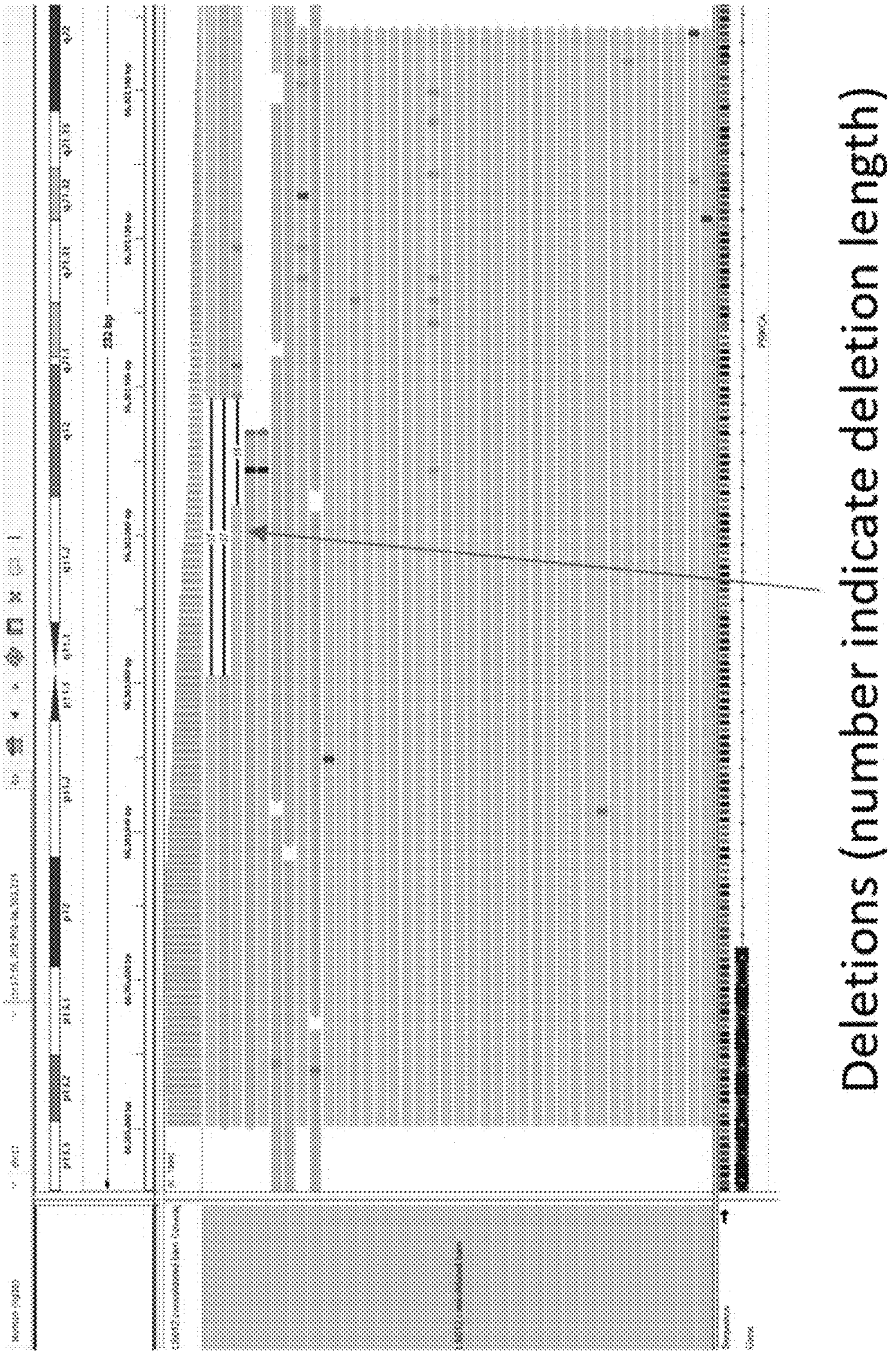
FIG. 3E is an exemplary result of deep amplicon sequencing shown in Integrated Genome Viewer, indicating additional off-target insertions (shown as "I") and deletions in chromosome 17 were detected by EDITED-Seq, but not by DISCOVER-Seq or GUIDE-Seq.
Figure 3F:
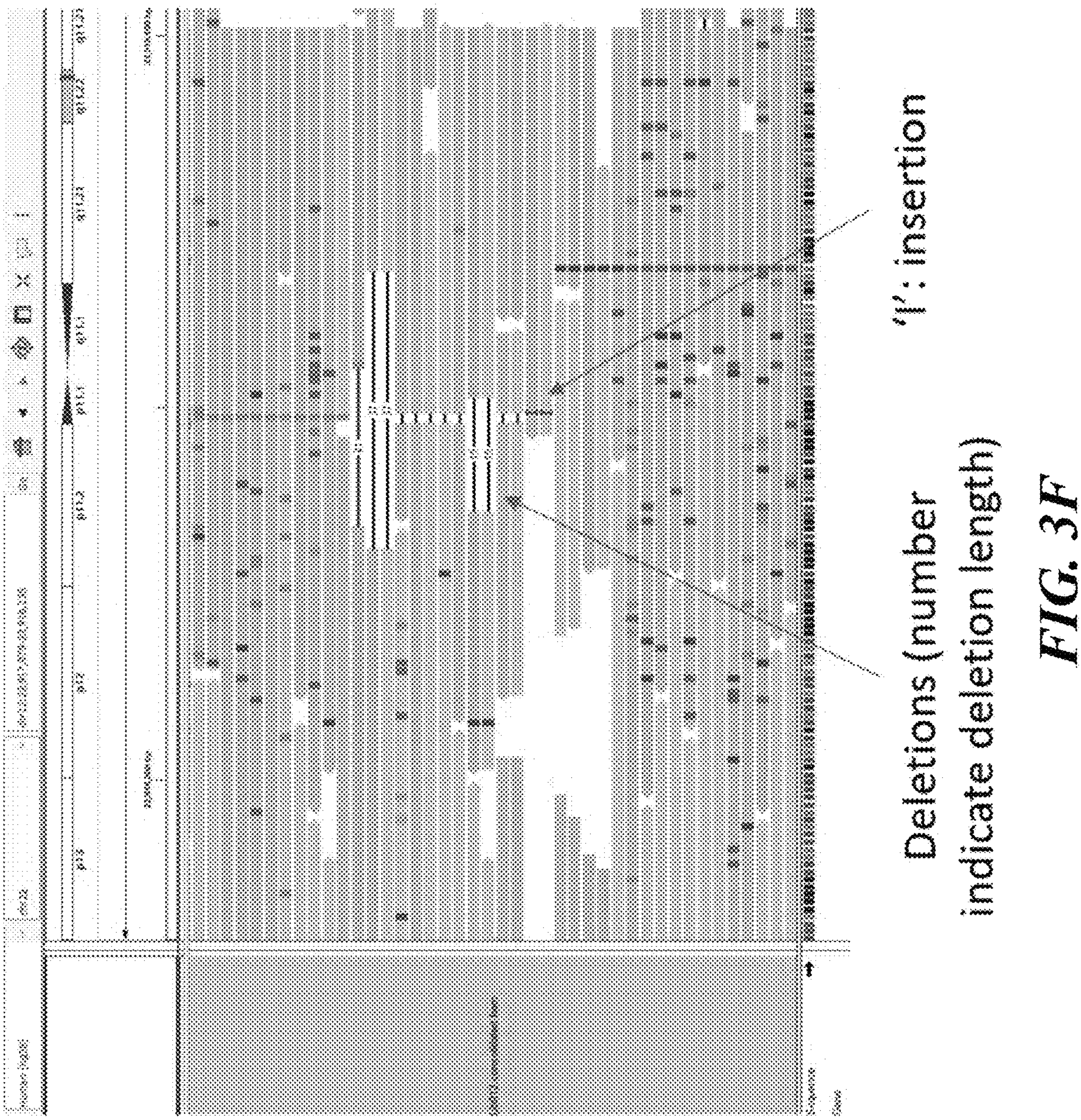
FIG. 3F is an exemplary result of deep amplicon sequencing shown in Integrated Genome Viewer, indicating additional off-target insertions (shown as "I") and deletions in chromosome 22 were detected by EDITED-Seq, but not by DISCOVER-Seq or GUIDE-Seq.
Figure 3G:
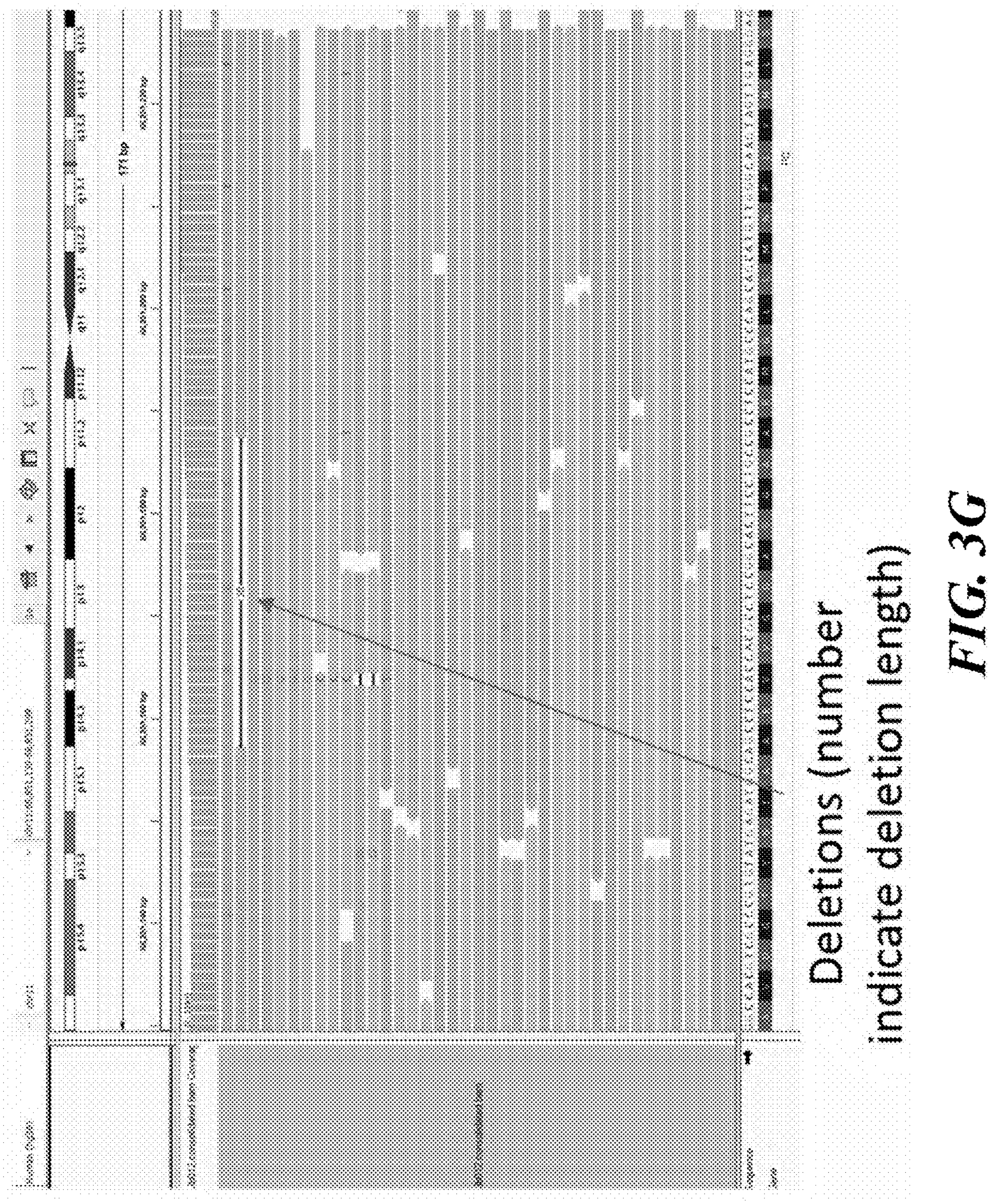
FIG. 3G is an exemplary result of deep amplicon sequencing shown in Integrated Genome Viewer, indicating additional off-target insertions (shown as "I") and deletions in chromosome 11 were detected by EDITED-Seq, but not by DISCOVER-Seq or GUIDE-Seq (reference nucleotide sequence SEQ ID NO: 1056; reference amino acid sequence SEQ ID no: 1057).
Figure 3H:
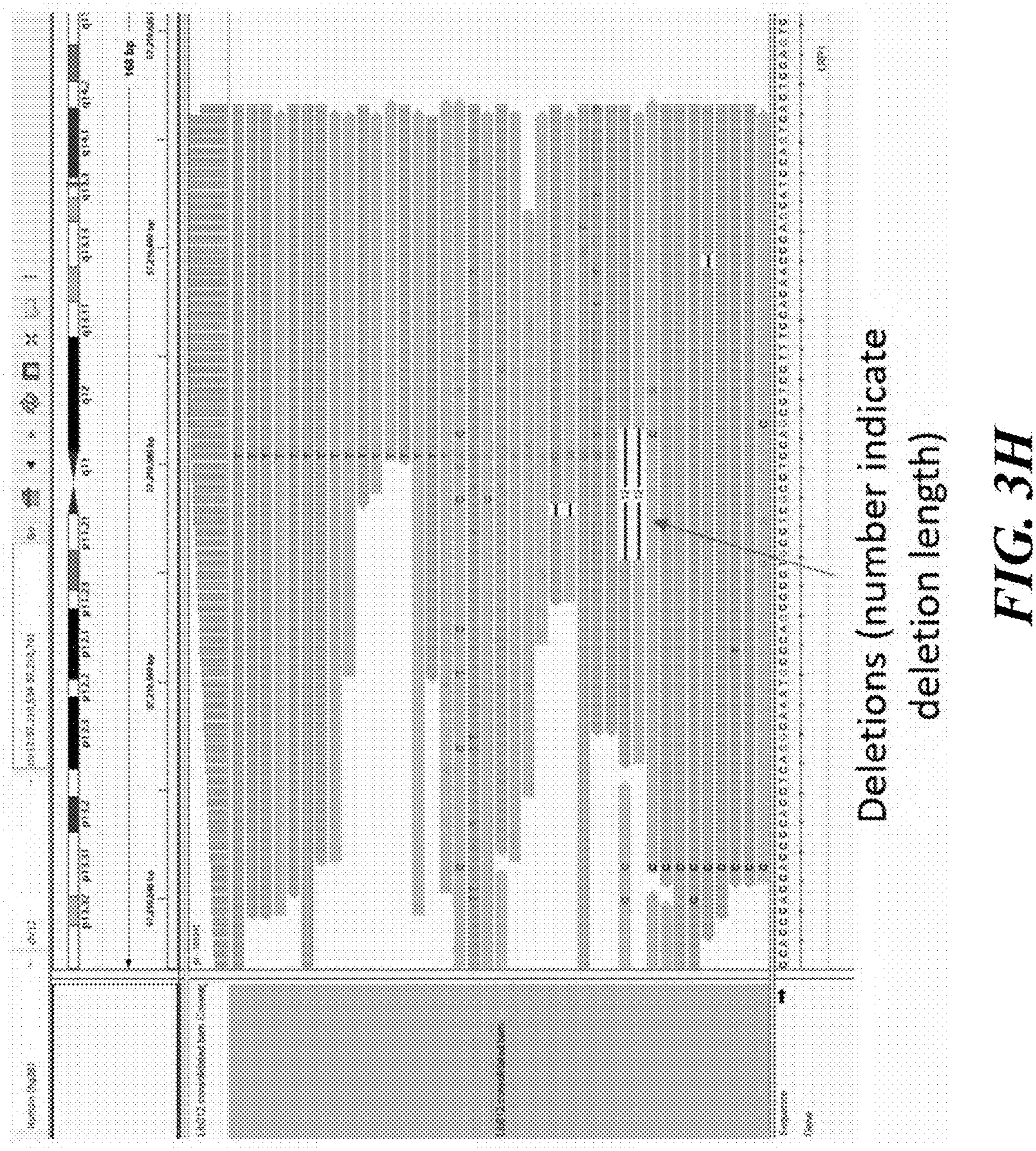
FIG. 3H is an exemplary result of deep amplicon sequencing shown in Integrated Genome Viewer, indicating additional off-target insertions (shown as "I") and deletions in chromosome 12 were detected by EDITED-Seq, but not by DISCOVER-Seq or GUIDE-Seq (reference nucleotide sequence SEQ ID NO: 1058).

Referring now to FIG. 3C, a diagram 330 shows Paranal distributions of identified (i.e., true) and missed (i.e., false) off-targets of EDITED-Seq, compared to GUIDE-Seq and DISCOVER-Seq, according to the same example embodiment of FIG. 3A. There were few sites with Indel discovered by amplicon NGS that had not been detected in translocation. EDITED-Seq missed the least number of true sites that were validated by amplicon NGS (false negatives). Some highly ranked sites discovered by GUIDE-Seq showed few translocations. It is supposed that protospacer sequence context might trigger the recombination between two DSB ends. The results showed that the relative ratio of false off-targets of EDITED-Seq over the true off targets is significantly lower than the same ratio of DISCOVER-Seq or GUIDE-Seq. EDITED-Seq is a more accurate method compared to DISCOVER-Seq and GUIDE-Seq because it has a significantly lower ratio of false off-targets.

Figure 3I:
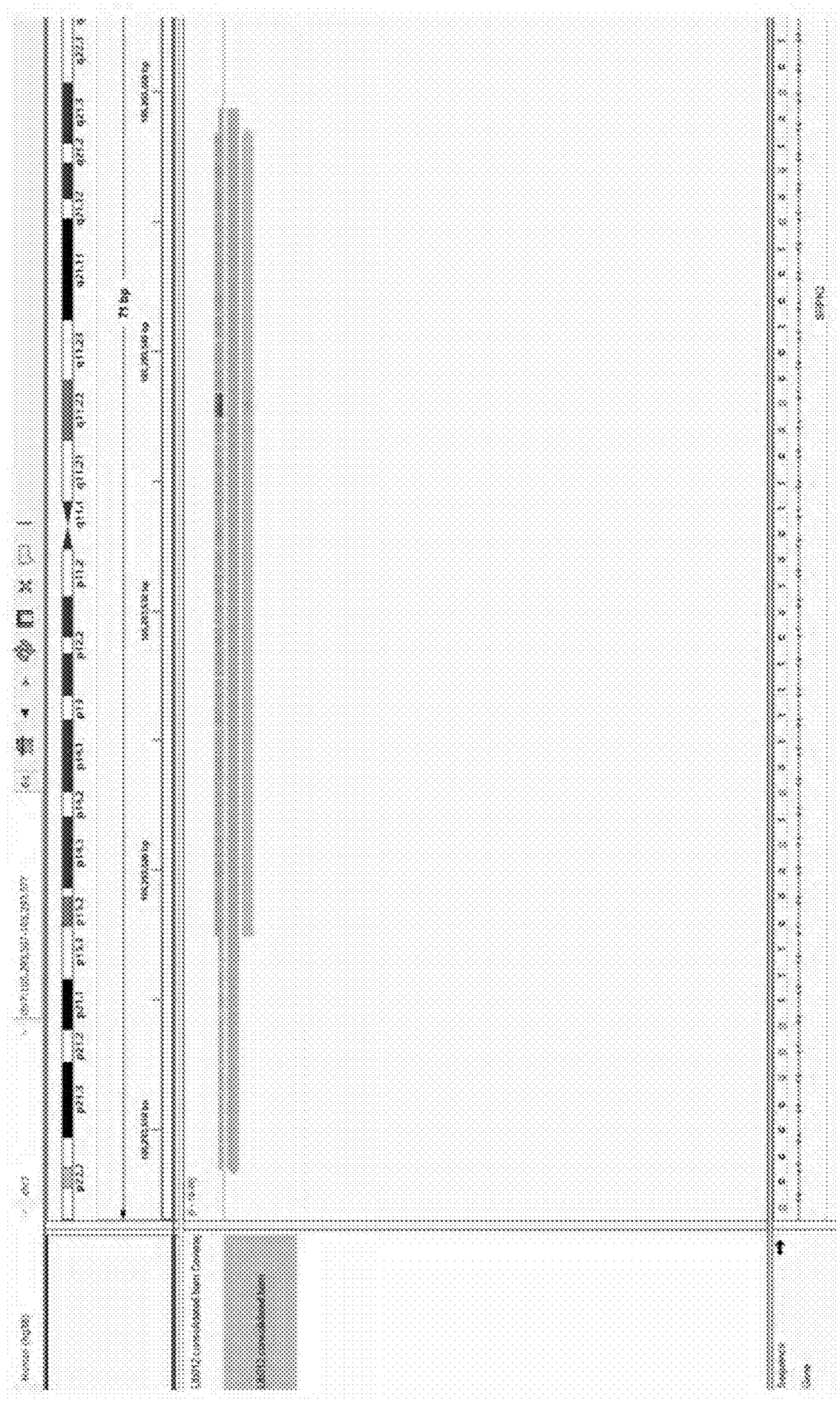
FIG. 3I is an exemplary result of deep amplicon sequencing shown in Integrated Genome Viewer, indicating additional translocation in chromosome 7 were detected by EDITED-Seq, but not by DISCOVER-Seq or GUIDE-Seq (reference nucleotide sequence SEQ ID NO: 1059).

Furthermore, the targets that were missed by DISCOVER-seq and GUIDE-seq but were identified by EDITED-seq were confirmed by deep amplicon sequencing. Six exemplary views from Integrated Genome Viewer illustrate the low-level insertions and deletions (see FIG. 3E to FIG. 3H), or translocation (see FIG. 3I).

Figure 3J:
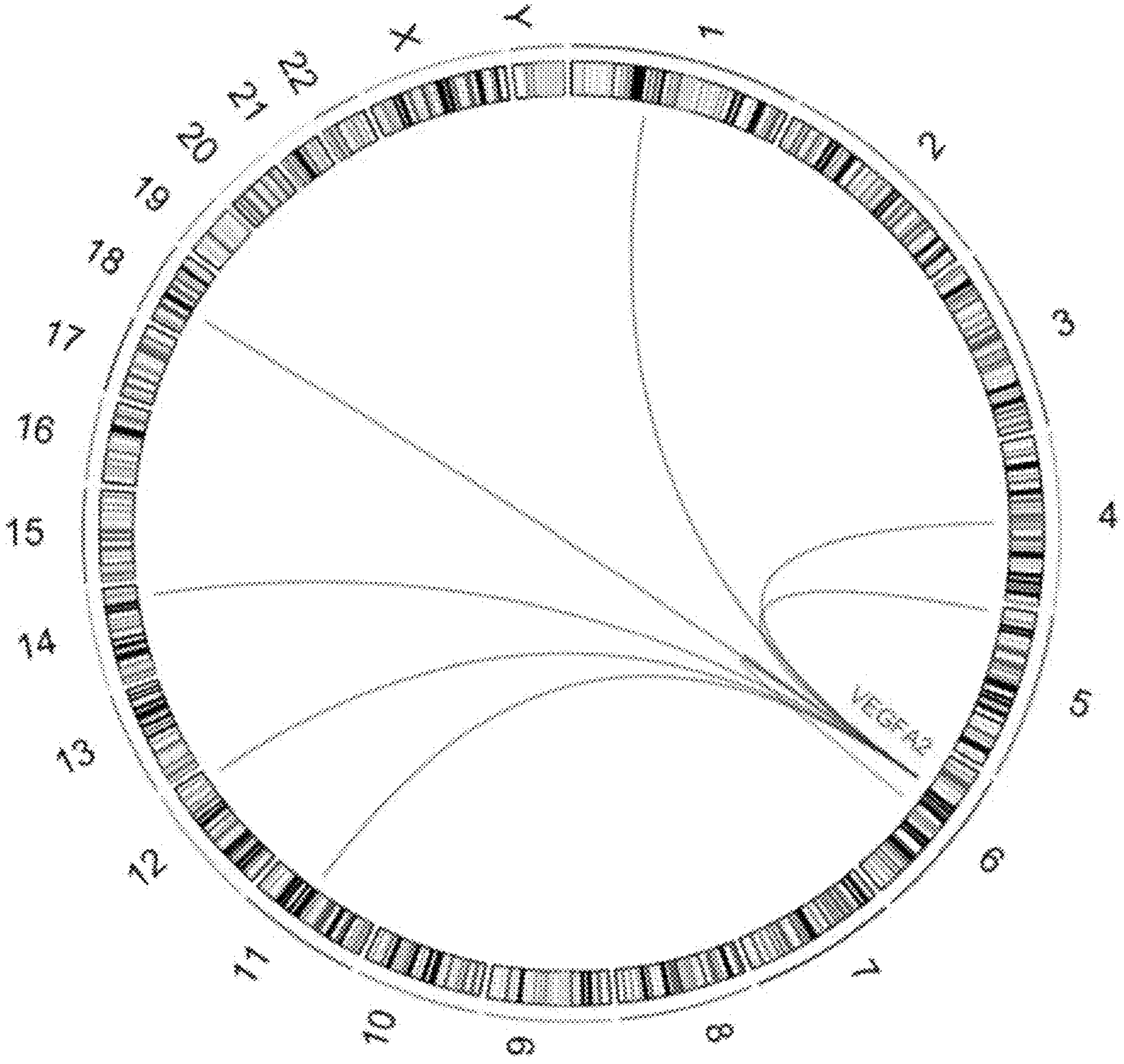
FIG. 3J is a cricos plot illustrating the translocation events detected by one set of primers for the on-target site of VEGFA_2.

In addition, a detailed analysis on translocation was carried out. Using only one set of primers for the on-target site in CRISPR-Cas9 targeting VEGFA_2 locus, 8 off-target sites were identified (see FIG. 3J). Briefly, the on-target site VEGFA2, colored in red in FIG. 3J and located on chromosome 6, were shown to form translocations with 8 off-target sites.

Figure 3K:
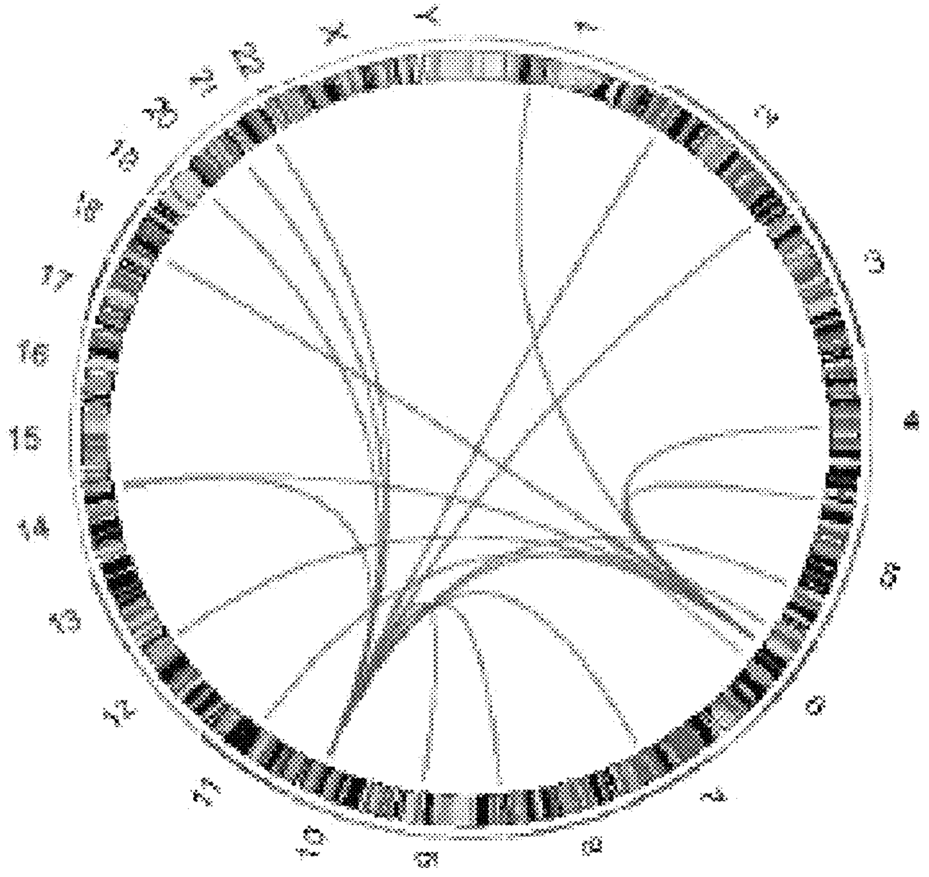
FIG. 3K is a cricos plot illustrating the translocation events detected by 1 off-target site predicted in-silicon in CRISPR-Cas9 targeting VEGFA_2 locus.
Figure 3L:
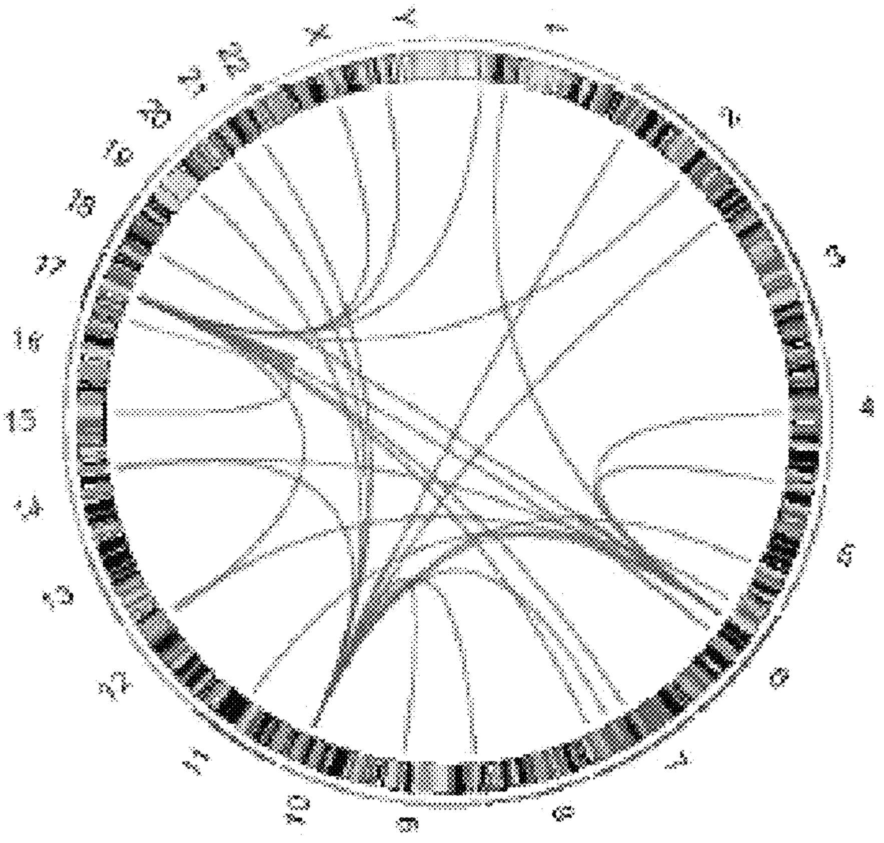
FIG. 3L is a cricos plot illustrating the translocation events detected by 2 off-target sites predicted in-silicon in CRISPR-Cas9 targeting VEGFA_2 locus.
Figure 3M:
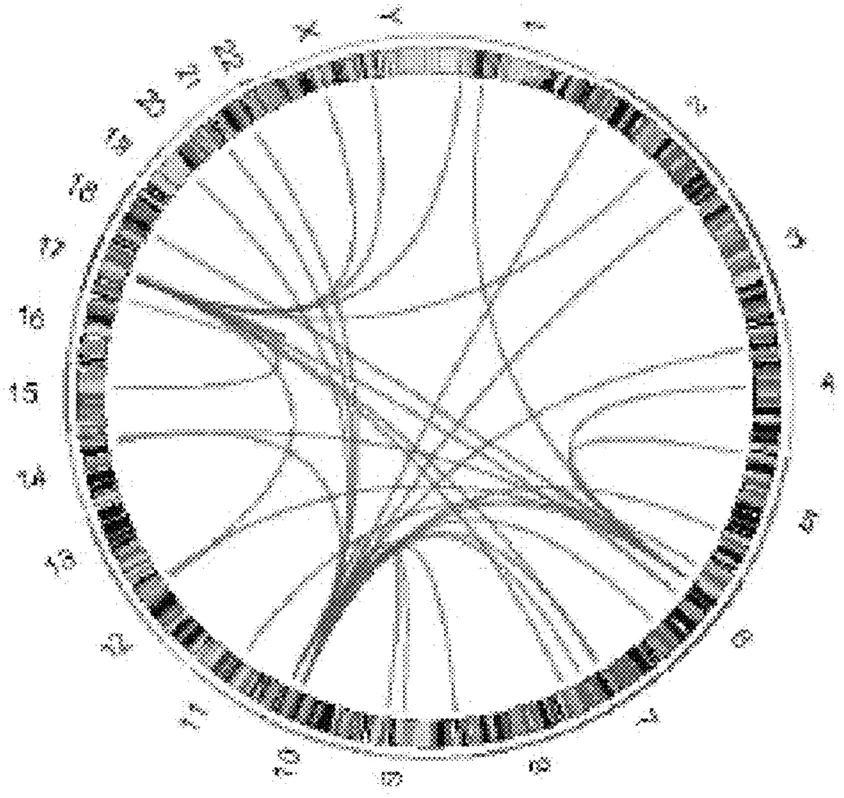
FIG. 3M is a cricos plot illustrating the translocation events detected by 3 off-target sites predicted in-silicon in CRISPR-Cas9 targeting VEGFA_2 locus.
Figure 3N:
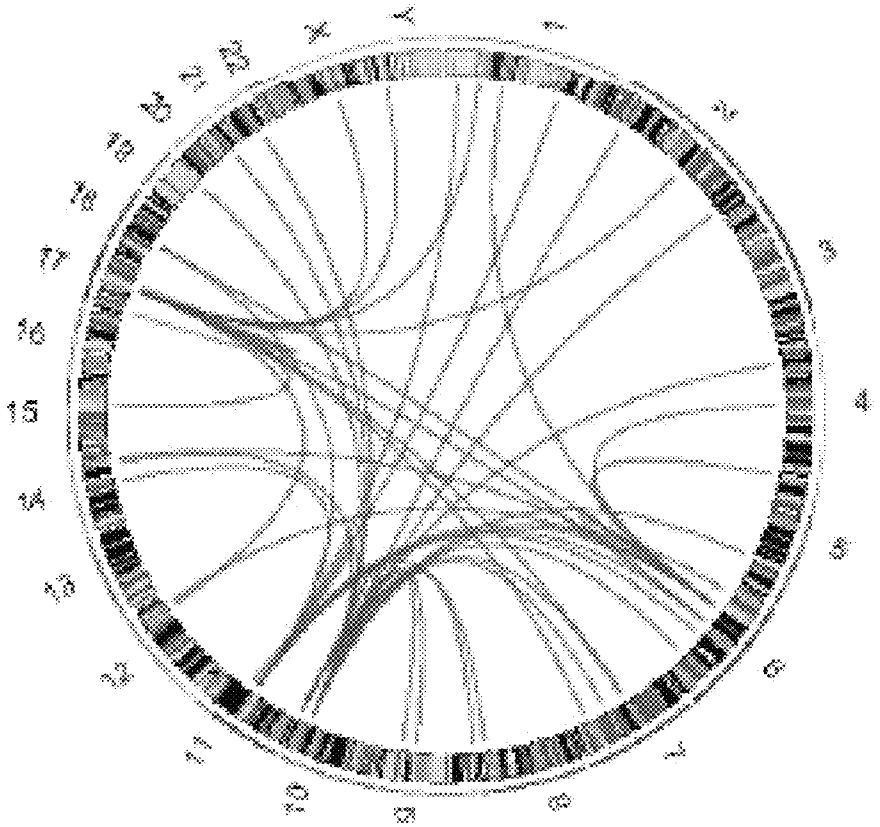
FIG. 3N is a cricos plot illustrating the translocation events detected by 4 off-target sites predicted in-silicon in CRISPR-Cas9 targeting VEGFA_2 locus.
Figure 3O:
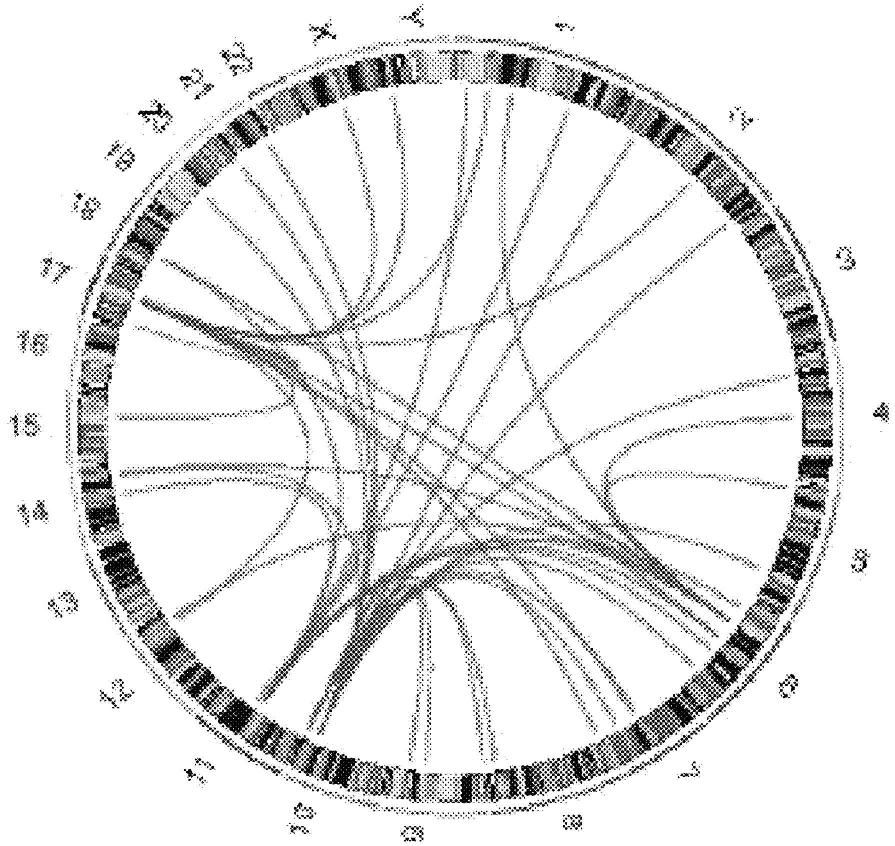
FIG. 3O is a cricos plot illustrating the translocation events detected by 5 off-target sites predicted in-silicon in CRISPR-Cas9 targeting VEGFA_2 locus.
Figure 3P:
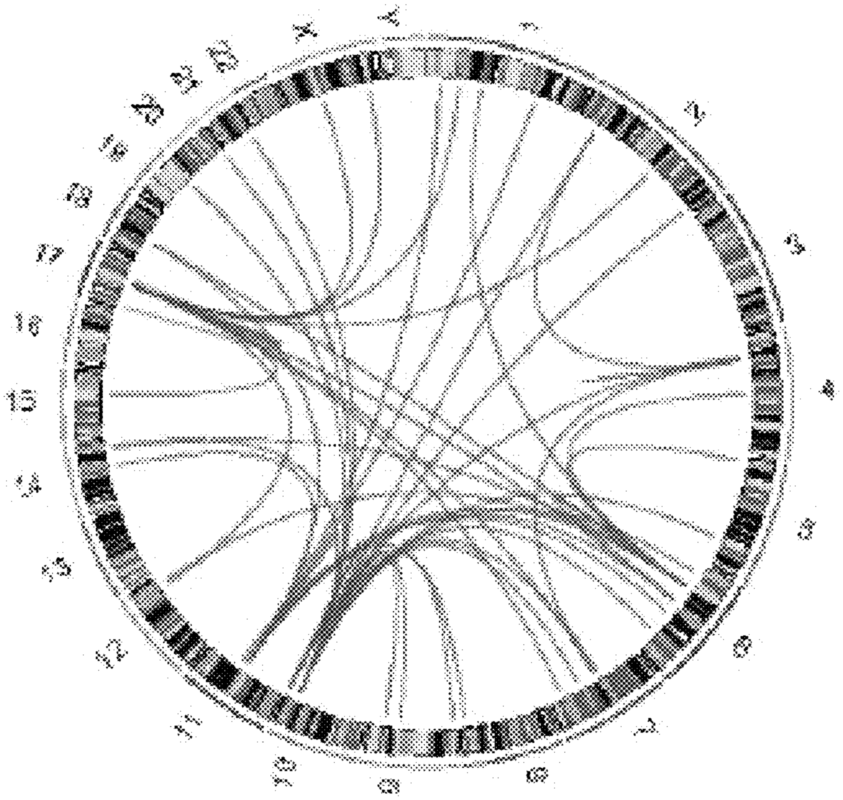
FIG. 3P is a cricos plot illustrating the translocation events detected by 6 off-target sites predicted in-silicon in CRISPR-Cas9 targeting VEGFA_2 locus.
Figure 3Q:
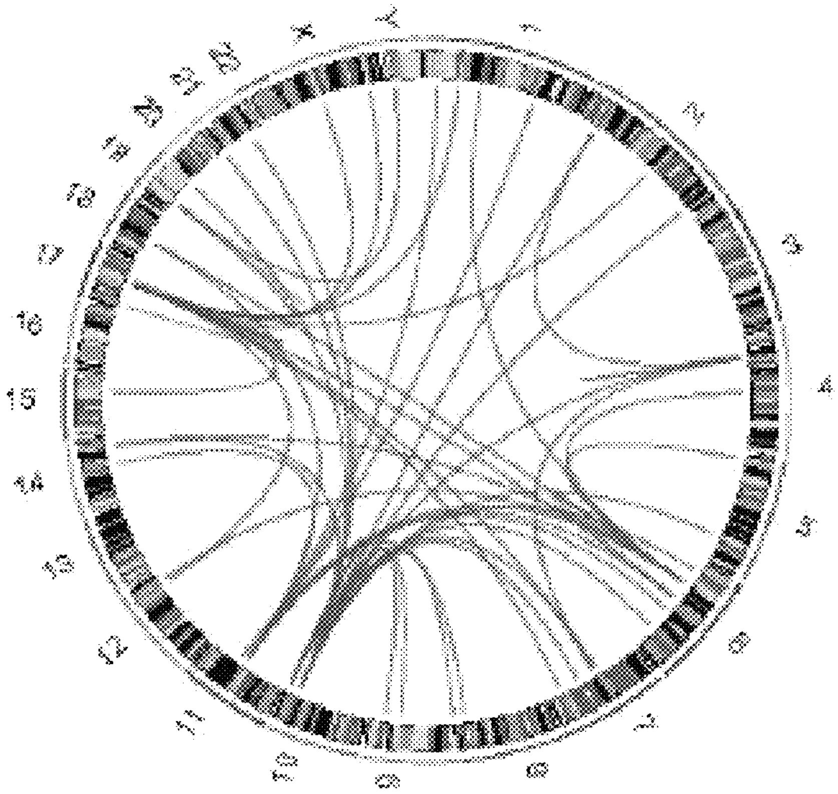
FIG. 3Q is a cricos plot illustrating the translocation events detected by 7 off-target sites predicted in-silicon in CRISPR-Cas9 targeting VEGFA_2 locus.
Figure 3R:
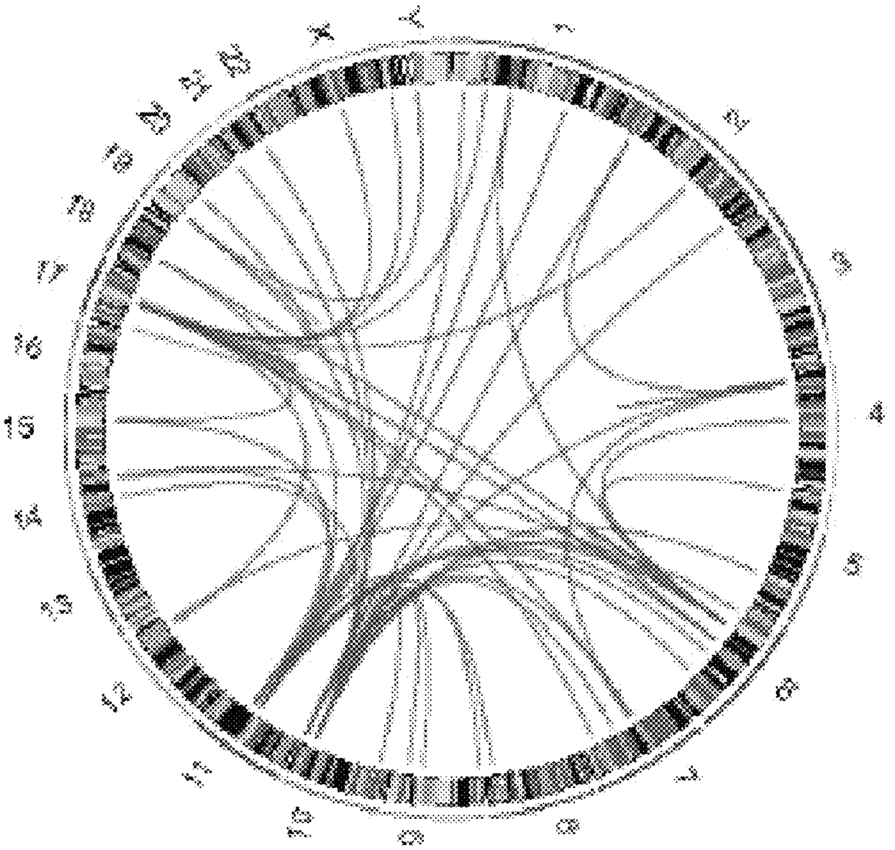
FIG. 3R is a cricos plot illustrating the translocation events detected by 8 off-target sites predicted in-silicon in CRISPR-Cas9 targeting VEGFA_2 locus.
Figure 3S:
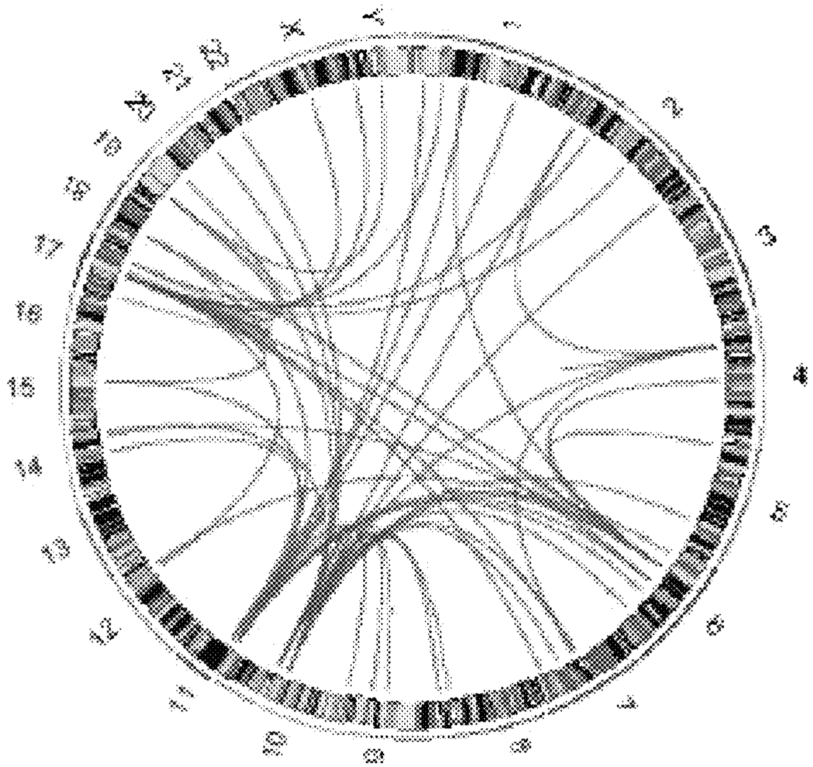
FIG. 3S is a cricos plot illustrating the translocation events detected by 9 off-target sites predicted in-silicon in CRISPR-Cas9 targeting VEGFA_2 locus.
Figure 3T:
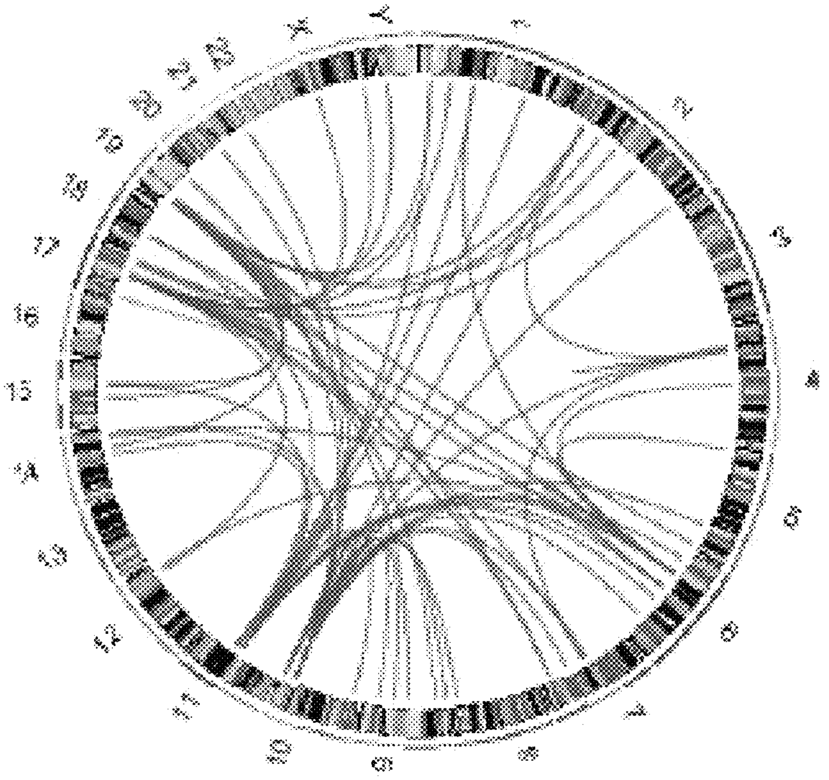
FIG. 3T is a cricos plot illustrating the translocation events detected by 10 off-target sites predicted in-silicon in CRISPR-Cas9 targeting VEGFA_2 locus.
Figure 3U:
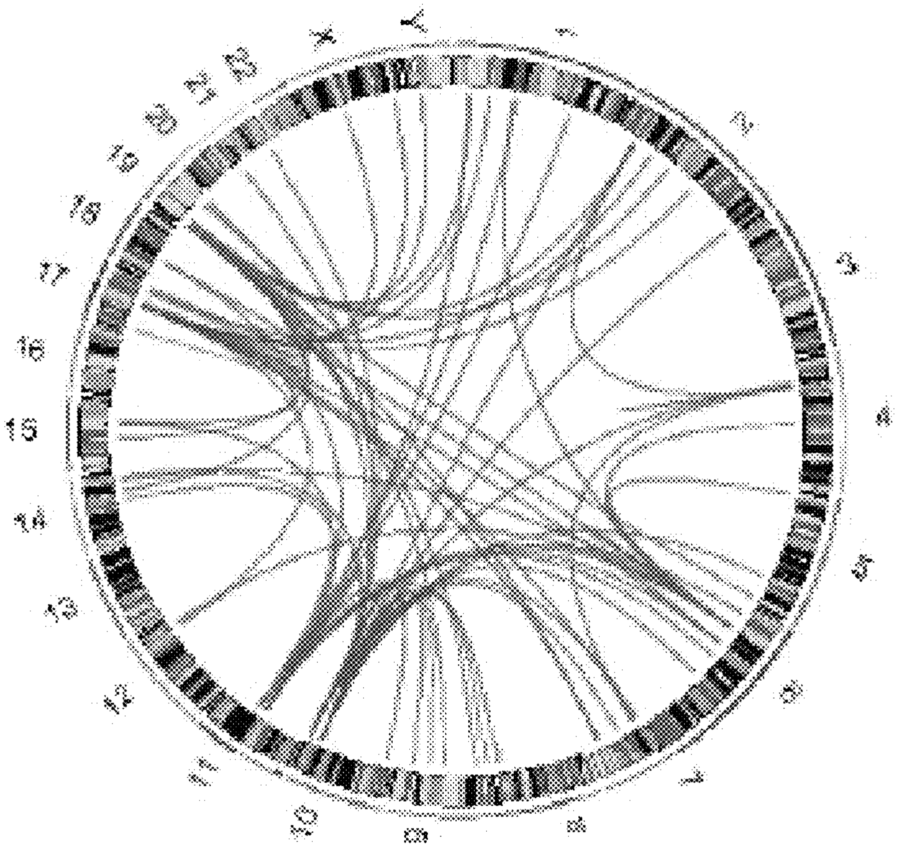
FIG. 3U is a cricos plot illustrating the translocation events detected by 11 off-target sites predicted in-silicon in CRISPR-Cas9 targeting VEGFA_2 locus.
Figure 3V:
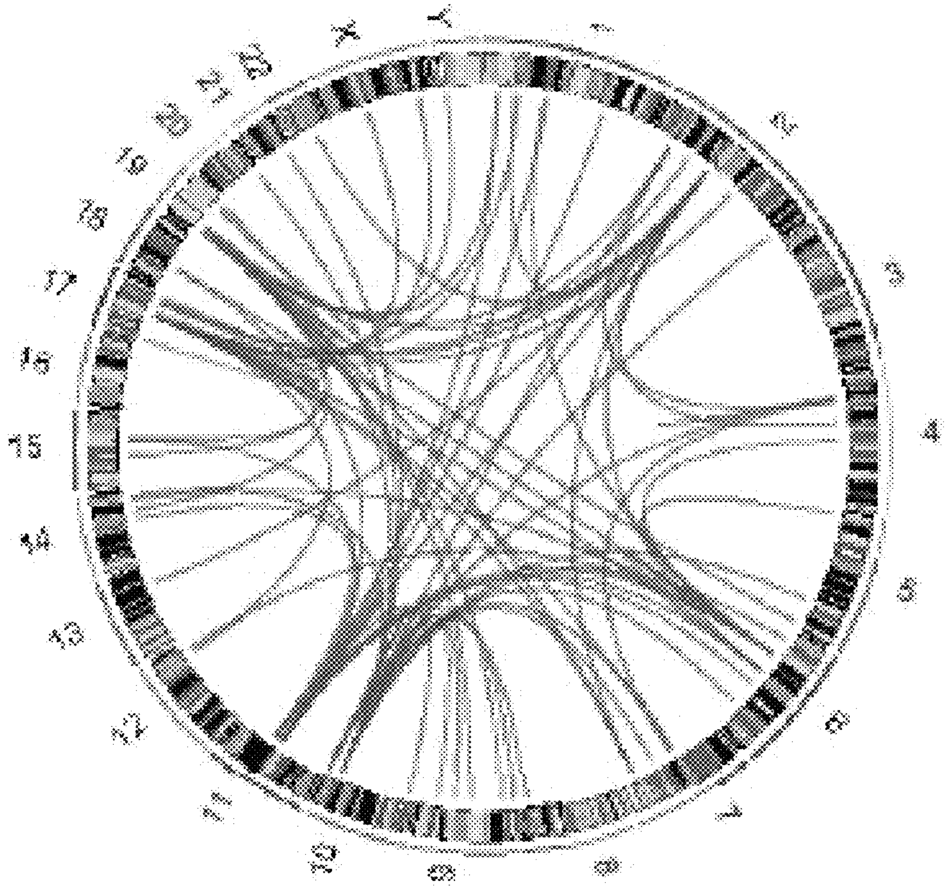
FIG. 3V is a cricos plot illustrating the translocation events detected by 12 off-target sites predicted in-silicon in CRISPR-Cas9 targeting VEGFA_2 locus.
Figure 3W:
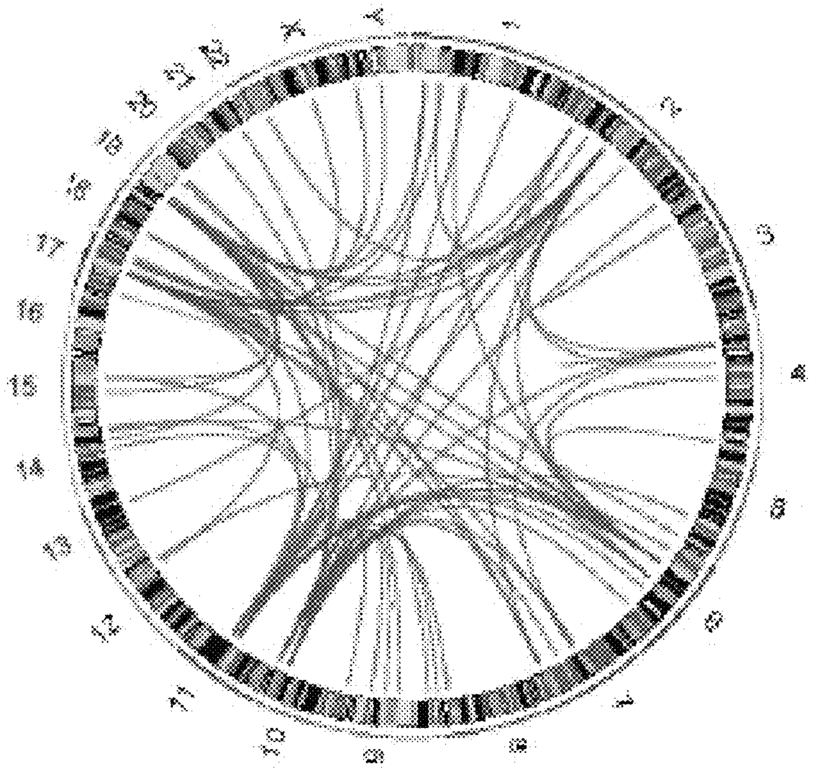
FIG. 3W is a cricos plot illustrating the translocation events detected by 13 off-target sites predicted in-silicon in CRISPR-Cas9 targeting VEGFA_2 locus.
Figure 3X:
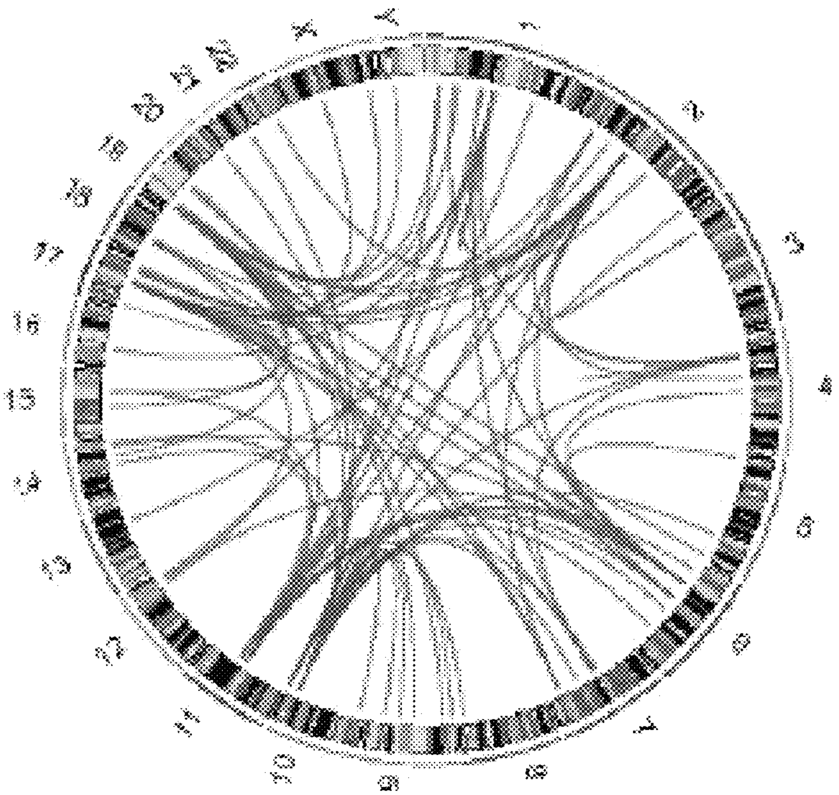
FIG. 3X is a cricos plot illustrating the translocation events detected by 14 off-target sites predicted in-silicon in CRISPR-Cas9 targeting VEGFA_2 locus.
Figure 3Y:
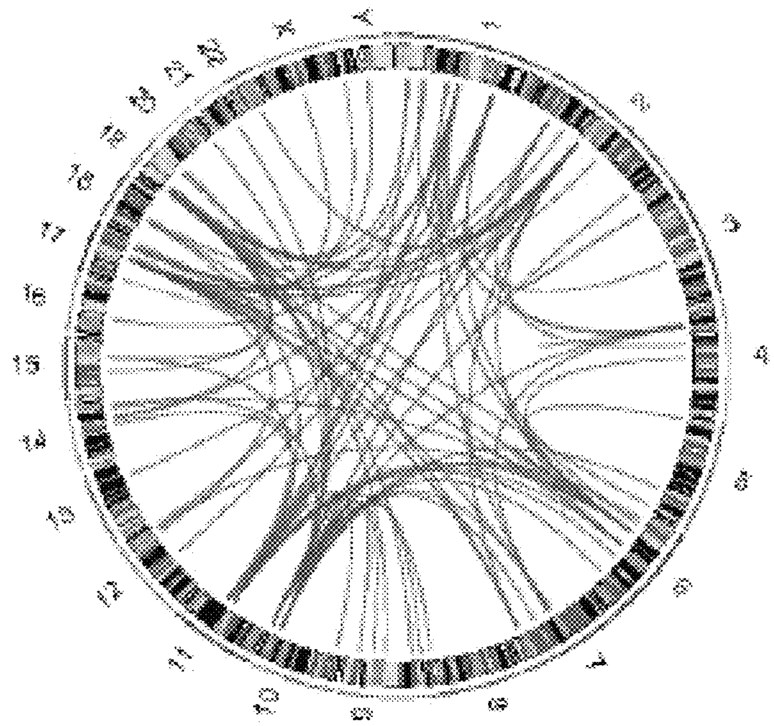
FIG. 3Y is a cricos plot illustrating the translocation events detected by 15 off-target sites predicted in-silicon in CRISPR-Cas9 targeting VEGFA_2 locus.
Figure 3Z:
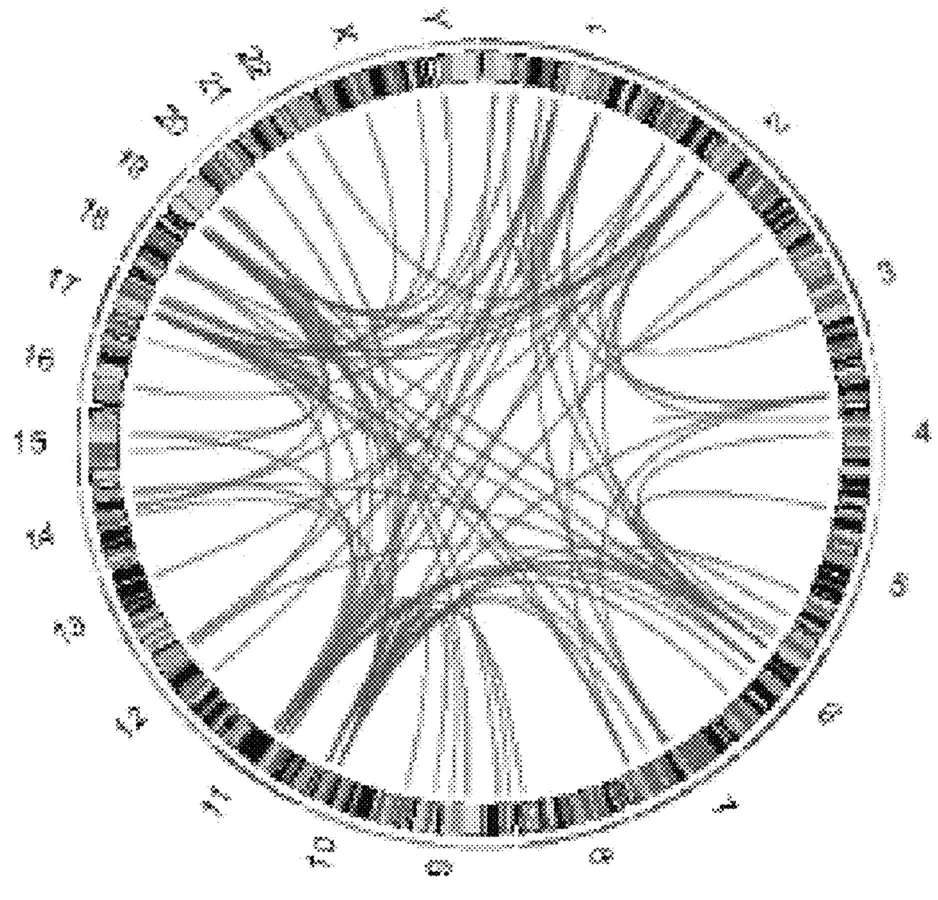
FIG. 3Z is a cricos plot illustrating the translocation events detected by 16 off-target sites predicted in-silicon in CRISPR-Cas9 targeting VEGFA_2 locus.
Figure 3A:
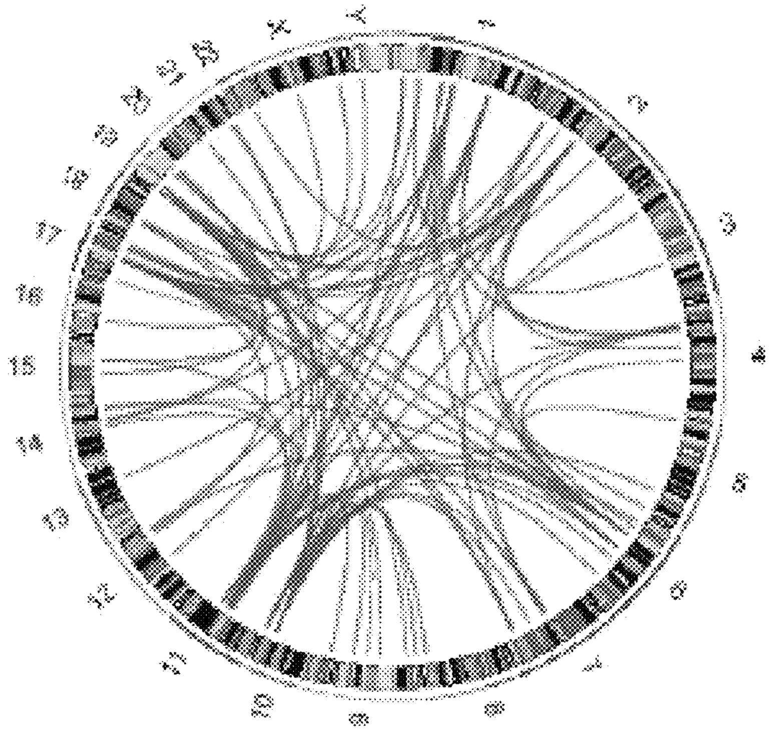
Figure 3A:
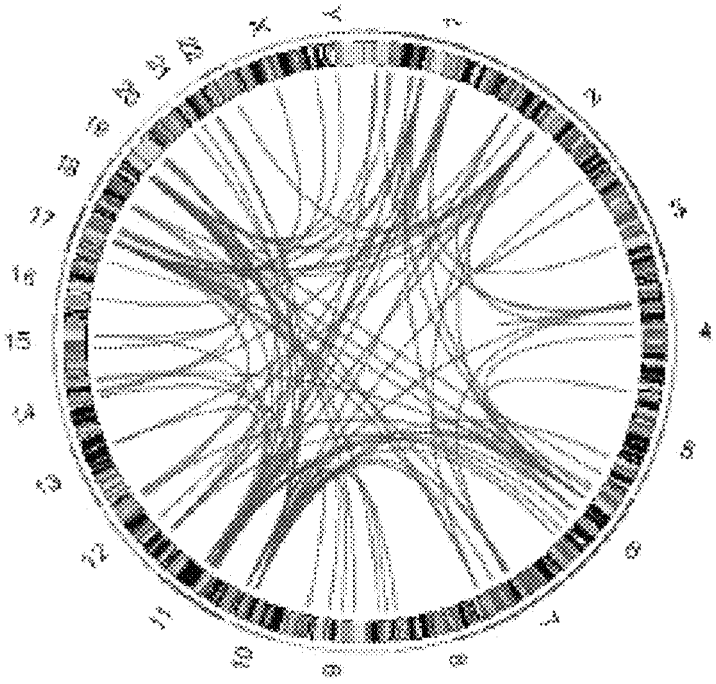
Figure 3A:
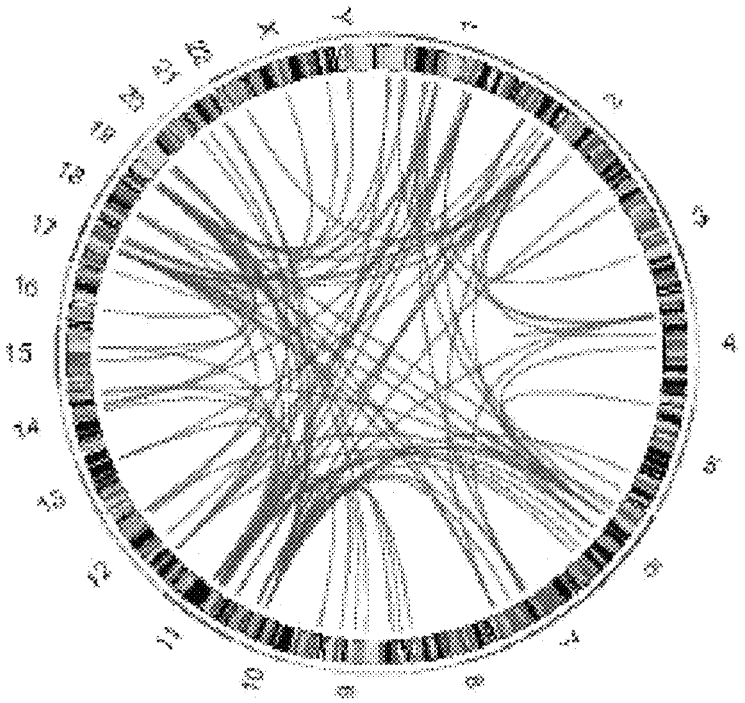
Figure 3A:
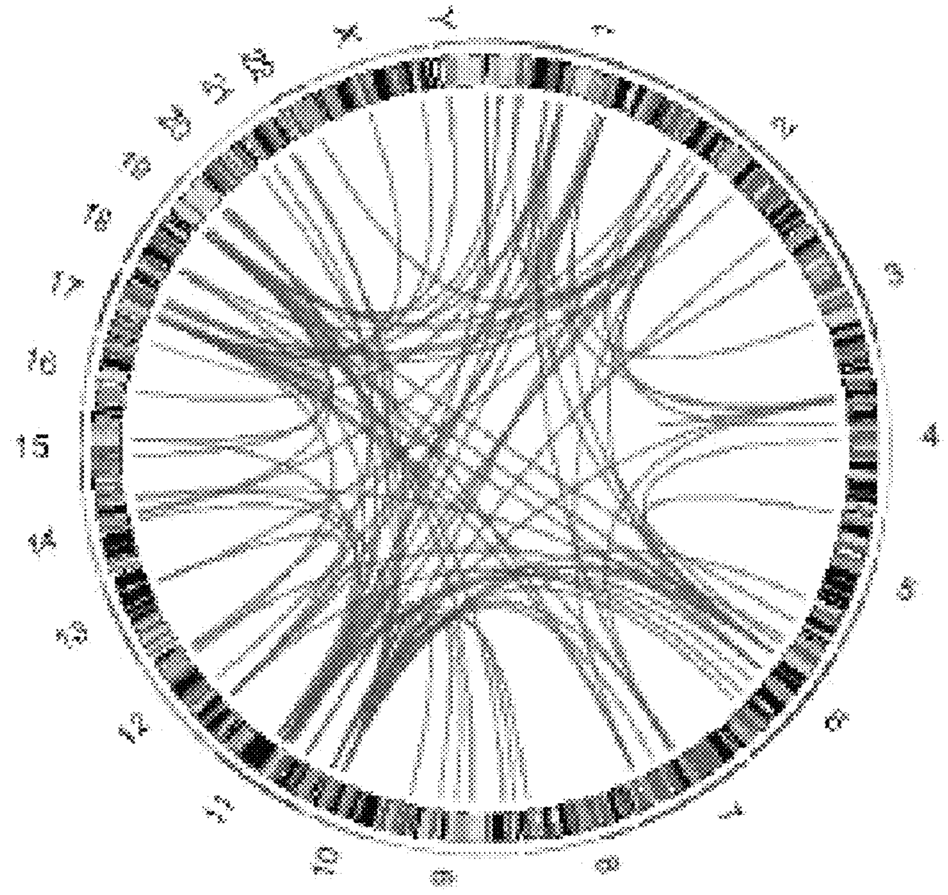

Furthermore, using increasing numbers of primers derived from in-silico predicted off-target sites, increasing numbers of novel off-target sites were detected via translocations between on- and off-targets, and between off- and off-target sites. Specifically, a comprehensive identification of genome-wide off-target sites when targeting VEGFA2 and using EDITED-seq was illustrated in FIG. 3K to FIG. 3AD. Using increasing numbers for 1 to 20 off-target sites (from in-silicon prediction) in data analysis, the numbers of total targeting sites identified were 23, 36, 43, 52, 54, 58, 61, 66, 68, 79, 81, 91, 93, 101, 107, 110, 113, 119, 122, 125, and 132, respectively.

Example 12. Off-Target Profiling in iPSC and Primary Cells Using EDITED-Seq

To test whether EDITED-Seq can act as a versatile implement in various types of cells, gene editing was conducted in iPSC (according to Example 6) and primary cells (according to Example 7), respectively, on four gene loci of functional importance, namely GAPDH, HBB, PD1 and TRAC. The sequences of anchored primers for GAPDH, HBB, PD1 and TRAC used in EDITED-Seq in this example embodiment is shown in Tables 4-7 respectively below.

TABLE 4

Sequences of anchored primers for GAPDH

| First PCR primer name | Sequence | SEQ ID NO: | Second PCR primer name | Sequence | SEQ ID NO: |
|---|---|---|---|---|---|
| NoName1_m1 | CCCCTTAGGGATAACAGGGTAATCTTGGCATGACCCAGGTCCATAC | 285 | NoName1_m2 | GTGACTGGAGTTCAGACGTGTGCTCTTCCGATCTGGTCCATACCAGGGCTGACC | 360 |
| NoName1_p1 | CCCCTTAGGGATAACAGGGTAATCAAGAGTCTGGGTGAATCAGCAGTC | 286 | NoName1_p2 | GTGACTGGAGTTCAGACGTGTGCTCTTCCGATCTAGTCAGGCAGGCGAGGAACA | 361 |
| NoName10_m1 | CCCCTTAGGGATAACAGGGTAATCAGGGGCCAGCAGCAAGGT | 287 | NoName10_m2 | GTGACTGGAGTTCAGACGTGTGCTCTTCCGATCTAGGTGAAGAATTTCATGCTGGCACAT | 362 |
| NoName11_p1 | CCCCTTAGGGATAACAGGGTAATCTGAGTCAGGAGGCAGAGATCCTC | 288 | NoName11_p2 | GTGACTGGAGTTCAGACGTGTGCTCTTCCGATCTCAAGACCCAGCGACCGACTCC | 363 |
| NoName12_m1 | CCCCTTAGGGATAACAGGGTAATCAAATCCCGTTGGCCCTCCTG | 289 | NoName12_m2 | GTGACTGGAGTTCAGACGTGTGCTCTTCCGATCTCTCCTGCTCAGCTGGCTCATGTC | 364 |

TABLE 4-continued

Sequences of anchored primers for GAPDH

| First PCR primer name | Sequence | SEQ ID NO: | Second PCR primer name | Sequence | SEQ ID NO: |
|---|---|---|---|---|---|
| NoName12_p1 | CCCCTTAGGGATAACAGGGTAATCGGGGCGTTGTGGGTCTGA | 290 | NoName12_p2 | GTGACTGGAGTTCAGACGTGTGCTCTTCCGATCTCTTAAAGATCCTCCGGCCACCATGTG | 365 |
| NoName13_m1 | CCCCTTAGGGATAACAGGGTAATCCCTAGGCCCCTCCCCTCT | 291 | NoName13_m2 | GTGACTGGAGTTCAGACGTGTGCTCTTCCGATCTGCCCCTCCCCTCTTCAAGG | 366 |
| NoName13_p1 | CCCCTTAGGGATAACAGGGTAATCCCAGGTGGTCTCCTCCGACT | 292 | NoName13_p2 | GTGACTGGAGTTCAGACGTGTGCTCTTCCGATCTTCAACAGCAACACCCACTCTTCC | 367 |
| NoName14_m1 | CCCCTTAGGGATAACAGGGTAATCAGGGGAGATGCTCAGTGTGGT | 293 | NoName14_m2 | GTGACTGGAGTTCAGACGTGTGCTCTTCCGATCTGTGTGGTGGGGGCTGAGC | 368 |
| NoName14_p1 | CCCCTTAGGGATAACAGGGTAATCTGAGCACAAGGTCGTCTCCTCT | 294 | NoName14_p2 | GTGACTGGAGTTCAGACGTGTGCTCTTCCGATCTCTCTGACTTTGACAGTGACACCCATT | 369 |
| NoName15_m1 | CCCCTTAGGGATAACAGGGTAATCTGGCAGATGAATAAGGCTCACTCCT | 295 | NoName15_m2 | GTGACTGGAGTTCAGACGTGTGCTCTTCCGATCTGGCTCACTCCTTCTCTTGTAGGTACT | 370 |
| NoName15_p1 | CCCCTTAGGGATAACAGGGTAATCTCCCTACAGAGATAAACAGACGCACA | 296 | NoName15_p2 | GTGACTGGAGTTCAGACGTGTGCTCTTCCGATCTGAGAGAGAGTAAGGTCAGGCATGTGG | 371 |
| NoName16_m1 | CCCCTTAGGGATAACAGGGTAATCCAGTTCTTTGGGTCCTCATCACAGT | 297 | NoName16_m2 | GTGACTGGAGTTCAGACGTGTGCTCTTCCGATCTTCATCACAGTTAATGTTGCAGCGGAA | 372 |
| NoName16_p1 | CCCCTTAGGGATAACAGGGTAATCAGCAACATACAGATGGGGTGGGA | 298 | NoName16_p2 | GTGACTGGAGTTCAGACGTGTGCTCTTCCGATCTGCTGGAGCTGTGGGGGCAA | 373 |
| NoName17_m1 | CCCCTTAGGGATAACAGGGTAATCGGATGCTTAGCTTCCGTTGGGTT | 299 | NoName17_m2 | GTGACTGGAGTTCAGACGTGTGCTCTTCCGATCTGCTTAGCTTCCGTTGGGTTGATGAGG | 374 |
| NoName17_p1 | CCCCTTAGGGATAACAGGGTAATCCTGGGCACGGTGGACAGC | 300 | NoName17_p2 | GTGACTGGAGTTCAGACGTGTGCTCTTCCGATCTCACGGTGGACAGCAGTGCA | 375 |
| NoName18_m1 | CCCCTTAGGGATAACAGGGTAATCCCTCTTCAAGTGGTCTGCATGGAA | 301 | NoName18_m2 | GTGACTGGAGTTCAGACGTGTGCTCTTCCGATCTGCATGGAAACTGTGAGGAGGGGAGT | 376 |
| NoName18_p1 | CCCCTTAGGGATAACAGGGTAATCGGTG | 302 | NoName18_p2 | GTGACTGGAGTTCAGACGTGTGCTCT | 377 |

TABLE 4-continued

Sequences of anchored primers for GAPDH

| First PCR primer name | Sequence | SEQ ID NO: | Second PCR primer name | Sequence | SEQ ID NO: |
|---|---|---|---|---|---|
| | GTCTCCTCCGATTTCAACA | | | TCCGATCTAGTGACACCCCCTCCTCCA | |
| NoName19_m1 | CCCCTTAGGGATAACAGGGTAATCTTGCGGGGAGGGGAGATTCT | 303 | NoName19_m2 | GTGACTGGAGTTCAGACGTGTGCTCTTCCGATCTAGGGAACTGGACACGTCAGGGA | 378 |
| NoName19_p1 | CCCCTTAGGGATAACAGGGTAATCCCCTACCTCACCGCCAATGTTT | 304 | NoName19_p2 | GTGACTGGAGTTCAGACGTGTGCTCTTCCGATCTACTTTGGTGGGCGTATAAGCAGTTT | 379 |
| NoName2_m1 | CCCCTTAGGGATAACAGGGTAATCGAGGAGGGGAGAGTCTCAGTGTT | 305 | NoName2_m2 | GTGACTGGAGTTCAGACGTGTGCTCTTCCGATCTAGGGGAGAGTCTCAGTGTTGTGGAG | 380 |
| NoName2_p1 | CCCCTTAGGGATAACAGGGTAATCACTTTAACAGCATCACCCACTCTTCC | 306 | NoName2_p2 | GTGACTGGAGTTCAGACGTGTGCTCTTCCGATCTGGCTACAGCAACAGGGTAGTAGACC | 381 |
| NoName20_m1 | CCCCTTAGGGATAACAGGGTAATCTTTCCTGTATTGCTTTTGCCTTGAGC | 307 | NoName20_m2 | GTGACTGGAGTTCAGACGTGTGCTCTTCCGATCTTGCCTTGAGCTTCTTACCCCAGTGAG | 382 |
| NoName20_p1 | CCCCTTAGGGATAACAGGGTAATCGGAGCCTGGACCACTAAGTCAC | 308 | NoName20_p2 | GTGACTGGAGTTCAGACGTGTGCTCTTCCGATCTTTCCAACCAAGGTACCTGTATTGGAC | 383 |
| NoName21_m1 | CCCCTTAGGGATAACAGGGTAATCGCGTGGAGGTGAGCTCATGTAG | 309 | NoName21_m2 | GTGACTGGAGTTCAGACGTGTGCTCTTCCGATCTCCCTGCTCACTGGAGAAGTTTTCCG | 384 |
| NoName21_p1 | CCCCTTAGGGATAACAGGGTAATCGGGCGCTCAGTAGGTGTGC | 310 | NoName21_p2 | GTGACTGGAGTTCAGACGTGTGCTCTTCCGATCTGCGCTCAGTAGGTGTGCAAGCAG | 385 |
| NoName22_m1 | CCCCTTAGGGATAACAGGGTAATCCTGTGGGCCATCTTCAAGTTCAGTCC | 311 | NoName22_m2 | GTGACTGGAGTTCAGACGTGTGCTCTTCCGATCTTCTCATTTCTGGACCTAGGCTGATGG | 386 |
| NoName22_p1 | CCCCTTAGGGATAACAGGGTAATCAAAAACCTCCACCCTTATGAAGCCT | 312 | NoName22_p2 | GTGACTGGAGTTCAGACGTGTGCTCTTCCGATCTTCCACCCTTATGAAGCCTCCTTCTAG | 387 |
| NoName23_m1 | CCCCTTAGGGATAACAGGGTAATCTCTCTGCTGTGTGCTGTCCAC | 313 | NoName23_m2 | GTGACTGGAGTTCAGACGTGTGCTCTTCCGATCTGTCCACTCACAGGGGTAGAACATGTT | 388 |
| NoName23_p1 | CCCCTTAGGGATAACAGGGTAATCAGCCCCTCCCTCTCCAGG | 314 | NoName23_p2 | GTGACTGGAGTTCAGACGTGTGCTCTTCCGATCTAGGTG | 389 |

TABLE 4-continued

Sequences of anchored primers for GAPDH

| First PCR primer name | Sequence | SEQ ID NO: | Second PCR primer name | Sequence | SEQ ID NO: |
|---|---|---|---|---|---|
| | A | | | GGGGACTGAGTGT GAC | |
| NoName24_m1 | CCCCTTAGGGATAA CAGGGTAATCGATG CTGGGGCTGGCACT | 315 | NoName24_m2 | GTGACTGGAGTTC AGACGTGTGCTCT TCCGATCTGCAAC AGGGTGGTGGAA CTCATGT | 390 |
| NoName24_p1 | CCCCTTAGGGATAA CAGGGTAATCACTG TGTCCAGGGGAGAT TCTCA | 316 | NoName24_p2 | GTGACTGGAGTTC AGACGTGTGCTCT TCCGATCTCAGTG TGGTAAGGGACTG AGTGCGT | 391 |
| NoName25_m1 | CCCCTTAGGGATAA CAGGGTAATCACTT ACGCTTAGGTGTGA TTTGCGAA | 317 | NoName25_m2 | GTGACTGGAGTTC AGACGTGTGCTCT TCCGATCTACACA TTGCTGCCATGAT CTGTCGTA | 392 |
| NoName26_m1 | CCCCTTAGGGATAA CAGGGTAATCCAGG CAAGGCTGAATGGA AGCG | 318 | NoName26_m2 | GTGACTGGAGTTC AGACGTGTGCTCT TCCGATCTGCTGA ATGGAAGCGAGTG AAGTGAGC | 393 |
| NoName26_p1 | CCCCTTAGGGATAA CAGGGTAATCCCTG GGGAAGGGCCATTC A | 319 | NoName26_p2 | GTGACTGGAGTTC AGACGTGTGCTCT TCCGATCTGGGCC ATTCACCCTTGATA TCATCA | 394 |
| NoName27_m1 | CCCCTTAGGGATAA CAGGGTAATCGGAG ACGGTGCAGGAGC TC | 320 | NoName27_m2 | GTGACTGGAGTTC AGACGTGTGCTCT TCCGATCTCTGAG CAGCGGGGAGGC T | 395 |
| NoName27_p1 | CCCCTTAGGGATAA CAGGGTAATCAGGA CCCTCCTCACGGGA TAC | 321 | NoName27_p2 | GTGACTGGAGTTC AGACGTGTGCTCT TCCGATCTACCCA GCTTTCAGCCAGA CC | 396 |
| NoName28_m1 | CCCCTTAGGGATAA CAGGGTAATCGTGT GGTGGGGGACTGA GC | 322 | NoName28_m2 | GTGACTGGAGTTC AGACGTGTGCTCT TCCGATCTGTGGG GGACTGAGCATGG CA | 397 |
| NoName28_p1 | CCCCTTAGGGATAA CAGGGTAATCGATG CTGGGGCTGCCATT G | 323 | NoName28_p2 | GTGACTGGAGTTC AGACGTGTGCTCT TCCGATCTGGCTG CCATTGCCCTCAG T | 398 |
| NoName29_m1 | CCCCTTAGGGATAA CAGGGTAATCCTCC TCACCACCCCCAAG G | 324 | NoName29_m2 | GTGACTGGAGTTC AGACGTGTGCTCT TCCGATCTGGTGG GGGCACAGTCCTG | 399 |
| NoName29_p1 | CCCCTTAGGGATAA CAGGGTAATCGGCC AAAGTCCGCCCCAA G | 325 | NoName29_p2 | GTGACTGGAGTTC AGACGTGTGCTCT TCCGATCTCCAAA GTCCGCCCCAAGG TCAAAA | 400 |
| NoName3_m1 | CCCCTTAGGGATAA CAGGGTAATCGGAG GCCCCAGGAACTTT CA | 326 | NoName3_m2 | GTGACTGGAGTTC AGACGTGTGCTCT TCCGATCTGGAGG AGAACGAGGCATG TCTTAC | 401 |

TABLE 4-continued

Sequences of anchored primers for GAPDH

| First PCR primer name | Sequence | SEQ ID NO: | Second PCR primer name | Sequence | SEQ ID NO: |
|---|---|---|---|---|---|
| NoName3_p1 | CCCCTTAGGGATAA CAGGGTAATCCCTC GGGAGGTGGGTAG TGT | 327 | NoName3_p2 | GTGACTGGAGTTC AGACGTGTGCTCT TCCGATCTCTCGG GAGGTGGGTAGTG TATGGTT | 402 |
| NoName30_m1 | CCCCTTAGGGATAA CAGGGTAATCGGAC CAGCTTGTTGAGGA CCCTA | 328 | NoName30_m2 | GTGACTGGAGTTC AGACGTGTGCTCT TCCGATCTCCAGC TTGTTGAGGACCC TAAAGGCT | 403 |
| NoName30_p1 | CCCCTTAGGGATAA CAGGGTAATCGAGC CTCATCAGTTGACC CCAA | 329 | NoName30_p2 | GTGACTGGAGTTC AGACGTGTGCTCT TCCGATCTTTGAC CCCAATGTCCTGC ATGTACTA | 404 |
| NoName31_m1 | CCCCTTAGGGATAA CAGGGTAATCGGGG TGCAGCCTGGAGA GA | 330 | NoName31_m2 | GTGACTGGAGTTC AGACGTGTGCTCT TCCGATCTGAGAG AGCTGGGTTGGCT GACAGA | 405 |
| NoName31_p1 | CCCCTTAGGGATAA CAGGGTAATCAGCT TTGCTGGGGTAACA GGACAC | 331 | NoName31_p2 | GTGACTGGAGTTC AGACGTGTGCTCT TCCGATCTGGGTA ACAGGACACATTG GCTGGGA | 406 |
| NoName32_p1 | CCCCTTAGGGATAA CAGGGTAATCGAAA CTATGAAACTACCA GGAGAAGT | 332 | NoName32_p2 | GTGACTGGAGTTC AGACGTGTGCTCT TCCGATCTCCAGG AGAAGTTTCCAGT GGGA | 407 |
| NoName33_m1 | CCCCTTAGGGATAA CAGGGTAATCGTTC AAAGCATCATCTGT GAATCAA | 333 | NoName33_m2 | GTGACTGGAGTTC AGACGTGTGCTCT TCCGATCTAGCAT CATCTGTGAATCA AAAGTTTT | 408 |
| NoName33_p1 | CCCCTTAGGGATAA CAGGGTAATCTCTG AGGCCAGCAAAAC CTTGA | 334 | NoName33_p2 | GTGACTGGAGTTC AGACGTGTGCTCT TCCGATCTGGCCA GCAAAACCTTGAC ATGTAAAC | 409 |
| NoName34_m1 | CCCCTTAGGGATAA CAGGGTAATCACTG ACACCTGGAGGCCT GA | 335 | NoName34_m2 | GTGACTGGAGTTC AGACGTGTGCTCT TCCGATCTACCTG GAGGCCTGACTTG CAG | 410 |
| NoName34_p1 | CCCCTTAGGGATAA CAGGGTAATCCTGG AGGGTGTATGCGTG CT | 336 | NoName34_p2 | GTGACTGGAGTTC AGACGTGTGCTCT TCCGATCTAGGGT GTATGCGTGCTCT CTGA | 411 |
| NoName35_m1 | CCCCTTAGGGATAA CAGGGTAATCCTGG GGTTGGCGTCACCT | 337 | NoName35_m2 | GTGACTGGAGTTC AGACGTGTGCTCT TCCGATCTGCGTC ACCTTGAACGACC ACTTTGT | 412 |
| NoName35_p1 | CCCCTTAGGGATAA CAGGGTAATCATTC TTCAGGGGGTCTGG CATGA | 338 | NoName35_p2 | GTGACTGGAGTTC AGACGTGTGCTCT TCCGATCTAGGGG GTCTGGCATGAAA ATGTGTTA | 413 |

TABLE 4-continued

Sequences of anchored primers for GAPDH

| First PCR primer name | Sequence | SEQ ID NO: | Second PCR primer name | Sequence | SEQ ID NO: |
|---|---|---|---|---|---|
| NoName36_m1 | CCCCTTAGGGATAA CAGGGTAATCCACC CATATGCACACCCA CATATACC | 339 | NoName36_m2 | GTGACTGGAGTTC AGACGTGTGCTCT TCCGATCTCACAC CCACATATACCTGC CAAAAGA | 414 |
| NoName37_m1 | CCCCTTAGGGATAA CAGGGTAATCGAAA ACGCCCTACTGCCC TAGAT | 340 | NoName37_m2 | GTGACTGGAGTTC AGACGTGTGCTCT TCCGATCTACGCC CTACTGCCCTAGA TTCTAATT | 415 |
| NoName37_p1 | CCCCTTAGGGATAA CAGGGTAATCAGTC CGCCCCCTTATCATC CTCTCTG | 341 | NoName37_p2 | GTGACTGGAGTTC AGACGTGTGCTCT TCCGATCTTGGGG GCTCTGGGGCTAC T | 416 |
| NoName38_m1 | CCCCTTAGGGATAA CAGGGTAATCCCAA CGTGGACATGAGGA TGCAT | 342 | NoName38_m2 | GTGACTGGAGTTC AGACGTGTGCTCT TCCGATCTACGTG GACATGAGGATGC ATTAAAGG | 417 |
| NoName38_p1 | CCCCTTAGGGATAA CAGGGTAATCTGGC TTCCCAACCTGAGG TTTTG | 343 | NoName38_p2 | GTGACTGGAGTTC AGACGTGTGCTCT TCCGATCTATCCCC TCTTCCCCAAGCC T | 418 |
| NoName39_m1 | CCCCTTAGGGATAA CAGGGTAATCGACA CAGGAGAACCCAC TGAACGC | 344 | NoName39_m2 | GTGACTGGAGTTC AGACGTGTGCTCT TCCGATCTGAACC CACTGAACGCTTC CACTTCCA | 419 |
| NoName39_p1 | CCCCTTAGGGATAA CAGGGTAATCTCTC CACAGTACAATGAG GCCATG | 345 | NoName39_p2 | GTGACTGGAGTTC AGACGTGTGCTCT TCCGATCTAGTAC AATGAGGCCATGC AGTTTCTT | 420 |
| NoName4_m1 | CCCCTTAGGGATAA CAGGGTAATCCGTG CACAGGGGACAGA AGC | 346 | NoName4_m2 | GTGACTGGAGTTC AGACGTGTGCTCT TCCGATCTACAGG GGACAGAAGCCAT GGG | 421 |
| NoName4_p1 | CCCCTTAGGGATAA CAGGGTAATCCCCA GGAGCTACGCCTCT G | 347 | NoName4_p2 | GTGACTGGAGTTC AGACGTGTGCTCT TCCGATCTCTACG CCTCTGCCCCATA CACG | 422 |
| NoName40_m1 | CCCCTTAGGGATAA CAGGGTAATCGGCT GGCATTGCTCTCAA CGA | 348 | NoName40_m2 | GTGACTGGAGTTC AGACGTGTGCTCT TCCGATCTTGGCA TTGCTCTCAACGA CCACTT | 423 |
| NoName40_p1 | CCCCTTAGGGATAA CAGGGTAATCCATG ACGAGGTCAGGCTC CCTAGGC | 349 | NoName40_p2 | GTGACTGGAGTTC AGACGTGTGCTCT TCCGATCTCCCTA GGCCCCTCCGTCT TCAG | 424 |
| NoName41_m1 | CCCCTTAGGGATAA CAGGGTAATCGTGG TGGACTTCGCAGAC CA | 350 | NoName41_m2 | GTGACTGGAGTTC AGACGTGTGCTCT TCCGATCTGGACT TCGCAGACCACAT GGC | 425 |

TABLE 4-continued

| Sequences of anchored primers for GAPDH | | | | | |
|---|---|---|---|---|---|
| First PCR primer name | Sequence | SEQ ID NO: | Second PCR primer name | Sequence | SEQ ID NO: |
| NoName5_m1 | CCCCTTAGGGATAA CAGGGTAATCGCCC AGCTTAAAACATGA GCCATTCA | 351 | NoName5_m2 | GTGACTGGAGTTC AGACGTGTGCTCT TCCGATCTGCCTC GGCTGGCCTTTAC TTG | 426 |
| NoName5_p1 | CCCCTTAGGGATAA CAGGGTAATCGGGA GACAATGGAGATCT ACCTCAGT | 352 | NoName5_p2 | GTGACTGGAGTTC AGACGTGTGCTCT TCCGATCTGGCAA AGTGAGACTAATC TAGCTGCT | 427 |
| NoName6_m1 | CCCCTTAGGGATAA CAGGGTAATCCCCA CTGGCGTCTTCAGC A | 353 | NoName6_m2 | GTGACTGGAGTTC AGACGTGTGCTCT TCCGATCTTCTTCA GCACTACGGAGAA GACTGG | 428 |
| NoName6_p1 | CCCCTTAGGGATAA CAGGGTAATCGCCA AGGGTGCCAAACG TTGATA | 354 | NoName6_p2 | GTGACTGGAGTTC AGACGTGTGCTCT TCCGATCTGTGCC AAACGTTGATAGT GCAGGA | 429 |
| NoName7_m1 | CCCCTTAGGGATAA CAGGGTAATCCAGC GTTTCAGGAAGGG AGAGG | 355 | NoName7_m2 | GTGACTGGAGTTC AGACGTGTGCTCT TCCGATCTTGCCC TGTGCTACTGGAA GGC | 430 |
| NoName7_p1 | CCCCTTAGGGATAA CAGGGTAATCTGTG CCCCCATGCATGCC | 356 | NoName7_p2 | GTGACTGGAGTTC AGACGTGTGCTCT TCCGATCTCCCCC ATGCATGCCTCAC TCTC | 431 |
| NoName8_m1 | CCCCTTAGGGATAA CAGGGTAATCGCAT TGCCCTCAACGACC ACTTTT | 357 | NoName8_m2 | GTGACTGGAGTTC AGACGTGTGCTCT TCCGATCTAGCAA CAGGGTGATGGAC CTC | 432 |
| NoName9_m1 | CCCCTTAGGGATAA CAGGGTAATCCTTA ACTCTCACAGGGCC ATGTAGTG | 358 | NoName9_m2 | GTGACTGGAGTTC AGACGTGTGCTCT TCCGATCTCAGGG CCATGTAGTGTCT TAAAGCTG | 433 |
| GAPDH_p1 | CCCCTTAGGGATAA CAGGGTAATCAGGG GTCTACATGGCAAC TGTG | 359 | GAPDH_p2 | GTGACTGGAGTTC AGACGTGTGCTCT TCCGATCTGAGGA GGGGAGATTCAGT GTGGT | 434 |

TABLE 5

| Sequences of anchored primers for HBB | | | | | |
|---|---|---|---|---|---|
| First PCR primer name | Sequence | SEQ ID NO: | Second PCR primer name | Sequence | SEQ ID NO: |
| NoName10_m1 | CCCCTTAGGGATAA CAGGGTAATCAGGT GTGACTCCTTTCCC AGATCA | 435 | NoName10_m2 | GTGACTGGAGTT CAGACGTGTGCT CTTCCGATCTGT GACTCCTTTCCC AGATCAGATAGC | 521 |

TABLE 5-continued

Sequences of anchored primers for HBB

| First PCR primer name | Sequence | SEQ ID NO: | Second PCR primer name | Sequence | SEQ ID NO: |
|---|---|---|---|---|---|
| NoName10_p1 | CCCCTTAGGGATAACAGGGTAATCAGAAGTCCTGGGTATGGAGGCTTTG | 436 | NoName10_p2 | GTGACTGGAGTTCAGACGTGTGCTCTTCCGATCTCCTGGGTATGGAGGCTTTGGCATTC | 522 |
| NoName11_m1 | CCCCTTAGGGATAACAGGGTAATCCCACTAGGCTAAGAGGTACACCGT | 437 | NoName11_m2 | GTGACTGGAGTTCAGACGTGTGCTCTTCCGATCTGGCTAAGAGGTACACCGTAACAGAGA | 523 |
| NoName11_p1 | CCCCTTAGGGATAACAGGGTAATCCCAGTGGCATCCCCTTTTGTCA | 438 | NoName11_p2 | GTGACTGGAGTTCAGACGTGTGCTCTTCCGATCTAGCATGTCATATGGCTAACACCGGTT | 524 |
| NoName12_m1 | CCCCTTAGGGATAACAGGGTAATCTTTGGCAGCGGTGATGAGGT | 439 | NoName12_m2 | GTGACTGGAGTTCAGACGTGTGCTCTTCCGATCTGAGGTTTCTCATCCTGCATGACGTAT | 525 |
| NoName12_p1 | CCCCTTAGGGATAACAGGGTAATCGCAAGGGTAACACCTGAGAAGGT | 440 | NoName12_p2 | GTGACTGGAGTTCAGACGTGTGCTCTTCCGATCTGTGTGGGGTAAGGGGAGCTG | 526 |
| NoName13_m1 | CCCCTTAGGGATAACAGGGTAATCTGGCAGGTGTAGCTTTTTCTGTTA | 441 | NoName13_m2 | GTGACTGGAGTTCAGACGTGTGCTCTTCCGATCTAGAACATTCTGTCATTCCAGTCAGA | 527 |
| NoName14_m1 | CCCCTTAGGGATAACAGGGTAATCGCGGATTAAAGGGAAGGGCTTCG | 442 | NoName14_m2 | GTGACTGGAGTTCAGACGTGTGCTCTTCCGATCTAGGGAAGGGCTTCGAATGAGAATGCT | 528 |
| NoName14_p1 | CCCCTTAGGGATAACAGGGTAATCGCCGTTACCATAAGTCAGCAGGT | 443 | NoName14_p2 | GTGACTGGAGTTCAGACGTGTGCTCTTCCGATCTCAGAAAGTCACTTCCAGCACTTGTGA | 529 |
| NoName15_m1 | CCCCTTAGGGATAACAGGGTAATCACCCAAGCGGCCCTTCCT | 444 | NoName15_m2 | GTGACTGGAGTTCAGACGTGTGCTCTTCCGATCTTCCTCCAGGCTTGACTTGGC | 530 |
| NoName15_p1 | CCCCTTAGGGATAACAGGGTAATCCTGCACACACATTGCCCACTTACA | 445 | NoName15_p2 | GTGACTGGAGTTCAGACGTGTGCTCTTCCGATCTCACCCCAGAACACGAGCAACT | 531 |
| NoName16_m1 | CCCCTTAGGGATAACAGGGTAATCGTGAAGTTGGACCAGCTGTCATACA | 446 | NoName16_m2 | GTGACTGGAGTTCAGACGTGTGCTCTTCCGATCTGTTGGACCAGCTGTCATACACACAAC | 532 |
| NoName16_p1 | CCCCTTAGGGATAACAGGGTAATCTGTGTGTCACATCAATTAATTTGTGC | 447 | NoName16_p2 | GTGACTGGAGTTCAGACGTGTGCTCTTCCGATCTTTGTGCACAGGTTTAAGAAACAAATA | 533 |

TABLE 5-continued

Sequences of anchored primers for HBB

| First PCR primer name | Sequence | SEQ ID NO: | Second PCR primer name | Sequence | SEQ ID NO: |
|---|---|---|---|---|---|
| NoName17_p1 | CCCCTTAGGGATAA CAGGGTAATCGCTC TGCAAGTACTGACT GCCT | 448 | NoName17_p2 | GTGACTGGAGTT CAGACGTGTGCT CTTCCGATCTGC AAGTACTGACTG CCTCCCCCTT | 534 |
| NoName18_m1 | CCCCTTAGGGATAA CAGGGTAATCATGA GGGGACACCAGAG GGAA | 449 | NoName18_m2 | GTGACTGGAGTT CAGACGTGTGCT CTTCCGATCTGG GACACCAGAGG GAAGTGAGG | 535 |
| NoName18_p1 | CCCCTTAGGGATAA CAGGGTAATCCCCT CTGGAGTCCCATCA TCAC | 450 | NoName18_p2 | GTGACTGGAGTT CAGACGTGTGCT CTTCCGATCTATC ACCATCTGGCAT CCCTTCAC | 536 |
| NoName19_m1 | CCCCTTAGGGATAA CAGGGTAATCTGCT GTGTCTGCTGTCCA TCC | 451 | NoName19_m2 | GTGACTGGAGTT CAGACGTGTGCT CTTCCGATCTGT GTCTGCTGTCCA TCCTTCACAT | 537 |
| NoName19_p1 | CCCCTTAGGGATAA CAGGGTAATCGCTG CTGCTGGAGAGCCA T | 452 | NoName19_p2 | GTGACTGGAGTT CAGACGTGTGCT CTTCCGATCTTGC TGGAGAGCCATC TTGAAACTAAG | 538 |
| NoName2_p1 | CCCCTTAGGGATAA CAGGGTAATCGTCG AACTGCATCCCCTG GTTT | 453 | NoName2_p2 | GTGACTGGAGTT CAGACGTGTGCT CTTCCGATCTGC CAGGGCAGCCTT CCAG | 539 |
| NoName20_p1 | CCCCTTAGGGATAA CAGGGTAATCGTTC CGCTACGTCAGTTG CCA | 454 | NoName20_p2 | GTGACTGGAGTT CAGACGTGTGCT CTTCCGATCTCGT CAGTTGCCACTT CTGTATCCA | 540 |
| NoName21_m1 | CCCCTTAGGGATAA CAGGGTAATCGGAA TGGCCACCCTTCCC T | 455 | NoName21_m2 | GTGACTGGAGTT CAGACGTGTGCT CTTCCGATCTACC CTTCCCTCCTTAT CAGAAATTGC | 541 |
| NoName21_p1 | CCCCTTAGGGATAA CAGGGTAATCCCTC CTGGAGGTCTCTCT TTAATGC | 456 | NoName21_p2 | GTGACTGGAGTT CAGACGTGTGCT CTTCCGATCTGC CCCTTTTCTCAC AGTGTGCA | 542 |
| NoName22_m1 | CCCCTTAGGGATAA CAGGGTAATCGTCA TTCTGCTGGGTGAC AATG | 457 | NoName22_m2 | GTGACTGGAGTT CAGACGTGTGCT CTTCCGATCTCAT TCTGCTGGGTGA CAATGAAATAT | 543 |
| NoName22_p1 | CCCCTTAGGGATAA CAGGGTAATCTCAC ACAGTGGTTAAGAC CCTTTGG | 458 | NoName22_p2 | GTGACTGGAGTT CAGACGTGTGCT CTTCCGATCTGT GGTTAAGACCCT TTGGCATGAGAG | 544 |
| NoName23_m1 | CCCCTTAGGGATAA CAGGGTAATCGTGG GCTAGAAGCTAAGA AGATCAGC | 459 | NoName23_m2 | GTGACTGGAGTT CAGACGTGTGCT CTTCCGATCTAG AAGCTAAGAAGA TCAGCCAGCAG | 545 |

TABLE 5-continued

Sequences of anchored primers for HBB

| First PCR primer name | Sequence | SEQ ID NO: | Second PCR primer name | Sequence | SEQ ID NO: |
|---|---|---|---|---|---|
| NoName23_p1 | CCCCTTAGGGATAA CAGGGTAATCAGTA CGATGCTGCTTCAC ATGGAAC | 460 | NoName23_p2 | GTGACTGGAGTT CAGACGTGTGCT CTTCCGATCTTCA CATGGAACCCAG CAGGAATC | 546 |
| NoName24_m1 | CCCCTTAGGGATAA CAGGGTAATCACGA CTGTTCTCACTGAG GGGTA | 461 | NoName24_m2 | GTGACTGGAGTT CAGACGTGTGCT CTTCCGATCTAG GAGGAAAGGGT GGAGCTGA | 547 |
| NoName24_p1 | CCCCTTAGGGATAA CAGGGTAATCGGGA GACTTACCAGCTTC CCGTA | 462 | NoName24_p2 | GTGACTGGAGTT CAGACGTGTGCT CTTCCGATCTACC AGCTTCCCGTATC TCCCT | 548 |
| NoName25_m1 | CCCCTTAGGGATAA CAGGGTAATCTAAG GCAGTGTGTTGGGT GCT | 463 | NoName25_m2 | GTGACTGGAGTT CAGACGTGTGCT CTTCCGATCTGCT GTTGCAGAAGGG ATAGTCAGAG | 549 |
| NoName25_p1 | CCCCTTAGGGATAA CAGGGTAATCCCTT CCTTCTCCACCCAA GTAGCTA | 464 | NoName25_p2 | GTGACTGGAGTT CAGACGTGTGCT CTTCCGATCTATG TGCCCTCTGTGT GCCTT | 550 |
| NoName26_m1 | CCCCTTAGGGATAA CAGGGTAATCCTCA CACTCTACCCTTGT GCTACG | 465 | NoName26_m2 | GTGACTGGAGTT CAGACGTGTGCT CTTCCGATCTCTC TACCCTTGTGCTA CGCTGTCT | 551 |
| NoName27_m1 | CCCCTTAGGGATAA CAGGGTAATCCAAC TGGGCATGCTCTCC TAGG | 466 | NoName27_m2 | GTGACTGGAGTT CAGACGTGTGCT CTTCCGATCTGC AAGGGGCCAGA AGGTCT | 552 |
| NoName27_p1 | CCCCTTAGGGATAA CAGGGTAATCCTGT GTGGCCCTCAGGTG TAA | 467 | NoName27_p2 | GTGACTGGAGTT CAGACGTGTGCT CTTCCGATCTGG CCCTCAGGTGTA ACTTACCCTCTC | 553 |
| NoName28_m1 | CCCCTTAGGGATAA CAGGGTAATCACCA CACCCGGCTCACTC T | 468 | NoName28_m2 | GTGACTGGAGTT CAGACGTGTGCT CTTCCGATCTCC ACACCCGGCTCA CTCTCCAATT | 554 |
| NoName29_p1 | CCCCTTAGGGATAA CAGGGTAATCGGAG GTTGCAGGTTGCTG GT | 469 | NoName29_p2 | GTGACTGGAGTT CAGACGTGTGCT CTTCCGATCTGTT GCTGGTTGCTGA GATCATGCCA | 555 |
| NoName3_m1 | CCCCTTAGGGATAA CAGGGTAATCGGCT GGAGTCCTGGTCCT G | 470 | NoName3_m2 | GTGACTGGAGTT CAGACGTGTGCT CTTCCGATCTCC AATCACGGGCCC TGGGA | 556 |
| NoName3_p1 | CCCCTTAGGGATAA CAGGGTAATCATGG TCACCGCCATTCAC GT | 471 | NoName3_p2 | GTGACTGGAGTT CAGACGTGTGCT CTTCCGATCTCC GCCATTCACGTG GTGCTTACTG | 557 |

TABLE 5-continued

Sequences of anchored primers for HBB

| First PCR primer name | Sequence | SEQ ID NO: | Second PCR primer name | Sequence | SEQ ID NO: |
|---|---|---|---|---|---|
| NoName30_m1 | CCCCTTAGGGATAACAGGGTAATCCTATCATTACCCACACCCCTGAGAC | 472 | NoName30_m2 | GTGACTGGAGTTCAGACGTGTGCTCTTCCGATCTCCCACACCCCTGAGACTGCATA | 558 |
| NoName30_p1 | CCCCTTAGGGATAACAGGGTAATCAGCTACCACGGTGACAGTAACATAGC | 473 | NoName30_p2 | GTGACTGGAGTTCAGACGTGTGCTCTTCCGATCTCGGTGACAGTAACATAGCCCAGGGA | 559 |
| NoName31_m1 | CCCCTTAGGGATAACAGGGTAATCAGCTGCCAGCCCACAAGAA | 474 | NoName31_m2 | GTGACTGGAGTTCAGACGTGTGCTCTTCCGATCTAAAATGGGGCCCTTAGTCCTACAATG | 560 |
| NoName31_p1 | CCCCTTAGGGATAACAGGGTAATCGGGAGACAGGGTATCCAGGCT | 475 | NoName31_p2 | GTGACTGGAGTTCAGACGTGTGCTCTTCCGATCTGAGACAGGGTATCCAGGCTGCATACA | 561 |
| NoName32_m1 | CCCCTTAGGGATAACAGGGTAATCAGTTCAGGGTCTGGTTCTGTGC | 476 | NoName32_m2 | GTGACTGGAGTTCAGACGTGTGCTCTTCCGATCTTTCAGGGTCTGGTTCTGTGCACATAA | 562 |
| NoName33_m1 | CCCCTTAGGGATAACAGGGTAATCCGGCATTCTTCCCGGCAATGA | 477 | NoName33_m2 | GTGACTGGAGTTCAGACGTGTGCTCTTCCGATCTGGCATTCTTCCCGGCAATGAAATCCT | 563 |
| NoName33_p1 | CCCCTTAGGGATAACAGGGTAATCTGACTCTCAGCACCTTGACACTCC | 478 | NoName33_p2 | GTGACTGGAGTTCAGACGTGTGCTCTTCCGATCTCAGCACCTTGACACTCCAGATGAACT | 564 |
| NoName34_m1 | CCCCTTAGGGATAACAGGGTAATCCTTTATATGTGGGGGATGGAAAAGAC | 479 | NoName34_m2 | GTGACTGGAGTTCAGACGTGTGCTCTTCCGATCTATGGAAAAGACAACCCATCATGGTAT | 565 |
| NoName35_m1 | CCCCTTAGGGATAACAGGGTAATCCAGTGCCTTTTCCTACTACACCACA | 480 | NoName35_m2 | GTGACTGGAGTTCAGACGTGTGCTCTTCCGATCTCCTACTACACCACACTGATGCCTCCA | 566 |
| NoName35_p1 | CCCCTTAGGGATAACAGGGTAATCCGAAGGAACCAAACGGAACTTGTGTA | 481 | NoName35_p2 | GTGACTGGAGTTCAGACGTGTGCTCTTCCGATCTTCTGGGTGGGAGCAGAGTACTCTT | 567 |
| NoName36_m1 | CCCCTTAGGGATAACAGGGTAATCAGCTCATCGAGGCACCAAACA | 482 | NoName36_m2 | GTGACTGGAGTTCAGACGTGTGCTCTTCCGATCTGTGGTGATTACAAGGCCACATCCTAC | 568 |
| NoName36_p1 | CCCCTTAGGGATAACAGGGTAATCATTTGTCCTGGAACCCATACTGCAT | 483 | NoName36_p2 | GTGACTGGAGTTCAGACGTGTGCTCTTCCGATCTCCTGGAACCCATACTGCATTAGGAAG | 569 |

TABLE 5-continued

Sequences of anchored primers for HBB

| First PCR primer name | Sequence | SEQ ID NO: | Second PCR primer name | Sequence | SEQ ID NO: |
|---|---|---|---|---|---|
| NoName37_m1 | CCCCTTAGGGATAACAGGGTAATCTGAAAGCATCAACTCTGGGAGCATG | 484 | NoName37_m2 | GTGACTGGAGTTCAGACGTGTGCTCTTCCGATCTAGCATGAAAAAGGCTGATGAGTGGGA | 570 |
| NoName37_p1 | CCCCTTAGGGATAACAGGGTAATCGCCACAGTTCCAGTGCATTCG | 485 | NoName37_p2 | GTGACTGGAGTTCAGACGTGTGCTCTTCCGATCTCCACAGTTCCAGTGCATTCGGAAGAA | 571 |
| NoName38_m1 | CCCCTTAGGGATAACAGGGTAATCGGCTCCCCAGAAGAAGAAGCCT | 486 | NoName38_m2 | GTGACTGGAGTTCAGACGTGTGCTCTTCCGATCTGCTTGCAGAACCACGAGCTGA | 572 |
| NoName38_p1 | CCCCTTAGGGATAACAGGGTAATCGCAAGTGGTAGGCATGGGTTAGAAGA | 487 | NoName38_p2 | GTGACTGGAGTTCAGACGTGTGCTCTTCCGATCTTCAGCTGTGCTTCTAATGTACACCCT | 573 |
| NoName39_m1 | CCCCTTAGGGATAACAGGGTAATCGCCCGGCAATCGTTTTCTAGGG | 488 | NoName39_m2 | GTGACTGGAGTTCAGACGTGTGCTCTTCCGATCTGCAATCGTTTTCTAGGGCACGACTTA | 574 |
| NoName39_p1 | CCCCTTAGGGATAACAGGGTAATCACCCCCAGGTCAGCAAGC | 489 | NoName39_p2 | GTGACTGGAGTTCAGACGTGTGCTCTTCCGATCTGTCAGCAAGCACTTGATCAGAGCATT | 575 |
| NoName4_m1 | CCCCTTAGGGATAACAGGGTAATCCTGATTAGGGTGGTTCGTTTTGACGT | 490 | NoName4_m2 | GTGACTGGAGTTCAGACGTGTGCTCTTCCGATCTGTGGTTCGTTTTGACGTGTCTGTTTC | 576 |
| NoName4_p1 | CCCCTTAGGGATAACAGGGTAATCGCACGACCGCGGCAGAGT | 491 | NoName4_p2 | GTGACTGGAGTTCAGACGTGTGCTCTTCCGATCTCACGACCGCGGCAGAGTTATCAG | 577 |
| NoName40_m1 | CCCCTTAGGGATAACAGGGTAATCAGCTGCTTCCCAGGCCTTG | 492 | NoName40_m2 | GTGACTGGAGTTCAGACGTGTGCTCTTCCGATCTCCCAGGCCTTGGCAATGAGTTTAGG | 578 |
| NoName40_p1 | CCCCTTAGGGATAACAGGGTAATCAATGCAGAGGCCAGGACACC | 493 | NoName40_p2 | GTGACTGGAGTTCAGACGTGTGCTCTTCCGATCTGGCCAGGACACCACCATCCC | 579 |
| NoName41_m1 | CCCCTTAGGGATAACAGGGTAATCTCATGTTGTGGTTGGAAGTGTGGAT | 494 | NoName41_m2 | GTGACTGGAGTTCAGACGTGTGCTCTTCCGATCTTGTGGTTGGAAGTGTGGATTACTGGT | 580 |
| NoName41_p1 | CCCCTTAGGGATAACAGGGTAATCTGGCTGGAAGATGGACGGAGA | 495 | NoName41_p2 | GTGACTGGAGTTCAGACGTGTGCTCTTCCGATCTTGGACGGAGAGTGGATCACAGATGAG | 581 |

TABLE 5-continued

Sequences of anchored primers for HBB

| First PCR primer name | Sequence | SEQ ID NO: | Second PCR primer name | Sequence | SEQ ID NO: |
|---|---|---|---|---|---|
| NoName42_m1 | CCCCTTAGGGATAA CAGGGTAATCCACC AGGCCACTCACCCA ATT | 496 | NoName42_m2 | GTGACTGGAGTT CAGACGTGTGCT CTTCCGATCTCC AGGCCACTCACC CAATTTGACATG | 582 |
| NoName43_m1 | CCCCTTAGGGATAA CAGGGTAATCGAGA CCAGTGATTTCAGA GTGGCTAG | 497 | NoName43_m2 | GTGACTGGAGTT CAGACGTGTGCT CTTCCGATCTTTC AGAGTGGCTAGG TGTTCACTGAT | 583 |
| NoName44_m1 | CCCCTTAGGGATAA CAGGGTAATCACCC CGAACTTGGTGATG CAGTAC | 498 | NoName44_m2 | GTGACTGGAGTT CAGACGTGTGCT CTTCCGATCTTAC GGGGAGCGGGC CGGGTT | 584 |
| NoName44_p1 | CCCCTTAGGGATAA CAGGGTAATCGGGT GGCTCAGAAGTGGT TCC | 499 | NoName44_p2 | GTGACTGGAGTT CAGACGTGTGCT CTTCCGATCTGCT CAGAAGTGGTTC CAGCCAAG | 585 |
| NoName45_m1 | CCCCTTAGGGATAA CAGGGTAATCGTAG GTGATAGGGAAACG CCGAAA | 500 | NoName45_m2 | GTGACTGGAGTT CAGACGTGTGCT CTTCCGATCTAG GGAAACGCCGA AAGTATTTTAGGT | 586 |
| NoName45_p1 | CCCCTTAGGGATAA CAGGGTAATCTCTG CAGAGCATGGAGG CAAC | 501 | NoName45_p2 | GTGACTGGAGTT CAGACGTGTGCT CTTCCGATCTGC AACTGCTCCCTG GTCTCTT | 587 |
| NoName46_m1 | CCCCTTAGGGATAA CAGGGTAATCAAGT CTGAAACGCTGCTC TGCTATT | 502 | NoName46_m2 | GTGACTGGAGTT CAGACGTGTGCT CTTCCGATCTCCT GTGATCCCTTCG AAGAATCTTGT | 588 |
| NoName47_m1 | CCCCTTAGGGATAA CAGGGTAATCGCAC CATTTCCACCCAGC TTTG | 503 | NoName47_m2 | GTGACTGGAGTT CAGACGTGTGCT CTTCCGATCTTCC ACCCAGCTTTGC TCAAGT | 589 |
| NoName47_p1 | CCCCTTAGGGATAA CAGGGTAATCCAAG TAGCTAGGACTCAA GGCACATG | 504 | NoName47_p2 | GTGACTGGAGTT CAGACGTGTGCT CTTCCGATCTCC ACCACGGCCAGA TCATTGA | 590 |
| NoName48_m1 | CCCCTTAGGGATAA CAGGGTAATCGGGG GCTGATATGGGTCA ACC | 505 | NoName48_m2 | GTGACTGGAGTT CAGACGTGTGCT CTTCCGATCTAAC TGGGTTGCCATG AATCTGCTG | 591 |
| NoName5_m1 | CCCCTTAGGGATAA CAGGGTAATCTGCA TCGAAGCTGGTGGA GAC | 506 | NoName5_m2 | GTGACTGGAGTT CAGACGTGTGCT CTTCCGATCTGC AGGGCTGAGGTG GAAAGCT | 592 |
| NoName5_p1 | CCCCTTAGGGATAA CAGGGTAATCCCAG ACCCTGACTCATGG ACACACC | 507 | NoName5_p2 | GTGACTGGAGTT CAGACGTGTGCT CTTCCGATCTGA CACACCCTCCCC CATCTGGCA | 593 |

TABLE 5-continued

Sequences of anchored primers for HBB

| First PCR primer name | Sequence | SEQ ID NO: | Second PCR primer name | Sequence | SEQ ID NO: |
|---|---|---|---|---|---|
| NoName6_m1 | CCCCTTAGGGATAACAGGGTAATCACGTTCCCGTCTGCTCAGTG | 508 | NoName6_m2 | GTGACTGGAGTTCAGACGTGTGCTCTTCCGATCTTGGGGTAAAGGGGACTCACTCT | 594 |
| NoName6_p1 | CCCCTTAGGGATAACAGGGTAATCGAGGTTGGACCAGCTGTCATACC | 509 | NoName6_p2 | GTGACTGGAGTTCAGACGTGTGCTCTTCCGATCTAGCTGCTTTACTGTCACACGTAGCAG | 595 |
| NoName7_m1 | CCCCTTAGGGATAACAGGGTAATCGCTAGTCTTTCCAGGCCACCCT | 510 | NoName7_m2 | GTGACTGGAGTTCAGACGTGTGCTCTTCCGATCTCCACCCTCTCCGAGCCACCT | 596 |
| NoName7_p1 | CCCCTTAGGGATAACAGGGTAATCTTGGCAAGCACTCCTCAATGGC | 511 | NoName7_p2 | GTGACTGGAGTTCAGACGTGTGCTCTTCCGATCTCCAGCTTACAGGCAGGGCTGT | 597 |
| NoName8_m1 | CCCCTTAGGGATAACAGGGTAATCGCAGAGAGGAGGGGCTAAAGGG | 512 | NoName8_m2 | GTGACTGGAGTTCAGACGTGTGCTCTTCCGATCTGGGGCAGGAAGGGAGAAGCAC | 598 |
| NoName8_p1 | CCCCTTAGGGATAACAGGGTAATCCTCCCATCCATACCCCCACCT | 513 | NoName8_p2 | GTGACTGGAGTTCAGACGTGTGCTCTTCCGATCTTCCACCCCCAACCTGAGAAGAC | 599 |
| NoName9_m1 | CCCCTTAGGGATAACAGGGTAATCGCCCCAACCCAAGCTAGTCTTTC | 514 | NoName9_m2 | GTGACTGGAGTTCAGACGTGTGCTCTTCCGATCTCCCAAGCTAGTCTTTCCAGGCCACT | 600 |
| OT1-NC_m1 | CCCCTTAGGGATAACAGGGTAATCCCTTTCCCGTTCTCCACCCAA | 515 | OT1-NC_m2 | GTGACTGGAGTTCAGACGTGTGCTCTTCCGATCTCCGTTCTCCACCCAATAGCTATGG | 601 |
| OT1-NC_p1 | CCCCTTAGGGATAACAGGGTAATCAGCAGTATGTCCAACTCCCAAATTG | 516 | OT1-NC_p2 | GTGACTGGAGTTCAGACGTGTGCTCTTCCGATCTTCCAACTCCCAAATTGAAAGCACAGC | 602 |
| OT2-NC_m1 | CCCCTTAGGGATAACAGGGTAATCACACAGGTTTTCTCCTCTCAGCCTA | 517 | OT2-NC_m2 | GTGACTGGAGTTCAGACGTGTGCTCTTCCGATCTTTCCCTTCCCTAGACCTGCCT | 603 |
| OT2-NC_p1 | CCCCTTAGGGATAACAGGGTAATCAACCTGGCTCCTTCGCTTCC | 518 | OT2-NC_p2 | GTGACTGGAGTTCAGACGTGTGCTCTTCCGATCTGGCTCCTTCGCTTCCATCTGATCAGG | 604 |

TABLE 5-continued

Sequences of anchored primers for HBB

| First PCR primer name | Sequence | SEQ ID NO: | Second PCR primer name | Sequence | SEQ ID NO: |
|---|---|---|---|---|---|
| HBB_m1 | CCCCTTAGGGATAA CAGGGTAATCCTCT GTCTCCACATGCCC AGTT | 519 | HBB_m2 | GTGACTGGAGTT CAGACGTGTGCT CTTCCGATCTGTC TCCACATGCCCA GTTTCTATTGG | 605 |
| HBB_p1 | CCCCTTAGGGATAA CAGGGTAATCCCAG GGCTGGGCATAAAA GTCAG | 520 | HBB_p2 | GTGACTGGAGTT CAGACGTGTGCT CTTCCGATCTTTC ACTAGCAACCTC AAACAGACACC | 606 |

TABLE_6

Sequences of anchored primers for PD1

| First PCR primer name | Sequence | SEQ ID NO: | Second PCR primer name | Sequence | SEQ ID NO: |
|---|---|---|---|---|---|
| NoName1_m1 | CCCCTTAGGGATAAC AGGGTAATCTGGGCT GAGAGCTAGCTTTAT GTGA | 607 | NoName1_m2 | GTGACTGGAGTTCA GACGTGTGCTCTTC CGATCTCAGTCACC ACACTGGGTAACTC CT | 699 |
| NoName1_p1 | CCCCTTAGGGATAAC AGGGTAATCAGGAG GCAGGGACGTGAAA C | 608 | NoName1_p2 | GTGACTGGAGTTCA GACGTGTGCTCTTC CGATCTGTGAAACG CTGGGGTGCAATTT C | 700 |
| NoName10_m1 | CCCCTTAGGGATAAC AGGGTAATCAGGTGA CTCCCTGGCTTTGC | 609 | NoName10_m2 | GTGACTGGAGTTCA GACGTGTGCTCTTC CGATCTTCCTCTTCC CCCAAGCTGGCTT | 701 |
| NoName10_p1 | CCCCTTAGGGATAAC AGGGTAATCTGATCT GAGGGGCTTGGCAG A | 610 | NoName10_p2 | GTGACTGGAGTTCA GACGTGTGCTCTTC CGATCTGGCAGAGA GGCACCCCAA | 702 |
| NoName11_m1 | CCCCTTAGGGATAAC AGGGTAATCCACATG TGGTACGTCTGGTCC AGT | 611 | NoName11_m2 | GTGACTGGAGTTCA GACGTGTGCTCTTC CGATCTCGTCTGGT CCAGTCAGCCTTGC | 703 |
| NoName11_p1 | CCCCTTAGGGATAAC AGGGTAATCACGACG GGTGTGTGGGTGA | 612 | NoName11_p2 | GTGACTGGAGTTCA GACGTGTGCTCTTC CGATCTCGGGTGTG TGGGTGACAAGCG | 704 |
| NoName12_m1 | CCCCTTAGGGATAAC AGGGTAATCCAGCTG GGGCGACATAGTGA | 613 | NoName12_m2 | GTGACTGGAGTTCA GACGTGTGCTCTTC CGATCTGGGGAGTT AATGTAAGGGAGGC AACA | 705 |
| NoName12_p1 | CCCCTTAGGGATAAC AGGGTAATCGGTAAC TGTAATATAGAGCCC ACCA | 614 | NoName12_p2 | GTGACTGGAGTTCA GACGTGTGCTCTTC CGATCTGAGCCCAC CACTCAGCTTT | 706 |
| NoName14_m1 | CCCCTTAGGGATAAC AGGGTAATCGGGGA GGGACAGGTTGTGA G | 615 | NoName14_m2 | GTGACTGGAGTTCA GACGTGTGCTCTTC CGATCTTGGGCTTG GAGTTAAGGGGCCT A | 707 |

TABLE_6-continued

Sequences of anchored primers for PD1

| First PCR primer name | Sequence | SEQ ID NO: | Second PCR primer name | Sequence | SEQ ID NO: |
|---|---|---|---|---|---|
| NoName14_p1 | CCCCTTAGGGATAACAGGGTAATCTGAATCACCAACTGCCAAACACGTG | 616 | NoName14_p2 | GTGACTGGAGTTCAGACGTGTGCTCTTCCGATCTCCAACTGCCAAACACGTGAATGAGGT | 708 |
| NoName15_m1 | CCCCTTAGGGATAACAGGGTAATCGGCCCCCAGTGAATCACCAATTG | 617 | NoName15_m2 | GTGACTGGAGTTCAGACGTGTGCTCTTCCGATCTATGAGGTCATCTGAGGCCATCCC | 709 |
| NoName16_m1 | CCCCTTAGGGATAACAGGGTAATCGCAGAATCAAGCCAGAGCATGC | 618 | NoName16_m2 | GTGACTGGAGTTCAGACGTGTGCTCTTCCGATCTAGCCAGAGCATGCCAAGCA | 710 |
| NoName16_p1 | CCCCTTAGGGATAACAGGGTAATCAGAGGTGAGGGCGAGCTAGA | 619 | NoName16_p2 | GTGACTGGAGTTCAGACGTGTGCTCTTCCGATCTCGAGCTAGAGTAGAAGGTGCCCCAT | 711 |
| NoName17_m1 | CCCCTTAGGGATAACAGGGTAATCTGCCAGTGATCTTTCCTTTCCCTCTG | 620 | NoName17_m2 | GTGACTGGAGTTCAGACGTGTGCTCTTCCGATCTCCTCTGATGTGTCGATGCCAGCCTT | 712 |
| NoName17_p1 | CCCCTTAGGGATAACAGGGTAATCCAACAGTCGGTGTCCTGATGGT | 621 | NoName17_p2 | GTGACTGGAGTTCAGACGTGTGCTCTTCCGATCTAGTCGGTGTCCTGATGGTAGAAAAC | 713 |
| NoName18_m1 | CCCCTTAGGGATAACAGGGTAATCTCCTGTGCCATGACCTTCACAC | 622 | NoName18_m2 | GTGACTGGAGTTCAGACGTGTGCTCTTCCGATCTAGCCAGTGATGAAAGGTGCCTCAA | 714 |
| NoName18_p1 | CCCCTTAGGGATAACAGGGTAATCATGGGGAGGCGGCAGTGA | 623 | NoName18_p2 | GTGACTGGAGTTCAGACGTGTGCTCTTCCGATCTAGCACAGGAGAGGGCCTCTG | 715 |
| NoName19_m1 | CCCCTTAGGGATAACAGGGTAATCGGGGCTGGGCAGTCACTC | 624 | NoName19_m2 | GTGACTGGAGTTCAGACGTGTGCTCTTCCGATCTTCCCCCAGCTCCCAAATCAATCAA | 716 |
| NoName19_p1 | CCCCTTAGGGATAACAGGGTAATCCCAGACTGCGGGTATGAGAGG | 625 | NoName19_p2 | GTGACTGGAGTTCAGACGTGTGCTCTTCCGATCTGGCAGCCTTTCCTTTTCACAGATG | 717 |
| NoName2_m1 | CCCCTTAGGGATAACAGGGTAATCGGCTCCGACGCTCCACAG | 626 | NoName2_m2 | GTGACTGGAGTTCAGACGTGTGCTCTTCCGATCTCCGACGCTCCACAGCCTGTC | 718 |
| NoName2_p1 | CCCCTTAGGGATAACAGGGTAATCCCCCTAGCGGCCCAGGCT | 627 | NoName2_p2 | GTGACTGGAGTTCAGACGTGTGCTCTTCCGATCTCGGCCCAGGCTCGGACTG | 719 |
| NoName20_m1 | CCCCTTAGGGATAACAGGGTAATCTCAGGCTCTAGCAGTCCCAGTA | 628 | NoName20_m2 | GTGACTGGAGTTCAGACGTGTGCTCTTCCGATCTAGGCTCTAGCAGTCCCAGTAATAAGT | 720 |

TABLE_6-continued

| Sequences of anchored primers for PD1 | | | | | |
|---|---|---|---|---|---|
| First PCR primer name | Sequence | SEQ ID NO: | Second PCR primer name | Sequence | SEQ ID NO: |
| NoName20_p1 | CCCCTTAGGGATAACAGGGTAATCGGCATGGTGAAGAAAGAATGCTAC | 629 | NoName20_p2 | GTGACTGGAGTTCAGACGTGTGCTCTTCCGATCTATGCTACACATACTTCACCTTAAGGG | 721 |
| NoName21_m1 | CCCCTTAGGGATAACAGGGTAATCAGGTTCTTGCTTAGAGGCATGATGAC | 630 | NoName21_m2 | GTGACTGGAGTTCAGACGTGTGCTCTTCCGATCTCAACTGTGGAGACTGACTGGCT | 722 |
| NoName21_p1 | CCCCTTAGGGATAACAGGGTAATCGCCCATGCTGTTCTTATAGCGGTA | 631 | NoName21_p2 | GTGACTGGAGTTCAGACGTGTGCTCTTCCGATCTGGGAGCCATACCTGAGAAGGAGA | 723 |
| NoName22_m1 | CCCCTTAGGGATAACAGGGTAATCTGTGCATACTCAGCTACTGTGCTCTA | 632 | NoName22_m2 | GTGACTGGAGTTCAGACGTGTGCTCTTCCGATCTTGAGCTTGAGGATCTGTCAGGCAA | 724 |
| NoName22_p1 | CCCCTTAGGGATAACAGGGTAATCTGCAGATGATCTGGCTGATGGAC | 633 | NoName22_p2 | GTGACTGGAGTTCAGACGTGTGCTCTTCCGATCTATGATCTGGCTGATGGACCAAACATC | 725 |
| NoName23_m1 | CCCCTTAGGGATAACAGGGTAATCCCAGATTCCCTGCTCAGCAAAGTA | 634 | NoName23_m2 | GTGACTGGAGTTCAGACGTGTGCTCTTCCGATCTACAGCGGCTGTTGCTCTTCC | 726 |
| NoName23_p1 | CCCCTTAGGGATAACAGGGTAATCCAACCACTGTGTAATAAGCCGCTTGT | 635 | NoName23_p2 | GTGACTGGAGTTCAGACGTGTGCTCTTCCGATCTCCGCTTGTACAACGGTCTTTCCTCAA | 727 |
| NoName24_p1 | CCCCTTAGGGATAACAGGGTAATCGCTAAACTTGGCACTGGCTTTCAC | 636 | NoName24_p2 | GTGACTGGAGTTCAGACGTGTGCTCTTCCGATCTATTTGCAGCTTCCTCTACACTTCCTG | 728 |
| NoName25_m1 | CCCCTTAGGGATAACAGGGTAATCAAACCCCACACACCACACGTAT | 637 | NoName25_m2 | GTGACTGGAGTTCAGACGTGTGCTCTTCCGATCTCACACCACACACGTCACAGAAACC | 729 |
| NoName25_p1 | CCCCTTAGGGATAACAGGGTAATCGGGGCTCCTGAGGGTGGA | 638 | NoName25_p2 | GTGACTGGAGTTCAGACGTGTGCTCTTCCGATCTAGAAGGGGTGGGAGGCCAA | 730 |
| NoName26_m1 | CCCCTTAGGGATAACAGGGTAATCTGTCTGCAGTCACCTGTCCAC | 639 | NoName26_m2 | GTGACTGGAGTTCAGACGTGTGCTCTTCCGATCTTCACCTGTCCACTCACAGCAC | 731 |
| NoName26_p1 | CCCCTTAGGGATAACAGGGTAATCCACTCCCAGGCGCTCGAGTT | 640 | NoName26_p2 | GTGACTGGAGTTCAGACGTGTGCTCTTCCGATCTGCGCTCGAGTTACAGGGCCACT | 732 |
| NoName27_m1 | CCCCTTAGGGATAACAGGGTAATCGGACAAACACCCACCCAGGT | 641 | NoName7_2m2 | GTGACTGGAGTTCAGACGTGTGCTCTTCCGATCTAGGTGATGTGATCTTCCTGCTTGCTC | 733 |

TABLE_6-continued

Sequences of anchored primers for PD1

| First PCR primer name | Sequence | SEQ ID NO: | Second PCR primer name | Sequence | SEQ ID NO: |
|---|---|---|---|---|---|
| NoName28_m1 | CCCCTTAGGGATAACAGGGTAATCTTTAACCTTCTTAGTAGCCAGGGAAT | 642 | NoName28_m2 | GTGACTGGAGTTCAGACGTGTGCTCTTCCGATCTAGCATTACACAACCCCTAGAAAGTC | 734 |
| NoName28_p1 | CCCCTTAGGGATAACAGGGTAATCTGCACATATTCCACGTGGGCATA | 643 | NoName28_p2 | GTGACTGGAGTTCAGACGTGTGCTCTTCCGATCTCACTGTGTCATATTGCCTGCATGTCT | 735 |
| NoName29_m1 | CCCCTTAGGGATAACAGGGTAATCCCACAGACATCAGAGCAGACACA | 644 | NoName29_m2 | GTGACTGGAGTTCAGACGTGTGCTCTTCCGATCTCCCCCAGCCCTAGTCCACA | 736 |
| NoName29_p1 | CCCCTTAGGGATAACAGGGTAATCACACCTGGTGAGGGCAACTG | 645 | NoName29_p2 | GTGACTGGAGTTCAGACGTGTGCTCTTCCGATCTGTGAGGGCAACTGACAAAAGCAATT | 737 |
| NoName3_m1 | CCCCTTAGGGATAACAGGGTAATCGAGGCCAGGTCCTACATTGAGC | 646 | NoName3_m2 | GTGACTGGAGTTCAGACGTGTGCTCTTCCGATCTGGCCAGGTCCTACATTGAGCAATCAT | 738 |
| NoName3_p1 | CCCCTTAGGGATAACAGGGTAATCTCTTTCTGTCAGAGGCAATGGT | 647 | NoName3_p2 | GTGACTGGAGTTCAGACGTGTGCTCTTCCGATCTGGCAATGGTGTCCACTTTGGA | 739 |
| NoName30_m1 | CCCCTTAGGGATAACAGGGTAATCCCCTGTCTGCCACCTGTTGTC | 648 | NoName30_m2 | GTGACTGGAGTTCAGACGTGTGCTCTTCCGATCTCCTGTCTGCCACCTGTTGTCATTAAC | 740 |
| NoName30_p1 | CCCCTTAGGGATAACAGGGTAATCGGCCTCTTCTCAATCCCAGTGC | 649 | NoName30_p2 | GTGACTGGAGTTCAGACGTGTGCTCTTCCGATCTCCTCTTCTCAATCCCAGTGCCTACTC | 741 |
| NoName31_m1 | CCCCTTAGGGATAACAGGGTAATCCATCCCTGACAGCAATGACTCACTC | 650 | NoName31_m2 | GTGACTGGAGTTCAGACGTGTGCTCTTCCGATCTCTGACAGCAATGACTCACTCCCCTTG | 742 |
| NoName31_p1 | CCCCTTAGGGATAACAGGGTAATCTGTGAGAGTCTGGCCTTTACTGGT | 651 | NoName31_p2 | GTGACTGGAGTTCAGACGTGTGCTCTTCCGATCTTGAATCAGGAGGGGCTATGTAGTTCT | 743 |
| NoName32_m1 | CCCCTTAGGGATAACAGGGTAATCTTGGACCTCCCCTGCGTGA | 652 | NoName32_m2 | GTGACTGGAGTTCAGACGTGTGCTCTTCCGATCTACCTCCCCTGCGTGAAACTGTTCTA | 744 |
| NoName32_p1 | CCCCTTAGGGATAACAGGGTAATCACTATGTGGACTGTGGGACTCTATGA | 653 | NoName32_p2 | GTGACTGGAGTTCAGACGTGTGCTCTTCCGATCTTGGACTGTGGGACTCTATGAATGTGG | 745 |
| NoName33_p1 | CCCCTTAGGGATAACAGGGTAATCTTTCAA | 654 | NoName33_p2 | GTGACTGGAGTTCAGACGTGTGCTCTTC | 746 |

TABLE_6-continued

Sequences of anchored primers for PD1

| First PCR primer name | Sequence | SEQ ID NO: | Second PCR primer name | Sequence | SEQ ID NO: |
|---|---|---|---|---|---|
| | AGGGGAATGTACTACCGT | | | CGATCTAGGGGAATGTACTACCGTCACTTT | |
| NoName34_m1 | CCCCTTAGGGATAACAGGGTAATCGGCCTGCAACCCCGCTAC | 655 | NoName34_m2 | GTGACTGGAGTTCAGACGTGTGCTCTTCCGATCTTGCAACCCCGCTACTTCCTCCT | 747 |
| NoName34_p1 | CCCCTTAGGGATAACAGGGTAATCGCTAGGCCCTGGAGATGCTAC | 656 | NoName34_p2 | GTGACTGGAGTTCAGACGTGTGCTCTTCCGATCTCAGGGATCAGGCCAGGTAAAACA | 748 |
| NoName35_m1 | CCCCTTAGGGATAACAGGGTAATCAGTCCAGCGTTTGAATCAGATCATGG | 657 | NoName35_m2 | GTGACTGGAGTTCAGACGTGTGCTCTTCCGATCTCATGGAAGATGGCTCTAGAGGAAGCT | 749 |
| NoName35_p1 | CCCCTTAGGGATAACAGGGTAATCCGTGGGCACTGAGAGCACCA | 658 | NoName35_p2 | GTGACTGGAGTTCAGACGTGTGCTCTTCCGATCTTGGGCACTGAGAGCACCATCATGG | 750 |
| NoName36_p1 | CCCCTTAGGGATAACAGGGTAATCGGATTGCAGGGTATCCACGTCTAAAT | 659 | NoName36_p2 | GTGACTGGAGTTCAGACGTGTGCTCTTCCGATCTATGCATGAAGGCCAGCACAATGGG | 751 |
| NoName37_m1 | CCCCTTAGGGATAACAGGGTAATCGTGTGTCTCACGTGGTGGGT | 660 | NoName37_m2 | GTGACTGGAGTTCAGACGTGTGCTCTTCCGATCTCACGTGGTGGGTGATTTTTATTCCAG | 752 |
| NoName37_p1 | CCCCTTAGGGATAACAGGGTAATCGGCTGGAATACCCTTTGTAGTTGGG | 661 | NoName37_p2 | GTGACTGGAGTTCAGACGTGTGCTCTTCCGATCTGGGGGCTGCCTGTGTGTTA | 753 |
| NoName38_m1 | CCCCTTAGGGATAACAGGGTAATCAGCAAGGCGTGGCTGGTG | 662 | NoName38_m2 | GTGACTGGAGTTCAGACGTGTGCTCTTCCGATCTCATGGGCAAGAGCATGCTGGTA | 754 |
| NoName38_p1 | CCCCTTAGGGATAACAGGGTAATCTCCAGTGCCCTATCAGAGTAATTCCT | 663 | NoName38_p2 | GTGACTGGAGTTCAGACGTGTGCTCTTCCGATCTCATAGCTTCTTTGCTGGCCGACCA | 755 |
| NoName39_m1 | CCCCTTAGGGATAACAGGGTAATCGAGGATGTAAGTAGCGCTTGTGAACA | 664 | NoName39_m2 | GTGACTGGAGTTCAGACGTGTGCTCTTCCGATCTCACAGCCCCAGGTCCTTTGCG | 756 |
| NoName39_p1 | CCCCTTAGGGATAACAGGGTAATCTGGAGACAGCGTAAGTGTCCCT | 665 | NoName39_p2 | GTGACTGGAGTTCAGACGTGTGCTCTTCCGATCTAGTGTCCCTGTCCTCACGCT | 757 |
| NoName4_m1 | CCCCTTAGGGATAACAGGGTAATCGCAATAAACACTGCCTAGAGCCTAT | 666 | NoName4_m2 | GTGACTGGAGTTCAGACGTGTGCTCTTCCGATCTCACTGCCTAGAGCCTATATTGCAAAG | 758 |
| NoName40_p1 | CCCCTTAGGGATAACAGGGTAATCGGCCTT | 667 | NoName40_p2 | GTGACTGGAGTTCAGACGTGTGCTCTTC | 759 |

TABLE_6-continued

Sequences of anchored primers for PD1

| First PCR primer name | Sequence | SEQ ID NO: | Second PCR primer name | Sequence | SEQ ID NO: |
|---|---|---|---|---|---|
| | AAAAATTGCTGCGCAGT | | | CGATCTCTTAAAAATTGCTGCGCAGTGGCTGT | |
| NoName41_m1 | CCCCTTAGGGATAACAGGGTAATCTGCTCAAGACAGGCCAAGGAC | 668 | NoName41_m2 | GTGACTGGAGTTCAGACGTGTGCTCTTCCGATCTGCTCAAGACAGGCCAAGGACTTAGAA | 760 |
| NoName41_p1 | CCCCTTAGGGATAACAGGGTAATCTCTTTTCTACTGGGCCTCCACCT | 669 | NoName41_p2 | GTGACTGGAGTTCAGACGTGTGCTCTTCCGATCTGCTGCTCCCTTCCCCTCCAC | 761 |
| NoName42_m1 | CCCCTTAGGGATAACAGGGTAATCGCTTCCTTAGCCTGAGGTCACTAAAA | 670 | NoName42_m2 | GTGACTGGAGTTCAGACGTGTGCTCTTCCGATCTGAGGTCACTAAAAATGGCCAGTCTGC | 762 |
| NoName42_p1 | CCCCTTAGGGATAACAGGGTAATCAATCCAACCTAATAAGCACAGGCACT | 671 | NoName42_p2 | GTGACTGGAGTTCAGACGTGTGCTCTTCCGATCTACTGAGTGCTGGCATCAGGATTC | 763 |
| NoName43_m1 | CCCCTTAGGGATAACAGGGTAATCTCCTAGGCTTCTTTCCTCTCCCA | 672 | NoName43_m2 | GTGACTGGAGTTCAGACGTGTGCTCTTCCGATCTCCAGTAGCCTGTAGTCAGAAAGAGTG | 764 |
| NoName43_p1 | CCCCTTAGGGATAACAGGGTAATCGGGGCCACTGAGACTCCTCT | 673 | NoName43_p2 | GTGACTGGAGTTCAGACGTGTGCTCTTCCGATCTCTCCTCTTAGGACAACCGACCATCCT | 765 |
| NoName44_m1 | CCCCTTAGGGATAACAGGGTAATCACCTTTGGAACGATGGGGGTATTTT | 674 | NoName44_m2 | GTGACTGGAGTTCAGACGTGTGCTCTTCCGATCTACCTCTTGTTTCTCAAAACGCTGTCG | 766 |
| NoName44_p1 | CCCCTTAGGGATAACAGGGTAATCCTGGAGCATCGACGAGGGTGA | 675 | NoName44_p2 | GTGACTGGAGTTCAGACGTGTGCTCTTCCGATCTCATCGACGAGGGTGAGCGCATG | 767 |
| NoName45_p1 | CCCCTTAGGGATAACAGGGTAATCGGAGCATCGACGAGGGTGAG | 676 | NoName45_p2 | GTGACTGGAGTTCAGACGTGTGCTCTTCCGATCTTCGACGAGGGTGAGCGCATG | 768 |
| NoName46_m1 | CCCCTTAGGGATAACAGGGTAATCGCCTGCATTCATTCGTCCACAATAC | 677 | NoName46_m2 | GTGACTGGAGTTCAGACGTGTGCTCTTCCGATCTGCCCTGGGCTTGGCATGAA | 769 |
| NoName46_p1 | CCCCTTAGGGATAACAGGGTAATCAGATGCTGAGAGTTTACCCCCTCTAC | 678 | NoName46_p2 | GTGACTGGAGTTCAGACGTGTGCTCTTCCGATCTCCCCCTCTACCTCCCACCTT | 770 |
| NoName47_m1 | CCCCTTAGGGATAACAGGGTAATCTTTTTCTCCCCAAACGTGAGAAGA | 679 | NoName47_m2 | GTGACTGGAGTTCAGACGTGTGCTCTTCCGATCTTCCCCAAACGTGAGAAGAAAAGAGA | 771 |
| NoName48_m1 | CCCCTTAGGGATAACAGGGTAATCACTGTT | 680 | NoName48_m2 | GTGACTGGAGTTCAGACGTGTGCTCTTC | 772 |

TABLE_6-continued

Sequences of anchored primers for PD1

| First PCR primer name | Sequence | SEQ ID NO: | Second PCR primer name | Sequence | SEQ ID NO: |
|---|---|---|---|---|---|
| | GGGGTGACTAACTGT | | | CGATCTGACTAACTGTCATGGTTTTCCCACG | |
| NoName48_p1 | CCCCTTAGGGATAACAGGGTAATCTTGCTAACAGTGGTGAGTTGTAATA | 681 | NoName48_p2 | GTGACTGGAGTTCAGACGTGTGCTCTTCCGATCTAACAGTGGTGAGTTGTAATACTAGCT | 773 |
| NoName49_p1 | CCCCTTAGGGATAACAGGGTAATCAGTTCCTGATCCGGCTCTGGA | 682 | NoName49_p2 | GTGACTGGAGTTCAGACGTGTGCTCTTCCGATCTTCCGGCTCTGGATTTGTGCACAG | 774 |
| NoName50_m1 | CCCCTTAGGGATAACAGGGTAATCCGAGAGGCTCCAGGACCATGACT | 683 | NoName50_m2 | GTGACTGGAGTTCAGACGTGTGCTCTTCCGATCTGCGCTGCACGGCCTCCAC | 775 |
| NoName50_p1 | CCCCTTAGGGATAACAGGGTAATCGGGCTGGCGGGGTGGGAA | 684 | NoName50_p2 | GTGACTGGAGTTCAGACGTGTGCTCTTCCGATCTGGGTGGGAAGGGAGGGTCAG | 776 |
| NoName51_m1 | CCCCTTAGGGATAACAGGGTAATCGTGCTGGCTGAATTAATAGGAGGCA | 685 | NoName51_m2 | GTGACTGGAGTTCAGACGTGTGCTCTTCCGATCTAATAGGAGGCACATCTCATCCATTGC | 777 |
| NoName51_p1 | CCCCTTAGGGATAACAGGGTAATCCAAGGTCTTTCAACTTGGGCCAGAT | 686 | NoName51_p2 | GTGACTGGAGTTCAGACGTGTGCTCTTCCGATCTGAGCACTGCAGGACGTTCAGCA | 778 |
| NoName52_m1 | CCCCTTAGGGATAACAGGGTAATCCCTTGGGTCCTGTCCTGGCA | 687 | NoName52_m2 | GTGACTGGAGTTCAGACGTGTGCTCTTCCGATCTTGCTATGAGCTGCCCCTGGGT | 779 |
| NoName52_p1 | CCCCTTAGGGATAACAGGGTAATCCGGGGTTCACTGGCCCAGA | 688 | NoName52_p2 | GTGACTGGAGTTCAGACGTGTGCTCTTCCGATCTTTCACTGGCCCAGAGCTGTGC | 780 |
| NoName6_m1 | CCCCTTAGGGATAACAGGGTAATCAAGGGAGCGGGGATTATGGC | 689 | NoName6_2 | GTGACTGGAGTTCAGACGTGTGCTCTTCCGATCTAGGACCAGGGTCATGACTAGCTAAA | 781 |
| NoName6_p1 | CCCCTTAGGGATAACAGGGTAATCGATCATGCACCCCGTCCTGAC | 690 | NoName6_p2 | GTGACTGGAGTTCAGACGTGTGCTCTTCCGATCTGTCCTGACCCTGACGCTGCAC | 782 |
| NoName7_m1 | CCCCTTAGGGATAACAGGGTAATCCAGACCTGCCGTGGACCTT | 691 | NoName7_m2 | GTGACTGGAGTTCAGACGTGTGCTCTTCCGATCTGCCGTGGACCTTGGCTTCC | 783 |
| NoName7_p1 | CCCCTTAGGGATAACAGGGTAATCAGCCGGCGCTAAGAGCAG | 692 | NoName7_p2 | GTGACTGGAGTTCAGACGTGTGCTCTTCCGATCTGGCGCTAAGAGCAGCTGACC | 784 |
| NoName8_m1 | CCCCTTAGGGATAACAGGGTAATCGCCTGGATCCCACCCTTGC | 693 | NoName8_m2 | GTGACTGGAGTTCAGACGTGTGCTCTTCCGATCTGTGTGGCACAGTGAGGGGTGT | 785 |

TABLE_6-continued

Sequences of anchored primers for PD1

| First PCR primer name | Sequence | SEQ ID NO: | Second PCR primer name | Sequence | SEQ ID NO: |
|---|---|---|---|---|---|
| NoName8_p1 | CCCCTTAGGGATAAC AGGGTAATCCTGGTC CCGCCGCAGCCT | 694 | NoName8_p2 | GTGACTGGAGTTCA GACGTGTGCTCTTC CGATCTCCGCCGCA GCCTCGCAGA | 786 |
| NoName9_m1 | CCCCTTAGGGATAAC AGGGTAATCGCCCTG GCTATTTGCAAACTG CAT | 695 | NoName9_m2 | GTGACTGGAGTTCA GACGTGTGCTCTTC CGATCTATGCTGTC CCAGTTCTCTCACC ACT | 787 |
| NoName9_p1 | CCCCTTAGGGATAAC AGGGTAATCACAGA GATGCAGATAGCCAG GTTAGA | 696 | NoName9_p2 | GTGACTGGAGTTCA GACGTGTGCTCTTC CGATCTGGCAGGGA TAGGTGAGCTTCAA A | 788 |
| PD1_m1 | CCCCTTAGGGATAAC AGGGTAATCGGGTGG AAGGTCCCTCCAG | 697 | PD1_m2 | GTGACTGGAGTTCA GACGTGTGCTCTTC CGATCTCCCTGGCT CTGGGACACCT | 789 |
| PD1_p1 | CCCCTTAGGGATAAC AGGGTAATCAGTGGA GAAGGCGGCACTC | 698 | PD1_p2 | GTGACTGGAGTTCA GACGTGTGCTCTTC CGATCTACTCTGGT GGGGCTGCTCCA | 790 |

TABLE_7

Sequences of anchored primers for TRAC

| First PCR primer name | Sequence | SEQ ID NO: | Second PCR primer name | Sequence | SEQ ID NO: |
|---|---|---|---|---|---|
| NoName1_m1 | CCCCTTAGGGATAAC AGGGTAATCAAGTAG GGCTCAGGGTCGAA GG | 791 | NoName1_m2 | GTGACTGGAGTTCA GACGTGTGCTCTTC CGATCTGGCTCAGG GTCGAAGGCTCACT | 876 |
| NoName1_p1 | CCCCTTAGGGATAAC AGGGTAATCGCAATG GCCGCTGGGAAAAA T | 792 | NoName1_p2 | GTGACTGGAGTTCA GACGTGTGCTCTTC CGATCTTCAAACCA TCGGGGGAAAAAT GACAA | 877 |
| NoName10_m1 | CCCCTTAGGGATAAC AGGGTAATCCTATCA TTGTAGATGGGGCCG GAAA | 793 | NoName10_m2 | GTGACTGGAGTTCA GACGTGTGCTCTTC CGATCTGTAGATGG GGCCGGAAAGTAG AAAAG | 878 |
| NoName10_p1 | CCCCTTAGGGATAAC AGGGTAATCGCCACT GCCACTGTAGCCT | 794 | NoName10_p2 | GTGACTGGAGTTCA GACGTGTGCTCTTC CGATCTCCCAGCTC CAAGTCCATCTGG | 879 |
| NoName12_m1 | CCCCTTAGGGATAAC AGGGTAATCCAACTC CAGGGCTCAAGCAA TCG | 795 | NoName12_m2 | GTGACTGGAGTTCA GACGTGTGCTCTTC CGATCTGCTACCAA GCCCCACCCT | 880 |
| NoName12_p1 | CCCCTTAGGGATAAC AGGGTAATCGCAGAC ATTTGACCACCCTAT ACCC | 796 | NoName12_p2 | GTGACTGGAGTTCA GACGTGTGCTCTTC CGATCTCACCCTATA CCCACCATACTCAC GTT | 881 |

TABLE_7-continued

| First PCR primer name | Sequence | SEQ ID NO: | Second PCR primer name | Sequence | SEQ ID NO: |
|---|---|---|---|---|---|
| Sequences of anchored primers for TRAC | | | | | |
| NoName13_m1 | CCCCTTAGGGATAACAGGGTAATCGCAGTAGGGAAGGGGCAACT | 797 | NoName13_m2 | GTGACTGGAGTTCAGACGTGTGCTCTTCCGATCTAGGGAAGGGGCAACTTTTCAAAATCT | 882 |
| NoName13_p1 | CCCCTTAGGGATAACAGGGTAATCGTCTTTCTCTGGCACCAAGCTTTTG | 798 | NoName13_p2 | GTGACTGGAGTTCAGACGTGTGCTCTTCCGATCTGCACCAAGCTTTTGTGATGCTCCAAC | 883 |
| NoName14_m1 | CCCCTTAGGGATAACAGGGTAATCTGGCACCTGCAGGAAACGGT | 799 | NoName14_m2 | GTGACTGGAGTTCAGACGTGTGCTCTTCCGATCTCACCTGCAGGAAACGGTTGCGTTC | 884 |
| NoName14_p1 | CCCCTTAGGGATAACAGGGTAATCCTGGGCCACCTGGTGTCG | 800 | NoName14_p2 | GTGACTGGAGTTCAGACGTGTGCTCTTCCGATCTGCTGGGCCGCCTGATCTACC | 885 |
| NoName15_m1 | CCCCTTAGGGATAACAGGGTAATCCCTTGGGCCAGTCACTGCA | 801 | NoName15_m2 | GTGACTGGAGTTCAGACGTGTGCTCTTCCGATCTGCCAGTCACTGCAGCTCTCT | 886 |
| NoName15_p1 | CCCCTTAGGGATAACAGGGTAATCTGACCACATGTCCACCGTTCAG | 802 | NoName15_p2 | GTGACTGGAGTTCAGACGTGTGCTCTTCCGATCTACATGTCCACCGTTCAGACACAGC | 887 |
| NoName16_m1 | CCCCTTAGGGATAACAGGGTAATCAGCTTGGGAGGCTGGTACTACTG | 803 | NoName16_m2 | GTGACTGGAGTTCAGACGTGTGCTCTTCCGATCTGGGAGGCTGGTACTACTGGGCATC | 888 |
| NoName16_p1 | CCCCTTAGGGATAACAGGGTAATCCCCAGACACTGCTTCCCTGGTA | 804 | NoName16_p2 | GTGACTGGAGTTCAGACGTGTGCTCTTCCGATCTAGACACTGCTTCCCTGGTAATGGAC | 889 |
| NoName17_p1 | CCCCTTAGGGATAACAGGGTAATCTTCCTCCTGCCAGGGTGCA | 805 | NoName17_p2 | GTGACTGGAGTTCAGACGTGTGCTCTTCCGATCTCCTGCCAGGGTGCAAGAACT | 890 |
| NoName18_m1 | CCCCTTAGGGATAACAGGGTAATCTGTACCATGAATGTTGTGGCGCAT | 806 | NoName18_m2 | GTGACTGGAGTTCAGACGTGTGCTCTTCCGATCTCCATGAATGTTGTGGCGCATTTTCAT | 891 |
| NoName18_p1 | CCCCTTAGGGATAACAGGGTAATCAGTCTGGGTCAAGTGCTGTGG | 807 | NoName18_p2 | GTGACTGGAGTTCAGACGTGTGCTCTTCCGATCTTGCTGTGGGCTCCTTTGCTT | 892 |
| NoName19_p1 | CCCCTTAGGGATAACAGGGTAATCGGAACAAAGGACCTACATGTGGCT | 808 | NoName19_p2 | GTGACTGGAGTTCAGACGTGTGCTCTTCCGATCTCAAAGGACCTACATGTGGCTCCAATT | 893 |
| NoName2_m1 | CCCCTTAGGGATAACAGGGTAATCACATAAGCGAAGGATCAGGAGAGT | 809 | NoName2_m2 | GTGACTGGAGTTCAGACGTGTGCTCTTCCGATCTGCGAAGGATCAGGAGAGTACTATTAG | 894 |

TABLE_7-continued

Sequences of anchored primers for TRAC

| First PCR primer name | Sequence | SEQ ID NO: | Second PCR primer name | Sequence | SEQ ID NO: |
|---|---|---|---|---|---|
| NoName20_m1 | CCCCTTAGGGATAAC AGGGTAATCTCTAGA GAACATCCGGCAATG CC | 810 | NoName20_m2 | GTGACTGGAGTTCA GACGTGTGCTCTTC CGATCTAGGGGTGG GAGAGTGCTACT | 895 |
| NoName21_m1 | CCCCTTAGGGATAAC AGGGTAATCCCTTAG GCCAAACATCCTTGA CCATA | 811 | NoName21_m2 | GTGACTGGAGTTCA GACGTGTGCTCTTC CGATCTTGTATGTTG GTTATGCGGGAAGA GAC | 896 |
| NoName21_p1 | CCCCTTAGGGATAAC AGGGTAATCTCCCCA AAGTCTAAGGAGGC TAAGA | 812 | NoName21_p2 | GTGACTGGAGTTCA GACGTGTGCTCTTC CGATCTTGGATTTC CAAAGAGAAGCCC TAGTC | 897 |
| NoName22_p1 | CCCCTTAGGGATAAC AGGGTAATCCCTGAA AAACGGATGAGACT TCAG | 813 | NoName22_p2 | GTGACTGGAGTTCA GACGTGTGCTCTTC CGATCTACGGATGA GACTTCAGTGAGTA C | 898 |
| NoName23_p1 | CCCCTTAGGGATAAC AGGGTAATCATTGTG CTTCAGATCCCGTGA CAT | 814 | NoName23_p2 | GTGACTGGAGTTCA GACGTGTGCTCTTC CGATCTTGCTTCAG ATCCCGTGACATCA GTGT | 899 |
| NoName24_m1 | CCCCTTAGGGATAAC AGGGTAATCGTGGGG ACTTGCTGCTGGT | 815 | NoName24_m2 | GTGACTGGAGTTCA GACGTGTGCTCTTC CGATCTAGTGGGGA CTTGCTGCTGGTAT CTAC | 900 |
| NoName24_p1 | CCCCTTAGGGATAAC AGGGTAATCAGCTCT GCTACATTCAGGTAA CAT | 816 | NoName24_p2 | GTGACTGGAGTTCA GACGTGTGCTCTTC CGATCTGCTACATT CAGGTAACATGTTT CTGC | 901 |
| NoName25_m1 | CCCCTTAGGGATAAC AGGGTAATCTCCCTC TTTAGCATCGCCAAA TCC | 817 | NoName25_m2 | GTGACTGGAGTTCA GACGTGTGCTCTTC CGATCTGCCAAATC CTCCCAGGTGCA | 902 |
| NoName25_p1 | CCCCTTAGGGATAAC AGGGTAATCTTGGTG GCCACAACTTAGGTG AGA | 818 | NoName25_p2 | GTGACTGGAGTTCA GACGTGTGCTCTTC CGATCTGGCCACAA CTTAGGTGAGAGTG ACGA | 903 |
| NoName26_m1 | CCCCTTAGGGATAAC AGGGTAATCCCCAGG TGTTGCTCATCAGTT CCTCT | 819 | NoName26_m2 | GTGACTGGAGTTCA GACGTGTGCTCTTC CGATCTCCTCTGAA CTAAGTGGGAGTTT GGC | 904 |
| NoName26_p1 | CCCCTTAGGGATAAC AGGGTAATCATCACT TTCTCAAGGGACATG CCAT | 820 | NoName26_p2 | GTGACTGGAGTTCA GACGTGTGCTCTTC CGATCTTGCCATTTC TCTAATCAAGGGGT GTG | 905 |
| NoName27_m1 | CCCCTTAGGGATAAC AGGGTAATCGTCTCA CAACTCCCAGTCTTG CTTTA | 821 | NoName27_m2 | GTGACTGGAGTTCA GACGTGTGCTCTTC CGATCTTCCCAGTC TTGCTTTATACTGTG CCT | 906 |
| NoName27_p1 | CCCCTTAGGGATAAC AGGGTAATCAACTGG | 822 | NoName27_p2 | GTGACTGGAGTTCA GACGTGTGCTCTTC | 907 |

TABLE_7-continued

| Sequences of anchored primers for TRAC | | | | | |
|---|---|---|---|---|---|
| First PCR primer name | Sequence | SEQ ID NO: | Second PCR primer name | Sequence | SEQ ID NO: |
| | GCTCGTTGGTTACCC T | | | CGATCTCTGGGCTC GTTGGTTACCCTATT CCT | |
| NoName28_m1 | CCCCTTAGGGATAAC AGGGTAATCTTTGGT TTGGTTGCTTTGCAG ACTAC | 823 | NoName28_m2 | GTGACTGGAGTTCA GACGTGTGCTCTTC CGATCTGAGGAGCT ACCAGGGCCCTA | 908 |
| NoName3_m1 | CCCCTTAGGGATAAC AGGGTAATCCTTTTC TGCTGTCACCCTCAA GGAT | 824 | NoName3_m2 | GTGACTGGAGTTCA GACGTGTGCTCTTC CGATCTACCTCATC ATTTCTCAGGCGAA AGG | 909 |
| NoName3_p1 | CCCCTTAGGGATAAC AGGGTAATCGAGTGA ATGCATGATTGTGTG ACCGA | 825 | NoName3_p2 | GTGACTGGAGTTCA GACGTGTGCTCTTC CGATCTGCATGATT GTGTGACCGAATGC CTCA | 910 |
| NoName30_m1 | CCCCTTAGGGATAAC AGGGTAATCTGCTAG TGTCGAGGTTTGCA | 826 | NoName30_m2 | GTGACTGGAGTTCA GACGTGTGCTCTTC CGATCTGGTTTGCA CCATAGAAAGCTGA G | 911 |
| NoName30_p1 | CCCCTTAGGGATAAC AGGGTAATCGTGGAG AAAGTGCTAAACAA GAAAA | 827 | NoName30_p2 | GTGACTGGAGTTCA GACGTGTGCTCTTC CGATCTGGTAAACC AGAACTATCTTTCT CTCC | 912 |
| NoName31_m1 | CCCCTTAGGGATAAC AGGGTAATCCTCCAG AGTCTATGCTCAACT GAA | 828 | NoName31_m2 | GTGACTGGAGTTCA GACGTGTGCTCTTC CGATCTGAACTTGA AATGCTTACAGCCA GAAT | 913 |
| NoName32_m1 | CCCCTTAGGGATAAC AGGGTAATCATGGCC ATAAGTTGAAATTTG CGT | 829 | NoName32_m2 | GTGACTGGAGTTCA GACGTGTGCTCTTC CGATCTCCATAAGT TGAAATTTGCGTTT CGGT | 914 |
| NoName33_m1 | CCCCTTAGGGATAAC AGGGTAATCGGGACC TCAGGTGCTGCTT | 830 | NoName33_m2 | GTGACTGGAGTTCA GACGTGTGCTCTTC CGATCTCCTCAGGT GCTGCTTCCTCAA | 915 |
| NoName33_p1 | CCCCTTAGGGATAAC AGGGTAATCTGATTC AATCTTACATGCGAC AGCCT | 831 | NoName33_p2 | GTGACTGGAGTTCA GACGTGTGCTCTTC CGATCTCATGCGAC AGCCTGATCCGTTT CT | 916 |
| NoName34_m1 | CCCCTTAGGGATAAC AGGGTAATCAGAGA AGCCTGTCAGGACC AT | 832 | NoName34_m2 | GTGACTGGAGTTCA GACGTGTGCTCTTC CGATCTGCCTGTCA GGACCATACAAATC TTAC | 917 |
| NoName34_p1 | CCCCTTAGGGATAAC AGGGTAATCTCACCG TCTACTTCTCTTGTGT G | 833 | NoName34_p2 | GTGACTGGAGTTCA GACGTGTGCTCTTC CGATCTTTCTCTTGT GTGATCCAGAGTTG ACA | 918 |
| NoName35_m1 | CCCCTTAGGGATAAC AGGGTAATCCCACAT GCAAATGAACGACA CTGAC | 834 | NoName35_m2 | GTGACTGGAGTTCA GACGTGTGCTCTTC CGATCTAACGACAC TGACAGAAAACAC TCACG | 919 |

TABLE_7-continued

Sequences of anchored primers for TRAC

| First PCR primer name | Sequence | SEQ ID NO: | Second PCR primer name | Sequence | SEQ ID NO: |
|---|---|---|---|---|---|
| NoName36_m1 | CCCCTTAGGGATAACAGGGTAATCGCAGCAATTTGGTCCCCCATGG | 835 | NoName36_m2 | GTGACTGGAGTTCAGACGTGTGCTCTTCCGATCTAGCAATTTGGTCCCCCATGGAGAGAC | 920 |
| NoName36_p1 | CCCCTTAGGGATAACAGGGTAATCTCAGACCGTGACTCAGTATGTTG | 836 | NoName36_p2 | GTGACTGGAGTTCAGACGTGTGCTCTTCCGATCTAAAACTTGACTGTTCATTGGGTTCAA | 921 |
| NoName37_m1 | CCCCTTAGGGATAACAGGGTAATCAGGCCCCTGTCTCTACCATCC | 837 | NoName37_m2 | GTGACTGGAGTTCAGACGTGTGCTCTTCCGATCTCCCCTGTCTCTACCATCCTAGACACC | 922 |
| NoName37_p1 | CCCCTTAGGGATAACAGGGTAATCGTGGAGAAGGCAGCCTCCCAA | 838 | NoName37_p2 | GTGACTGGAGTTCAGACGTGTGCTCTTCCGATCTAGAAGGCAGCCTCCCAAAGCACT | 923 |
| NoName38_m1 | CCCCTTAGGGATAACAGGGTAATCTGCCTGGAGTGGTGTCTGGT | 839 | NoName38_m2 | GTGACTGGAGTTCAGACGTGTGCTCTTCCGATCTGCCTGGAGTGGTGTCTGGTACAATGA | 924 |
| NoName38_p1 | CCCCTTAGGGATAACAGGGTAATCACAGACCTCAGAGCCCAGTCC | 840 | NoName38_p2 | GTGACTGGAGTTCAGACGTGTGCTCTTCCGATCTGTCCCTGGCCTTAAAGAAATGACAGA | 925 |
| NoName39_m1 | CCCCTTAGGGATAACAGGGTAATCGCACACAGCCAACAAGATGACTCA | 841 | NoName39_m2 | GTGACTGGAGTTCAGACGTGTGCTCTTCCGATCTAGCCTTGATTACTGTTCCCACTAGC | 926 |
| NoName39_p1 | CCCCTTAGGGATAACAGGGTAATCCCCCTGTTTTTACCTCAACCTTAGGG | 842 | NoName39_p2 | GTGACTGGAGTTCAGACGTGTGCTCTTCCGATCTGGGCTTCCTTGCTTTGGTTACTGT | 927 |
| NoName4_m1 | CCCCTTAGGGATAACAGGGTAATCTCACTGCTGCCCCCACAAG | 843 | NoName4_m2 | GTGACTGGAGTTCAGACGTGTGCTCTTCCGATCTCACTGCTGCCCCCACAAGCTTAAC | 928 |
| NoName4_p1 | CCCCTTAGGGATAACAGGGTAATCGGCCAGGCCGGAGTCAGG | 844 | NoName4_p2 | GTGACTGGAGTTCAGACGTGTGCTCTTCCGATCTGCCGGAGTCAGGGGCATC | 929 |
| NoName40_m1 | CCCCTTAGGGATAACAGGGTAATCTTGGAATGGCAATCCGTTGGAAATG | 845 | NoName40_m2 | GTGACTGGAGTTCAGACGTGTGCTCTTCCGATCTATGGCAATCCGTTGGAAATGTCTTCT | 930 |
| NoName40_p1 | CCCCTTAGGGATAACAGGGTAATCTGGAACTGTGGGCATAAGCATATGTC | 846 | NoName40_p2 | GTGACTGGAGTTCAGACGTGTGCTCTTCCGATCTCCCATACCCCACTCCCACTACT | 931 |
| NoName41_m1 | CCCCTTAGGGATAACAGGGTAATCACAGGT | 847 | NoName41_m2 | GTGACTGGAGTTCAGACGTGTGCTCTTC | 932 |

TABLE_7-continued

| Sequences of anchored primers for TRAC | | | | | |
|---|---|---|---|---|---|
| First PCR primer name | Sequence | SEQ ID NO: | Second PCR primer name | Sequence | SEQ ID NO: |
| | TTCAGGCGGAGTGGA | | | CGATCTCAGGTTTCAGGCGGAGTGGAAGAAGT | |
| NoName41_p1 | CCCCTTAGGGATAACAGGGTAATCAGGAGGAATTAACCCTGTGAACATCG | 848 | NoName41_p2 | GTGACTGGAGTTCAGACGTGTGCTCTTCCGATCTAACCCTGTGAACATCGTGATTCCAG | 933 |
| NoName42_p1 | CCCCTTAGGGATAACAGGGTAATCTTTCACAAGAACGGTACTGGCCAAT | 849 | NoName42_p2 | GTGACTGGAGTTCAGACGTGTGCTCTTCCGATCTCGGTACTGGCCAATGAAATTTTCCCA | 934 |
| NoName43_m1 | CCCCTTAGGGATAACAGGGTAATCATAAGAGGTGAACTAGCAAGCAGAGC | 850 | NoName43_m2 | GTGACTGGAGTTCAGACGTGTGCTCTTCCGATCTTTGGCTCTCTGGATTGTTCCTCTAAA | 935 |
| NoName43_p1 | CCCCTTAGGGATAACAGGGTAATCAGAGTGTAAGCTCACCCTACAGTCT | 851 | NoName43_p2 | GTGACTGGAGTTCAGACGTGTGCTCTTCCGATCTCACCCTACAGTCTATGTTCCAGGTCA | 936 |
| NoName44_m1 | CCCCTTAGGGATAACAGGGTAATCGACAGCAAGTCCAGACTAAGGCA | 852 | NoName44_m2 | GTGACTGGAGTTCAGACGTGTGCTCTTCCGATCTCCAGACTAAGGCAAGCAACTGTAACA | 937 |
| NoName44_p1 | CCCCTTAGGGATAACAGGGTAATCGAGGTAGGGTTCTTCGTGTTGGC | 853 | NoName44_p2 | GTGACTGGAGTTCAGACGTGTGCTCTTCCGATCTCTTCGTGTTGGCCAGGTGGGT | 938 |
| NoName45_m1 | CCCCTTAGGGATAACAGGGTAATCCCTAAGTGGAGTTGACCTGTACAAGG | 854 | NoName45_m2 | GTGACTGGAGTTCAGACGTGTGCTCTTCCGATCTTGAAGCTGAGTTACCTGGGAGCTC | 939 |
| NoName45_p1 | CCCCTTAGGGATAACAGGGTAATCCTTCAGCCACTCCCTTATGAGGTAG | 855 | NoName45_p2 | GTGACTGGAGTTCAGACGTGTGCTCTTCCGATCTCTTACGGGAAAGCAAGTTGACTTTGC | 940 |
| NoName46_m1 | CCCCTTAGGGATAACAGGGTAATCACACCAGGCTACAAGTCTCCTGA | 856 | NoName46_m2 | GTGACTGGAGTTCAGACGTGTGCTCTTCCGATCTACAAAACAAAACCCTCCGGATGGTCT | 941 |
| NoName46_p1 | CCCCTTAGGGATAACAGGGTAATCCCCTGCTCCTGTCTGCCTGATTA | 857 | NoName46_p2 | GTGACTGGAGTTCAGACGTGTGCTCTTCCGATCTTGCTCCTGTCTGCCTGATTACTTACT | 942 |
| NoName47_m1 | CCCCTTAGGGATAACAGGGTAATCAAGGCTTGTTCACCCTGAGGAG | 858 | NoName47_m2 | GTGACTGGAGTTCAGACGTGTGCTCTTCCGATCTGGTCATGCCTCCAACCTGCA | 943 |
| NoName47_p1 | CCCCTTAGGGATAACAGGGTAATCGGAAAGCTAAAAGATTTGCGTTGACT | 859 | NoName47_p2 | GTGACTGGAGTTCAGACGTGTGCTCTTCCGATCTTTGCGTTGACTTAAATGAAAGTGTCC | 944 |

TABLE_7-continued

Sequences of anchored primers for TRAC

| First PCR primer name | Sequence | SEQ ID NO: | Second PCR primer name | Sequence | SEQ ID NO: |
|---|---|---|---|---|---|
| NoName48_p1 | CCCCTTAGGGATAACAGGGTAATCTCCTTCCACGGAGTTCACTGAGT | 860 | NoName48_p2 | GTGACTGGAGTTCAGACGTGTGCTCTTCCGATCTACTGTCGGGAGAAGGCGTCT | 945 |
| NoName49_m1 | CCCCTTAGGGATAACAGGGTAATCAGCTTTGGCCCCTAGGATTCTG | 861 | NoName49_m2 | GTGACTGGAGTTCAGACGTGTGCTCTTCCGATCTTGATCTGTTTGTGAATGGCTCAGACA | 946 |
| NoName49_p1 | CCCCTTAGGGATAACAGGGTAATCCTCTGGGTGCGGGGGAACT | 862 | NoName49_p2 | GTGACTGGAGTTCAGACGTGTGCTCTTCCGATCTACTCTGGGTGCGGGGGAACTTATTTG | 947 |
| NoName5_m1 | CCCCTTAGGGATAACAGGGTAATCTCCAGTGATCTAGTAACTCCGTGGT | 863 | NoName5_m2 | GTGACTGGAGTTCAGACGTGTGCTCTTCCGATCTCCGTGGTGGATTTAACTCCCCTATTG | 948 |
| NoName5_p1 | CCCCTTAGGGATAACAGGGTAATCCCTTCAGAAACTAGTTAGCCCTGT | 864 | NoName5_p2 | GTGACTGGAGTTCAGACGTGTGCTCTTCCGATCTAGCATTCTGCCTCTGACAGG | 949 |
| NoName50_m1 | CCCCTTAGGGATAACAGGGTAATCATGGTCCAAGGTCAGCTGGCGGACA | 865 | NoName50_m2 | GTGACTGGAGTTCAGACGTGTGCTCTTCCGATCTTCCAAGGTCAGCTGGCGGACA | 950 |
| NoName50_p1 | CCCCTTAGGGATAACAGGGTAATCAGGACCCACCACGGATTCCT | 866 | NoName50_p2 | GTGACTGGAGTTCAGACGTGTGCTCTTCCGATCTACGGATTCCTGCTGTACTGGCTAAAG | 951 |
| NoName6_m1 | CCCCTTAGGGATAACAGGGTAATCACTGCCTCCTCCTTAGTCGAT | 867 | NoName6_m2 | GTGACTGGAGTTCAGACGTGTGCTCTTCCGATCTTGCCTCCTCCTTAGTCGATTCTTACC | 952 |
| NoName6_p1 | CCCCTTAGGGATAACAGGGTAATCGCTGTAGACAGATTGGCCTCAGTT | 868 | NoName6_p2 | GTGACTGGAGTTCAGACGTGTGCTCTTCCGATCTAACAAGTGTCCCTGGCAAATGTGA | 953 |
| NoName7_m1 | CCCCTTAGGGATAACAGGGTAATCCCAAGGTATGGGGGCTAACCATT | 869 | NoName7_m2 | GTGACTGGAGTTCAGACGTGTGCTCTTCCGATCTGGGGGCTAACCATTGGCAATTGAA | 954 |
| NoName7_p1 | CCCCTTAGGGATAACAGGGTAATCTTCTGGAAATTCGTCGAAGGATGGTC | 870 | NoName7_p2 | GTGACTGGAGTTCAGACGTGTGCTCTTCCGATCTTTCGTCGAAGGATGGTCTCTCTGTTG | 955 |
| NoName8_m1 | CCCCTTAGGGATAACAGGGTAATCAGCTGTGCTCTTCCGTTTCAGTG | 871 | NoName8_m2 | GTGACTGGAGTTCAGACGTGTGCTCTTCCGATCTTGTGCTCTTCCGTTTCAGTGTGAAAA | 956 |
| NoName8_p1 | CCCCTTAGGGATAACAGGGTAATCCCACGAGGCGTATTCATCTGC | 872 | NoName8_p2 | GTGACTGGAGTTCAGACGTGTGCTCTTCCGATCTATCTGCATG | 957 |

TABLE_7-continued

Sequences of anchored primers for TRAC

| First PCR primer name | Sequence | SEQ ID NO: | Second PCR primer name | Sequence | SEQ ID NO: |
|---|---|---|---|---|---|
| | AT | | | CATGAGTCCTGACTTC | |
| NoName9_m1 | CCCCTTAGGGATAACAGGGTAATCAATGGAACCACACTACATCAAGTTA | 873 | NoName9_m2 | GTGACTGGAGTTCAGACGTGTGCTCTTCCGATCTATCAAGTTACATAGAAATGGGGAGGT | 958 |
| TRAC_m1 | CCCCTTAGGGATAACAGGGTAATCCCTGACCCTGCCGTGTACCAG | 874 | TRAC_m2 | GTGACTGGAGTTCAGACGTGTGCTCTTCCGATCTCCTGCCGTGTACCAGCTGAGAGAC | 959 |
| TRAC_p1 | CCCCTTAGGGATAACAGGGTAATCCCTGCGAAGGCACCAAAGC | 875 | TRAC_p2 | GTGACTGGAGTTCAGACGTGTGCTCTTCCGATCTGCTGTTGTTGAAGGCGTTTGCA | 960 |

Figure 4C:
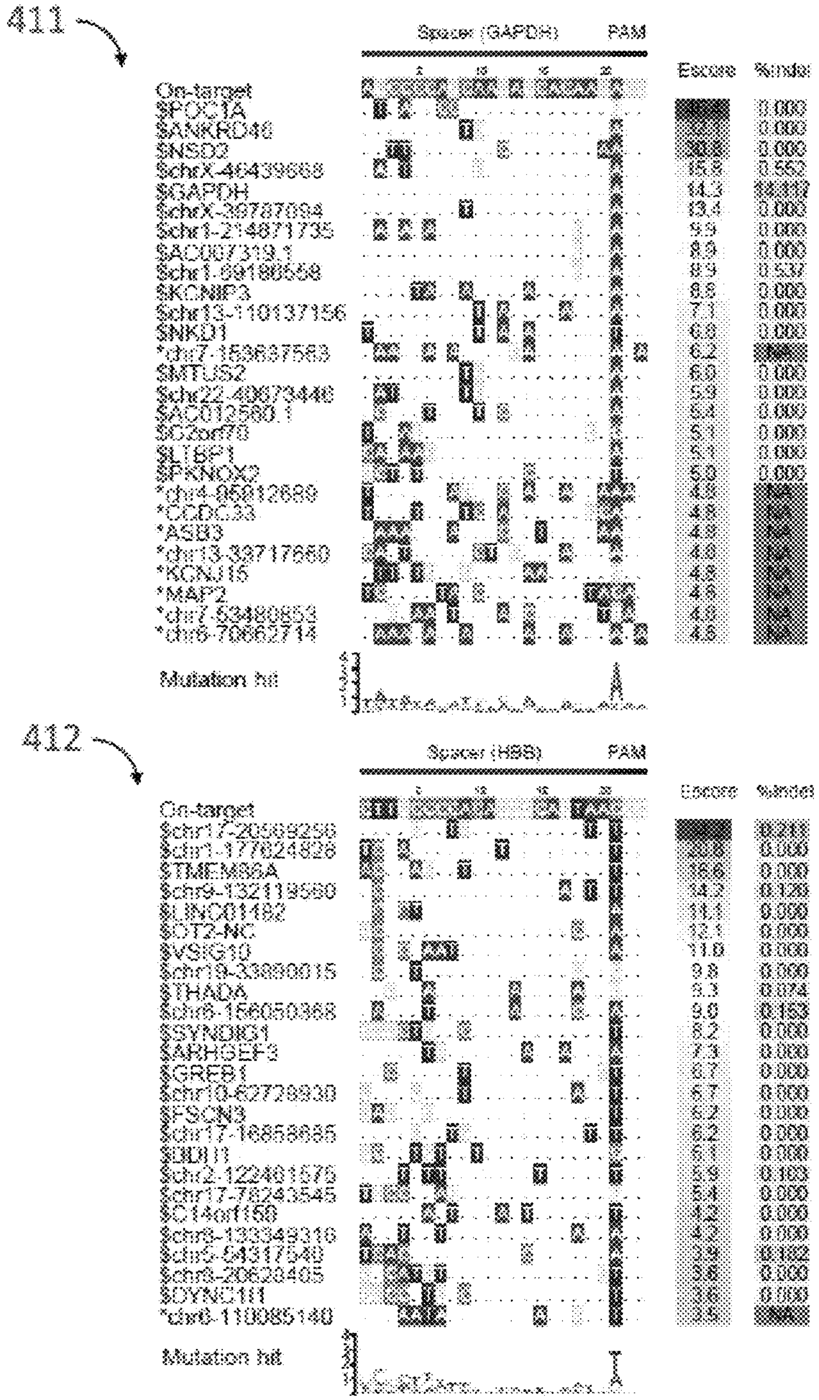
FIG. 4C is a chart which show off-target sites (Chart 411, SEQ ID NOs: 1060-1084; Chart 412, SEQ ID NOs: 1085-1109) in the iPSC at GAPDH and HBB sites, according to the same example embodiment of FIG. 4A.
Figure 4D:
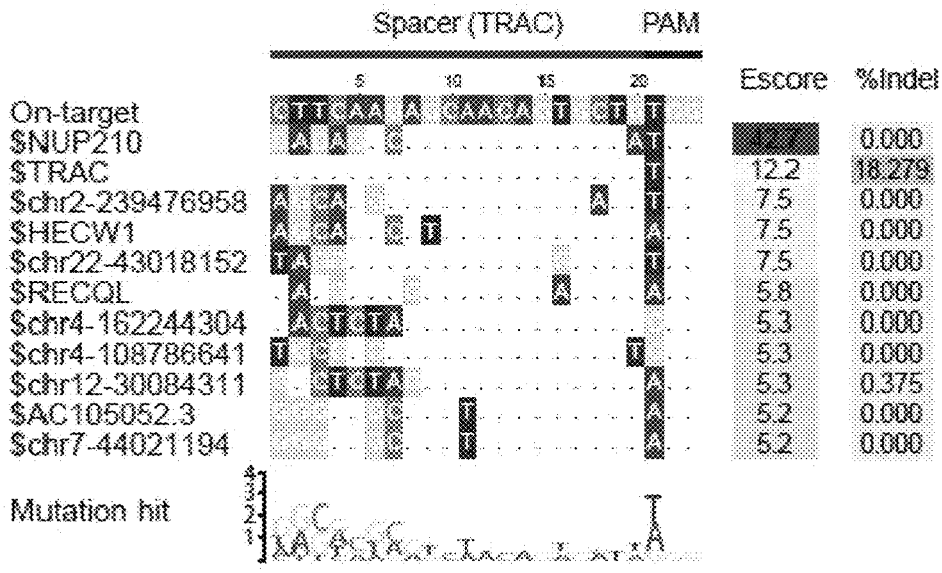
FIG. 4D is a chart which shows off-targets (Chart 421, SEQ ID NOs: 1110-1119; Chart 422, SEQ ID NOs: 1120-1130) in the T-cell at TRAC and PD-1 sites, according to the same example embodiment of FIG. 4B.
Figure 4D:
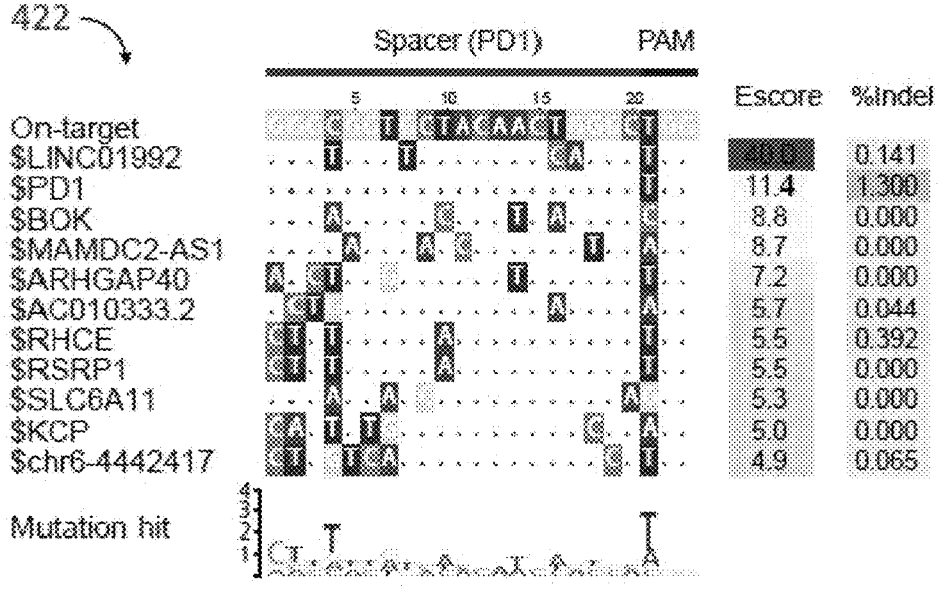

Referring now to FIG. 4C and FIG. 4D. Chart 411 and chart 412 in FIG. 4C shows off-targets in the iPSC in Example 6 at GAPDH and HBB sites, respectively. Chart 421 and chart 422 in FIG. 4D show off-targets in the T-cell in example 6 at TRAC and PD-1 sites, respectively. As shown in charts 411, 412, 421 and 422, there were 10-26 sites identified as off-targets through fusion detection, while 10%-40% of which were also confirmed by Indel detection. In addition, several sites were validated with Indel frequencies below 0.1%, while translocation could still be detected. Generally, the on-target sites accounted for 7%-20% gene fusions, except HBB locus fetching no fusion partner, as shown in chart 412 (FIG. 4C). It indicated that the sequence contexts flanking DSB end might impact translocation frequency.

Example 13. Off-Target Profiling and Translocation Dynamics In Vivo

Figure 5B:
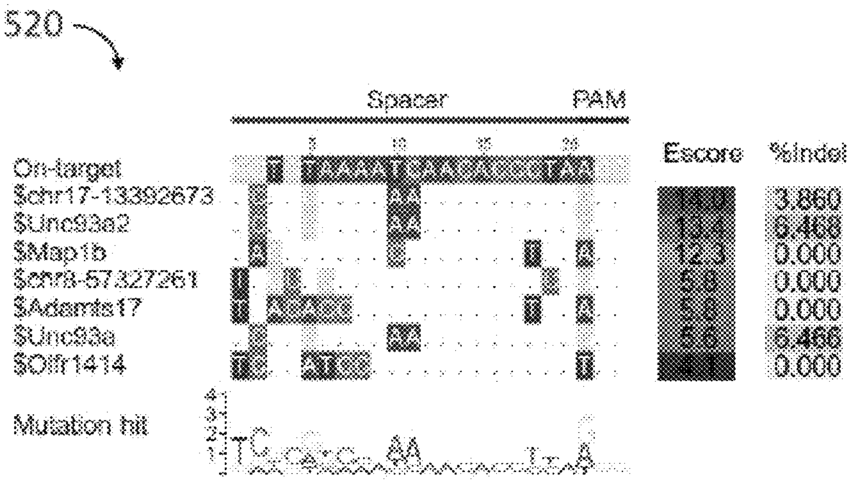
FIG. 5B and FIG. 5C are charts which show off-targets (Chart 520, SEQ ID NOs: 1131-1136; Chart 530, SEQ ID NOs: 1131-1134) in a mouse at ALB site after 15 or 60 days, respectively, according to the same example embodiment of FIG. 5A.
Figure 5C:
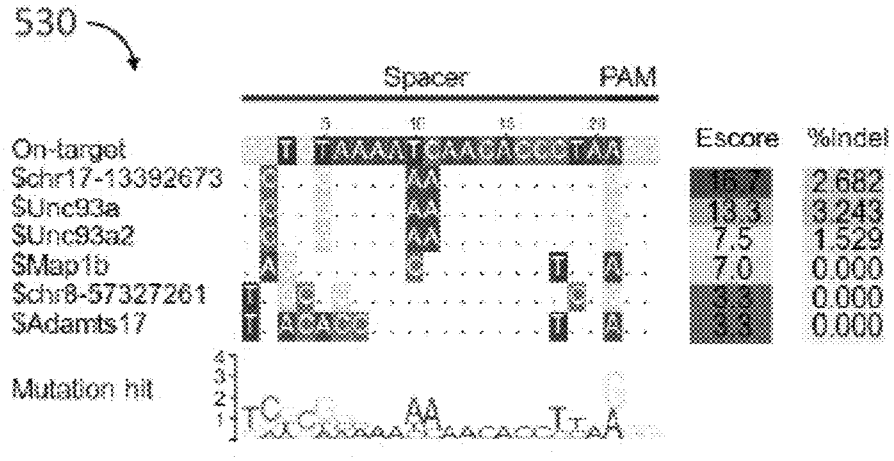

EDITED-Seq was further used to scan off-targets in CRISPR-edited mouse which was edited according to Example 7. Referring to FIGS. 5B and 5C, charts 520 and 530 show off-targets in a mouse at ALB site after 15 or 60 days, respectively.

Example 14. Summary of Results

In summary, the above results showed that EDITED-Seq can capture all types of off-target events by using an anchored multiplex enrichment of several in-silico predicted genomic loci. Using human tumor-, immune-, and induced pluripotent stem cells and mouse in vivo experiments, the present disclosure showed that EDITED-Seq can identify novel (translocations) off-target sites and quantify editing efficiencies of known off-target sites (InDels), and is compatible with therapeutics pipelines without the need for extra cell manipulations. Most off-target sites (about 90%) that were confirmed by InDels also presented in the form of translocations by EDITED-Seq, albeit translocation frequencies varied in different cell types and genomic contexts. In addition, there were 30%-60% of novel off-target sites that never been detected previously by other existing methods such as DISCOVER-Seq or GUIDE-Seq. The present disclosure demonstrates that EDITED-Seq is sensitive and versatile methods for the detection and evaluation of CRISPR editing efficiency and off-target events and would be compatible with future CRISPR based gene therapy of various genetic diseases.

Example 15. Discussion

DSBs within genome that created by Cas9 can activate DNA repair pathways, thus resulting in three major kinds of sealed DNA strand formed between different types of double strand breaks (DSBs), including on-target sites, off-target sites, and background: unchanged, mutation (insertion/deletion (Indels) and base mutation), and translocation. Directed by single protospacer RNA, in principle, Cas9 can just make two DSBs at the on-target locus in a diploid human cell. If there is no other unwanted cut, it is unlikely to detect gene fusion. From this view, gene fusion or chromosome arrangement could be observed at undesired cutting site (i.e., off-target). In the example embodiments as described above, the performance of EDITED-Seq, DISCOVER-Seq and GUIDE-Seq in detection of off-targets were compared.

GUIDE-Seq requires an extra double-strand oligonucleotide (dsODN) during wet lab process to generate dsODN insertions at CRISPR editing sites in the genome, which is incompatible with in vivo editing scenarios, and is an undesired extra step for ex vivo editing scenarios. ODN-inserted genome is actually artifact genome derivation, not the nature status of edited one created by nuclease.

DISCOVER-Seq snapshots the intermediate status of MER11, one of key components of the onset double-stranded break (DSB) repair, bound to DSB end to capture genome-wide cutting lesions created by Cas9. Therefore, the sensitivity and specificity of DISCOVER-Seq highly depends on the quality of MER11 antibody, implying uncontrollable fluctuations in outcome as well as a time-consuming procedure if a validation should be conducted via amplicon Next Generation Sequencing (NGS).

In contrast with the two methods above, EDITED-Seq is a versatile approach to detect genome-wide in situ edited off-targets without any artificial perturbation during the mutagenesis (e.g., mutation and translocation) progression induced by genome-editing nucleases. There might be a concern that gene translocation/arrangement just accounts for a small proportion of nuclease-induced mutagenesis, thus potentially limiting the sensitivity of EDITED-Seq. The two steps can significantly improve such potential limitation. Most off-target sites (about 90%) that were confirmed by InDels also presented in the form of translocations by EDITED-Seq, albeit translocation frequencies varied in different cell types and genomic contexts.

There are considerable differences in outcome off-target between repairing DSB and post-repair. Some sites identified by DISCOVER-Seq actually showed few final mutagenesis edit (FIG. 2A and FIG. 2B), indicating biased DSB repair levels at distinguished off-target sites. EDITED-Seq can directly readout the sequence-altered off-targets post DSB repair, representing a clinically useful approach as the most critical concern during gene editing is how many genomic loci as well as genomes are altered in a biopsy pool rather than which locus is cleaved or bound by Cas-nuclease. In this view, EDITED-Seq provides the genome-wide bona fide information of in situ sequence alternation induced by CRISPR, with an economical and straightforward fashion unlike whole genome sequencing. The performance of EDITED-Seq in iPSC and in vivo further extend its application as a parallel quality control step for clinical gene therapy bioproduct.

The exemplary embodiments of the present disclosure are thus fully described. Although the description referred to particular embodiments, it will be clear to one skilled in the art that the present disclosure may be practiced with variation of these specific details. The methods/steps discussed in one figure can be added to or exchanged with methods/steps in other figures. Hence this disclosure should not be construed as limited to the embodiments set forth herein.

What is claimed is:

1. A method of evaluating gene editing efficiency from a sample comprising a plurality of single-strand nucleic acid fragments, comprising:

(a) contacting a universal oligonucleotide adaptor with the sample to produce a ligation product, wherein the universal oligonucleotide adaptor is configured for ligating to a 5' end of the single-strand nucleic acid fragments;

(b) amplifying the ligation product by performing a first PCR with a first target-specific primer to form a PCR product, wherein the first target-specific primer is configured for annealing to the single-strand nucleic acid fragments at an on-target site, a predicted off-target site, or a known off-target site;

(c) amplifying the PCR product by a second PCR with a sequencing specific adaptor primer and a second target-specific primer nested relative to the first target-specific primer, to form a sequencing library;

(d) quantifying and reading the sequencing library to form sequencing results; and (e) mapping the sequencing results to a reference genome and evaluating gene editing efficiency.

2. The method of claim 1, wherein the predicted off-target site is predicted in silico based on software comprising E-CRISP, Cas-OFFinder, and/or CRISPRscan.

3. The method of claim 2, wherein the E-CRISP has a cutoff of mismatch <=10, 9, 8, 7, or 6; the Cas-OFFinder has a mismatch <=6, 5, 4, 3, or 2 and a bulge <=3, 2, or 1; and the CRISPRscan has no threshold.

4. The method of claim 1, wherein (e) further comprises: detecting translocation by obtaining a split read and a discordant read or determining an insertion and deletion (indel) frequency.

5. The method of claim 4, wherein the split read and the discordant read are obtained by: identifying potential candidate translocations and estimating protospacer similarity to an on-target spacer and a cutting frequency determinant (CFD).

6. The method of claim 4, wherein the indel frequency is obtained by:

(a) aligning the mapped results by GATK-realigner to form aligned results;

(b) filtering the aligned results not spanning a corresponding spacer region;

(c) predicting an insertion and deletion occurring around 5-bp upstream or downstream of a cleavage site; and (d) determining the indel frequency by an indel value of the sample with an elimination by a corresponding value of a negative control.

7. A method of identifying genome-wide gene editing off-target sites from a sample comprising a plurality of single-strand nucleic acid fragments, comprising:

(a) contacting a universal oligonucleotide adaptor with the sample to produce a ligation product, wherein the universal oligonucleotide adaptor is configured for ligating to a 5' end of the single-strand nucleic acid fragments;

(b) amplifying the ligation product by a first PCR with a first set of target-specific primers to form a PCR product, wherein the target-specific primers in the first set are configured for annealing to the single-strand nucleic acid fragments at an on-target site and one or more predicted and/or known off-targets sites;

(c) amplifying the PCR product by a second PCR with a second set of target-specific primers and a universal oligonucleotide adaptor primer to form a sequencing library, wherein each member of the second set of target-specific primers is nested relative to a corresponding primer of the first set of target-specific primers; and (d) sequencing the sequencing library to identify off-target sites.

8. The method of claim 7, wherein the predicted off-target sites in (b) are computationally predicted off-target sites.

9. The method of claim 8, wherein the computationally predicted off-target sites are top 100, 90, 80, 70, 60, 50, 40, 30, 20, or 10 off-target sites predicted based on software comprising E-CRISP, Cas-OFFinder, or CRISPRscan.

10. The method of claim 9, wherein the E-CRISP has a cutoff of mismatch <=10, 9, 8, 7, or 6; the Cas-OFFinder has a mismatch <=6, 5, 4, 3, or 2 and a bulge <=3, 2, or 1; and the CRISPRscan has no threshold.

11. The method of claim 7, wherein the method further comprises: detecting translocation by obtaining a split read and a discordant read or determining an insertion and deletion (indel) frequency.

12. The method of claim 11, wherein the split read and the discordant read are obtained by: identifying potential candidate translocations and estimating protospacer similarity to an on-target spacer and a cutting frequency determinant (CFD).

13. The method of claim 11, wherein the indel frequency is obtained by: quantifying and reading the sequencing library to form sequencing results; mapping the sequencing results to a reference genome and evaluating gene editing efficiency; aligning the mapped results by GATK-realigner to form aligned results; filtering the aligned results not spanning a corresponding spacer region; predicting an insertion and deletion occurring around 5-bp upstream or downstream of a cleavage site; and determining the indel frequency by an indel value of the sample with an elimination by a corresponding value of a negative control.

14. The method of claim 7, wherein prior to (a), the method further comprises at least one of: blocking a 3' end of the single-strand nucleic acid fragments; phosphorylating a 5' end of the single-strand nucleic acid fragments; or adenylating the single-strand nucleic acid fragments to produce a 3'-adenosine overhang on the single-strand nucleic acid fragments.

15. The method of claim 7, wherein the universal oligonucleotide adaptor comprises: a 3' recessive end, the 3' recessive end configured for ligating to the 5' end of the single-strand nucleic acid fragments; and/or a 5' protrude end comprising three to twenty bases of random or degenerate nucleotides; wherein a duplex portion of the universal oligonucleotide adaptor is of sufficient length to remain in duplex form in (a).

16. The method of claim 15, wherein the universal oligonucleotide adaptor comprises a hairpin loop connecting a portion of the duplex form.

17. The method of claim 7, wherein the universal oligonucleotide adaptor comprises a single strand segment comprising three to twenty random nucleotides as a unique molecular index (UMI) for tracing individual original molecules.

18. The method of claim 7, wherein (c) further comprises forming the sequencing library with a sequencing specific adaptor pair.

19. The method of claim 18, wherein the method, after (c), further comprises: sequencing the sequencing library using a sequencing primer pair, wherein the sequencing primer pair is at least partially complementary to opposite strands of the sequencing library, respectively.

* * * * *

SEQUENCE LISTING

```
Sequence total quantity: 1136
SEQ ID NO: 1           moltype = DNA  length = 25
FEATURE                Location/Qualifiers
misc_feature           1..25
                       note = Synthetic oligonucleotide
source                 1..25
                       mol_type = other DNA
                       organism = synthetic construct
SEQUENCE: 1
caccggaccc cctccacccc gcctc                                        25

SEQ ID NO: 2           moltype = DNA  length = 25
FEATURE                Location/Qualifiers
misc_feature           1..25
                       note = Synthetic oligonucleotide
source                 1..25
                       mol_type = other DNA
                       organism = synthetic construct
SEQUENCE: 2
aaacgaggcg gggtggaggg ggtcc                                        25

SEQ ID NO: 3           moltype = DNA  length = 25
FEATURE                Location/Qualifiers
misc_feature           1..25
                       note = Synthetic oligonucleotide
source                 1..25
                       mol_type = other DNA
                       organism = synthetic construct
SEQUENCE: 3
caccgcttgc cccacagggc agtaa                                        25

SEQ ID NO: 4           moltype = DNA  length = 25
FEATURE                Location/Qualifiers
misc_feature           1..25
                       note = Synthetic oligonucleotide
source                 1..25
                       mol_type = other DNA
                       organism = synthetic construct
SEQUENCE: 4
aaacttactg ccctgtgggg caagc                                        25

SEQ ID NO: 5           moltype = DNA  length = 25
FEATURE                Location/Qualifiers
misc_feature           1..25
                       note = Synthetic oligonucleotide
source                 1..25
                       mol_type = other DNA
                       organism = synthetic construct
SEQUENCE: 5
caccggggcg gtgctacaac tgggc                                        25

SEQ ID NO: 6           moltype = DNA  length = 25
FEATURE                Location/Qualifiers
misc_feature           1..25
                       note = Synthetic oligonucleotide
```

```
source                  1..25
                        mol_type = other DNA
                        organism = synthetic construct
SEQUENCE: 6
aaacgcccag ttgtagcacc gcccc                                        25

SEQ ID NO: 7            moltype = DNA  length = 25
FEATURE                 Location/Qualifiers
misc_feature            1..25
                        note = Synthetic oligonucleotide
source                  1..25
                        mol_type = other DNA
                        organism = synthetic construct
SEQUENCE: 7
caccgcttca agagcaacag tgctg                                        25

SEQ ID NO: 8            moltype = DNA  length = 25
FEATURE                 Location/Qualifiers
misc_feature            1..25
                        note = Synthetic oligonucleotide
source                  1..25
                        mol_type = other DNA
                        organism = synthetic construct
SEQUENCE: 8
aaaccagcac tgttgctctt gaagc                                        25

SEQ ID NO: 9            moltype = DNA  length = 25
FEATURE                 Location/Qualifiers
misc_feature            1..25
                        note = Synthetic oligonucleotide
source                  1..25
                        mol_type = other DNA
                        organism = synthetic construct
SEQUENCE: 9
caccgggtgt aaaatcaaca cccta                                        25

SEQ ID NO: 10           moltype = DNA  length = 25
FEATURE                 Location/Qualifiers
misc_feature            1..25
                        note = Synthetic oligonucleotide
source                  1..25
                        mol_type = other DNA
                        organism = synthetic construct
SEQUENCE: 10
aaactagggt gttgatttta caccc                                        25

SEQ ID NO: 11           moltype = DNA  length = 25
FEATURE                 Location/Qualifiers
misc_feature            1..25
                        note = Synthetic oligonucleotide
source                  1..25
                        mol_type = other DNA
                        organism = synthetic construct
SEQUENCE: 11
caccgagccc cagcaagagc acaag                                        25

SEQ ID NO: 12           moltype = DNA  length = 25
FEATURE                 Location/Qualifiers
misc_feature            1..25
                        note = Synthetic oligonucleotide
source                  1..25
                        mol_type = other DNA
                        organism = synthetic construct
SEQUENCE: 12
aaaccttgtg ctcttgctgg ggctc                                        25

SEQ ID NO: 13           moltype = DNA  length = 70
FEATURE                 Location/Qualifiers
misc_feature            1..70
                        note = Synthetic oligonucleotide
misc_difference         30..37
                        note = a, c, t, g, unknown or other
source                  1..70
                        mol_type = other DNA
                        organism = synthetic construct
SEQUENCE: 13
aatgatacgg cgaccaccga gatctacacn nnnnnnnaca ctctttccct acacgacgct  60
cttccgatct                                                         70
```

```
SEQ ID NO: 14          moltype = DNA  length = 65
FEATURE                Location/Qualifiers
misc_feature           1..65
                       note = Synthetic oligonucleotide
misc_difference        25..32
                       note = a, c, t, g, unknown or other
source                 1..65
                       mol_type = other DNA
                       organism = synthetic construct
SEQUENCE: 14
caagcagaag acggcatacg agatnnnnnn nngtgactgg agttcagacg tgtgctcttc  60
cgatc                                                              65

SEQ ID NO: 15          moltype = DNA  length = 45
FEATURE                Location/Qualifiers
misc_feature           1..45
                       note = Synthetic oligonucleotide
source                 1..45
                       mol_type = other DNA
                       organism = synthetic construct
SEQUENCE: 15
ccccttaggg ataacagggt aatccaactg ccatatgccc tgggt                  45

SEQ ID NO: 16          moltype = DNA  length = 42
FEATURE                Location/Qualifiers
misc_feature           1..42
                       note = Synthetic oligonucleotide
source                 1..42
                       mol_type = other DNA
                       organism = synthetic construct
SEQUENCE: 16
ccccttaggg ataacagggt aatccggcgg gtgggtcaca aa                     42

SEQ ID NO: 17          moltype = DNA  length = 43
FEATURE                Location/Qualifiers
misc_feature           1..43
                       note = Synthetic oligonucleotide
source                 1..43
                       mol_type = other DNA
                       organism = synthetic construct
SEQUENCE: 17
ccccttaggg ataacagggt aatccacagg acagggtcag cgt                    43

SEQ ID NO: 18          moltype = DNA  length = 50
FEATURE                Location/Qualifiers
misc_feature           1..50
                       note = Synthetic oligonucleotide
source                 1..50
                       mol_type = other DNA
                       organism = synthetic construct
SEQUENCE: 18
ccccttaggg ataacagggt aatcggcccc tacaatacta tcttgaccct             50

SEQ ID NO: 19          moltype = DNA  length = 47
FEATURE                Location/Qualifiers
misc_feature           1..47
                       note = Synthetic oligonucleotide
source                 1..47
                       mol_type = other DNA
                       organism = synthetic construct
SEQUENCE: 19
ccccttaggg ataacagggt aatctgagag acagggtctt gctgttg                47

SEQ ID NO: 20          moltype = DNA  length = 46
FEATURE                Location/Qualifiers
misc_feature           1..46
                       note = Synthetic oligonucleotide
source                 1..46
                       mol_type = other DNA
                       organism = synthetic construct
SEQUENCE: 20
ccccttaggg ataacagggt aatcccaact tggtgggggt agagtg                 46

SEQ ID NO: 21          moltype = DNA  length = 42
FEATURE                Location/Qualifiers
misc_feature           1..42
                       note = Synthetic oligonucleotide
source                 1..42
                       mol_type = other DNA
```

```
                        organism = synthetic construct
SEQUENCE: 21
ccccttaggg ataacagggt aatctcacgc agacgccccc at                     42

SEQ ID NO: 22           moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 22
ccccttaggg ataacagggt aatcagcctg gagttaaggg tgtctcc                47

SEQ ID NO: 23           moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 23
ccccttaggg ataacagggt aatcccccag gagcgtggat gactac                 46

SEQ ID NO: 24           moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 24
ccccttaggg ataacagggt aatcgcaggt gaggccgtgc ag                     42

SEQ ID NO: 25           moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 25
ccccttaggg ataacagggt aatctgagtt atgtggtccc ctctaggaa              49

SEQ ID NO: 26           moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 26
ccccttaggg ataacagggt aatcagcgtc gtctcctgga gctc                   44

SEQ ID NO: 27           moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 27
ccccttaggg ataacagggt aatctgatgg catcaaaatg tgtgtccagt             50

SEQ ID NO: 28           moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 28
ccccttaggg ataacagggt aatcggaggt ggcttcactt aggaggtc               48

SEQ ID NO: 29           moltype = DNA  length = 44
FEATURE                 Location/Qualifiers
misc_feature            1..44
                        note = Synthetic oligonucleotide
source                  1..44
```

```
                         mol_type = other DNA
                         organism = synthetic construct
SEQUENCE: 29
ccccttaggg ataacagggt aatcagcaag gctgacacca ggtg                    44

SEQ ID NO: 30            moltype = DNA  length = 45
FEATURE                  Location/Qualifiers
misc_feature             1..45
                         note = Synthetic oligonucleotide
source                   1..45
                         mol_type = other DNA
                         organism = synthetic construct
SEQUENCE: 30
ccccttaggg ataacagggt aatcggctgg gatctgggga gagag                   45

SEQ ID NO: 31            moltype = DNA  length = 49
FEATURE                  Location/Qualifiers
misc_feature             1..49
                         note = Synthetic oligonucleotide
source                   1..49
                         mol_type = other DNA
                         organism = synthetic construct
SEQUENCE: 31
ccccttaggg ataacagggt aatcaatcat caggtgcaag gcaagactg               49

SEQ ID NO: 32            moltype = DNA  length = 47
FEATURE                  Location/Qualifiers
misc_feature             1..47
                         note = Synthetic oligonucleotide
source                   1..47
                         mol_type = other DNA
                         organism = synthetic construct
SEQUENCE: 32
ccccttaggg ataacagggt aatctctgac tggagttccc ttcacca                 47

SEQ ID NO: 33            moltype = DNA  length = 45
FEATURE                  Location/Qualifiers
misc_feature             1..45
                         note = Synthetic oligonucleotide
source                   1..45
                         mol_type = other DNA
                         organism = synthetic construct
SEQUENCE: 33
ccccttaggg ataacagggt aatcgaggag cctggacaga cgaag                   45

SEQ ID NO: 34            moltype = DNA  length = 46
FEATURE                  Location/Qualifiers
misc_feature             1..46
                         note = Synthetic oligonucleotide
source                   1..46
                         mol_type = other DNA
                         organism = synthetic construct
SEQUENCE: 34
ccccttaggg ataacagggt aatcgctgcc agaagcctgt agagat                  46

SEQ ID NO: 35            moltype = DNA  length = 45
FEATURE                  Location/Qualifiers
misc_feature             1..45
                         note = Synthetic oligonucleotide
source                   1..45
                         mol_type = other DNA
                         organism = synthetic construct
SEQUENCE: 35
ccccttaggg ataacagggt aatcagctcg ggggtgatta gttgc                   45

SEQ ID NO: 36            moltype = DNA  length = 42
FEATURE                  Location/Qualifiers
misc_feature             1..42
                         note = Synthetic oligonucleotide
source                   1..42
                         mol_type = other DNA
                         organism = synthetic construct
SEQUENCE: 36
ccccttaggg ataacagggt aatcgccgtg gcccgacacc ta                      42

SEQ ID NO: 37            moltype = DNA  length = 48
FEATURE                  Location/Qualifiers
misc_feature             1..48
                         note = Synthetic oligonucleotide
```

```
source                  1..48
                        mol_type = other DNA
                        organism = synthetic construct
SEQUENCE: 37
ccccttaggg ataacagggt aatctaagaa gggcccccttg atgaggtc            48

SEQ ID NO: 38           moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 38
ccccttaggg ataacagggt aatcgggaga ggtgggtcaa ctttgg              46

SEQ ID NO: 39           moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 39
ccccttaggg ataacagggt aatcgagggt gggcgtggct atgta               45

SEQ ID NO: 40           moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 40
ccccttaggg ataacagggt aatcatgaag ctggactgca ccatcg              46

SEQ ID NO: 41           moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 41
ccccttaggg ataacagggt aatctgggga ggggcgaagg tc                  42

SEQ ID NO: 42           moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 42
ccccttaggg ataacagggt aatcccgggt cctgcgtccc tt                  42

SEQ ID NO: 43           moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 43
ccccttaggg ataacagggt aatcccgcag cctccagatg ca                  42

SEQ ID NO: 44           moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 44
ccccttaggg ataacagggt aatcctgagg ctcttatcaa acaactgcca          50

SEQ ID NO: 45           moltype = DNA  length = 42
FEATURE                 Location/Qualifiers
misc_feature            1..42
```

```
                        note = Synthetic oligonucleotide
source                  1..42
                        mol_type = other DNA
                        organism = synthetic construct
SEQUENCE: 45
ccccttaggg ataacagggt aatccgagtc ccggcgctgt cc                     42

SEQ ID NO: 46           moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 46
ccccttaggg ataacagggt aatccctcct cggtccgctg ag                     42

SEQ ID NO: 47           moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 47
ccccttaggg ataacagggt aatccaatct ctgacttgga cagctgca               48

SEQ ID NO: 48           moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 48
ccccttaggg ataacagggt aatctcgatg atggcctatg ggttgaaaa              49

SEQ ID NO: 49           moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 49
ccccttaggg ataacagggt aatctgtgct tcttccaagc tgcgt                  45

SEQ ID NO: 50           moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 50
ccccttaggg ataacagggt aatctgtgat tttcctggct ttagcgcta              49

SEQ ID NO: 51           moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 51
ccccttaggg ataacagggt aatctctaca accaagccca tttgtcca               48

SEQ ID NO: 52           moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 52
ccccttaggg ataacagggt aatcagcctc tctaccattt gtgctga                47

SEQ ID NO: 53           moltype = DNA  length = 43
FEATURE                 Location/Qualifiers
```

```
misc_feature           1..43
                       note = Synthetic oligonucleotide
source                 1..43
                       mol_type = other DNA
                       organism = synthetic construct
SEQUENCE: 53
ccccttaggg ataacagggt aatccctgcc agggttgcat ggg                    43

SEQ ID NO: 54          moltype = DNA  length = 45
FEATURE                Location/Qualifiers
misc_feature           1..45
                       note = Synthetic oligonucleotide
source                 1..45
                       mol_type = other DNA
                       organism = synthetic construct
SEQUENCE: 54
ccccttaggg ataacagggt aatcttgtcc ccaccctcgt cactc                  45

SEQ ID NO: 55          moltype = DNA  length = 42
FEATURE                Location/Qualifiers
misc_feature           1..42
                       note = Synthetic oligonucleotide
source                 1..42
                       mol_type = other DNA
                       organism = synthetic construct
SEQUENCE: 55
ccccttaggg ataacagggt aatcggcagg gacccggcga ca                     42

SEQ ID NO: 56          moltype = DNA  length = 43
FEATURE                Location/Qualifiers
misc_feature           1..43
                       note = Synthetic oligonucleotide
source                 1..43
                       mol_type = other DNA
                       organism = synthetic construct
SEQUENCE: 56
ccccttaggg ataacagggt aatcggaagg gaggcgctag gca                    43

SEQ ID NO: 57          moltype = DNA  length = 42
FEATURE                Location/Qualifiers
misc_feature           1..42
                       note = Synthetic oligonucleotide
source                 1..42
                       mol_type = other DNA
                       organism = synthetic construct
SEQUENCE: 57
ccccttaggg ataacagggt aatcgctggg cctgcacgct ca                     42

SEQ ID NO: 58          moltype = DNA  length = 43
FEATURE                Location/Qualifiers
misc_feature           1..43
                       note = Synthetic oligonucleotide
source                 1..43
                       mol_type = other DNA
                       organism = synthetic construct
SEQUENCE: 58
ccccttaggg ataacagggt aatcgacagc caccctgctc cac                    43

SEQ ID NO: 59          moltype = DNA  length = 43
FEATURE                Location/Qualifiers
misc_feature           1..43
                       note = Synthetic oligonucleotide
source                 1..43
                       mol_type = other DNA
                       organism = synthetic construct
SEQUENCE: 59
ccccttaggg ataacagggt aatccctagc aacggccctg gca                    43

SEQ ID NO: 60          moltype = DNA  length = 44
FEATURE                Location/Qualifiers
misc_feature           1..44
                       note = Synthetic oligonucleotide
source                 1..44
                       mol_type = other DNA
                       organism = synthetic construct
SEQUENCE: 60
ccccttaggg ataacagggt aatcccctac cctgccgcgc tcct                   44

SEQ ID NO: 61          moltype = DNA  length = 43
```

```
FEATURE                 Location/Qualifiers
misc_feature            1..43
                        note = Synthetic oligonucleotide
source                  1..43
                        mol_type = other DNA
                        organism = synthetic construct
SEQUENCE: 61
ccccttaggg ataacagggt aatcggcacc tcattgggga cgt                   43

SEQ ID NO: 62           moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 62
ccccttaggg ataacagggt aatctgctct gaaccgaggc cttg                  44

SEQ ID NO: 63           moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 63
ccccttaggg ataacagggt aatcgcaggg ccccagagag gt                    42

SEQ ID NO: 64           moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 64
ccccttaggg ataacagggt aatcgcagcg acgccactct ttatct                46

SEQ ID NO: 65           moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 65
ccccttaggg ataacagggt aatccgcgct gacagctgtt gc                    42

SEQ ID NO: 66           moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 66
ccccttaggg ataacagggt aatctgagtt tcatgctcag tccctgca              48

SEQ ID NO: 67           moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 67
ccccttaggg ataacagggt aatcagggct ctggggtgac tcc                   43

SEQ ID NO: 68           moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 68
ccccttaggg ataacagggt aatcctccct actcaacccc gagccctcct            50
```

```
SEQ ID NO: 69          moltype = DNA  length = 42
FEATURE                Location/Qualifiers
misc_feature           1..42
                       note = Synthetic oligonucleotide
source                 1..42
                       mol_type = other DNA
                       organism = synthetic construct
SEQUENCE: 69
ccccttaggg ataacagggt aatcgcgcca gaccagctcc ga                    42

SEQ ID NO: 70          moltype = DNA  length = 42
FEATURE                Location/Qualifiers
misc_feature           1..42
                       note = Synthetic oligonucleotide
source                 1..42
                       mol_type = other DNA
                       organism = synthetic construct
SEQUENCE: 70
ccccttaggg ataacagggt aatcctcctt gcccggggta gg                    42

SEQ ID NO: 71          moltype = DNA  length = 50
FEATURE                Location/Qualifiers
misc_feature           1..50
                       note = Synthetic oligonucleotide
source                 1..50
                       mol_type = other DNA
                       organism = synthetic construct
SEQUENCE: 71
ccccttaggg ataacagggt aatccttctc atccttgtat cagctgcctt            50

SEQ ID NO: 72          moltype = DNA  length = 48
FEATURE                Location/Qualifiers
misc_feature           1..48
                       note = Synthetic oligonucleotide
source                 1..48
                       mol_type = other DNA
                       organism = synthetic construct
SEQUENCE: 72
ccccttaggg ataacagggt aatcgggaga gtgccattct cagcctaa              48

SEQ ID NO: 73          moltype = DNA  length = 43
FEATURE                Location/Qualifiers
misc_feature           1..43
                       note = Synthetic oligonucleotide
source                 1..43
                       mol_type = other DNA
                       organism = synthetic construct
SEQUENCE: 73
ccccttaggg ataacagggt aatcggtgga tcacgcagtc gga                   43

SEQ ID NO: 74          moltype = DNA  length = 44
FEATURE                Location/Qualifiers
misc_feature           1..44
                       note = Synthetic oligonucleotide
source                 1..44
                       mol_type = other DNA
                       organism = synthetic construct
SEQUENCE: 74
ccccttaggg ataacagggt aatccatgag cacacccacc acca                  44

SEQ ID NO: 75          moltype = DNA  length = 45
FEATURE                Location/Qualifiers
misc_feature           1..45
                       note = Synthetic oligonucleotide
source                 1..45
                       mol_type = other DNA
                       organism = synthetic construct
SEQUENCE: 75
ccccttaggg ataacagggt aatcgccttg tcccacatca cagca                 45

SEQ ID NO: 76          moltype = DNA  length = 50
FEATURE                Location/Qualifiers
misc_feature           1..50
                       note = Synthetic oligonucleotide
source                 1..50
                       mol_type = other DNA
                       organism = synthetic construct
SEQUENCE: 76
ccccttaggg ataacagggt aatccgcctg ggactacttc tcgtttgaaa            50
```

```
SEQ ID NO: 77          moltype = DNA  length = 42
FEATURE                Location/Qualifiers
misc_feature           1..42
                       note = Synthetic oligonucleotide
source                 1..42
                       mol_type = other DNA
                       organism = synthetic construct
SEQUENCE: 77
ccccttaggg ataacagggt aatcccccca acgtggcctc ag                    42

SEQ ID NO: 78          moltype = DNA  length = 45
FEATURE                Location/Qualifiers
misc_feature           1..45
                       note = Synthetic oligonucleotide
source                 1..45
                       mol_type = other DNA
                       organism = synthetic construct
SEQUENCE: 78
ccccttaggg ataacagggt aatccacagc tgtccaaacg aggct                 45

SEQ ID NO: 79          moltype = DNA  length = 46
FEATURE                Location/Qualifiers
misc_feature           1..46
                       note = Synthetic oligonucleotide
source                 1..46
                       mol_type = other DNA
                       organism = synthetic construct
SEQUENCE: 79
ccccttaggg ataacagggt aatcggatgc aactgagggc tcctta                46

SEQ ID NO: 80          moltype = DNA  length = 43
FEATURE                Location/Qualifiers
misc_feature           1..43
                       note = Synthetic oligonucleotide
source                 1..43
                       mol_type = other DNA
                       organism = synthetic construct
SEQUENCE: 80
ccccttaggg ataacagggt aatcggaagg tcgctgggaa gcc                   43

SEQ ID NO: 81          moltype = DNA  length = 42
FEATURE                Location/Qualifiers
misc_feature           1..42
                       note = Synthetic oligonucleotide
source                 1..42
                       mol_type = other DNA
                       organism = synthetic construct
SEQUENCE: 81
ccccttaggg ataacagggt aatctgccca gcctccctgc ag                    42

SEQ ID NO: 82          moltype = DNA  length = 45
FEATURE                Location/Qualifiers
misc_feature           1..45
                       note = Synthetic oligonucleotide
source                 1..45
                       mol_type = other DNA
                       organism = synthetic construct
SEQUENCE: 82
ccccttaggg ataacagggt aatcagctcc tctgtgtgac atgcc                 45

SEQ ID NO: 83          moltype = DNA  length = 49
FEATURE                Location/Qualifiers
misc_feature           1..49
                       note = Synthetic oligonucleotide
source                 1..49
                       mol_type = other DNA
                       organism = synthetic construct
SEQUENCE: 83
ccccttaggg ataacagggt aatcaccaac cagctaacac tgctatgca             49

SEQ ID NO: 84          moltype = DNA  length = 46
FEATURE                Location/Qualifiers
misc_feature           1..46
                       note = Synthetic oligonucleotide
source                 1..46
                       mol_type = other DNA
                       organism = synthetic construct
SEQUENCE: 84
```

```
ccccttaggg ataacagggt aatcactcag gtgtgctggc actgat                46

SEQ ID NO: 85          moltype = DNA  length = 49
FEATURE                Location/Qualifiers
misc_feature           1..49
                       note = Synthetic oligonucleotide
source                 1..49
                       mol_type = other DNA
                       organism = synthetic construct
SEQUENCE: 85
ccccttaggg ataacagggt aatcacatac aaccagttca cccagttac             49

SEQ ID NO: 86          moltype = DNA  length = 49
FEATURE                Location/Qualifiers
misc_feature           1..49
                       note = Synthetic oligonucleotide
source                 1..49
                       mol_type = other DNA
                       organism = synthetic construct
SEQUENCE: 86
ccccttaggg ataacagggt aatcggtgtg tgtttgctgt taccgctta             49

SEQ ID NO: 87          moltype = DNA  length = 44
FEATURE                Location/Qualifiers
misc_feature           1..44
                       note = Synthetic oligonucleotide
source                 1..44
                       mol_type = other DNA
                       organism = synthetic construct
SEQUENCE: 87
ccccttaggg ataacagggt aatccctgga gcgaaggcct ggag                  44

SEQ ID NO: 88          moltype = DNA  length = 45
FEATURE                Location/Qualifiers
misc_feature           1..45
                       note = Synthetic oligonucleotide
source                 1..45
                       mol_type = other DNA
                       organism = synthetic construct
SEQUENCE: 88
ccccttaggg ataacagggt aatctactga tgggggtgag ctcca                 45

SEQ ID NO: 89          moltype = DNA  length = 47
FEATURE                Location/Qualifiers
misc_feature           1..47
                       note = Synthetic oligonucleotide
source                 1..47
                       mol_type = other DNA
                       organism = synthetic construct
SEQUENCE: 89
ccccttaggg ataacagggt aatctgtgtc tctgctttct gttggca               47

SEQ ID NO: 90          moltype = DNA  length = 46
FEATURE                Location/Qualifiers
misc_feature           1..46
                       note = Synthetic oligonucleotide
source                 1..46
                       mol_type = other DNA
                       organism = synthetic construct
SEQUENCE: 90
ccccttaggg ataacagggt aatctcttca agcagcccac cttctg                46

SEQ ID NO: 91          moltype = DNA  length = 42
FEATURE                Location/Qualifiers
misc_feature           1..42
                       note = Synthetic oligonucleotide
source                 1..42
                       mol_type = other DNA
                       organism = synthetic construct
SEQUENCE: 91
ccccttaggg ataacagggt aatcactccc gccggttcca ag                    42

SEQ ID NO: 92          moltype = DNA  length = 44
FEATURE                Location/Qualifiers
misc_feature           1..44
                       note = Synthetic oligonucleotide
source                 1..44
                       mol_type = other DNA
                       organism = synthetic construct
```

```
SEQUENCE: 92
ccccttaggg ataacagggt aatcccaaag cacaggtggg gact                  44

SEQ ID NO: 93          moltype = DNA  length = 44
FEATURE                Location/Qualifiers
misc_feature           1..44
                       note = Synthetic oligonucleotide
source                 1..44
                       mol_type = other DNA
                       organism = synthetic construct
SEQUENCE: 93
ccccttaggg ataacagggt aatccagctg cttgggctcc gttg                  44

SEQ ID NO: 94          moltype = DNA  length = 43
FEATURE                Location/Qualifiers
misc_feature           1..43
                       note = Synthetic oligonucleotide
source                 1..43
                       mol_type = other DNA
                       organism = synthetic construct
SEQUENCE: 94
ccccttaggg ataacagggt aatcccccag gccacaggaa acc                   43

SEQ ID NO: 95          moltype = DNA  length = 45
FEATURE                Location/Qualifiers
misc_feature           1..45
                       note = Synthetic oligonucleotide
source                 1..45
                       mol_type = other DNA
                       organism = synthetic construct
SEQUENCE: 95
ccccttaggg ataacagggt aatcgctagg gtggctgtga ctcag                 45

SEQ ID NO: 96          moltype = DNA  length = 46
FEATURE                Location/Qualifiers
misc_feature           1..46
                       note = Synthetic oligonucleotide
source                 1..46
                       mol_type = other DNA
                       organism = synthetic construct
SEQUENCE: 96
ccccttaggg ataacagggt aatccctctg gcttcccatg ggtgag                46

SEQ ID NO: 97          moltype = DNA  length = 49
FEATURE                Location/Qualifiers
misc_feature           1..49
                       note = Synthetic oligonucleotide
source                 1..49
                       mol_type = other DNA
                       organism = synthetic construct
SEQUENCE: 97
ccccttaggg ataacagggt aatcctccct gagaagagct gaacatagc             49

SEQ ID NO: 98          moltype = DNA  length = 48
FEATURE                Location/Qualifiers
misc_feature           1..48
                       note = Synthetic oligonucleotide
source                 1..48
                       mol_type = other DNA
                       organism = synthetic construct
SEQUENCE: 98
ccccttaggg ataacagggt aatctcaacc cttcccatga ctgaggtg              48

SEQ ID NO: 99          moltype = DNA  length = 42
FEATURE                Location/Qualifiers
misc_feature           1..42
                       note = Synthetic oligonucleotide
source                 1..42
                       mol_type = other DNA
                       organism = synthetic construct
SEQUENCE: 99
ccccttaggg ataacagggt aatccccaac cccctgcagc tg                    42

SEQ ID NO: 100         moltype = DNA  length = 47
FEATURE                Location/Qualifiers
misc_feature           1..47
                       note = Synthetic oligonucleotide
source                 1..47
                       mol_type = other DNA
```

```
                       organism = synthetic construct
SEQUENCE: 100
ccccttaggg ataacagggt aatctcaaaa tcccaagggc attgttc             47

SEQ ID NO: 101         moltype = DNA  length = 50
FEATURE                Location/Qualifiers
misc_feature           1..50
                       note = Synthetic oligonucleotide
source                 1..50
                       mol_type = other DNA
                       organism = synthetic construct
SEQUENCE: 101
ccccttaggg ataacagggt aatccattgt gtcttcttgg taccctttt           50

SEQ ID NO: 102         moltype = DNA  length = 46
FEATURE                Location/Qualifiers
misc_feature           1..46
                       note = Synthetic oligonucleotide
source                 1..46
                       mol_type = other DNA
                       organism = synthetic construct
SEQUENCE: 102
ccccttaggg ataacagggt aatcagatca cacgaggcag agggaa              46

SEQ ID NO: 103         moltype = DNA  length = 46
FEATURE                Location/Qualifiers
misc_feature           1..46
                       note = Synthetic oligonucleotide
source                 1..46
                       mol_type = other DNA
                       organism = synthetic construct
SEQUENCE: 103
ccccttaggg ataacagggt aatcgcaatc tcacctcctc cctctc              46

SEQ ID NO: 104         moltype = DNA  length = 43
FEATURE                Location/Qualifiers
misc_feature           1..43
                       note = Synthetic oligonucleotide
source                 1..43
                       mol_type = other DNA
                       organism = synthetic construct
SEQUENCE: 104
ccccttaggg ataacagggt aatcagccaa acacagaaag gcc                 43

SEQ ID NO: 105         moltype = DNA  length = 45
FEATURE                Location/Qualifiers
misc_feature           1..45
                       note = Synthetic oligonucleotide
source                 1..45
                       mol_type = other DNA
                       organism = synthetic construct
SEQUENCE: 105
ccccttaggg ataacagggt aatcgtgagc catgatcgtg cactc               45

SEQ ID NO: 106         moltype = DNA  length = 47
FEATURE                Location/Qualifiers
misc_feature           1..47
                       note = Synthetic oligonucleotide
source                 1..47
                       mol_type = other DNA
                       organism = synthetic construct
SEQUENCE: 106
ccccttaggg ataacagggt aatcactaca ttggaggagt gtgtacc             47

SEQ ID NO: 107         moltype = DNA  length = 45
FEATURE                Location/Qualifiers
misc_feature           1..45
                       note = Synthetic oligonucleotide
source                 1..45
                       mol_type = other DNA
                       organism = synthetic construct
SEQUENCE: 107
ccccttaggg ataacagggt aatcctctgc tttcccctcc cacct               45

SEQ ID NO: 108         moltype = DNA  length = 47
FEATURE                Location/Qualifiers
misc_feature           1..47
                       note = Synthetic oligonucleotide
source                 1..47
```

```
                        mol_type = other DNA
                        organism = synthetic construct
SEQUENCE: 108
ccccttaggg ataacagggt aatcctgccc tgttggataa cccttct              47

SEQ ID NO: 109          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 109
ccccttaggg ataacagggt aatccttgga aagggatgct ctgaatacct           50

SEQ ID NO: 110          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 110
ccccttaggg ataacagggt aatcagctgc actttctccc ggacaa               46

SEQ ID NO: 111          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 111
ccccttaggg ataacagggt aatctgttgt taaggctgtt ggcatctgt            49

SEQ ID NO: 112          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 112
ccccttaggg ataacagggt aatcaggaaa acacggttgc atcctga              47

SEQ ID NO: 113          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 113
ccccttaggg ataacagggt aatcgcacca gctcttcggc caag                 44

SEQ ID NO: 114          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 114
ccccttaggg ataacagggt aatctccgtg tgtttgactc cctcaac              47

SEQ ID NO: 115          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 115
ccccttaggg ataacagggt aatcggcggt gtcagcaaag ctagg                45

SEQ ID NO: 116          moltype = DNA  length = 43
FEATURE                 Location/Qualifiers
misc_feature            1..43
                        note = Synthetic oligonucleotide
```

```
source                  1..43
                        mol_type = other DNA
                        organism = synthetic construct
SEQUENCE: 116
ccccttaggg ataacagggt aatcagcacc gatgaggcat ggg                  43

SEQ ID NO: 117          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 117
ccccttaggg ataacagggt aatcgtgctg cctccccctc tggta                45

SEQ ID NO: 118          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 118
ccccttaggg ataacagggt aatcggagtg actggatgct gggtt                45

SEQ ID NO: 119          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 119
ccccttaggg ataacagggt aatcggagag gggcctggaa gattctc              47

SEQ ID NO: 120          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 120
ccccttaggg ataacagggt aatcgggtag acttgacata agcacca              47

SEQ ID NO: 121          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 121
ccccttaggg ataacagggt aatcaagaaa aggggctgct gggt                 44

SEQ ID NO: 122          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 122
ccccttaggg ataacagggt aatcgacgtg attcgagttc ctggca               46

SEQ ID NO: 123          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 123
ccccttaggg ataacagggt aatcgggtct ggggtcctga aatgac               46

SEQ ID NO: 124          moltype = DNA  length = 49
FEATURE                 Location/Qualifiers
misc_feature            1..49
```

```
                        note = Synthetic oligonucleotide
source                  1..49
                        mol_type = other DNA
                        organism = synthetic construct
SEQUENCE: 124
ccccttaggg ataacagggt aatccccact agatcctgtc acaattccc              49

SEQ ID NO: 125          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 125
ccccttaggg ataacagggt aatctgtgct cccgctccca tgag                   44

SEQ ID NO: 126          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 126
ccccttaggg ataacagggt aatctgcaca agaacctgct gtctaaactt             50

SEQ ID NO: 127          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 127
ccccttaggg ataacagggt aatcacgacg gccgcacagt gg                     42

SEQ ID NO: 128          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 128
ccccttaggg ataacagggt aatccccgcc cactctcgac tctt                   44

SEQ ID NO: 129          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 129
ccccttaggg ataacagggt aatcccagga ctccccaggt gct                    43

SEQ ID NO: 130          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 130
ccccttaggg ataacagggt aatcctctag cccgaaaagc caagct                 46

SEQ ID NO: 131          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 131
ccccttaggg ataacagggt aatcctctgc cagatgctgc tcgt                   44

SEQ ID NO: 132          moltype = DNA  length = 47
FEATURE                 Location/Qualifiers
```

```
misc_feature          1..47
                      note = Synthetic oligonucleotide
source                1..47
                      mol_type = other DNA
                      organism = synthetic construct
SEQUENCE: 132
ccccttaggg ataacagggt aatcgctgtt gcaggtccag aggacac             47

SEQ ID NO: 133        moltype = DNA  length = 45
FEATURE               Location/Qualifiers
misc_feature          1..45
                      note = Synthetic oligonucleotide
source                1..45
                      mol_type = other DNA
                      organism = synthetic construct
SEQUENCE: 133
ccccttaggg ataacagggt aatcgaagac gtgggttctg gcaga               45

SEQ ID NO: 134        moltype = DNA  length = 42
FEATURE               Location/Qualifiers
misc_feature          1..42
                      note = Synthetic oligonucleotide
source                1..42
                      mol_type = other DNA
                      organism = synthetic construct
SEQUENCE: 134
ccccttaggg ataacagggt aatccccccg tcccctctgc ca                  42

SEQ ID NO: 135        moltype = DNA  length = 43
FEATURE               Location/Qualifiers
misc_feature          1..43
                      note = Synthetic oligonucleotide
source                1..43
                      mol_type = other DNA
                      organism = synthetic construct
SEQUENCE: 135
ccccttaggg ataacagggt aatctgcctg tgtccggagc tgt                 43

SEQ ID NO: 136        moltype = DNA  length = 43
FEATURE               Location/Qualifiers
misc_feature          1..43
                      note = Synthetic oligonucleotide
source                1..43
                      mol_type = other DNA
                      organism = synthetic construct
SEQUENCE: 136
ccccttaggg ataacagggt aatccctacc ggggcaagac agc                 43

SEQ ID NO: 137        moltype = DNA  length = 50
FEATURE               Location/Qualifiers
misc_feature          1..50
                      note = Synthetic oligonucleotide
source                1..50
                      mol_type = other DNA
                      organism = synthetic construct
SEQUENCE: 137
ccccttaggg ataacagggt aatctggtga caactaccac tctagaattt          50

SEQ ID NO: 138        moltype = DNA  length = 49
FEATURE               Location/Qualifiers
misc_feature          1..49
                      note = Synthetic oligonucleotide
source                1..49
                      mol_type = other DNA
                      organism = synthetic construct
SEQUENCE: 138
ccccttaggg ataacagggt aatctgtcct aaaacccctg cttggattt           49

SEQ ID NO: 139        moltype = DNA  length = 46
FEATURE               Location/Qualifiers
misc_feature          1..46
                      note = Synthetic oligonucleotide
source                1..46
                      mol_type = other DNA
                      organism = synthetic construct
SEQUENCE: 139
ccccttaggg ataacagggt aatctgcgga acacaggagc tagtct              46

SEQ ID NO: 140        moltype = DNA  length = 48
```

```
FEATURE                 Location/Qualifiers
misc_feature            1..48
                        note = Synthetic oligonucleotide
source                  1..48
                        mol_type = other DNA
                        organism = synthetic construct
SEQUENCE: 140
ccccttaggg ataacagggt aatctcagta gctccccaac gttactgt                48

SEQ ID NO: 141          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 141
ccccttaggg ataacagggt aatcctgtct cccaaaatca ggcctgt                 47

SEQ ID NO: 142          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 142
ccccttaggg ataacagggt aatctttgtg cgccctgccc tt                      42

SEQ ID NO: 143          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 143
ccccttaggg ataacagggt aatcggggag gagggtgttt acgg                    44

SEQ ID NO: 144          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 144
ccccttaggg ataacagggt aatcaggcag tgcaggcgtt ataaact                 47

SEQ ID NO: 145          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 145
ccccttaggg ataacagggt aatccacttt ccctggggct tgctta                  46

SEQ ID NO: 146          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 146
ccccttaggg ataacagggt aatcggaagg ggcgtgggaa gcg                     43

SEQ ID NO: 147          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 147
ccccttaggg ataacagggt aatcccgcag acagagcaag cgcgtt                  46
```

```
SEQ ID NO: 148          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 148
ccccttaggg ataacagggt aatcgcccca gctaccacct cctc                   44

SEQ ID NO: 149          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 149
ccccttaggg ataacagggt aatccgcgga ccacggctcc tc                     42

SEQ ID NO: 150          moltype = DNA  length = 56
FEATURE                 Location/Qualifiers
misc_feature            1..56
                        note = Synthetic oligonucleotide
source                  1..56
                        mol_type = other DNA
                        organism = synthetic construct
SEQUENCE: 150
gtgactggag ttcagacgtg tgctcttccg atctgccctg ggtctctgaa gaagct      56

SEQ ID NO: 151          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 151
gtgactggag ttcagacgtg tgctcttccg atctggcggg tggtcacaa aataaaatgt  60

SEQ ID NO: 152          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 152
gtgactggag ttcagacgtg tgctcttccg atctacagga cagggtcagc gtttaaga    58

SEQ ID NO: 153          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 153
gtgactggag ttcagacgtg tgctcttccg atctaagttt gctggccctg gtttaga     57

SEQ ID NO: 154          moltype = DNA  length = 56
FEATURE                 Location/Qualifiers
misc_feature            1..56
                        note = Synthetic oligonucleotide
source                  1..56
                        mol_type = other DNA
                        organism = synthetic construct
SEQUENCE: 154
gtgactggag ttcagacgtg tgctcttccg atcttgcagt acagtgatgg gaccgt      56

SEQ ID NO: 155          moltype = DNA  length = 53
FEATURE                 Location/Qualifiers
misc_feature            1..53
                        note = Synthetic oligonucleotide
source                  1..53
                        mol_type = other DNA
                        organism = synthetic construct
SEQUENCE: 155
gtgactggag ttcagacgtg tgctcttccg atctccttag ggggccagca gtg         53
```

```
SEQ ID NO: 156          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 156
gtgactggag ttcagacgtg tgctcttccg atctgcagac gcccccatca agcc        54

SEQ ID NO: 157          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 157
gtgactggag ttcagacgtg tgctcttccg atcttggagt taagggtgtc tccgaggtg   59

SEQ ID NO: 158          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 158
gtgactggag ttcagacgtg tgctcttccg atctgcgcgc accccttcc ca          52

SEQ ID NO: 159          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 159
gtgactggag ttcagacgtg tgctcttccg atctggtgag gccgtgcagt tggtc       55

SEQ ID NO: 160          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 160
gtgactggag ttcagacgtg tgctcttccg atctaagcct cttgaacatg ccgaaatgta  60

SEQ ID NO: 161          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 161
gtgactggag ttcagacgtg tgctcttccg atcttcgtct cctggagctc tggacac     57

SEQ ID NO: 162          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 162
gtgactggag ttcagacgtg tgctcttccg atctccacct gtggctgata gtgacgtct   59

SEQ ID NO: 163          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 163
```

```
gtgactggag ttcagacgtg tgctcttccg atctaggtct ggggagcgga gtcc        54

SEQ ID NO: 164          moltype = DNA  length = 53
FEATURE                 Location/Qualifiers
misc_feature            1..53
                        note = Synthetic oligonucleotide
source                  1..53
                        mol_type = other DNA
                        organism = synthetic construct
SEQUENCE: 164
gtgactggag ttcagacgtg tgctcttccg atctaccgcc tccaccccca agg         53

SEQ ID NO: 165          moltype = DNA  length = 56
FEATURE                 Location/Qualifiers
misc_feature            1..56
                        note = Synthetic oligonucleotide
source                  1..56
                        mol_type = other DNA
                        organism = synthetic construct
SEQUENCE: 165
gtgactggag ttcagacgtg tgctcttccg atctggatct ggggagagag gtgacc      56

SEQ ID NO: 166          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 166
gtgactggag ttcagacgtg tgctcttccg atcttgtatg tatgcaaagc cccgtcacg   59

SEQ ID NO: 167          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 167
gtgactggag ttcagacgtg tgctcttccg atctgactgg agttcccttc accatttcaa  60

SEQ ID NO: 168          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 168
gtgactggag ttcagacgtg tgctcttccg atctcctgga cagacgaagg cagca       55

SEQ ID NO: 169          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 169
gtgactggag ttcagacgtg tgctcttccg atctgcctgt agagatcaag gctgctc     57

SEQ ID NO: 170          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 170
gtgactggag ttcagacgtg tgctcttccg atcttcgggg gtgattagtt gctttttgtt  60

SEQ ID NO: 171          moltype = DNA  length = 55
FEATURE                 Location/Qualifiers
misc_feature            1..55
                        note = Synthetic oligonucleotide
source                  1..55
                        mol_type = other DNA
                        organism = synthetic construct
```

```
SEQUENCE: 171
gtgactggag ttcagacgtg tgctcttccg atctcccgac acctaccggc tctcc       55

SEQ ID NO: 172         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 172
gtgactggag ttcagacgtg tgctcttccg atctggtcct ggtgctgttc agcccatctt  60

SEQ ID NO: 173         moltype = DNA  length = 56
FEATURE                Location/Qualifiers
misc_feature           1..56
                       note = Synthetic oligonucleotide
source                 1..56
                       mol_type = other DNA
                       organism = synthetic construct
SEQUENCE: 173
gtgactggag ttcagacgtg tgctcttccg atctggtggg tcaactttgg cagggt      56

SEQ ID NO: 174         moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 174
gtgactggag ttcagacgtg tgctcttccg atctggtggg cgtggctatg taaacgga    58

SEQ ID NO: 175         moltype = DNA  length = 56
FEATURE                Location/Qualifiers
misc_feature           1..56
                       note = Synthetic oligonucleotide
source                 1..56
                       mol_type = other DNA
                       organism = synthetic construct
SEQUENCE: 175
gtgactggag ttcagacgtg tgctcttccg atctctggac tgcaccatcg ctcagg      56

SEQ ID NO: 176         moltype = DNA  length = 56
FEATURE                Location/Qualifiers
misc_feature           1..56
                       note = Synthetic oligonucleotide
source                 1..56
                       mol_type = other DNA
                       organism = synthetic construct
SEQUENCE: 176
gtgactggag ttcagacgtg tgctcttccg atctaaggga gtctcaggcc cgtgag      56

SEQ ID NO: 177         moltype = DNA  length = 55
FEATURE                Location/Qualifiers
misc_feature           1..55
                       note = Synthetic oligonucleotide
source                 1..55
                       mol_type = other DNA
                       organism = synthetic construct
SEQUENCE: 177
gtgactggag ttcagacgtg tgctcttccg atctgtcctg cgtcccttcc cctga       55

SEQ ID NO: 178         moltype = DNA  length = 52
FEATURE                Location/Qualifiers
misc_feature           1..52
                       note = Synthetic oligonucleotide
source                 1..52
                       mol_type = other DNA
                       organism = synthetic construct
SEQUENCE: 178
gtgactggag ttcagacgtg tgctcttccg atctgcaccg gcagccacct gt          52

SEQ ID NO: 179         moltype = DNA  length = 58
FEATURE                Location/Qualifiers
misc_feature           1..58
                       note = Synthetic oligonucleotide
source                 1..58
                       mol_type = other DNA
```

```
                         organism = synthetic construct
SEQUENCE: 179
gtgactggag ttcagacgtg tgctcttccg atctaactgc cactactccc gtcctcag    58

SEQ ID NO: 180           moltype = DNA  length = 53
FEATURE                  Location/Qualifiers
misc_feature             1..53
                         note = Synthetic oligonucleotide
source                   1..53
                         mol_type = other DNA
                         organism = synthetic construct
SEQUENCE: 180
gtgactggag ttcagacgtg tgctcttccg atcttgtccg cgtctgtgtc ggt         53

SEQ ID NO: 181           moltype = DNA  length = 52
FEATURE                  Location/Qualifiers
misc_feature             1..52
                         note = Synthetic oligonucleotide
source                   1..52
                         mol_type = other DNA
                         organism = synthetic construct
SEQUENCE: 181
gtgactggag ttcagacgtg tgctcttccg atctcccggg cctcgagcag ac          52

SEQ ID NO: 182           moltype = DNA  length = 57
FEATURE                  Location/Qualifiers
misc_feature             1..57
                         note = Synthetic oligonucleotide
source                   1..57
                         mol_type = other DNA
                         organism = synthetic construct
SEQUENCE: 182
gtgactggag ttcagacgtg tgctcttccg atctcttgga cagctgcagt actccct     57

SEQ ID NO: 183           moltype = DNA  length = 55
FEATURE                  Location/Qualifiers
misc_feature             1..55
                         note = Synthetic oligonucleotide
source                   1..55
                         mol_type = other DNA
                         organism = synthetic construct
SEQUENCE: 183
gtgactggag ttcagacgtg tgctcttccg atctagtgcg gtggagaaag gcaag       55

SEQ ID NO: 184           moltype = DNA  length = 58
FEATURE                  Location/Qualifiers
misc_feature             1..58
                         note = Synthetic oligonucleotide
source                   1..58
                         mol_type = other DNA
                         organism = synthetic construct
SEQUENCE: 184
gtgactggag ttcagacgtg tgctcttccg atctgcgtct ctttggaccc gtacttgc    58

SEQ ID NO: 185           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 185
gtgactggag ttcagacgtg tgctcttccg atcttcctgg ctttagcgct atacgtttga  60

SEQ ID NO: 186           moltype = DNA  length = 57
FEATURE                  Location/Qualifiers
misc_feature             1..57
                         note = Synthetic oligonucleotide
source                   1..57
                         mol_type = other DNA
                         organism = synthetic construct
SEQUENCE: 186
gtgactggag ttcagacgtg tgctcttccg atctcatttg tccaggaacc cctagcc     57

SEQ ID NO: 187           moltype = DNA  length = 60
FEATURE                  Location/Qualifiers
misc_feature             1..60
                         note = Synthetic oligonucleotide
source                   1..60
```

```
                        mol_type = other DNA
                        organism = synthetic construct
SEQUENCE: 187
gtgactggag ttcagacgtg tgctcttccg atctaccatt tgtgctgatc tgtgggtatc  60

SEQ ID NO: 188          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 188
gtgactggag ttcagacgtg tgctcttccg atctcagggt tgcatgggaa cttcctctg   59

SEQ ID NO: 189          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 189
gtgactggag ttcagacgtg tgctcttccg atctcccacc ctcgtcactc tctgacc     57

SEQ ID NO: 190          moltype = DNA  length = 53
FEATURE                 Location/Qualifiers
misc_feature            1..53
                        note = Synthetic oligonucleotide
source                  1..53
                        mol_type = other DNA
                        organism = synthetic construct
SEQUENCE: 190
gtgactggag ttcagacgtg tgctcttccg atctccggcg acactgggga atg         53

SEQ ID NO: 191          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 191
gtgactggag ttcagacgtg tgctcttccg atctcccggg ctccgtgcaa ac          52

SEQ ID NO: 192          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 192
gtgactggag ttcagacgtg tgctcttccg atctaggccc cctggagctg ca          52

SEQ ID NO: 193          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 193
gtgactggag ttcagacgtg tgctcttccg atctccaccc tgctccacac acct        54

SEQ ID NO: 194          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 194
gtgactggag ttcagacgtg tgctcttccg atctacggcc ctggcaccac ct          52

SEQ ID NO: 195          moltype = DNA  length = 53
FEATURE                 Location/Qualifiers
misc_feature            1..53
                        note = Synthetic oligonucleotide
```

```
source                1..53
                      mol_type = other DNA
                      organism = synthetic construct
SEQUENCE: 195
gtgactggag ttcagacgtg tgctcttccg atctctgccg cgctcctcct tcc         53

SEQ ID NO: 196        moltype = DNA  length = 60
FEATURE               Location/Qualifiers
misc_feature          1..60
                      note = Synthetic oligonucleotide
source                1..60
                      mol_type = other DNA
                      organism = synthetic construct
SEQUENCE: 196
gtgactggag ttcagacgtg tgctcttccg atctcctcat tggggacgtc tgttgtgaaa  60

SEQ ID NO: 197        moltype = DNA  length = 59
FEATURE               Location/Qualifiers
misc_feature          1..59
                      note = Synthetic oligonucleotide
source                1..59
                      mol_type = other DNA
                      organism = synthetic construct
SEQUENCE: 197
gtgactggag ttcagacgtg tgctcttccg atctagtccc cagttacgga gacaaatct   59

SEQ ID NO: 198        moltype = DNA  length = 60
FEATURE               Location/Qualifiers
misc_feature          1..60
                      note = Synthetic oligonucleotide
source                1..60
                      mol_type = other DNA
                      organism = synthetic construct
SEQUENCE: 198
gtgactggag ttcagacgtg tgctcttccg atctggcccc agagaggtga ggtcactata  60

SEQ ID NO: 199        moltype = DNA  length = 53
FEATURE               Location/Qualifiers
misc_feature          1..53
                      note = Synthetic oligonucleotide
source                1..53
                      mol_type = other DNA
                      organism = synthetic construct
SEQUENCE: 199
gtgactggag ttcagacgtg tgctcttccg atctggtacc ccgtgcctca gct         53

SEQ ID NO: 200        moltype = DNA  length = 57
FEATURE               Location/Qualifiers
misc_feature          1..57
                      note = Synthetic oligonucleotide
source                1..57
                      mol_type = other DNA
                      organism = synthetic construct
SEQUENCE: 200
gtgactggag ttcagacgtg tgctcttccg atctccaggt tgtttatctg ggcctct     57

SEQ ID NO: 201        moltype = DNA  length = 58
FEATURE               Location/Qualifiers
misc_feature          1..58
                      note = Synthetic oligonucleotide
source                1..58
                      mol_type = other DNA
                      organism = synthetic construct
SEQUENCE: 201
gtgactggag ttcagacgtg tgctcttccg atctgcagga cacagcacag gtaaggga    58

SEQ ID NO: 202        moltype = DNA  length = 58
FEATURE               Location/Qualifiers
misc_feature          1..58
                      note = Synthetic oligonucleotide
source                1..58
                      mol_type = other DNA
                      organism = synthetic construct
SEQUENCE: 202
gtgactggag ttcagacgtg tgctcttccg atctctgggg tgactccaag gcttttcg    58

SEQ ID NO: 203        moltype = DNA  length = 54
FEATURE               Location/Qualifiers
misc_feature          1..54
```

```
                        note = Synthetic oligonucleotide
source                  1..54
                        mol_type = other DNA
                        organism = synthetic construct
SEQUENCE: 203
gtgactggag ttcagacgtg tgctcttccg atctccccga gccctcctct cttg        54

SEQ ID NO: 204          moltype = DNA  length = 53
FEATURE                 Location/Qualifiers
misc_feature            1..53
                        note = Synthetic oligonucleotide
source                  1..53
                        mol_type = other DNA
                        organism = synthetic construct
SEQUENCE: 204
gtgactggag ttcagacgtg tgctcttccg atctagctcc gactccgctc gct         53

SEQ ID NO: 205          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 205
gtgactggag ttcagacgtg tgctcttccg atctttgccc ggggtaggaa agtga       55

SEQ ID NO: 206          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 206
gtgactggag ttcagacgtg tgctcttccg atctgtatca gctgccttct catcacaaga  60

SEQ ID NO: 207          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 207
gtgactggag ttcagacgtg tgctcttccg atctgtgcca ttctcagcct aaaaggtaga  60

SEQ ID NO: 208          moltype = DNA  length = 53
FEATURE                 Location/Qualifiers
misc_feature            1..53
                        note = Synthetic oligonucleotide
source                  1..53
                        mol_type = other DNA
                        organism = synthetic construct
SEQUENCE: 208
gtgactggag ttcagacgtg tgctcttccg atctacgcag tcggaggcca tcc         53

SEQ ID NO: 209          moltype = DNA  length = 56
FEATURE                 Location/Qualifiers
misc_feature            1..56
                        note = Synthetic oligonucleotide
source                  1..56
                        mol_type = other DNA
                        organism = synthetic construct
SEQUENCE: 209
gtgactggag ttcagacgtg tgctcttccg atctagcaca cccaccacca ctccta      56

SEQ ID NO: 210          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 210
gtgactggag ttcagacgtg tgctcttccg atctcttgtc ccacatcaca gcaaactct   59

SEQ ID NO: 211          moltype = DNA  length = 53
FEATURE                 Location/Qualifiers
```

```
misc_feature            1..53
                        note = Synthetic oligonucleotide
source                  1..53
                        mol_type = other DNA
                        organism = synthetic construct
SEQUENCE: 211
gtgactggag ttcagacgtg tgctcttccg atctcggggc tgcggaagga tcc         53

SEQ ID NO: 212          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 212
gtgactggag ttcagacgtg tgctcttccg atctcaacgt ggcctcagct gctc        54

SEQ ID NO: 213          moltype = DNA  length = 53
FEATURE                 Location/Qualifiers
misc_feature            1..53
                        note = Synthetic oligonucleotide
source                  1..53
                        mol_type = other DNA
                        organism = synthetic construct
SEQUENCE: 213
gtgactggag ttcagacgtg tgctcttccg atctacgagg ctggctcccc act         53

SEQ ID NO: 214          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 214
gtgactggag ttcagacgtg tgctcttccg atctctcctt agaaagtcat gccccaggag  60

SEQ ID NO: 215          moltype = DNA  length = 53
FEATURE                 Location/Qualifiers
misc_feature            1..53
                        note = Synthetic oligonucleotide
source                  1..53
                        mol_type = other DNA
                        organism = synthetic construct
SEQUENCE: 215
gtgactggag ttcagacgtg tgctcttccg atctgggctg ggaggggatt ggc         53

SEQ ID NO: 216          moltype = DNA  length = 56
FEATURE                 Location/Qualifiers
misc_feature            1..56
                        note = Synthetic oligonucleotide
source                  1..56
                        mol_type = other DNA
                        organism = synthetic construct
SEQUENCE: 216
gtgactggag ttcagacgtg tgctcttccg atctgcctcc ctgcaggatg attggc      56

SEQ ID NO: 217          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 217
gtgactggag ttcagacgtg tgctcttccg atctatgcca cagatgacta ttgcacacct  60

SEQ ID NO: 218          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 218
gtgactggag ttcagacgtg tgctcttccg atctacctca ggggccgctg ca          52

SEQ ID NO: 219          moltype = DNA  length = 57
```

```
FEATURE                Location/Qualifiers
misc_feature           1..57
                       note = Synthetic oligonucleotide
source                 1..57
                       mol_type = other DNA
                       organism = synthetic construct
SEQUENCE: 219
gtgactggag ttcagacgtg tgctcttccg atctgctggc actgatctgt ggtccca     57

SEQ ID NO: 220         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 220
gtgactggag ttcagacgtg tgctcttccg atctaaccag ttcacccagt tacagtagac  60

SEQ ID NO: 221         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 221
gtgactggag ttcagacgtg tgctcttccg atctaccgct taaattaacc ctgagtgacg  60

SEQ ID NO: 222         moltype = DNA  length = 52
FEATURE                Location/Qualifiers
misc_feature           1..52
                       note = Synthetic oligonucleotide
source                 1..52
                       mol_type = other DNA
                       organism = synthetic construct
SEQUENCE: 222
gtgactggag ttcagacgtg tgctcttccg atcttagcgt gcggcccgag ct          52

SEQ ID NO: 223         moltype = DNA  length = 54
FEATURE                Location/Qualifiers
misc_feature           1..54
                       note = Synthetic oligonucleotide
source                 1..54
                       mol_type = other DNA
                       organism = synthetic construct
SEQUENCE: 223
gtgactggag ttcagacgtg tgctcttccg atctgggggt gagctccaac tctg        54

SEQ ID NO: 224         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 224
gtgactggag ttcagacgtg tgctcttccg atctatgtat ctggcattac agctgagcag  60

SEQ ID NO: 225         moltype = DNA  length = 54
FEATURE                Location/Qualifiers
misc_feature           1..54
                       note = Synthetic oligonucleotide
source                 1..54
                       mol_type = other DNA
                       organism = synthetic construct
SEQUENCE: 225
gtgactggag ttcagacgtg tgctcttccg atctcagcca ctgcaccgac ttca        54

SEQ ID NO: 226         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 226
gtgactggag ttcagacgtg tgctcttccg atctcggttc caagttatcg gagtgagcca  60
```

```
SEQ ID NO: 227          moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 227
gtgactggag ttcagacgtg tgctcttccg atctggactc atagcctggg ggtaaatgtt  60

SEQ ID NO: 228          moltype = DNA  length = 56
FEATURE                Location/Qualifiers
misc_feature           1..56
                       note = Synthetic oligonucleotide
source                 1..56
                       mol_type = other DNA
                       organism = synthetic construct
SEQUENCE: 228
gtgactggag ttcagacgtg tgctcttccg atcttgcttg ggctccgttg caatcc      56

SEQ ID NO: 229          moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 229
gtgactggag ttcagacgtg tgctcttccg atctaaacca ggggagaggg ccatagag    58

SEQ ID NO: 230          moltype = DNA  length = 55
FEATURE                Location/Qualifiers
misc_feature           1..55
                       note = Synthetic oligonucleotide
source                 1..55
                       mol_type = other DNA
                       organism = synthetic construct
SEQUENCE: 230
gtgactggag ttcagacgtg tgctcttccg atctgctgtg actcagagcc atggc       55

SEQ ID NO: 231          moltype = DNA  length = 57
FEATURE                Location/Qualifiers
misc_feature           1..57
                       note = Synthetic oligonucleotide
source                 1..57
                       mol_type = other DNA
                       organism = synthetic construct
SEQUENCE: 231
gtgactggag ttcagacgtg tgctcttccg atctggcttc ccatgggtga gtcctgt     57

SEQ ID NO: 232          moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 232
gtgactggag ttcagacgtg tgctcttccg atctgaagag ctgaacatag ccaggcaatt  60

SEQ ID NO: 233          moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 233
gtgactggag ttcagacgtg tgctcttccg atcttgactg aggtggatga acccctaagc  60

SEQ ID NO: 234          moltype = DNA  length = 56
FEATURE                Location/Qualifiers
misc_feature           1..56
                       note = Synthetic oligonucleotide
source                 1..56
                       mol_type = other DNA
                       organism = synthetic construct
SEQUENCE: 234
gtgactggag ttcagacgtg tgctcttccg atctaacccc ctgcagctgc tcacaa      56
```

```
SEQ ID NO: 235         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 235
gtgactggag ttcagacgtg tgctcttccg atctaaatcc caagggcatt gttcacataa  60

SEQ ID NO: 236         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 236
gtgactggag ttcagacgtg tgctcttccg atctaccctt tttgaaaatt agttgcccat  60

SEQ ID NO: 237         moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 237
gtgactggag ttcagacgtg tgctcttccg atctgaggca gagggaacta caggtgca    58

SEQ ID NO: 238         moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 238
gtgactggag ttcagacgtg tgctcttccg atctcctccc tctcctacca acttcatcc   59

SEQ ID NO: 239         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 239
gtgactggag ttcagacgtg tgctcttccg atctccaaac acagaaaggc catttattgt  60

SEQ ID NO: 240         moltype = DNA  length = 56
FEATURE                Location/Qualifiers
misc_feature           1..56
                       note = Synthetic oligonucleotide
source                 1..56
                       mol_type = other DNA
                       organism = synthetic construct
SEQUENCE: 240
gtgactggag ttcagacgtg tgctcttccg atctccatga tcgtgcactc tagcct      56

SEQ ID NO: 241         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 241
gtgactggag ttcagacgtg tgctcttccg atctaggagt gtgtaccatt taaggatgtg  60

SEQ ID NO: 242         moltype = DNA  length = 53
FEATURE                Location/Qualifiers
misc_feature           1..53
                       note = Synthetic oligonucleotide
source                 1..53
                       mol_type = other DNA
                       organism = synthetic construct
SEQUENCE: 242
```

```
gtgactggag ttcagacgtg tgctcttccg atctcccacc tggccctgca aga         53

SEQ ID NO: 243          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 243
gtgactggag ttcagacgtg tgctcttccg atcttctctg cccctggaca gattctatag  60

SEQ ID NO: 244          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 244
gtgactggag ttcagacgtg tgctcttccg atctgggccc tgctgcacta tgatcaa     57

SEQ ID NO: 245          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 245
gtgactggag ttcagacgtg tgctcttccg atctgggcca gcttcatgac ctgaaacc    58

SEQ ID NO: 246          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 246
gtgactggag ttcagacgtg tgctcttccg atcttgcacc tggctgcacc ac          52

SEQ ID NO: 247          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 247
gtgactggag ttcagacgtg tgctcttccg atctcatcct gaatgctcgt tgagtggatg  60

SEQ ID NO: 248          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 248
gtgactggag ttcagacgtg tgctcttccg atctggccaa gcccatgtag tactgcag    58

SEQ ID NO: 249          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 249
gtgactggag ttcagacgtg tgctcttccg atctccctca actacttgcc caacatgc    58

SEQ ID NO: 250          moltype = DNA  length = 60
FEATURE                 Location/Qualifiers
misc_feature            1..60
                        note = Synthetic oligonucleotide
source                  1..60
                        mol_type = other DNA
                        organism = synthetic construct
```

SEQUENCE: 250
gtgactggag ttcagacgtg tgctcttccg atctcggtgt cagcaaagct aggtaaggag 60

SEQ ID NO: 251 moltype = DNA length = 59
FEATURE Location/Qualifiers
misc_feature 1..59
note = Synthetic oligonucleotide
source 1..59
mol_type = other DNA
organism = synthetic construct
SEQUENCE: 251
gtgactggag ttcagacgtg tgctcttccg atctccgatg aggcatgggt tatgaagta 59

SEQ ID NO: 252 moltype = DNA length = 56
FEATURE Location/Qualifiers
misc_feature 1..56
note = Synthetic oligonucleotide
source 1..56
mol_type = other DNA
organism = synthetic construct
SEQUENCE: 252
gtgactggag ttcagacgtg tgctcttccg atctcccctc tggtatgccc cctcat 56

SEQ ID NO: 253 moltype = DNA length = 58
FEATURE Location/Qualifiers
misc_feature 1..58
note = Synthetic oligonucleotide
source 1..58
mol_type = other DNA
organism = synthetic construct
SEQUENCE: 253
gtgactggag ttcagacgtg tgctcttccg atcttgactg gatgctgggt tgtggaaa 58

SEQ ID NO: 254 moltype = DNA length = 55
FEATURE Location/Qualifiers
misc_feature 1..55
note = Synthetic oligonucleotide
source 1..55
mol_type = other DNA
organism = synthetic construct
SEQUENCE: 254
gtgactggag ttcagacgtg tgctcttccg atctttctcc cccgaggcct cagaa 55

SEQ ID NO: 255 moltype = DNA length = 60
FEATURE Location/Qualifiers
misc_feature 1..60
note = Synthetic oligonucleotide
source 1..60
mol_type = other DNA
organism = synthetic construct
SEQUENCE: 255
gtgactggag ttcagacgtg tgctcttccg atctgacttg acataagcac catacttcgg 60

SEQ ID NO: 256 moltype = DNA length = 54
FEATURE Location/Qualifiers
misc_feature 1..54
note = Synthetic oligonucleotide
source 1..54
mol_type = other DNA
organism = synthetic construct
SEQUENCE: 256
gtgactggag ttcagacgtg tgctcttccg atctgggctg ctgggtagga cctg 54

SEQ ID NO: 257 moltype = DNA length = 60
FEATURE Location/Qualifiers
misc_feature 1..60
note = Synthetic oligonucleotide
source 1..60
mol_type = other DNA
organism = synthetic construct
SEQUENCE: 257
gtgactggag ttcagacgtg tgctcttccg atctcgtgat tcgagttcct ggcaatgcta 60

SEQ ID NO: 258 moltype = DNA length = 56
FEATURE Location/Qualifiers
misc_feature 1..56
note = Synthetic oligonucleotide
source 1..56
mol_type = other DNA

```
                        organism = synthetic construct
SEQUENCE: 258
gtgactggag ttcagacgtg tgctcttccg atctggtcct gaaatgaccc ccaagg      56

SEQ ID NO: 259          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 259
gtgactggag ttcagacgtg tgctcttccg atctcgcagc ctattgtctc ctggt       55

SEQ ID NO: 260          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 260
gtgactggag ttcagacgtg tgctcttccg atctgcacgc cgtggccgaa ca          52

SEQ ID NO: 261          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 261
gtgactggag ttcagacgtg tgctcttccg atctaacttc cataccagca gcagttcc    58

SEQ ID NO: 262          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 262
gtgactggag ttcagacgtg tgctcttccg atctccgctc gggccgctga ct          52

SEQ ID NO: 263          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 263
gtgactggag ttcagacgtg tgctcttccg atctcgccca ctctcgactc ttcaggtag   59

SEQ ID NO: 264          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 264
gtgactggag ttcagacgtg tgctcttccg atctactccc caggtgctga agagacg     57

SEQ ID NO: 265          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 265
gtgactggag ttcagacgtg tgctcttccg atctgcaggg ggtccgagtg ca          52

SEQ ID NO: 266          moltype = DNA  length = 53
FEATURE                 Location/Qualifiers
misc_feature            1..53
                        note = Synthetic oligonucleotide
source                  1..53
```

```
                        mol_type = other DNA
                        organism = synthetic construct
SEQUENCE: 266
gtgactggag ttcagacgtg tgctcttccg atcttgctgc tcgttgcctg gca         53

SEQ ID NO: 267          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 267
gtgactggag ttcagacgtg tgctcttccg atctcacttg aggtggacgt cagtttctgg  60

SEQ ID NO: 268          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 268
gtgactggag ttcagacgtg tgctcttccg atctgtgggt tctggcagaa gttcctatgt  60

SEQ ID NO: 269          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 269
gtgactggag ttcagacgtg tgctcttccg atctcccctc tgccaccccc at          52

SEQ ID NO: 270          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 270
gtgactggag ttcagacgtg tgctcttccg atctcctgtg tccggagctg tttctgc     57

SEQ ID NO: 271          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 271
gtgactggag ttcagacgtg tgctcttccg atctcctggc tggaaaggca accc        54

SEQ ID NO: 272          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 272
gtgactggag ttcagacgtg tgctcttccg atctaccact ctagaatttg gcaagatgt   59

SEQ ID NO: 273          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 273
gtgactggag ttcagacgtg tgctcttccg atctatttct ccacctaggt gtgctctctc  60

SEQ ID NO: 274          moltype = DNA  length = 59
FEATURE                 Location/Qualifiers
misc_feature            1..59
                        note = Synthetic oligonucleotide
```

```
source                  1..59
                        mol_type = other DNA
                        organism = synthetic construct
SEQUENCE: 274
gtgactggag ttcagacgtg tgctcttccg atctgaacac aggagctagt ctgggaaga   59

SEQ ID NO: 275          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 275
gtgactggag ttcagacgtg tgctcttccg atctcgttac tgtgcattga agtcacctga  60

SEQ ID NO: 276          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 276
gtgactggag ttcagacgtg tgctcttccg atctgcctgt tcttgcacct ggattcttac  60

SEQ ID NO: 277          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 277
gtgactggag ttcagacgtg tgctcttccg atctgcgccc tgcccttcgg ataa        54

SEQ ID NO: 278          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 278
gtgactggag ttcagacgtg tgctcttccg atctacggtt atctttgcga cttaggctca  60

SEQ ID NO: 279          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 279
gtgactggag ttcagacgtg tgctcttccg atctgcgtta taaactcccc gaatcttgga  60

SEQ ID NO: 280          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 280
gtgactggag ttcagacgtg tgctcttccg atcttccctg gggcttgctt agtaaagtag  60

SEQ ID NO: 281          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 281
gtgactggag ttcagacgtg tgctcttccg atctaggtgg ccggcccagg gt          52

SEQ ID NO: 282          moltype = DNA  length = 52
FEATURE                 Location/Qualifiers
misc_feature            1..52
```

```
                        note = Synthetic oligonucleotide
source                  1..52
                        mol_type = other DNA
                        organism = synthetic construct
SEQUENCE: 282
gtgactggag ttcagacgtg tgctcttccg atcttcgggc cggggcgtct ga          52

SEQ ID NO: 283          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 283
gtgactggag ttcagacgtg tgctcttccg atctcggcgg cggacagtgg ac          52

SEQ ID NO: 284          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 284
gtgactggag ttcagacgtg tgctcttccg atctccgaag cgagaacagc ccagaagtt   59

SEQ ID NO: 285          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 285
ccccttaggg ataacagggt aatcttggca tgacccaggt ccatac                 46

SEQ ID NO: 286          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 286
ccccttaggg ataacagggt aatcaagagt ctgggtgaat cagcagtc               48

SEQ ID NO: 287          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 287
ccccttaggg ataacagggt aatcaggggc cagcagcaag gt                     42

SEQ ID NO: 288          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 288
ccccttaggg ataacagggt aatctgagtc aggaggcaga gatcctc                47

SEQ ID NO: 289          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 289
ccccttaggg ataacagggt aatcaaatcc cgttggccct cctg                   44

SEQ ID NO: 290          moltype = DNA  length = 42
FEATURE                 Location/Qualifiers
```

```
misc_feature          1..42
                      note = Synthetic oligonucleotide
source                1..42
                      mol_type = other DNA
                      organism = synthetic construct
SEQUENCE: 290
ccccttaggg ataacagggt aatcggggcg ttgtgggtct ga                  42

SEQ ID NO: 291        moltype = DNA  length = 42
FEATURE               Location/Qualifiers
misc_feature          1..42
                      note = Synthetic oligonucleotide
source                1..42
                      mol_type = other DNA
                      organism = synthetic construct
SEQUENCE: 291
ccccttaggg ataacagggt aatccctagg cccctcccct ct                  42

SEQ ID NO: 292        moltype = DNA  length = 44
FEATURE               Location/Qualifiers
misc_feature          1..44
                      note = Synthetic oligonucleotide
source                1..44
                      mol_type = other DNA
                      organism = synthetic construct
SEQUENCE: 292
ccccttaggg ataacagggt aatcccaggt ggtctcctcc gact                44

SEQ ID NO: 293        moltype = DNA  length = 45
FEATURE               Location/Qualifiers
misc_feature          1..45
                      note = Synthetic oligonucleotide
source                1..45
                      mol_type = other DNA
                      organism = synthetic construct
SEQUENCE: 293
ccccttaggg ataacagggt aatcagggga gatgctcagt gtggt               45

SEQ ID NO: 294        moltype = DNA  length = 46
FEATURE               Location/Qualifiers
misc_feature          1..46
                      note = Synthetic oligonucleotide
source                1..46
                      mol_type = other DNA
                      organism = synthetic construct
SEQUENCE: 294
ccccttaggg ataacagggt aatctgagca caaggtcgtc tcctct              46

SEQ ID NO: 295        moltype = DNA  length = 49
FEATURE               Location/Qualifiers
misc_feature          1..49
                      note = Synthetic oligonucleotide
source                1..49
                      mol_type = other DNA
                      organism = synthetic construct
SEQUENCE: 295
ccccttaggg ataacagggt aatctggcag atgaataagg ctcactcct           49

SEQ ID NO: 296        moltype = DNA  length = 50
FEATURE               Location/Qualifiers
misc_feature          1..50
                      note = Synthetic oligonucleotide
source                1..50
                      mol_type = other DNA
                      organism = synthetic construct
SEQUENCE: 296
ccccttaggg ataacagggt aatctcccta cagagataaa cagacgcaca          50

SEQ ID NO: 297        moltype = DNA  length = 49
FEATURE               Location/Qualifiers
misc_feature          1..49
                      note = Synthetic oligonucleotide
source                1..49
                      mol_type = other DNA
                      organism = synthetic construct
SEQUENCE: 297
ccccttaggg ataacagggt aatccagttc tttgggtcct catcacagt           49

SEQ ID NO: 298        moltype = DNA  length = 47
```

```
FEATURE                Location/Qualifiers
misc_feature           1..47
                       note = Synthetic oligonucleotide
source                 1..47
                       mol_type = other DNA
                       organism = synthetic construct
SEQUENCE: 298
ccccttaggg ataacagggt aatcagcaac atacagatgg ggtggga              47

SEQ ID NO: 299         moltype = DNA  length = 47
FEATURE                Location/Qualifiers
misc_feature           1..47
                       note = Synthetic oligonucleotide
source                 1..47
                       mol_type = other DNA
                       organism = synthetic construct
SEQUENCE: 299
ccccttaggg ataacagggt aatcggatgc ttagcttccg ttgggtt              47

SEQ ID NO: 300         moltype = DNA  length = 42
FEATURE                Location/Qualifiers
misc_feature           1..42
                       note = Synthetic oligonucleotide
source                 1..42
                       mol_type = other DNA
                       organism = synthetic construct
SEQUENCE: 300
ccccttaggg ataacagggt aatcctgggc acggtggaca gc                   42

SEQ ID NO: 301         moltype = DNA  length = 48
FEATURE                Location/Qualifiers
misc_feature           1..48
                       note = Synthetic oligonucleotide
source                 1..48
                       mol_type = other DNA
                       organism = synthetic construct
SEQUENCE: 301
ccccttaggg ataacagggt aatccctctt caagtggtct gcatggaa             48

SEQ ID NO: 302         moltype = DNA  length = 47
FEATURE                Location/Qualifiers
misc_feature           1..47
                       note = Synthetic oligonucleotide
source                 1..47
                       mol_type = other DNA
                       organism = synthetic construct
SEQUENCE: 302
ccccttaggg ataacagggt aatcggtggt ctcctccgat ttcaaca              47

SEQ ID NO: 303         moltype = DNA  length = 44
FEATURE                Location/Qualifiers
misc_feature           1..44
                       note = Synthetic oligonucleotide
source                 1..44
                       mol_type = other DNA
                       organism = synthetic construct
SEQUENCE: 303
ccccttaggg ataacagggt aatcttgcgg ggaggggaga ttct                 44

SEQ ID NO: 304         moltype = DNA  length = 46
FEATURE                Location/Qualifiers
misc_feature           1..46
                       note = Synthetic oligonucleotide
source                 1..46
                       mol_type = other DNA
                       organism = synthetic construct
SEQUENCE: 304
ccccttaggg ataacagggt aatcccctac ctcaccgcca atgttt               46

SEQ ID NO: 305         moltype = DNA  length = 47
FEATURE                Location/Qualifiers
misc_feature           1..47
                       note = Synthetic oligonucleotide
source                 1..47
                       mol_type = other DNA
                       organism = synthetic construct
SEQUENCE: 305
ccccttaggg ataacagggt aatcgaggag gggagagtct cagtgtt              47
```

```
SEQ ID NO: 306          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 306
ccccttaggg ataacagggt aatcacttta acagcatcac ccactcttcc             50

SEQ ID NO: 307          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 307
ccccttaggg ataacagggt aatctttcct gtattgcttt tgccttgagc             50

SEQ ID NO: 308          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 308
ccccttaggg ataacagggt aatcggagcc tggaccacta agtcac                 46

SEQ ID NO: 309          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 309
ccccttaggg ataacagggt aatcgcgtgg aggtgagctc atgtag                 46

SEQ ID NO: 310          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 310
ccccttaggg ataacagggt aatcgggcgc tcagtaggtg tgc                    43

SEQ ID NO: 311          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 311
ccccttaggg ataacagggt aatcctgtgg gccatcttca agttcagtcc             50

SEQ ID NO: 312          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 312
ccccttaggg ataacagggt aatcaaaaac ctccaccctt atgaagcct              49

SEQ ID NO: 313          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 313
ccccttaggg ataacagggt aatctctctg ctgtgtgctg tccac                  45
```

```
SEQ ID NO: 314          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 314
cccettaggg ataacagggt aatcagcccc tccctctcca gga                    43

SEQ ID NO: 315          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 315
cccettaggg ataacagggt aatcgatgct ggggctggca ct                     42

SEQ ID NO: 316          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 316
cccettaggg ataacagggt aatcactgtg tccaggggag attctca                47

SEQ ID NO: 317          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 317
cccettaggg ataacagggt aatcacttac gcttaggtgt gatttgcgaa             50

SEQ ID NO: 318          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 318
cccettaggg ataacagggt aatccaggca aggctgaatg gaagcg                 46

SEQ ID NO: 319          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 319
cccettaggg ataacagggt aatccctggg gaagggccat tca                    43

SEQ ID NO: 320          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 320
cccettaggg ataacagggt aatcggagac ggtgcaggag ctc                    43

SEQ ID NO: 321          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 321
```

```
ccccttaggg ataacagggt aatcaggacc ctcctcacgg gatac                  45

SEQ ID NO: 322          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 322
ccccttaggg ataacagggt aatcgtgtgg tgggggactg agc                    43

SEQ ID NO: 323          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 323
ccccttaggg ataacagggt aatcgatgct ggggctgcca ttg                    43

SEQ ID NO: 324          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 324
ccccttaggg ataacagggt aatcctcctc accaccccca agg                    43

SEQ ID NO: 325          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 325
ccccttaggg ataacagggt aatcggccaa agtccgcccc aag                    43

SEQ ID NO: 326          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 326
ccccttaggg ataacagggt aatcggaggc cccaggaact ttca                   44

SEQ ID NO: 327          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 327
ccccttaggg ataacagggt aatccctcgg gaggtgggta gtgt                   44

SEQ ID NO: 328          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 328
ccccttaggg ataacagggt aatcggacca gcttgttgag gacccta                47

SEQ ID NO: 329          moltype = DNA  length = 46
FEATURE                 Location/Qualifiers
misc_feature            1..46
                        note = Synthetic oligonucleotide
source                  1..46
                        mol_type = other DNA
                        organism = synthetic construct
```

```
SEQUENCE: 329
ccccttaggg ataacagggt aatcgagcct catcagttga ccccaa                46

SEQ ID NO: 330          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 330
ccccttaggg ataacagggt aatcggggtg cagcctggag aga                   43

SEQ ID NO: 331          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 331
ccccttaggg ataacagggt aatcagcttt gctggggtaa caggacac              48

SEQ ID NO: 332          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 332
ccccttaggg ataacagggt aatcgaaact atgaaactac caggagaagt            50

SEQ ID NO: 333          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 333
ccccttaggg ataacagggt aatcgttcaa agcatcatct gtgaatcaa             49

SEQ ID NO: 334          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 334
ccccttaggg ataacagggt aatctctgag gccagcaaaa ccttga                46

SEQ ID NO: 335          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 335
ccccttaggg ataacagggt aatcactgac acctggaggc ctga                  44

SEQ ID NO: 336          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 336
ccccttaggg ataacagggt aatcctggag ggtgtatgcg tgct                  44

SEQ ID NO: 337          moltype = DNA  length = 42
FEATURE                 Location/Qualifiers
misc_feature            1..42
                        note = Synthetic oligonucleotide
source                  1..42
                        mol_type = other DNA
```

```
                         organism = synthetic construct
SEQUENCE: 337
ccccttaggg ataacagggt aatcctgggg ttggcgtcac ct                    42

SEQ ID NO: 338           moltype = DNA  length = 47
FEATURE                  Location/Qualifiers
misc_feature             1..47
                         note = Synthetic oligonucleotide
source                   1..47
                         mol_type = other DNA
                         organism = synthetic construct
SEQUENCE: 338
ccccttaggg ataacagggt aatcattctt caggggtct ggcatga                47

SEQ ID NO: 339           moltype = DNA  length = 50
FEATURE                  Location/Qualifiers
misc_feature             1..50
                         note = Synthetic oligonucleotide
source                   1..50
                         mol_type = other DNA
                         organism = synthetic construct
SEQUENCE: 339
ccccttaggg ataacagggt aatccaccca tatgcacacc cacatatacc            50

SEQ ID NO: 340           moltype = DNA  length = 47
FEATURE                  Location/Qualifiers
misc_feature             1..47
                         note = Synthetic oligonucleotide
source                   1..47
                         mol_type = other DNA
                         organism = synthetic construct
SEQUENCE: 340
ccccttaggg ataacagggt aatcgaaaac gccctactgc cctagat               47

SEQ ID NO: 341           moltype = DNA  length = 50
FEATURE                  Location/Qualifiers
misc_feature             1..50
                         note = Synthetic oligonucleotide
source                   1..50
                         mol_type = other DNA
                         organism = synthetic construct
SEQUENCE: 341
ccccttaggg ataacagggt aatcagtccg ccccttatc atcctctctg             50

SEQ ID NO: 342           moltype = DNA  length = 47
FEATURE                  Location/Qualifiers
misc_feature             1..47
                         note = Synthetic oligonucleotide
source                   1..47
                         mol_type = other DNA
                         organism = synthetic construct
SEQUENCE: 342
ccccttaggg ataacagggt aatcccaacg tggacatgag gatgcat               47

SEQ ID NO: 343           moltype = DNA  length = 47
FEATURE                  Location/Qualifiers
misc_feature             1..47
                         note = Synthetic oligonucleotide
source                   1..47
                         mol_type = other DNA
                         organism = synthetic construct
SEQUENCE: 343
ccccttaggg ataacagggt aatctggctt cccaacctga ggttttg               47

SEQ ID NO: 344           moltype = DNA  length = 48
FEATURE                  Location/Qualifiers
misc_feature             1..48
                         note = Synthetic oligonucleotide
source                   1..48
                         mol_type = other DNA
                         organism = synthetic construct
SEQUENCE: 344
ccccttaggg ataacagggt aatcgacaca ggagaaccca ctgaacgc              48

SEQ ID NO: 345           moltype = DNA  length = 48
FEATURE                  Location/Qualifiers
misc_feature             1..48
                         note = Synthetic oligonucleotide
source                   1..48
```

```
                        mol_type = other DNA
                        organism = synthetic construct
SEQUENCE: 345
ccccttaggg ataacagggt aatctctcca cagtacaatg aggccatg                48

SEQ ID NO: 346          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 346
ccccttaggg ataacagggt aatccgtgca caggggacag aagc                    44

SEQ ID NO: 347          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 347
ccccttaggg ataacagggt aatccccagg agctacgcct ctg                     43

SEQ ID NO: 348          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 348
ccccttaggg ataacagggt aatcggctgg cattgctctc aacga                   45

SEQ ID NO: 349          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 349
ccccttaggg ataacagggt aatccatgac gaggtcaggc tccctaggc               49

SEQ ID NO: 350          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 350
ccccttaggg ataacagggt aatcgtggtg gacttcgcag acca                    44

SEQ ID NO: 351          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 351
ccccttaggg ataacagggt aatcgcccag cttaaaacat gagccattca              50

SEQ ID NO: 352          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 352
ccccttaggg ataacagggt aatcgggaga caatggagat ctacctcagt              50

SEQ ID NO: 353          moltype = DNA  length = 43
FEATURE                 Location/Qualifiers
misc_feature            1..43
                        note = Synthetic oligonucleotide
```

```
source                  1..43
                        mol_type = other DNA
                        organism = synthetic construct
SEQUENCE: 353
cccettaggg ataacagggt aatccccact ggcgtcttca gca                   43

SEQ ID NO: 354          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 354
cccettaggg ataacagggt aatcgccaag ggtgccaaac gttgata               47

SEQ ID NO: 355          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 355
cccettaggg ataacagggt aatccagcgt ttcaggaagg gagagg                46

SEQ ID NO: 356          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 356
cccettaggg ataacagggt aatctgtgcc cccatgcatg cc                    42

SEQ ID NO: 357          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 357
cccettaggg ataacagggt aatcgcattg ccctcaacga ccactttt              48

SEQ ID NO: 358          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 358
cccettaggg ataacagggt aatccttaac tctcacaggg ccatgtagtg            50

SEQ ID NO: 359          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 359
cccettaggg ataacagggt aatcaggggt ctacatggca actgtg                46

SEQ ID NO: 360          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 360
gtgactggag ttcagacgtg tgctcttccg atctggtcca taccagggct gacc        54

SEQ ID NO: 361          moltype = DNA  length = 54
FEATURE                 Location/Qualifiers
misc_feature            1..54
```

```
                        note = Synthetic oligonucleotide
source                  1..54
                        mol_type = other DNA
                        organism = synthetic construct
SEQUENCE: 361
gtgactggag ttcagacgtg tgctcttccg atctagtcag gcaggcgagg aaca        54

SEQ ID NO: 362          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 362
gtgactggag ttcagacgtg tgctcttccg atctaggtga agaatttcat gctggcacat  60

SEQ ID NO: 363          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 363
gtgactggag ttcagacgtg tgctcttccg atctcaagac ccagcgaccg actcc       55

SEQ ID NO: 364          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 364
gtgactggag ttcagacgtg tgctcttccg atctctcctg ctcagctggc tcatgtc     57

SEQ ID NO: 365          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 365
gtgactggag ttcagacgtg tgctcttccg atctcttaaa gatcctccgg ccaccatgtg  60

SEQ ID NO: 366          moltype = DNA  length = 53
FEATURE                 Location/Qualifiers
misc_feature            1..53
                        note = Synthetic oligonucleotide
source                  1..53
                        mol_type = other DNA
                        organism = synthetic construct
SEQUENCE: 366
gtgactggag ttcagacgtg tgctcttccg atctgcccct cccctcttca agg         53

SEQ ID NO: 367          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 367
gtgactggag ttcagacgtg tgctcttccg atcttcaaca gcaacaccca ctcttcc     57

SEQ ID NO: 368          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 368
gtgactggag ttcagacgtg tgctcttccg atctgtgtgg tgggggctga gc          52

SEQ ID NO: 369          moltype = DNA  length = 60
FEATURE                 Location/Qualifiers
```

```
misc_feature            1..60
                        note = Synthetic oligonucleotide
source                  1..60
                        mol_type = other DNA
                        organism = synthetic construct
SEQUENCE: 369
gtgactggag ttcagacgtg tgctcttccg atctctctga ctttgacagt gacacccatt  60

SEQ ID NO: 370          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 370
gtgactggag ttcagacgtg tgctcttccg atctggctca ctccttctct tgtaggtact  60

SEQ ID NO: 371          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 371
gtgactggag ttcagacgtg tgctcttccg atctgagaga gagtaaggtc aggcatgtgg  60

SEQ ID NO: 372          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 372
gtgactggag ttcagacgtg tgctcttccg atcttcatca cagttaatgt tgcagcggaa  60

SEQ ID NO: 373          moltype = DNA  length = 53
FEATURE                 Location/Qualifiers
misc_feature            1..53
                        note = Synthetic oligonucleotide
source                  1..53
                        mol_type = other DNA
                        organism = synthetic construct
SEQUENCE: 373
gtgactggag ttcagacgtg tgctcttccg atctgctgga gctgtggggg caa         53

SEQ ID NO: 374          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 374
gtgactggag ttcagacgtg tgctcttccg atctgcttag cttccgttgg gttgatgagg  60

SEQ ID NO: 375          moltype = DNA  length = 53
FEATURE                 Location/Qualifiers
misc_feature            1..53
                        note = Synthetic oligonucleotide
source                  1..53
                        mol_type = other DNA
                        organism = synthetic construct
SEQUENCE: 375
gtgactggag ttcagacgtg tgctcttccg atctcacggt ggacagcagt gca         53

SEQ ID NO: 376          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 376
gtgactggag ttcagacgtg tgctcttccg atctgcatgg aaactgtgag gaggggagt   59

SEQ ID NO: 377          moltype = DNA  length = 53
```

```
FEATURE                Location/Qualifiers
misc_feature           1..53
                       note = Synthetic oligonucleotide
source                 1..53
                       mol_type = other DNA
                       organism = synthetic construct
SEQUENCE: 377
gtgactggag ttcagacgtg tgctcttccg atctagtgac accccctcct cca         53

SEQ ID NO: 378         moltype = DNA  length = 56
FEATURE                Location/Qualifiers
misc_feature           1..56
                       note = Synthetic oligonucleotide
source                 1..56
                       mol_type = other DNA
                       organism = synthetic construct
SEQUENCE: 378
gtgactggag ttcagacgtg tgctcttccg atctagggaa ctggacacgt caggga      56

SEQ ID NO: 379         moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 379
gtgactggag ttcagacgtg tgctcttccg atctactttg gtgggcgtat aagcagttt   59

SEQ ID NO: 380         moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 380
gtgactggag ttcagacgtg tgctcttccg atctagggga gagtctcagt gttgtggag   59

SEQ ID NO: 381         moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 381
gtgactggag ttcagacgtg tgctcttccg atctggctac agcaacaggg tagtagacc   59

SEQ ID NO: 382         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 382
gtgactggag ttcagacgtg tgctcttccg atcttgcctt gagcttctta ccccagtgag  60

SEQ ID NO: 383         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 383
gtgactggag ttcagacgtg tgctcttccg atctttccaa ccaaggtacc tgtattggac  60

SEQ ID NO: 384         moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 384
gtgactggag ttcagacgtg tgctcttccg atctccctgc tcactggaga agttttccg   59
```

```
SEQ ID NO: 385         moltype = DNA  length = 57
FEATURE                Location/Qualifiers
misc_feature           1..57
                       note = Synthetic oligonucleotide
source                 1..57
                       mol_type = other DNA
                       organism = synthetic construct
SEQUENCE: 385
gtgactggag ttcagacgtg tgctcttccg atctgcgctc agtaggtgtg caagcag     57

SEQ ID NO: 386         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 386
gtgactggag ttcagacgtg tgctcttccg atcttctcat ttctggacct aggctgatgg  60

SEQ ID NO: 387         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 387
gtgactggag ttcagacgtg tgctcttccg atcttccacc cttatgaagc ctccttctag  60

SEQ ID NO: 388         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 388
gtgactggag ttcagacgtg tgctcttccg atctgtccac tcacaggggt agaacatgtt  60

SEQ ID NO: 389         moltype = DNA  length = 55
FEATURE                Location/Qualifiers
misc_feature           1..55
                       note = Synthetic oligonucleotide
source                 1..55
                       mol_type = other DNA
                       organism = synthetic construct
SEQUENCE: 389
gtgactggag ttcagacgtg tgctcttccg atctaggtgg gggactgagt gtgac       55

SEQ ID NO: 390         moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 390
gtgactggag ttcagacgtg tgctcttccg atctgcaaca gggtggtgga actcatgt    58

SEQ ID NO: 391         moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 391
gtgactggag ttcagacgtg tgctcttccg atctcagtgt ggtaagggac tgagtgcgt   59

SEQ ID NO: 392         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 392
gtgactggag ttcagacgtg tgctcttccg atctacacat tgctgccatg atctgtcgta  60
```

```
SEQ ID NO: 393          moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 393
gtgactggag ttcagacgtg tgctcttccg atctgctgaa tggaagcgag tgaagtgagc  60

SEQ ID NO: 394          moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 394
gtgactggag ttcagacgtg tgctcttccg atctgggcca ttcacccttg atatcatca   59

SEQ ID NO: 395          moltype = DNA  length = 52
FEATURE                Location/Qualifiers
misc_feature           1..52
                       note = Synthetic oligonucleotide
source                 1..52
                       mol_type = other DNA
                       organism = synthetic construct
SEQUENCE: 395
gtgactggag ttcagacgtg tgctcttccg atctctgagc agcggggagg ct          52

SEQ ID NO: 396          moltype = DNA  length = 54
FEATURE                Location/Qualifiers
misc_feature           1..54
                       note = Synthetic oligonucleotide
source                 1..54
                       mol_type = other DNA
                       organism = synthetic construct
SEQUENCE: 396
gtgactggag ttcagacgtg tgctcttccg atctacccag ctttcagcca gacc        54

SEQ ID NO: 397          moltype = DNA  length = 54
FEATURE                Location/Qualifiers
misc_feature           1..54
                       note = Synthetic oligonucleotide
source                 1..54
                       mol_type = other DNA
                       organism = synthetic construct
SEQUENCE: 397
gtgactggag ttcagacgtg tgctcttccg atctgtgggg gactgagcat ggca        54

SEQ ID NO: 398          moltype = DNA  length = 53
FEATURE                Location/Qualifiers
misc_feature           1..53
                       note = Synthetic oligonucleotide
source                 1..53
                       mol_type = other DNA
                       organism = synthetic construct
SEQUENCE: 398
gtgactggag ttcagacgtg tgctcttccg atctggctgc cattgccctc agt         53

SEQ ID NO: 399          moltype = DNA  length = 52
FEATURE                Location/Qualifiers
misc_feature           1..52
                       note = Synthetic oligonucleotide
source                 1..52
                       mol_type = other DNA
                       organism = synthetic construct
SEQUENCE: 399
gtgactggag ttcagacgtg tgctcttccg atctggtggg ggcacagtcc tg          52

SEQ ID NO: 400          moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 400
```

```
gtgactggag ttcagacgtg tgctcttccg atctccaaag tccgccccaa ggtcaaaa    58

SEQ ID NO: 401         moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 401
gtgactggag ttcagacgtg tgctcttccg atctggagga gaacgaggca tgtcttac    58

SEQ ID NO: 402         moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 402
gtgactggag ttcagacgtg tgctcttccg atctctcggg aggtgggtag tgtatggtt   59

SEQ ID NO: 403         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 403
gtgactggag ttcagacgtg tgctcttccg atctccagct tgttgaggac cctaaaggct  60

SEQ ID NO: 404         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 404
gtgactggag ttcagacgtg tgctcttccg atctttgacc ccaatgtcct gcatgtacta  60

SEQ ID NO: 405         moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 405
gtgactggag ttcagacgtg tgctcttccg atctgagaga gctgggttgg ctgacaga    58

SEQ ID NO: 406         moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 406
gtgactggag ttcagacgtg tgctcttccg atctgggtaa caggacacat tggctggga   59

SEQ ID NO: 407         moltype = DNA  length = 56
FEATURE                Location/Qualifiers
misc_feature           1..56
                       note = Synthetic oligonucleotide
source                 1..56
                       mol_type = other DNA
                       organism = synthetic construct
SEQUENCE: 407
gtgactggag ttcagacgtg tgctcttccg atctccagga gaagtttcca gtggga      56

SEQ ID NO: 408         moltype = DNA  length = 60
FEATURE                Location/Qualifiers
misc_feature           1..60
                       note = Synthetic oligonucleotide
source                 1..60
                       mol_type = other DNA
                       organism = synthetic construct
```

```
SEQUENCE: 408
gtgactggag ttcagacgtg tgctcttccg atctagcatc atctgtgaat caaaagtttt  60

SEQ ID NO: 409         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 409
gtgactggag ttcagacgtg tgctcttccg atctggccag caaaaccttg acatgtaaac  60

SEQ ID NO: 410         moltype = DNA  length = 55
FEATURE                Location/Qualifiers
misc_feature           1..55
                       note = Synthetic oligonucleotide
source                 1..55
                       mol_type = other DNA
                       organism = synthetic construct
SEQUENCE: 410
gtgactggag ttcagacgtg tgctcttccg atctacctgg aggcctgact tgcag       55

SEQ ID NO: 411         moltype = DNA  length = 56
FEATURE                Location/Qualifiers
misc_feature           1..56
                       note = Synthetic oligonucleotide
source                 1..56
                       mol_type = other DNA
                       organism = synthetic construct
SEQUENCE: 411
gtgactggag ttcagacgtg tgctcttccg atctagggtg tatgcgtgct ctctga      56

SEQ ID NO: 412         moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 412
gtgactggag ttcagacgtg tgctcttccg atctgcgtca ccttgaacga ccactttgt   59

SEQ ID NO: 413         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 413
gtgactggag ttcagacgtg tgctcttccg atctaggggg tctggcatga aaatgtgtta  60

SEQ ID NO: 414         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 414
gtgactggag ttcagacgtg tgctcttccg atctcacacc cacatatacc tgccaaaaga  60

SEQ ID NO: 415         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 415
gtgactggag ttcagacgtg tgctcttccg atctacgccc tactgcccta gattctaatt  60

SEQ ID NO: 416         moltype = DNA  length = 53
FEATURE                Location/Qualifiers
misc_feature           1..53
                       note = Synthetic oligonucleotide
source                 1..53
                       mol_type = other DNA
```

```
                        organism = synthetic construct
SEQUENCE: 416
gtgactggag ttcagacgtg tgctcttccg atcttggggg ctctggggct act         53

SEQ ID NO: 417          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 417
gtgactggag ttcagacgtg tgctcttccg atctacgtgg acatgaggat gcattaaagg  60

SEQ ID NO: 418          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 418
gtgactggag ttcagacgtg tgctcttccg atctatcccc tcttccccaa gcct        54

SEQ ID NO: 419          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 419
gtgactggag ttcagacgtg tgctcttccg atctgaaccc actgaacgct tccacttcca  60

SEQ ID NO: 420          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 420
gtgactggag ttcagacgtg tgctcttccg atctagtaca atgaggccat gcagtttctt  60

SEQ ID NO: 421          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 421
gtgactggag ttcagacgtg tgctcttccg atctacaggg gacagaagcc atggg       55

SEQ ID NO: 422          moltype = DNA  length = 56
FEATURE                 Location/Qualifiers
misc_feature            1..56
                        note = Synthetic oligonucleotide
source                  1..56
                        mol_type = other DNA
                        organism = synthetic construct
SEQUENCE: 422
gtgactggag ttcagacgtg tgctcttccg atctctacgc ctctgcccca tacacg      56

SEQ ID NO: 423          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 423
gtgactggag ttcagacgtg tgctcttccg atcttggcat tgctctcaac gaccactt    58

SEQ ID NO: 424          moltype = DNA  length = 56
FEATURE                 Location/Qualifiers
misc_feature            1..56
                        note = Synthetic oligonucleotide
source                  1..56
```

```
                        mol_type = other DNA
                        organism = synthetic construct
SEQUENCE: 424
gtgactggag ttcagacgtg tgctcttccg atctccctag gcccctccgt cttcag      56

SEQ ID NO: 425          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 425
gtgactggag ttcagacgtg tgctcttccg atctggactt cgcagaccac atggc       55

SEQ ID NO: 426          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 426
gtgactggag ttcagacgtg tgctcttccg atctgcctcg gctggccttt acttg       55

SEQ ID NO: 427          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 427
gtgactggag ttcagacgtg tgctcttccg atctggcaaa gtgagactaa tctagctgct  60

SEQ ID NO: 428          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 428
gtgactggag ttcagacgtg tgctcttccg atcttcttca gcactacgga gaagactgg   59

SEQ ID NO: 429          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 429
gtgactggag ttcagacgtg tgctcttccg atctgtgcca aacgttgata gtgcagga    58

SEQ ID NO: 430          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 430
gtgactggag ttcagacgtg tgctcttccg atcttgccct gtgctactgg aaggc       55

SEQ ID NO: 431          moltype = DNA  length = 56
FEATURE                 Location/Qualifiers
misc_feature            1..56
                        note = Synthetic oligonucleotide
source                  1..56
                        mol_type = other DNA
                        organism = synthetic construct
SEQUENCE: 431
gtgactggag ttcagacgtg tgctcttccg atctccccca tgcatgcctc actctc      56

SEQ ID NO: 432          moltype = DNA  length = 55
FEATURE                 Location/Qualifiers
misc_feature            1..55
                        note = Synthetic oligonucleotide
```

```
source                  1..55
                        mol_type = other DNA
                        organism = synthetic construct
SEQUENCE: 432
gtgactggag ttcagacgtg tgctcttccg atctagcaac agggtgatgg acctc       55

SEQ ID NO: 433          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 433
gtgactggag ttcagacgtg tgctcttccg atctcagggc catgtagtgt cttaaagctg  60

SEQ ID NO: 434          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 434
gtgactggag ttcagacgtg tgctcttccg atctgaggag gggagattca gtgtggt     57

SEQ ID NO: 435          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 435
ccccttaggg ataacagggt aatcaggtgt gactcctttc ccagatca               48

SEQ ID NO: 436          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 436
ccccttaggg ataacagggt aatcagaagt cctgggtatg gaggctttg              49

SEQ ID NO: 437          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 437
ccccttaggg ataacagggt aatcccacta ggctaagagg tacaccgt               48

SEQ ID NO: 438          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 438
ccccttaggg ataacagggt aatcccagtg gcatcccctt ttgtca                 46

SEQ ID NO: 439          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 439
ccccttaggg ataacagggt aatctttggc agcggtgatg aggt                   44

SEQ ID NO: 440          moltype = DNA  length = 47
FEATURE                 Location/Qualifiers
misc_feature            1..47
```

```
                        note = Synthetic oligonucleotide
source                  1..47
                        mol_type = other DNA
                        organism = synthetic construct
SEQUENCE: 440
ccccttaggg ataacagggt aatcgcaagg gtaacacctg agaaggt               47

SEQ ID NO: 441          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 441
ccccttaggg ataacagggt aatctggcag gtgtagcttt ttctgtta              48

SEQ ID NO: 442          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 442
ccccttaggg ataacagggt aatcgcggat taaagggaag ggcttcg               47

SEQ ID NO: 443          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 443
ccccttaggg ataacagggt aatcgccgtt accataagtc agcaggt               47

SEQ ID NO: 444          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 444
ccccttaggg ataacagggt aatcacccaa gcggcccttc ct                    42

SEQ ID NO: 445          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 445
ccccttaggg ataacagggt aatcctgcac acacattgcc cacttaca              48

SEQ ID NO: 446          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 446
ccccttaggg ataacagggt aatcgtgaag ttggaccagc tgtcataca             49

SEQ ID NO: 447          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 447
ccccttaggg ataacagggt aatctgtgtg tcacatcaat taatttgtgc            50

SEQ ID NO: 448          moltype = DNA  length = 46
FEATURE                 Location/Qualifiers
```

```
misc_feature            1..46
                        note = Synthetic oligonucleotide
source                  1..46
                        mol_type = other DNA
                        organism = synthetic construct
SEQUENCE: 448
ccccttaggg ataacagggt aatcgctctg caagtactga ctgcct                   46

SEQ ID NO: 449          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 449
ccccttaggg ataacagggt aatcatgagg ggacaccaga gggaa                    45

SEQ ID NO: 450          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 450
ccccttaggg ataacagggt aatcccctct ggagtcccat catcac                   46

SEQ ID NO: 451          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 451
ccccttaggg ataacagggt aatctgctgt gtctgctgtc catcc                    45

SEQ ID NO: 452          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 452
ccccttaggg ataacagggt aatcgctgct gctggagagc cat                      43

SEQ ID NO: 453          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 453
ccccttaggg ataacagggt aatcgtcgaa ctgcatcccc tggttt                   46

SEQ ID NO: 454          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 454
ccccttaggg ataacagggt aatcgttccg ctacgtcagt tgcca                    45

SEQ ID NO: 455          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 455
ccccttaggg ataacagggt aatcggaatg gccacccttc cct                      43

SEQ ID NO: 456          moltype = DNA  length = 49
```

```
FEATURE                Location/Qualifiers
misc_feature           1..49
                       note = Synthetic oligonucleotide
source                 1..49
                       mol_type = other DNA
                       organism = synthetic construct
SEQUENCE: 456
ccccttaggg ataacagggt aatccctcct ggaggtctct ctttaatgc            49

SEQ ID NO: 457         moltype = DNA  length = 46
FEATURE                Location/Qualifiers
misc_feature           1..46
                       note = Synthetic oligonucleotide
source                 1..46
                       mol_type = other DNA
                       organism = synthetic construct
SEQUENCE: 457
ccccttaggg ataacagggt aatcgtcatt ctgctgggtg acaatg               46

SEQ ID NO: 458         moltype = DNA  length = 49
FEATURE                Location/Qualifiers
misc_feature           1..49
                       note = Synthetic oligonucleotide
source                 1..49
                       mol_type = other DNA
                       organism = synthetic construct
SEQUENCE: 458
ccccttaggg ataacagggt aatctcacac agtggttaag accctttgg            49

SEQ ID NO: 459         moltype = DNA  length = 50
FEATURE                Location/Qualifiers
misc_feature           1..50
                       note = Synthetic oligonucleotide
source                 1..50
                       mol_type = other DNA
                       organism = synthetic construct
SEQUENCE: 459
ccccttaggg ataacagggt aatcgtgggc tagaagctaa gaagatcagc           50

SEQ ID NO: 460         moltype = DNA  length = 49
FEATURE                Location/Qualifiers
misc_feature           1..49
                       note = Synthetic oligonucleotide
source                 1..49
                       mol_type = other DNA
                       organism = synthetic construct
SEQUENCE: 460
ccccttaggg ataacagggt aatcagtacg atgctgcttc acatggaac            49

SEQ ID NO: 461         moltype = DNA  length = 47
FEATURE                Location/Qualifiers
misc_feature           1..47
                       note = Synthetic oligonucleotide
source                 1..47
                       mol_type = other DNA
                       organism = synthetic construct
SEQUENCE: 461
ccccttaggg ataacagggt aatcacgact gttctcactg aggggta              47

SEQ ID NO: 462         moltype = DNA  length = 47
FEATURE                Location/Qualifiers
misc_feature           1..47
                       note = Synthetic oligonucleotide
source                 1..47
                       mol_type = other DNA
                       organism = synthetic construct
SEQUENCE: 462
ccccttaggg ataacagggt aatcgggaga cttaccagct tcccgta              47

SEQ ID NO: 463         moltype = DNA  length = 45
FEATURE                Location/Qualifiers
misc_feature           1..45
                       note = Synthetic oligonucleotide
source                 1..45
                       mol_type = other DNA
                       organism = synthetic construct
SEQUENCE: 463
ccccttaggg ataacagggt aatctaaggc agtgtgttgg gtgct                45
```

```
SEQ ID NO: 464          moltype = DNA  length = 49
FEATURE                Location/Qualifiers
misc_feature           1..49
                       note = Synthetic oligonucleotide
source                 1..49
                       mol_type = other DNA
                       organism = synthetic construct
SEQUENCE: 464
ccccttaggg ataacagggt aatcccttcc ttctccaccc aagtagcta               49

SEQ ID NO: 465          moltype = DNA  length = 48
FEATURE                Location/Qualifiers
misc_feature           1..48
                       note = Synthetic oligonucleotide
source                 1..48
                       mol_type = other DNA
                       organism = synthetic construct
SEQUENCE: 465
ccccttaggg ataacagggt aatcctcaca ctctaccctt gtgctacg                48

SEQ ID NO: 466          moltype = DNA  length = 46
FEATURE                Location/Qualifiers
misc_feature           1..46
                       note = Synthetic oligonucleotide
source                 1..46
                       mol_type = other DNA
                       organism = synthetic construct
SEQUENCE: 466
ccccttaggg ataacagggt aatccaactg ggcatgctct cctagg                  46

SEQ ID NO: 467          moltype = DNA  length = 45
FEATURE                Location/Qualifiers
misc_feature           1..45
                       note = Synthetic oligonucleotide
source                 1..45
                       mol_type = other DNA
                       organism = synthetic construct
SEQUENCE: 467
ccccttaggg ataacagggt aatcctgtgt ggccctcagg tgtaa                   45

SEQ ID NO: 468          moltype = DNA  length = 43
FEATURE                Location/Qualifiers
misc_feature           1..43
                       note = Synthetic oligonucleotide
source                 1..43
                       mol_type = other DNA
                       organism = synthetic construct
SEQUENCE: 468
ccccttaggg ataacagggt aatcaccaca cccggctcac tct                     43

SEQ ID NO: 469          moltype = DNA  length = 44
FEATURE                Location/Qualifiers
misc_feature           1..44
                       note = Synthetic oligonucleotide
source                 1..44
                       mol_type = other DNA
                       organism = synthetic construct
SEQUENCE: 469
ccccttaggg ataacagggt aatcggaggt tgcaggttgc tggt                    44

SEQ ID NO: 470          moltype = DNA  length = 43
FEATURE                Location/Qualifiers
misc_feature           1..43
                       note = Synthetic oligonucleotide
source                 1..43
                       mol_type = other DNA
                       organism = synthetic construct
SEQUENCE: 470
ccccttaggg ataacagggt aatcggctgg agtcctggtc ctg                     43

SEQ ID NO: 471          moltype = DNA  length = 44
FEATURE                Location/Qualifiers
misc_feature           1..44
                       note = Synthetic oligonucleotide
source                 1..44
                       mol_type = other DNA
                       organism = synthetic construct
SEQUENCE: 471
ccccttaggg ataacagggt aatcatggtc accgccattc acgt                    44
```

```
SEQ ID NO: 472          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 472
ccccttaggg ataacagggt aatcctatca ttacccacac ccctgagac             49

SEQ ID NO: 473          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 473
ccccttaggg ataacagggt aatcagctac cacggtgaca gtaacatagc            50

SEQ ID NO: 474          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 474
ccccttaggg ataacagggt aatcagctgc cagcccacaa gaa                   43

SEQ ID NO: 475          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 475
ccccttaggg ataacagggt aatcgggaga cagggtatcc aggct                 45

SEQ ID NO: 476          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 476
ccccttaggg ataacagggt aatcagttca gggtctggtt ctgtgc                46

SEQ ID NO: 477          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 477
ccccttaggg ataacagggt aatccggcat tcttcccggc aatga                 45

SEQ ID NO: 478          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 478
ccccttaggg ataacagggt aatctgactc tcagcacctt gacactcc              48

SEQ ID NO: 479          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 479
```

```
ccccttaggg ataacagggt aatcctttat atgtggggga tggaaaagac            50

SEQ ID NO: 480          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 480
ccccttaggg ataacagggt aatccagtgc cttttcctac tacaccaca             49

SEQ ID NO: 481          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 481
ccccttaggg ataacagggt aatccgaagg aaccaaacgg aacttgtgta            50

SEQ ID NO: 482          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 482
ccccttaggg ataacagggt aatcagctca tcgaggcacc aaaca                 45

SEQ ID NO: 483          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 483
ccccttaggg ataacagggt aatcatttgt cctggaaccc atactgcat             49

SEQ ID NO: 484          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 484
ccccttaggg ataacagggt aatctgaaag catcaactct gggagcatg             49

SEQ ID NO: 485          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 485
ccccttaggg ataacagggt aatcgccaca gttccagtgc attcg                 45

SEQ ID NO: 486          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 486
ccccttaggg ataacagggt aatcggctcc ccagaagaag aagcct                46

SEQ ID NO: 487          moltype = DNA  length = 50
FEATURE                 Location/Qualifiers
misc_feature            1..50
                        note = Synthetic oligonucleotide
source                  1..50
                        mol_type = other DNA
                        organism = synthetic construct
```

```
SEQUENCE: 487
ccccttaggg ataacagggt aatcgcaagt ggtaggcatg ggttagaaga            50

SEQ ID NO: 488         moltype = DNA  length = 46
FEATURE                Location/Qualifiers
misc_feature           1..46
                       note = Synthetic oligonucleotide
source                 1..46
                       mol_type = other DNA
                       organism = synthetic construct
SEQUENCE: 488
ccccttaggg ataacagggt aatcgcccgg caatcgtttt ctaggg                46

SEQ ID NO: 489         moltype = DNA  length = 42
FEATURE                Location/Qualifiers
misc_feature           1..42
                       note = Synthetic oligonucleotide
source                 1..42
                       mol_type = other DNA
                       organism = synthetic construct
SEQUENCE: 489
ccccttaggg ataacagggt aatcaccccc aggtcagcaa gc                    42

SEQ ID NO: 490         moltype = DNA  length = 50
FEATURE                Location/Qualifiers
misc_feature           1..50
                       note = Synthetic oligonucleotide
source                 1..50
                       mol_type = other DNA
                       organism = synthetic construct
SEQUENCE: 490
ccccttaggg ataacagggt aatcctgatt agggtggttc gttttgacgt            50

SEQ ID NO: 491         moltype = DNA  length = 42
FEATURE                Location/Qualifiers
misc_feature           1..42
                       note = Synthetic oligonucleotide
source                 1..42
                       mol_type = other DNA
                       organism = synthetic construct
SEQUENCE: 491
ccccttaggg ataacagggt aatcgcacga ccgcggcaga gt                    42

SEQ ID NO: 492         moltype = DNA  length = 43
FEATURE                Location/Qualifiers
misc_feature           1..43
                       note = Synthetic oligonucleotide
source                 1..43
                       mol_type = other DNA
                       organism = synthetic construct
SEQUENCE: 492
ccccttaggg ataacagggt aatcagctgc ttcccaggcc ttg                   43

SEQ ID NO: 493         moltype = DNA  length = 44
FEATURE                Location/Qualifiers
misc_feature           1..44
                       note = Synthetic oligonucleotide
source                 1..44
                       mol_type = other DNA
                       organism = synthetic construct
SEQUENCE: 493
ccccttaggg ataacagggt aatcaatgca gaggccagga cacc                  44

SEQ ID NO: 494         moltype = DNA  length = 49
FEATURE                Location/Qualifiers
misc_feature           1..49
                       note = Synthetic oligonucleotide
source                 1..49
                       mol_type = other DNA
                       organism = synthetic construct
SEQUENCE: 494
ccccttaggg ataacagggt aatctcatgt tgtggttgga agtgtggat             49

SEQ ID NO: 495         moltype = DNA  length = 45
FEATURE                Location/Qualifiers
misc_feature           1..45
                       note = Synthetic oligonucleotide
source                 1..45
                       mol_type = other DNA
```

```
                         organism = synthetic construct
SEQUENCE: 495
ccccttaggg ataacagggt aatctggctg gaagatggac ggaga               45

SEQ ID NO: 496           moltype = DNA  length = 45
FEATURE                  Location/Qualifiers
misc_feature             1..45
                         note = Synthetic oligonucleotide
source                   1..45
                         mol_type = other DNA
                         organism = synthetic construct
SEQUENCE: 496
ccccttaggg ataacagggt aatccaccag gccactcacc caatt               45

SEQ ID NO: 497           moltype = DNA  length = 50
FEATURE                  Location/Qualifiers
misc_feature             1..50
                         note = Synthetic oligonucleotide
source                   1..50
                         mol_type = other DNA
                         organism = synthetic construct
SEQUENCE: 497
ccccttaggg ataacagggt aatcgagacc agtgatttca gagtggctag          50

SEQ ID NO: 498           moltype = DNA  length = 48
FEATURE                  Location/Qualifiers
misc_feature             1..48
                         note = Synthetic oligonucleotide
source                   1..48
                         mol_type = other DNA
                         organism = synthetic construct
SEQUENCE: 498
ccccttaggg ataacagggt aatcaccccg aacttggtga tgcagtac            48

SEQ ID NO: 499           moltype = DNA  length = 45
FEATURE                  Location/Qualifiers
misc_feature             1..45
                         note = Synthetic oligonucleotide
source                   1..45
                         mol_type = other DNA
                         organism = synthetic construct
SEQUENCE: 499
ccccttaggg ataacagggt aatcgggtgg ctcagaagtg gttcc               45

SEQ ID NO: 500           moltype = DNA  length = 48
FEATURE                  Location/Qualifiers
misc_feature             1..48
                         note = Synthetic oligonucleotide
source                   1..48
                         mol_type = other DNA
                         organism = synthetic construct
SEQUENCE: 500
ccccttaggg ataacagggt aatcgtaggt gatagggaaa cgccgaaa            48

SEQ ID NO: 501           moltype = DNA  length = 45
FEATURE                  Location/Qualifiers
misc_feature             1..45
                         note = Synthetic oligonucleotide
source                   1..45
                         mol_type = other DNA
                         organism = synthetic construct
SEQUENCE: 501
ccccttaggg ataacagggt aatctctgca gagcatggag gcaac               45

SEQ ID NO: 502           moltype = DNA  length = 49
FEATURE                  Location/Qualifiers
misc_feature             1..49
                         note = Synthetic oligonucleotide
source                   1..49
                         mol_type = other DNA
                         organism = synthetic construct
SEQUENCE: 502
ccccttaggg ataacagggt aatcaagtct gaaacgctgc tctgctatt           49

SEQ ID NO: 503           moltype = DNA  length = 46
FEATURE                  Location/Qualifiers
misc_feature             1..46
                         note = Synthetic oligonucleotide
source                   1..46
```

```
                        mol_type = other DNA
                        organism = synthetic construct
SEQUENCE: 503
ccccttaggg ataacagggt aatcgcacca tttccaccca gctttg             46

SEQ ID NO: 504          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 504
ccccttaggg ataacagggt aatccaagta gctaggactc aaggcacatg         50

SEQ ID NO: 505          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 505
ccccttaggg ataacagggt aatcgggggc tgatatgggt caacc              45

SEQ ID NO: 506          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 506
ccccttaggg ataacagggt aatctgcatc gaagctggtg gagac              45

SEQ ID NO: 507          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 507
ccccttaggg ataacagggt aatcccagac cctgactcat ggacacacc          49

SEQ ID NO: 508          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 508
ccccttaggg ataacagggt aatcacgttc ccgtctgctc agtg               44

SEQ ID NO: 509          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 509
ccccttaggg ataacagggt aatcgaggtt ggaccagctg tcatacc            47

SEQ ID NO: 510          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 510
ccccttaggg ataacagggt aatcgctagt ctttccaggc caccct             46

SEQ ID NO: 511          moltype = DNA  length = 46
FEATURE                 Location/Qualifiers
misc_feature            1..46
                        note = Synthetic oligonucleotide
```

```
source                  1..46
                        mol_type = other DNA
                        organism = synthetic construct
SEQUENCE: 511
ccccttaggg ataacagggt aatcttggca agcactcctc aatggc                  46

SEQ ID NO: 512          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 512
ccccttaggg ataacagggt aatcgcagag aggaggggct aaaggg                  46

SEQ ID NO: 513          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 513
ccccttaggg ataacagggt aatcctccca tccatacccc cacct                   45

SEQ ID NO: 514          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 514
ccccttaggg ataacagggt aatcgcccca acccaagcta gtctttc                 47

SEQ ID NO: 515          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 515
ccccttaggg ataacagggt aatccctttc ccgttctcca cccaa                   45

SEQ ID NO: 516          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 516
ccccttaggg ataacagggt aatcagcagt atgtccaact cccaaattg               49

SEQ ID NO: 517          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 517
ccccttaggg ataacagggt aatcacacag gttttctcct ctcagccta               49

SEQ ID NO: 518          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 518
ccccttaggg ataacagggt aatcaacctg gctccttcgc ttcc                    44

SEQ ID NO: 519          moltype = DNA  length = 46
FEATURE                 Location/Qualifiers
misc_feature            1..46
```

```
                      note = Synthetic oligonucleotide
source                1..46
                      mol_type = other DNA
                      organism = synthetic construct
SEQUENCE: 519
ccccttaggg ataacagggt aatcctctgt ctccacatgc ccagtt                 46

SEQ ID NO: 520        moltype = DNA  length = 47
FEATURE               Location/Qualifiers
misc_feature          1..47
                      note = Synthetic oligonucleotide
source                1..47
                      mol_type = other DNA
                      organism = synthetic construct
SEQUENCE: 520
ccccttaggg ataacagggt aatcccaggg ctgggcataa aagtcag                47

SEQ ID NO: 521        moltype = DNA  length = 60
FEATURE               Location/Qualifiers
misc_feature          1..60
                      note = Synthetic oligonucleotide
source                1..60
                      mol_type = other DNA
                      organism = synthetic construct
SEQUENCE: 521
gtgactggag ttcagacgtg tgctcttccg atctgtgact cctttcccag atcagatagc  60

SEQ ID NO: 522        moltype = DNA  length = 59
FEATURE               Location/Qualifiers
misc_feature          1..59
                      note = Synthetic oligonucleotide
source                1..59
                      mol_type = other DNA
                      organism = synthetic construct
SEQUENCE: 522
gtgactggag ttcagacgtg tgctcttccg atctcctggg tatggaggct ttggcattc   59

SEQ ID NO: 523        moltype = DNA  length = 60
FEATURE               Location/Qualifiers
misc_feature          1..60
                      note = Synthetic oligonucleotide
source                1..60
                      mol_type = other DNA
                      organism = synthetic construct
SEQUENCE: 523
gtgactggag ttcagacgtg tgctcttccg atctggctaa gaggtacacc gtaacagaga  60

SEQ ID NO: 524        moltype = DNA  length = 60
FEATURE               Location/Qualifiers
misc_feature          1..60
                      note = Synthetic oligonucleotide
source                1..60
                      mol_type = other DNA
                      organism = synthetic construct
SEQUENCE: 524
gtgactggag ttcagacgtg tgctcttccg atctagcatg tcatatggct aacaccggtt  60

SEQ ID NO: 525        moltype = DNA  length = 60
FEATURE               Location/Qualifiers
misc_feature          1..60
                      note = Synthetic oligonucleotide
source                1..60
                      mol_type = other DNA
                      organism = synthetic construct
SEQUENCE: 525
gtgactggag ttcagacgtg tgctcttccg atctgaggtt tctcatcctg catgacgtat  60

SEQ ID NO: 526        moltype = DNA  length = 54
FEATURE               Location/Qualifiers
misc_feature          1..54
                      note = Synthetic oligonucleotide
source                1..54
                      mol_type = other DNA
                      organism = synthetic construct
SEQUENCE: 526
gtgactggag ttcagacgtg tgctcttccg atctgtgtgg ggtaagggga gctg        54

SEQ ID NO: 527        moltype = DNA  length = 59
FEATURE               Location/Qualifiers
```

```
misc_feature           1..59
                       note = Synthetic oligonucleotide
source                 1..59
                       mol_type = other DNA
                       organism = synthetic construct
SEQUENCE: 527
gtgactggag ttcagacgtg tgctcttccg atctagaaca ttctgtcatt ccagtcaga   59

SEQ ID NO: 528         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 528
gtgactggag ttcagacgtg tgctcttccg atctagggaa gggcttcgaa tgagaatgct  60

SEQ ID NO: 529         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 529
gtgactggag ttcagacgtg tgctcttccg atctcagaaa gtcacttcca gcacttgtga  60

SEQ ID NO: 530         moltype = DNA  length = 54
FEATURE                Location/Qualifiers
misc_feature           1..54
                       note = Synthetic oligonucleotide
source                 1..54
                       mol_type = other DNA
                       organism = synthetic construct
SEQUENCE: 530
gtgactggag ttcagacgtg tgctcttccg atcttcctcc aggcttgact tggc        54

SEQ ID NO: 531         moltype = DNA  length = 55
FEATURE                Location/Qualifiers
misc_feature           1..55
                       note = Synthetic oligonucleotide
source                 1..55
                       mol_type = other DNA
                       organism = synthetic construct
SEQUENCE: 531
gtgactggag ttcagacgtg tgctcttccg atctcacccc agaacacgag caact       55

SEQ ID NO: 532         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 532
gtgactggag ttcagacgtg tgctcttccg atctgttgga ccagctgtca tacacacaac  60

SEQ ID NO: 533         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 533
gtgactggag ttcagacgtg tgctcttccg atctttgtgc acaggtttaa gaaacaaata  60

SEQ ID NO: 534         moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 534
gtgactggag ttcagacgtg tgctcttccg atctgcaagt actgactgcc tccccctt    58

SEQ ID NO: 535         moltype = DNA  length = 56
```

```
FEATURE                 Location/Qualifiers
misc_feature            1..56
                        note = Synthetic oligonucleotide
source                  1..56
                        mol_type = other DNA
                        organism = synthetic construct
SEQUENCE: 535
gtgactggag ttcagacgtg tgctcttccg atctgggaca ccagagggaa gtgagg      56

SEQ ID NO: 536          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 536
gtgactggag ttcagacgtg tgctcttccg atctatcacc atctggcatc ccttcac     57

SEQ ID NO: 537          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 537
gtgactggag ttcagacgtg tgctcttccg atctgtgtct gctgtccatc cttcacat    58

SEQ ID NO: 538          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 538
gtgactggag ttcagacgtg tgctcttccg atcttgctgg agagccatct tgaaactaag  60

SEQ ID NO: 539          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 539
gtgactggag ttcagacgtg tgctcttccg atctgccagg gcagccttcc ag          52

SEQ ID NO: 540          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 540
gtgactggag ttcagacgtg tgctcttccg atctcgtcag ttgccacttc tgtatcca    58

SEQ ID NO: 541          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 541
gtgactggag ttcagacgtg tgctcttccg atctaccctt ccctccttat cagaaattgc  60

SEQ ID NO: 542          moltype = DNA  length = 56
FEATURE                 Location/Qualifiers
misc_feature            1..56
                        note = Synthetic oligonucleotide
source                  1..56
                        mol_type = other DNA
                        organism = synthetic construct
SEQUENCE: 542
gtgactggag ttcagacgtg tgctcttccg atctgcccct tttctcacag tgtgca      56
```

-continued

```
SEQ ID NO: 543          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 543
gtgactggag ttcagacgtg tgctcttccg atctcattct gctgggtgac aatgaaatat  60

SEQ ID NO: 544          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 544
gtgactggag ttcagacgtg tgctcttccg atctgtggtt aagacccttt ggcatgagag  60

SEQ ID NO: 545          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 545
gtgactggag ttcagacgtg tgctcttccg atctagaagc taagaagatc agccagcag   59

SEQ ID NO: 546          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 546
gtgactggag ttcagacgtg tgctcttccg atcttcacat ggaacccagc aggaatc     57

SEQ ID NO: 547          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 547
gtgactggag ttcagacgtg tgctcttccg atctaggagg aaagggtgga gctga       55

SEQ ID NO: 548          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 548
gtgactggag ttcagacgtg tgctcttccg atctaccagc ttcccgtatc tccct       55

SEQ ID NO: 549          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 549
gtgactggag ttcagacgtg tgctcttccg atctgctgtt gcagaaggga tagtcagag   59

SEQ ID NO: 550          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 550
gtgactggag ttcagacgtg tgctcttccg atctatgtgc cctctgtgtg cctt        54
```

```
SEQ ID NO: 551         moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 551
gtgactggag ttcagacgtg tgctcttccg atctctctac ccttgtgcta cgctgtct    58

SEQ ID NO: 552         moltype = DNA  length = 53
FEATURE                Location/Qualifiers
misc_feature           1..53
                       note = Synthetic oligonucleotide
source                 1..53
                       mol_type = other DNA
                       organism = synthetic construct
SEQUENCE: 552
gtgactggag ttcagacgtg tgctcttccg atctgcaagg ggccagaagg tct         53

SEQ ID NO: 553         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 553
gtgactggag ttcagacgtg tgctcttccg atctggccct caggtgtaac ttaccctctc  60

SEQ ID NO: 554         moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 554
gtgactggag ttcagacgtg tgctcttccg atctccacac ccggctcact ctccaatt    58

SEQ ID NO: 555         moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 555
gtgactggag ttcagacgtg tgctcttccg atctgttgct ggttgctgag atcatgcca   59

SEQ ID NO: 556         moltype = DNA  length = 53
FEATURE                Location/Qualifiers
misc_feature           1..53
                       note = Synthetic oligonucleotide
source                 1..53
                       mol_type = other DNA
                       organism = synthetic construct
SEQUENCE: 556
gtgactggag ttcagacgtg tgctcttccg atctccaatc acgggccctg gga         53

SEQ ID NO: 557         moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 557
gtgactggag ttcagacgtg tgctcttccg atctccgcca ttcacgtggt gcttactg    58

SEQ ID NO: 558         moltype = DNA  length = 56
FEATURE                Location/Qualifiers
misc_feature           1..56
                       note = Synthetic oligonucleotide
source                 1..56
                       mol_type = other DNA
                       organism = synthetic construct
SEQUENCE: 558
```

```
gtgactggag ttcagacgtg tgctcttccg atctcccaca cccctgagac tgcata      56

SEQ ID NO: 559         moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 559
gtgactggag ttcagacgtg tgctcttccg atctcggtga cagtaacata gcccaggga   59

SEQ ID NO: 560         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 560
gtgactggag ttcagacgtg tgctcttccg atctaaaatg gggcccttag tcctacaatg  60

SEQ ID NO: 561         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 561
gtgactggag ttcagacgtg tgctcttccg atctgagaca gggtatccag gctgcataca  60

SEQ ID NO: 562         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 562
gtgactggag ttcagacgtg tgctcttccg atctttcagg gtctggttct gtgcacataa  60

SEQ ID NO: 563         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 563
gtgactggag ttcagacgtg tgctcttccg atctggcatt cttcccggca atgaaatcct  60

SEQ ID NO: 564         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 564
gtgactggag ttcagacgtg tgctcttccg atctcagcac cttgacactc cagatgaact  60

SEQ ID NO: 565         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 565
gtgactggag ttcagacgtg tgctcttccg atctatggaa aagacaaccc atcatggtat  60

SEQ ID NO: 566         moltype = DNA  length = 60
FEATURE                Location/Qualifiers
misc_feature           1..60
                       note = Synthetic oligonucleotide
source                 1..60
                       mol_type = other DNA
                       organism = synthetic construct
```

```
SEQUENCE: 566
gtgactggag ttcagacgtg tgctcttccg atctcctact acaccacact gatgcctcca  60

SEQ ID NO: 567         moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 567
gtgactggag ttcagacgtg tgctcttccg atcttctggg tgggagcaga gtactctt    58

SEQ ID NO: 568         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 568
gtgactggag ttcagacgtg tgctcttccg atctgtggtg attacaaggc cacatcctac  60

SEQ ID NO: 569         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 569
gtgactggag ttcagacgtg tgctcttccg atctcctgga acccatactg cattaggaag  60

SEQ ID NO: 570         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 570
gtgactggag ttcagacgtg tgctcttccg atctagcatg aaaaaggctg atgagtggga  60

SEQ ID NO: 571         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 571
gtgactggag ttcagacgtg tgctcttccg atctccacag ttccagtgca ttcggaagaa  60

SEQ ID NO: 572         moltype = DNA  length = 55
FEATURE                Location/Qualifiers
misc_feature           1..55
                       note = Synthetic oligonucleotide
source                 1..55
                       mol_type = other DNA
                       organism = synthetic construct
SEQUENCE: 572
gtgactggag ttcagacgtg tgctcttccg atctgcttgc agaaccacga gctga       55

SEQ ID NO: 573         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 573
gtgactggag ttcagacgtg tgctcttccg atcttcagct gtgcttctaa tgtacaccct  60

SEQ ID NO: 574         moltype = DNA  length = 60
FEATURE                Location/Qualifiers
misc_feature           1..60
                       note = Synthetic oligonucleotide
source                 1..60
                       mol_type = other DNA
```

```
                        organism = synthetic construct
SEQUENCE: 574
gtgactggag ttcagacgtg tgctcttccg atctgcaatc gttttctagg gcacgactta  60

SEQ ID NO: 575          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 575
gtgactggag ttcagacgtg tgctcttccg atctgtcagc aagcacttga tcagagcatt  60

SEQ ID NO: 576          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 576
gtgactggag ttcagacgtg tgctcttccg atctgtggtt cgttttgacg tgtctgtttc  60

SEQ ID NO: 577          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 577
gtgactggag ttcagacgtg tgctcttccg atctcacgac cgcggcagag ttatcag     57

SEQ ID NO: 578          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 578
gtgactggag ttcagacgtg tgctcttccg atctcccagg ccttggcaat gagtttagg   59

SEQ ID NO: 579          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 579
gtgactggag ttcagacgtg tgctcttccg atctggccag gacaccacca tccc        54

SEQ ID NO: 580          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 580
gtgactggag ttcagacgtg tgctcttccg atcttgtggt tggaagtgtg gattactggt  60

SEQ ID NO: 581          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 581
gtgactggag ttcagacgtg tgctcttccg atcttggacg gagagtggat cacagatgag  60

SEQ ID NO: 582          moltype = DNA  length = 60
FEATURE                 Location/Qualifiers
misc_feature            1..60
                        note = Synthetic oligonucleotide
source                  1..60
```

```
                        mol_type = other DNA
                        organism = synthetic construct
SEQUENCE: 582
gtgactggag ttcagacgtg tgctcttccg atctccaggc cactcaccca atttgacatg  60

SEQ ID NO: 583          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 583
gtgactggag ttcagacgtg tgctcttccg atctttcaga gtggctaggt gttcactgat  60

SEQ ID NO: 584          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 584
gtgactggag ttcagacgtg tgctcttccg atcttacggg gagcgggccg ggtt        54

SEQ ID NO: 585          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 585
gtgactggag ttcagacgtg tgctcttccg atctgctcag aagtggttcc agccaag     57

SEQ ID NO: 586          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 586
gtgactggag ttcagacgtg tgctcttccg atctagggaa acgccgaaag tattttaggt  60

SEQ ID NO: 587          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 587
gtgactggag ttcagacgtg tgctcttccg atctgcaact gctccctggt ctctt       55

SEQ ID NO: 588          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 588
gtgactggag ttcagacgtg tgctcttccg atctcctgtg atcccttcga agaatcttgt  60

SEQ ID NO: 589          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 589
gtgactggag ttcagacgtg tgctcttccg atcttccacc cagctttgct caagt       55

SEQ ID NO: 590          moltype = DNA  length = 55
FEATURE                 Location/Qualifiers
misc_feature            1..55
                        note = Synthetic oligonucleotide
```

```
source                  1..55
                        mol_type = other DNA
                        organism = synthetic construct
SEQUENCE: 590
gtgactggag ttcagacgtg tgctcttccg atctccacca cggccagatc attga       55

SEQ ID NO: 591          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 591
gtgactggag ttcagacgtg tgctcttccg atctaactgg gttgccatga atctgctg    58

SEQ ID NO: 592          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 592
gtgactggag ttcagacgtg tgctcttccg atctgcaggg ctgaggtgga aagct       55

SEQ ID NO: 593          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 593
gtgactggag ttcagacgtg tgctcttccg atctgacaca ccctccccca tctggca     57

SEQ ID NO: 594          moltype = DNA  length = 56
FEATURE                 Location/Qualifiers
misc_feature            1..56
                        note = Synthetic oligonucleotide
source                  1..56
                        mol_type = other DNA
                        organism = synthetic construct
SEQUENCE: 594
gtgactggag ttcagacgtg tgctcttccg atcttggggt aaaggggact cactct      56

SEQ ID NO: 595          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 595
gtgactggag ttcagacgtg tgctcttccg atctagctgc tttactgtca cacgtagcag  60

SEQ ID NO: 596          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 596
gtgactggag ttcagacgtg tgctcttccg atctccaccc tctccgagcc acct        54

SEQ ID NO: 597          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 597
gtgactggag ttcagacgtg tgctcttccg atctccagct tacaggcagg gctgt       55

SEQ ID NO: 598          moltype = DNA  length = 55
FEATURE                 Location/Qualifiers
misc_feature            1..55
```

```
                        note = Synthetic oligonucleotide
source                  1..55
                        mol_type = other DNA
                        organism = synthetic construct
SEQUENCE: 598
gtgactggag ttcagacgtg tgctcttccg atctggggca ggaagggaga agcac       55

SEQ ID NO: 599          moltype = DNA  length = 56
FEATURE                 Location/Qualifiers
misc_feature            1..56
                        note = Synthetic oligonucleotide
source                  1..56
                        mol_type = other DNA
                        organism = synthetic construct
SEQUENCE: 599
gtgactggag ttcagacgtg tgctcttccg atcttccacc cccaacctga gaagac      56

SEQ ID NO: 600          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 600
gtgactggag ttcagacgtg tgctcttccg atctcccaag ctagtctttc caggccact   59

SEQ ID NO: 601          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 601
gtgactggag ttcagacgtg tgctcttccg atctccgttc tccacccaat agctatgg    58

SEQ ID NO: 602          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 602
gtgactggag ttcagacgtg tgctcttccg atcttccaac tcccaaattg aaagcacagc  60

SEQ ID NO: 603          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 603
gtgactggag ttcagacgtg tgctcttccg atctttccct tccctagacc tgcct       55

SEQ ID NO: 604          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 604
gtgactggag ttcagacgtg tgctcttccg atctggctcc ttcgcttcca tctgatcagg  60

SEQ ID NO: 605          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 605
gtgactggag ttcagacgtg tgctcttccg atctgtctcc acatgcccag tttctattgg  60

SEQ ID NO: 606          moltype = DNA  length = 60
FEATURE                 Location/Qualifiers
```

```
misc_feature           1..60
                       note = Synthetic oligonucleotide
source                 1..60
                       mol_type = other DNA
                       organism = synthetic construct
SEQUENCE: 606
gtgactggag ttcagacgtg tgctcttccg atctttcact agcaacctca aacagacacc  60

SEQ ID NO: 607         moltype = DNA  length = 49
FEATURE                Location/Qualifiers
misc_feature           1..49
                       note = Synthetic oligonucleotide
source                 1..49
                       mol_type = other DNA
                       organism = synthetic construct
SEQUENCE: 607
ccccttaggg ataacagggt aatctgggct gagagctagc tttatgtga              49

SEQ ID NO: 608         moltype = DNA  length = 44
FEATURE                Location/Qualifiers
misc_feature           1..44
                       note = Synthetic oligonucleotide
source                 1..44
                       mol_type = other DNA
                       organism = synthetic construct
SEQUENCE: 608
ccccttaggg ataacagggt aatcaggagg cagggacgtg aaac                   44

SEQ ID NO: 609         moltype = DNA  length = 44
FEATURE                Location/Qualifiers
misc_feature           1..44
                       note = Synthetic oligonucleotide
source                 1..44
                       mol_type = other DNA
                       organism = synthetic construct
SEQUENCE: 609
ccccttaggg ataacagggt aatcaggtga ctccctggct ttgc                   44

SEQ ID NO: 610         moltype = DNA  length = 45
FEATURE                Location/Qualifiers
misc_feature           1..45
                       note = Synthetic oligonucleotide
source                 1..45
                       mol_type = other DNA
                       organism = synthetic construct
SEQUENCE: 610
ccccttaggg ataacagggt aatctgatct gaggggcttg gcaga                  45

SEQ ID NO: 611         moltype = DNA  length = 48
FEATURE                Location/Qualifiers
misc_feature           1..48
                       note = Synthetic oligonucleotide
source                 1..48
                       mol_type = other DNA
                       organism = synthetic construct
SEQUENCE: 611
ccccttaggg ataacagggt aatccacatg tggtacgtct ggtccagt               48

SEQ ID NO: 612         moltype = DNA  length = 43
FEATURE                Location/Qualifiers
misc_feature           1..43
                       note = Synthetic oligonucleotide
source                 1..43
                       mol_type = other DNA
                       organism = synthetic construct
SEQUENCE: 612
ccccttaggg ataacagggt aatcacgacg ggtgtgtggg tga                    43

SEQ ID NO: 613         moltype = DNA  length = 44
FEATURE                Location/Qualifiers
misc_feature           1..44
                       note = Synthetic oligonucleotide
source                 1..44
                       mol_type = other DNA
                       organism = synthetic construct
SEQUENCE: 613
ccccttaggg ataacagggt aatccagctg gggcgacata gtga                   44

SEQ ID NO: 614         moltype = DNA  length = 49
```

```
FEATURE                Location/Qualifiers
misc_feature           1..49
                       note = Synthetic oligonucleotide
source                 1..49
                       mol_type = other DNA
                       organism = synthetic construct
SEQUENCE: 614
ccccttaggg ataacagggt aatcggtaac tgtaatatag agcccacca              49

SEQ ID NO: 615         moltype = DNA  length = 44
FEATURE                Location/Qualifiers
misc_feature           1..44
                       note = Synthetic oligonucleotide
source                 1..44
                       mol_type = other DNA
                       organism = synthetic construct
SEQUENCE: 615
ccccttaggg ataacagggt aatcggggag ggacaggttg tgag                   44

SEQ ID NO: 616         moltype = DNA  length = 49
FEATURE                Location/Qualifiers
misc_feature           1..49
                       note = Synthetic oligonucleotide
source                 1..49
                       mol_type = other DNA
                       organism = synthetic construct
SEQUENCE: 616
ccccttaggg ataacagggt aatctgaatc accaactgcc aaacacgtg              49

SEQ ID NO: 617         moltype = DNA  length = 47
FEATURE                Location/Qualifiers
misc_feature           1..47
                       note = Synthetic oligonucleotide
source                 1..47
                       mol_type = other DNA
                       organism = synthetic construct
SEQUENCE: 617
ccccttaggg ataacagggt aatcggcccc cagtgaatca ccaattg                47

SEQ ID NO: 618         moltype = DNA  length = 46
FEATURE                Location/Qualifiers
misc_feature           1..46
                       note = Synthetic oligonucleotide
source                 1..46
                       mol_type = other DNA
                       organism = synthetic construct
SEQUENCE: 618
ccccttaggg ataacagggt aatcgcagaa tcaagccaga gcatgc                 46

SEQ ID NO: 619         moltype = DNA  length = 44
FEATURE                Location/Qualifiers
misc_feature           1..44
                       note = Synthetic oligonucleotide
source                 1..44
                       mol_type = other DNA
                       organism = synthetic construct
SEQUENCE: 619
ccccttaggg ataacagggt aatcagaggt gagggcgagc taga                   44

SEQ ID NO: 620         moltype = DNA  length = 50
FEATURE                Location/Qualifiers
misc_feature           1..50
                       note = Synthetic oligonucleotide
source                 1..50
                       mol_type = other DNA
                       organism = synthetic construct
SEQUENCE: 620
ccccttaggg ataacagggt aatctgccag tgatctttcc tttccctctg             50

SEQ ID NO: 621         moltype = DNA  length = 46
FEATURE                Location/Qualifiers
misc_feature           1..46
                       note = Synthetic oligonucleotide
source                 1..46
                       mol_type = other DNA
                       organism = synthetic construct
SEQUENCE: 621
ccccttaggg ataacagggt aatccaacag tcggtgtcct gatggt                 46
```

```
SEQ ID NO: 622          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 622
ccccttaggg ataacagggt aatctcctgt gccatgacct tcacac                46

SEQ ID NO: 623          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 623
ccccttaggg ataacagggt aatcatgggg aggcggcagt ga                    42

SEQ ID NO: 624          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 624
ccccttaggg ataacagggt aatcggggct gggcagtcac tc                    42

SEQ ID NO: 625          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 625
ccccttaggg ataacagggt aatcccagac tgcgggtatg agagg                 45

SEQ ID NO: 626          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 626
ccccttaggg ataacagggt aatcggctcc gacgctccac ag                    42

SEQ ID NO: 627          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 627
ccccttaggg ataacagggt aatcccccta gcggcccagg ct                    42

SEQ ID NO: 628          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 628
ccccttaggg ataacagggt aatctcaggc tctagcagtc ccagta                46

SEQ ID NO: 629          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 629
ccccttaggg ataacagggt aatcggcatg gtgaagaaag aatgctac              48
```

```
SEQ ID NO: 630          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 630
cccottaggg ataacagggt aatcaggttc ttgcttagag gcatgatgac            50

SEQ ID NO: 631          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 631
cccottaggg ataacagggt aatcgcccat gctgttctta tagcggta              48

SEQ ID NO: 632          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 632
cccottaggg ataacagggt aatctgtgca tactcagcta ctgtgctcta            50

SEQ ID NO: 633          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 633
cccottaggg ataacagggt aatctgcaga tgatctggct gatggac               47

SEQ ID NO: 634          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 634
cccottaggg ataacagggt aatcccagat tccctgctca gcaaagta              48

SEQ ID NO: 635          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 635
cccottaggg ataacagggt aatccaacca ctgtgtaata agccgcttgt            50

SEQ ID NO: 636          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 636
cccottaggg ataacagggt aatcgctaaa cttggcactg gctttcac              48

SEQ ID NO: 637          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 637
```

```
ccccttaggg ataacagggt aatcaaaccc cacacaccac acgtat              46

SEQ ID NO: 638          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 638
ccccttaggg ataacagggt aatcggggct cctgagggtg ga                  42

SEQ ID NO: 639          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 639
ccccttaggg ataacagggt aatctgtctg cagtcacctg tccac               45

SEQ ID NO: 640          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 640
ccccttaggg ataacagggt aatccactcc caggcgctcg agtt                44

SEQ ID NO: 641          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 641
ccccttaggg ataacagggt aatcggacaa acacccaccc aggt                44

SEQ ID NO: 642          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 642
ccccttaggg ataacagggt aatctttaac cttcttagta gccagggaat          50

SEQ ID NO: 643          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 643
ccccttaggg ataacagggt aatctgcaca tattccacgt gggcata             47

SEQ ID NO: 644          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 644
ccccttaggg ataacagggt aatcccacag acatcagagc agacaca             47

SEQ ID NO: 645          moltype = DNA  length = 44
FEATURE                 Location/Qualifiers
misc_feature            1..44
                        note = Synthetic oligonucleotide
source                  1..44
                        mol_type = other DNA
                        organism = synthetic construct
```

```
SEQUENCE: 645
ccccttaggg ataacagggt aatcacacct ggtgagggca actg                44

SEQ ID NO: 646          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 646
ccccttaggg ataacagggt aatcgaggcc aggtcctaca ttgagc              46

SEQ ID NO: 647          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 647
ccccttaggg ataacagggt aatctctttc tgtcagaggc aatggt              46

SEQ ID NO: 648          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 648
ccccttaggg ataacagggt aatcccctgt ctgccacctg ttgtc               45

SEQ ID NO: 649          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 649
ccccttaggg ataacagggt aatcggcctc ttctcaatcc cagtgc              46

SEQ ID NO: 650          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 650
ccccttaggg ataacagggt aatccatccc tgacagcaat gactcactc           49

SEQ ID NO: 651          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 651
ccccttaggg ataacagggt aatctgtgag agtctggcct ttactggt            48

SEQ ID NO: 652          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 652
ccccttaggg ataacagggt aatcttggac ctcccctgcg tga                 43

SEQ ID NO: 653          moltype = DNA  length = 50
FEATURE                 Location/Qualifiers
misc_feature            1..50
                        note = Synthetic oligonucleotide
source                  1..50
                        mol_type = other DNA
```

```
                        organism = synthetic construct
SEQUENCE: 653
ccccttaggg ataacagggt aatcactatg tggactgtgg gactctatga               50

SEQ ID NO: 654          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 654
ccccttaggg ataacagggt aatctttcaa aggggaatgt actaccgt                 48

SEQ ID NO: 655          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 655
ccccttaggg ataacagggt aatcggcctg caaccccgct ac                       42

SEQ ID NO: 656          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 656
ccccttaggg ataacagggt aatcgctagg ccctggagat gctac                    45

SEQ ID NO: 657          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 657
ccccttaggg ataacagggt aatcagtcca gcgtttgaat cagatcatgg               50

SEQ ID NO: 658          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 658
ccccttaggg ataacagggt aatccgtggg cactgagagc acca                     44

SEQ ID NO: 659          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 659
ccccttaggg ataacagggt aatcggattg cagggtatcc acgtctaaat               50

SEQ ID NO: 660          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 660
ccccttaggg ataacagggt aatcgtgtgt ctcacgtggt gggt                     44

SEQ ID NO: 661          moltype = DNA  length = 49
FEATURE                 Location/Qualifiers
misc_feature            1..49
                        note = Synthetic oligonucleotide
source                  1..49
```

```
                        mol_type = other DNA
                        organism = synthetic construct
SEQUENCE: 661
ccccttaggg ataacagggt aatcggctgg aatacccttt gtagttggg             49

SEQ ID NO: 662          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 662
ccccttaggg ataacagggt aatcagcaag gcgtggctgg tg                    42

SEQ ID NO: 663          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 663
ccccttaggg ataacagggt aatctccagt gccctatcag agtaattcct            50

SEQ ID NO: 664          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 664
ccccttaggg ataacagggt aatcgaggat gtaagtagcg cttgtgaaca            50

SEQ ID NO: 665          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 665
ccccttaggg ataacagggt aatctggaga cagcgtaagt gtccct                46

SEQ ID NO: 666          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 666
ccccttaggg ataacagggt aatcgcaata aacactgcct agagcctat             49

SEQ ID NO: 667          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 667
ccccttaggg ataacagggt aatcggcctt aaaaattgct gcgcagt               47

SEQ ID NO: 668          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 668
ccccttaggg ataacagggt aatctgctca agacaggcca aggac                 45

SEQ ID NO: 669          moltype = DNA  length = 47
FEATURE                 Location/Qualifiers
misc_feature            1..47
                        note = Synthetic oligonucleotide
```

```
source                  1..47
                        mol_type = other DNA
                        organism = synthetic construct
SEQUENCE: 669
ccccttaggg ataacagggt aatctctttt ctactgggcc tccacct              47

SEQ ID NO: 670          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 670
ccccttaggg ataacagggt aatcgcttcc ttagcctgag gtcactaaaa           50

SEQ ID NO: 671          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 671
ccccttaggg ataacagggt aatcaatcca acctaataag cacaggcact           50

SEQ ID NO: 672          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 672
ccccttaggg ataacagggt aatctcctag gcttctttcc tctccca              47

SEQ ID NO: 673          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 673
ccccttaggg ataacagggt aatcggggcc actgagactc ctct                 44

SEQ ID NO: 674          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 674
ccccttaggg ataacagggt aatcaccttt ggaacgatgg gggtatttt            49

SEQ ID NO: 675          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 675
ccccttaggg ataacagggt aatcctggag catcgacgag ggtga                45

SEQ ID NO: 676          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 676
ccccttaggg ataacagggt aatcggagca tcgacgaggg tgag                 44

SEQ ID NO: 677          moltype = DNA  length = 49
FEATURE                 Location/Qualifiers
misc_feature            1..49
```

```
                        note = Synthetic oligonucleotide
source                  1..49
                        mol_type = other DNA
                        organism = synthetic construct
SEQUENCE: 677
ccccttaggg ataacagggt aatcgcctgc attcattcgt ccacaatac             49

SEQ ID NO: 678          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 678
ccccttaggg ataacagggt aatcagatgc tgagagttta ccccctctac            50

SEQ ID NO: 679          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 679
ccccttaggg ataacagggt aatctttttc tccccaaacg tgagaaga              48

SEQ ID NO: 680          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 680
ccccttaggg ataacagggt aatcactgtt ggggtgacta actgt                 45

SEQ ID NO: 681          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 681
ccccttaggg ataacagggt aatcttgcta acagtggtga gttgtaata             49

SEQ ID NO: 682          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 682
ccccttaggg ataacagggt aatcagttcc tgatccggct ctgga                 45

SEQ ID NO: 683          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 683
ccccttaggg ataacagggt aatccgagag gctccaggac catgact               47

SEQ ID NO: 684          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 684
ccccttaggg ataacagggt aatcgggctg gcggggtggg aa                    42

SEQ ID NO: 685          moltype = DNA  length = 49
FEATURE                 Location/Qualifiers
```

```
misc_feature            1..49
                        note = Synthetic oligonucleotide
source                  1..49
                        mol_type = other DNA
                        organism = synthetic construct
SEQUENCE: 685
cccettaggg ataacagggt aatcgtgctg gctgaattaa taggaggca            49

SEQ ID NO: 686          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 686
cccettaggg ataacagggt aatccaaggt ctttcaactt gggccagat            49

SEQ ID NO: 687          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 687
cccettaggg ataacagggt aatcccttgg gtcctgtcct ggca                 44

SEQ ID NO: 688          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 688
cccettaggg ataacagggt aatccggggt tcactggccc aga                  43

SEQ ID NO: 689          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 689
cccettaggg ataacagggt aatcaaggga gcggggatta tggc                 44

SEQ ID NO: 690          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 690
cccettaggg ataacagggt aatcgatcat gcaccccgtc ctgac                45

SEQ ID NO: 691          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 691
cccettaggg ataacagggt aatccagacc tgccgtggac ctt                  43

SEQ ID NO: 692          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 692
cccettaggg ataacagggt aatcagccgg cgctaagagc ag                   42

SEQ ID NO: 693          moltype = DNA  length = 43
```

```
FEATURE                 Location/Qualifiers
misc_feature            1..43
                        note = Synthetic oligonucleotide
source                  1..43
                        mol_type = other DNA
                        organism = synthetic construct
SEQUENCE: 693
ccccttaggg ataacagggt aatcgcctgg atcccaccct tgc                      43

SEQ ID NO: 694          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 694
ccccttaggg ataacagggt aatcctggtc ccgccgcagc ct                       42

SEQ ID NO: 695          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 695
ccccttaggg ataacagggt aatcgccctg gctatttgca aactgcat                 48

SEQ ID NO: 696          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 696
ccccttaggg ataacagggt aatcacagag atgcagatag ccaggttaga               50

SEQ ID NO: 697          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 697
ccccttaggg ataacagggt aatcgggtgg aaggtccctc cag                      43

SEQ ID NO: 698          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 698
ccccttaggg ataacagggt aatcagtgga gaaggcggca ctc                      43

SEQ ID NO: 699          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 699
gtgactggag ttcagacgtg tgctcttccg atctcagtca ccacactggg taactcct      58

SEQ ID NO: 700          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 700
gtgactggag ttcagacgtg tgctcttccg atctgtgaaa cgctggggtg caatttc       57
```

```
SEQ ID NO: 701          moltype = DNA  length = 56
FEATURE                 Location/Qualifiers
misc_feature            1..56
                        note = Synthetic oligonucleotide
source                  1..56
                        mol_type = other DNA
                        organism = synthetic construct
SEQUENCE: 701
gtgactggag ttcagacgtg tgctcttccg atcttcctct tcccccaagc tggctt      56

SEQ ID NO: 702          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 702
gtgactggag ttcagacgtg tgctcttccg atctggcaga gaggcacccc aa          52

SEQ ID NO: 703          moltype = DNA  length = 56
FEATURE                 Location/Qualifiers
misc_feature            1..56
                        note = Synthetic oligonucleotide
source                  1..56
                        mol_type = other DNA
                        organism = synthetic construct
SEQUENCE: 703
gtgactggag ttcagacgtg tgctcttccg atctcgtctg gtccagtcag ccttgc      56

SEQ ID NO: 704          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 704
gtgactggag ttcagacgtg tgctcttccg atctcgggtg tgtgggtgac aagcg       55

SEQ ID NO: 705          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 705
gtgactggag ttcagacgtg tgctcttccg atctggggag ttaatgtaag ggaggcaaca  60

SEQ ID NO: 706          moltype = DNA  length = 53
FEATURE                 Location/Qualifiers
misc_feature            1..53
                        note = Synthetic oligonucleotide
source                  1..53
                        mol_type = other DNA
                        organism = synthetic construct
SEQUENCE: 706
gtgactggag ttcagacgtg tgctcttccg atctgagccc accactcagc ttt         53

SEQ ID NO: 707          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 707
gtgactggag ttcagacgtg tgctcttccg atcttgggct tggagttaag gggccta     57

SEQ ID NO: 708          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 708
gtgactggag ttcagacgtg tgctcttccg atctccaact gccaaacacg tgaatgaggt  60
```

SEQ ID NO: 709 moltype = DNA length = 57
FEATURE Location/Qualifiers
misc_feature 1..57
note = Synthetic oligonucleotide
source 1..57
mol_type = other DNA
organism = synthetic construct
SEQUENCE: 709
gtgactggag ttcagacgtg tgctcttccg atctatgagg tcatctgagg ccatccc 57

SEQ ID NO: 710 moltype = DNA length = 53
FEATURE Location/Qualifiers
misc_feature 1..53
note = Synthetic oligonucleotide
source 1..53
mol_type = other DNA
organism = synthetic construct
SEQUENCE: 710
gtgactggag ttcagacgtg tgctcttccg atctagccag agcatgccaa gca 53

SEQ ID NO: 711 moltype = DNA length = 59
FEATURE Location/Qualifiers
misc_feature 1..59
note = Synthetic oligonucleotide
source 1..59
mol_type = other DNA
organism = synthetic construct
SEQUENCE: 711
gtgactggag ttcagacgtg tgctcttccg atctcgagct agagtagaag gtgccccat 59

SEQ ID NO: 712 moltype = DNA length = 59
FEATURE Location/Qualifiers
misc_feature 1..59
note = Synthetic oligonucleotide
source 1..59
mol_type = other DNA
organism = synthetic construct
SEQUENCE: 712
gtgactggag ttcagacgtg tgctcttccg atctcctctg atgtgtcgat gccagcctt 59

SEQ ID NO: 713 moltype = DNA length = 59
FEATURE Location/Qualifiers
misc_feature 1..59
note = Synthetic oligonucleotide
source 1..59
mol_type = other DNA
organism = synthetic construct
SEQUENCE: 713
gtgactggag ttcagacgtg tgctcttccg atctagtcgg tgtcctgatg gtagaaaac 59

SEQ ID NO: 714 moltype = DNA length = 58
FEATURE Location/Qualifiers
misc_feature 1..58
note = Synthetic oligonucleotide
source 1..58
mol_type = other DNA
organism = synthetic construct
SEQUENCE: 714
gtgactggag ttcagacgtg tgctcttccg atctagccag tgatgaaagg tgcctcaa 58

SEQ ID NO: 715 moltype = DNA length = 54
FEATURE Location/Qualifiers
misc_feature 1..54
note = Synthetic oligonucleotide
source 1..54
mol_type = other DNA
organism = synthetic construct
SEQUENCE: 715
gtgactggag ttcagacgtg tgctcttccg atctagcaca ggagagggcc tctg 54

SEQ ID NO: 716 moltype = DNA length = 58
FEATURE Location/Qualifiers
misc_feature 1..58
note = Synthetic oligonucleotide
source 1..58
mol_type = other DNA
organism = synthetic construct
SEQUENCE: 716

```
gtgactggag ttcagacgtg tgctcttccg atcttccccc agctcccaaa tcaatcaa    58

SEQ ID NO: 717         moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 717
gtgactggag ttcagacgtg tgctcttccg atctggcagc ctttcctttt cacagatg    58

SEQ ID NO: 718         moltype = DNA  length = 54
FEATURE                Location/Qualifiers
misc_feature           1..54
                       note = Synthetic oligonucleotide
source                 1..54
                       mol_type = other DNA
                       organism = synthetic construct
SEQUENCE: 718
gtgactggag ttcagacgtg tgctcttccg atctccgacg ctccacagcc tgtc        54

SEQ ID NO: 719         moltype = DNA  length = 52
FEATURE                Location/Qualifiers
misc_feature           1..52
                       note = Synthetic oligonucleotide
source                 1..52
                       mol_type = other DNA
                       organism = synthetic construct
SEQUENCE: 719
gtgactggag ttcagacgtg tgctcttccg atctcggccc aggctcggac tg          52

SEQ ID NO: 720         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 720
gtgactggag ttcagacgtg tgctcttccg atctaggctc tagcagtccc agtaataagt  60

SEQ ID NO: 721         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 721
gtgactggag ttcagacgtg tgctcttccg atctatgcta cacatacttc accttaaggg  60

SEQ ID NO: 722         moltype = DNA  length = 56
FEATURE                Location/Qualifiers
misc_feature           1..56
                       note = Synthetic oligonucleotide
source                 1..56
                       mol_type = other DNA
                       organism = synthetic construct
SEQUENCE: 722
gtgactggag ttcagacgtg tgctcttccg atctcaactg tggagactga ctggct      56

SEQ ID NO: 723         moltype = DNA  length = 57
FEATURE                Location/Qualifiers
misc_feature           1..57
                       note = Synthetic oligonucleotide
source                 1..57
                       mol_type = other DNA
                       organism = synthetic construct
SEQUENCE: 723
gtgactggag ttcagacgtg tgctcttccg atctgggagc catacctgag aaggaga     57

SEQ ID NO: 724         moltype = DNA  length = 58
FEATURE                Location/Qualifiers
misc_feature           1..58
                       note = Synthetic oligonucleotide
source                 1..58
                       mol_type = other DNA
                       organism = synthetic construct
```

```
SEQUENCE: 724
gtgactggag ttcagacgtg tgctcttccg atcttgagct tgaggatctg tcaggcaa    58

SEQ ID NO: 725          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 725
gtgactggag ttcagacgtg tgctcttccg atctatgatc tggctgatgg accaaacatc  60

SEQ ID NO: 726          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 726
gtgactggag ttcagacgtg tgctcttccg atctacagcg gctgttgctc ttcc        54

SEQ ID NO: 727          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 727
gtgactggag ttcagacgtg tgctcttccg atctccgctt gtacaacggt ctttcctcaa  60

SEQ ID NO: 728          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 728
gtgactggag ttcagacgtg tgctcttccg atctatttgc agcttcctct acacttcctg  60

SEQ ID NO: 729          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 729
gtgactggag ttcagacgtg tgctcttccg atctcacacc acacacgtca cagaaacc    58

SEQ ID NO: 730          moltype = DNA  length = 53
FEATURE                 Location/Qualifiers
misc_feature            1..53
                        note = Synthetic oligonucleotide
source                  1..53
                        mol_type = other DNA
                        organism = synthetic construct
SEQUENCE: 730
gtgactggag ttcagacgtg tgctcttccg atctagaagg ggtgggaggc caa         53

SEQ ID NO: 731          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 731
gtgactggag ttcagacgtg tgctcttccg atcttcacct gtccactcac agcac       55

SEQ ID NO: 732          moltype = DNA  length = 56
FEATURE                 Location/Qualifiers
misc_feature            1..56
                        note = Synthetic oligonucleotide
source                  1..56
                        mol_type = other DNA
```

```
                         organism = synthetic construct
SEQUENCE: 732
gtgactggag ttcagacgtg tgctcttccg atctgcgctc gagttacagg gccact      56

SEQ ID NO: 733           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 733
gtgactggag ttcagacgtg tgctcttccg atctaggtga tgtgatcttc ctgcttgctc  60

SEQ ID NO: 734           moltype = DNA  length = 59
FEATURE                  Location/Qualifiers
misc_feature             1..59
                         note = Synthetic oligonucleotide
source                   1..59
                         mol_type = other DNA
                         organism = synthetic construct
SEQUENCE: 734
gtgactggag ttcagacgtg tgctcttccg atctagcatt acacaacccc tagaaagtc   59

SEQ ID NO: 735           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 735
gtgactggag ttcagacgtg tgctcttccg atctcactgt gtcatattgc ctgcatgtct  60

SEQ ID NO: 736           moltype = DNA  length = 53
FEATURE                  Location/Qualifiers
misc_feature             1..53
                         note = Synthetic oligonucleotide
source                   1..53
                         mol_type = other DNA
                         organism = synthetic construct
SEQUENCE: 736
gtgactggag ttcagacgtg tgctcttccg atctccccca gccctagtcc aca         53

SEQ ID NO: 737           moltype = DNA  length = 59
FEATURE                  Location/Qualifiers
misc_feature             1..59
                         note = Synthetic oligonucleotide
source                   1..59
                         mol_type = other DNA
                         organism = synthetic construct
SEQUENCE: 737
gtgactggag ttcagacgtg tgctcttccg atctgtgagg gcaactgaca aaagcaatt   59

SEQ ID NO: 738           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 738
gtgactggag ttcagacgtg tgctcttccg atctggccag gtcctacatt gagcaatcat  60

SEQ ID NO: 739           moltype = DNA  length = 55
FEATURE                  Location/Qualifiers
misc_feature             1..55
                         note = Synthetic oligonucleotide
source                   1..55
                         mol_type = other DNA
                         organism = synthetic construct
SEQUENCE: 739
gtgactggag ttcagacgtg tgctcttccg atctggcaat ggtgtccact ttgga       55

SEQ ID NO: 740           moltype = DNA  length = 60
FEATURE                  Location/Qualifiers
misc_feature             1..60
                         note = Synthetic oligonucleotide
source                   1..60
```

```
                         mol_type = other DNA
                         organism = synthetic construct
SEQUENCE: 740
gtgactggag ttcagacgtg tgctcttccg atctcctgtc tgccacctgt tgtcattaac  60

SEQ ID NO: 741           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 741
gtgactggag ttcagacgtg tgctcttccg atctcctctt ctcaatccca gtgcctactc  60

SEQ ID NO: 742           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 742
gtgactggag ttcagacgtg tgctcttccg atctctgaca gcaatgactc actccccttg  60

SEQ ID NO: 743           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 743
gtgactggag ttcagacgtg tgctcttccg atcttgaatc aggaggggct atgtagttct  60

SEQ ID NO: 744           moltype = DNA  length = 59
FEATURE                  Location/Qualifiers
misc_feature             1..59
                         note = Synthetic oligonucleotide
source                   1..59
                         mol_type = other DNA
                         organism = synthetic construct
SEQUENCE: 744
gtgactggag ttcagacgtg tgctcttccg atctacctcc cctgcgtgaa actgttcta   59

SEQ ID NO: 745           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 745
gtgactggag ttcagacgtg tgctcttccg atcttggact gtgggactct atgaatgtgg  60

SEQ ID NO: 746           moltype = DNA  length = 58
FEATURE                  Location/Qualifiers
misc_feature             1..58
                         note = Synthetic oligonucleotide
source                   1..58
                         mol_type = other DNA
                         organism = synthetic construct
SEQUENCE: 746
gtgactggag ttcagacgtg tgctcttccg atctagggga atgtactacc gtcacttt    58

SEQ ID NO: 747           moltype = DNA  length = 56
FEATURE                  Location/Qualifiers
misc_feature             1..56
                         note = Synthetic oligonucleotide
source                   1..56
                         mol_type = other DNA
                         organism = synthetic construct
SEQUENCE: 747
gtgactggag ttcagacgtg tgctcttccg atcttgcaac cccgctactt cctcct      56

SEQ ID NO: 748           moltype = DNA  length = 57
FEATURE                  Location/Qualifiers
misc_feature             1..57
                         note = Synthetic oligonucleotide
```

```
source                  1..57
                        mol_type = other DNA
                        organism = synthetic construct
SEQUENCE: 748
gtgactggag ttcagacgtg tgctcttccg atctcaggga tcaggccagg taaaaca     57

SEQ ID NO: 749          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 749
gtgactggag ttcagacgtg tgctcttccg atctcatgga agatggctct agaggaagct  60

SEQ ID NO: 750          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 750
gtgactggag ttcagacgtg tgctcttccg atcttgggca ctgagagcac catcatgg    58

SEQ ID NO: 751          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 751
gtgactggag ttcagacgtg tgctcttccg atctatgcat gaaggccagc acaatggg    58

SEQ ID NO: 752          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 752
gtgactggag ttcagacgtg tgctcttccg atctcacgtg gtgggtgatt tttattccag  60

SEQ ID NO: 753          moltype = DNA  length = 53
FEATURE                 Location/Qualifiers
misc_feature            1..53
                        note = Synthetic oligonucleotide
source                  1..53
                        mol_type = other DNA
                        organism = synthetic construct
SEQUENCE: 753
gtgactggag ttcagacgtg tgctcttccg atctgggggc tgcctgtgtg tta         53

SEQ ID NO: 754          moltype = DNA  length = 56
FEATURE                 Location/Qualifiers
misc_feature            1..56
                        note = Synthetic oligonucleotide
source                  1..56
                        mol_type = other DNA
                        organism = synthetic construct
SEQUENCE: 754
gtgactggag ttcagacgtg tgctcttccg atctcatggg caagagcatg ctggta      56

SEQ ID NO: 755          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 755
gtgactggag ttcagacgtg tgctcttccg atctcatagc ttctttgctg gccgacca    58

SEQ ID NO: 756          moltype = DNA  length = 55
FEATURE                 Location/Qualifiers
misc_feature            1..55
```

```
                         note = Synthetic oligonucleotide
source                   1..55
                         mol_type = other DNA
                         organism = synthetic construct
SEQUENCE: 756
gtgactggag ttcagacgtg tgctcttccg atctcacagc cccaggtcct ttgcg       55

SEQ ID NO: 757           moltype = DNA  length = 54
FEATURE                  Location/Qualifiers
misc_feature             1..54
                         note = Synthetic oligonucleotide
source                   1..54
                         mol_type = other DNA
                         organism = synthetic construct
SEQUENCE: 757
gtgactggag ttcagacgtg tgctcttccg atctagtgtc cctgtcctca cgct        54

SEQ ID NO: 758           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 758
gtgactggag ttcagacgtg tgctcttccg atctcactgc ctagagccta tattgcaaag  60

SEQ ID NO: 759           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 759
gtgactggag ttcagacgtg tgctcttccg atctcttaaa aattgctgcg cagtggctgt  60

SEQ ID NO: 760           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 760
gtgactggag ttcagacgtg tgctcttccg atctgctcaa gacaggccaa ggacttagaa  60

SEQ ID NO: 761           moltype = DNA  length = 54
FEATURE                  Location/Qualifiers
misc_feature             1..54
                         note = Synthetic oligonucleotide
source                   1..54
                         mol_type = other DNA
                         organism = synthetic construct
SEQUENCE: 761
gtgactggag ttcagacgtg tgctcttccg atctgctgct cccttcccct ccac        54

SEQ ID NO: 762           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 762
gtgactggag ttcagacgtg tgctcttccg atctgaggtc actaaaaatg gccagtctgc  60

SEQ ID NO: 763           moltype = DNA  length = 57
FEATURE                  Location/Qualifiers
misc_feature             1..57
                         note = Synthetic oligonucleotide
source                   1..57
                         mol_type = other DNA
                         organism = synthetic construct
SEQUENCE: 763
gtgactggag ttcagacgtg tgctcttccg atctactgag tgctggcatc aggattc     57

SEQ ID NO: 764           moltype = DNA  length = 60
FEATURE                  Location/Qualifiers
```

```
misc_feature           1..60
                       note = Synthetic oligonucleotide
source                 1..60
                       mol_type = other DNA
                       organism = synthetic construct
SEQUENCE: 764
gtgactggag ttcagacgtg tgctcttccg atctccagta gcctgtagtc agaaagagtg  60

SEQ ID NO: 765         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 765
gtgactggag ttcagacgtg tgctcttccg atctctcctc ttaggacaac cgaccatcct  60

SEQ ID NO: 766         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 766
gtgactggag ttcagacgtg tgctcttccg atctacctct tgtttctcaa aacgctgtcg  60

SEQ ID NO: 767         moltype = DNA  length = 56
FEATURE                Location/Qualifiers
misc_feature           1..56
                       note = Synthetic oligonucleotide
source                 1..56
                       mol_type = other DNA
                       organism = synthetic construct
SEQUENCE: 767
gtgactggag ttcagacgtg tgctcttccg atctcatcga cgagggtgag cgcatg      56

SEQ ID NO: 768         moltype = DNA  length = 54
FEATURE                Location/Qualifiers
misc_feature           1..54
                       note = Synthetic oligonucleotide
source                 1..54
                       mol_type = other DNA
                       organism = synthetic construct
SEQUENCE: 768
gtgactggag ttcagacgtg tgctcttccg atcttcgacg agggtgagcg catg        54

SEQ ID NO: 769         moltype = DNA  length = 53
FEATURE                Location/Qualifiers
misc_feature           1..53
                       note = Synthetic oligonucleotide
source                 1..53
                       mol_type = other DNA
                       organism = synthetic construct
SEQUENCE: 769
gtgactggag ttcagacgtg tgctcttccg atctgccctg ggcttggcat gaa         53

SEQ ID NO: 770         moltype = DNA  length = 54
FEATURE                Location/Qualifiers
misc_feature           1..54
                       note = Synthetic oligonucleotide
source                 1..54
                       mol_type = other DNA
                       organism = synthetic construct
SEQUENCE: 770
gtgactggag ttcagacgtg tgctcttccg atctccccct ctacctccca cctt        54

SEQ ID NO: 771         moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 771
gtgactggag ttcagacgtg tgctcttccg atcttcccca aacgtgagaa gaaaagaga   59

SEQ ID NO: 772         moltype = DNA  length = 59
```

```
FEATURE                Location/Qualifiers
misc_feature           1..59
                       note = Synthetic oligonucleotide
source                 1..59
                       mol_type = other DNA
                       organism = synthetic construct
SEQUENCE: 772
gtgactggag ttcagacgtg tgctcttccg atctgactaa ctgtcatggt tttcccacg   59

SEQ ID NO: 773         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 773
gtgactggag ttcagacgtg tgctcttccg atctaacagt ggtgagttgt aatactagct  60

SEQ ID NO: 774         moltype = DNA  length = 57
FEATURE                Location/Qualifiers
misc_feature           1..57
                       note = Synthetic oligonucleotide
source                 1..57
                       mol_type = other DNA
                       organism = synthetic construct
SEQUENCE: 774
gtgactggag ttcagacgtg tgctcttccg atcttccggc tctggatttg tgcacag     57

SEQ ID NO: 775         moltype = DNA  length = 52
FEATURE                Location/Qualifiers
misc_feature           1..52
                       note = Synthetic oligonucleotide
source                 1..52
                       mol_type = other DNA
                       organism = synthetic construct
SEQUENCE: 775
gtgactggag ttcagacgtg tgctcttccg atctgcgctg cacggcctcc ac          52

SEQ ID NO: 776         moltype = DNA  length = 54
FEATURE                Location/Qualifiers
misc_feature           1..54
                       note = Synthetic oligonucleotide
source                 1..54
                       mol_type = other DNA
                       organism = synthetic construct
SEQUENCE: 776
gtgactggag ttcagacgtg tgctcttccg atctgggtgg gaagggaggg tcag        54

SEQ ID NO: 777         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 777
gtgactggag ttcagacgtg tgctcttccg atctaatagg aggcacatct catccattgc  60

SEQ ID NO: 778         moltype = DNA  length = 56
FEATURE                Location/Qualifiers
misc_feature           1..56
                       note = Synthetic oligonucleotide
source                 1..56
                       mol_type = other DNA
                       organism = synthetic construct
SEQUENCE: 778
gtgactggag ttcagacgtg tgctcttccg atctgagcac tgcaggacgt tcagca      56

SEQ ID NO: 779         moltype = DNA  length = 55
FEATURE                Location/Qualifiers
misc_feature           1..55
                       note = Synthetic oligonucleotide
source                 1..55
                       mol_type = other DNA
                       organism = synthetic construct
SEQUENCE: 779
gtgactggag ttcagacgtg tgctcttccg atcttgctat gagctgcccc tgggt       55
```

```
SEQ ID NO: 780          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 780
gtgactggag ttcagacgtg tgctcttccg atctttcact ggcccagagc tgtgc       55

SEQ ID NO: 781          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 781
gtgactggag ttcagacgtg tgctcttccg atctaggacc agggtcatga ctagctaaa   59

SEQ ID NO: 782          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 782
gtgactggag ttcagacgtg tgctcttccg atctgtcctg accctgacgc tgcac       55

SEQ ID NO: 783          moltype = DNA  length = 53
FEATURE                 Location/Qualifiers
misc_feature            1..53
                        note = Synthetic oligonucleotide
source                  1..53
                        mol_type = other DNA
                        organism = synthetic construct
SEQUENCE: 783
gtgactggag ttcagacgtg tgctcttccg atctgccgtg gaccttggct tcc         53

SEQ ID NO: 784          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 784
gtgactggag ttcagacgtg tgctcttccg atctggcgct aagagcagct gacc        54

SEQ ID NO: 785          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 785
gtgactggag ttcagacgtg tgctcttccg atctgtgtgg cacagtgagg ggtgt       55

SEQ ID NO: 786          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 786
gtgactggag ttcagacgtg tgctcttccg atctccgccg cagcctcgca ga          52

SEQ ID NO: 787          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 787
gtgactggag ttcagacgtg tgctcttccg atctatgctg tcccagttct ctcaccact   59
```

```
SEQ ID NO: 788          moltype = DNA  length = 57
FEATURE                Location/Qualifiers
misc_feature           1..57
                       note = Synthetic oligonucleotide
source                 1..57
                       mol_type = other DNA
                       organism = synthetic construct
SEQUENCE: 788
gtgactggag ttcagacgtg tgctcttccg atctggcagg gataggtgag cttcaaa     57

SEQ ID NO: 789          moltype = DNA  length = 53
FEATURE                Location/Qualifiers
misc_feature           1..53
                       note = Synthetic oligonucleotide
source                 1..53
                       mol_type = other DNA
                       organism = synthetic construct
SEQUENCE: 789
gtgactggag ttcagacgtg tgctcttccg atctccctgg ctctgggaca cct         53

SEQ ID NO: 790          moltype = DNA  length = 54
FEATURE                Location/Qualifiers
misc_feature           1..54
                       note = Synthetic oligonucleotide
source                 1..54
                       mol_type = other DNA
                       organism = synthetic construct
SEQUENCE: 790
gtgactggag ttcagacgtg tgctcttccg atctactctg gtggggctgc tcca        54

SEQ ID NO: 791          moltype = DNA  length = 46
FEATURE                Location/Qualifiers
misc_feature           1..46
                       note = Synthetic oligonucleotide
source                 1..46
                       mol_type = other DNA
                       organism = synthetic construct
SEQUENCE: 791
ccccttaggg ataacagggt aatcaagtag ggctcagggt cgaagg                 46

SEQ ID NO: 792          moltype = DNA  length = 45
FEATURE                Location/Qualifiers
misc_feature           1..45
                       note = Synthetic oligonucleotide
source                 1..45
                       mol_type = other DNA
                       organism = synthetic construct
SEQUENCE: 792
ccccttaggg ataacagggt aatcgcaatg gccgctggga aaaat                  45

SEQ ID NO: 793          moltype = DNA  length = 49
FEATURE                Location/Qualifiers
misc_feature           1..49
                       note = Synthetic oligonucleotide
source                 1..49
                       mol_type = other DNA
                       organism = synthetic construct
SEQUENCE: 793
ccccttaggg ataacagggt aatcctatca ttgtagatgg ggccggaaa              49

SEQ ID NO: 794          moltype = DNA  length = 43
FEATURE                Location/Qualifiers
misc_feature           1..43
                       note = Synthetic oligonucleotide
source                 1..43
                       mol_type = other DNA
                       organism = synthetic construct
SEQUENCE: 794
ccccttaggg ataacagggt aatcgccact gccactgtag cct                    43

SEQ ID NO: 795          moltype = DNA  length = 47
FEATURE                Location/Qualifiers
misc_feature           1..47
                       note = Synthetic oligonucleotide
source                 1..47
                       mol_type = other DNA
                       organism = synthetic construct
SEQUENCE: 795
```

```
ccccttaggg ataacagggt aatccaactc cagggctcaa gcaatcg              47

SEQ ID NO: 796          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 796
ccccttaggg ataacagggt aatcgcagac atttgaccac cctataccc            49

SEQ ID NO: 797          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 797
ccccttaggg ataacagggt aatcgcagta gggaaggggc aact                 44

SEQ ID NO: 798          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 798
ccccttaggg ataacagggt aatcgtcttt ctctggcacc aagcttttg            49

SEQ ID NO: 799          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 799
ccccttaggg ataacagggt aatctggcac ctgcaggaaa cggt                 44

SEQ ID NO: 800          moltype = DNA  length = 42
FEATURE                 Location/Qualifiers
misc_feature            1..42
                        note = Synthetic oligonucleotide
source                  1..42
                        mol_type = other DNA
                        organism = synthetic construct
SEQUENCE: 800
ccccttaggg ataacagggt aatcctgggc cacctggtgt cg                   42

SEQ ID NO: 801          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 801
ccccttaggg ataacagggt aatcccttgg gccagtcact gca                  43

SEQ ID NO: 802          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 802
ccccttaggg ataacagggt aatctgacca catgtccacc gttcag               46

SEQ ID NO: 803          moltype = DNA  length = 47
FEATURE                 Location/Qualifiers
misc_feature            1..47
                        note = Synthetic oligonucleotide
source                  1..47
                        mol_type = other DNA
                        organism = synthetic construct
```

```
SEQUENCE: 803
ccccttaggg ataacagggt aatcagcttg ggaggctggt actactg              47

SEQ ID NO: 804          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 804
ccccttaggg ataacagggt aatccccaga cactgcttcc ctggta               46

SEQ ID NO: 805          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 805
ccccttaggg ataacagggt aatcttcctc ctgccagggt gca                  43

SEQ ID NO: 806          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 806
ccccttaggg ataacagggt aatctgtacc atgaatgttg tggcgcat             48

SEQ ID NO: 807          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 807
ccccttaggg ataacagggt aatcagtctg ggtcaagtgc tgtgg                45

SEQ ID NO: 808          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 808
ccccttaggg ataacagggt aatcggaaca aaggacctac atgtggct             48

SEQ ID NO: 809          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 809
ccccttaggg ataacagggt aatcacataa gcgaaggatc aggagagt             48

SEQ ID NO: 810          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 810
ccccttaggg ataacagggt aatctctaga gaacatccgg caatgcc              47

SEQ ID NO: 811          moltype = DNA  length = 50
FEATURE                 Location/Qualifiers
misc_feature            1..50
                        note = Synthetic oligonucleotide
source                  1..50
                        mol_type = other DNA
```

```
                       organism = synthetic construct
SEQUENCE: 811
ccccttaggg ataacagggt aatcccttag gccaaacatc cttgaccata             50

SEQ ID NO: 812         moltype = DNA  length = 49
FEATURE                Location/Qualifiers
misc_feature           1..49
                       note = Synthetic oligonucleotide
source                 1..49
                       mol_type = other DNA
                       organism = synthetic construct
SEQUENCE: 812
ccccttaggg ataacagggt aatctcccca aagtctaagg aggctaaga              49

SEQ ID NO: 813         moltype = DNA  length = 48
FEATURE                Location/Qualifiers
misc_feature           1..48
                       note = Synthetic oligonucleotide
source                 1..48
                       mol_type = other DNA
                       organism = synthetic construct
SEQUENCE: 813
ccccttaggg ataacagggt aatccctgaa aaacggatga gacttcag               48

SEQ ID NO: 814         moltype = DNA  length = 48
FEATURE                Location/Qualifiers
misc_feature           1..48
                       note = Synthetic oligonucleotide
source                 1..48
                       mol_type = other DNA
                       organism = synthetic construct
SEQUENCE: 814
ccccttaggg ataacagggt aatcattgtg cttcagatcc cgtgacat               48

SEQ ID NO: 815         moltype = DNA  length = 43
FEATURE                Location/Qualifiers
misc_feature           1..43
                       note = Synthetic oligonucleotide
source                 1..43
                       mol_type = other DNA
                       organism = synthetic construct
SEQUENCE: 815
ccccttaggg ataacagggt aatcgtgggg acttgctgct ggt                    43

SEQ ID NO: 816         moltype = DNA  length = 48
FEATURE                Location/Qualifiers
misc_feature           1..48
                       note = Synthetic oligonucleotide
source                 1..48
                       mol_type = other DNA
                       organism = synthetic construct
SEQUENCE: 816
ccccttaggg ataacagggt aatcagctct gctacattca ggtaacat               48

SEQ ID NO: 817         moltype = DNA  length = 48
FEATURE                Location/Qualifiers
misc_feature           1..48
                       note = Synthetic oligonucleotide
source                 1..48
                       mol_type = other DNA
                       organism = synthetic construct
SEQUENCE: 817
ccccttaggg ataacagggt aatctccctc tttagcatcg ccaaatcc               48

SEQ ID NO: 818         moltype = DNA  length = 48
FEATURE                Location/Qualifiers
misc_feature           1..48
                       note = Synthetic oligonucleotide
source                 1..48
                       mol_type = other DNA
                       organism = synthetic construct
SEQUENCE: 818
ccccttaggg ataacagggt aatcttggtg gccacaactt aggtgaga               48

SEQ ID NO: 819         moltype = DNA  length = 50
FEATURE                Location/Qualifiers
misc_feature           1..50
                       note = Synthetic oligonucleotide
source                 1..50
```

```
                        mol_type = other DNA
                        organism = synthetic construct
SEQUENCE: 819
ccccttaggg ataacagggt aatccccagg tgttgctcat cagttcctct              50

SEQ ID NO: 820          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 820
ccccttaggg ataacagggt aatcatcact ttctcaaggg acatgccat               49

SEQ ID NO: 821          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 821
ccccttaggg ataacagggt aatcgtctca caactcccag tcttgcttta              50

SEQ ID NO: 822          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 822
ccccttaggg ataacagggt aatcaactgg gctcgttggt taccct                  46

SEQ ID NO: 823          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 823
ccccttaggg ataacagggt aatctttggt ttggttgctt tgcagactac              50

SEQ ID NO: 824          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 824
ccccttaggg ataacagggt aatccttttc tgctgtcacc ctcaaggat               49

SEQ ID NO: 825          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 825
ccccttaggg ataacagggt aatcgagtga atgcatgatt gtgtgaccga              50

SEQ ID NO: 826          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 826
ccccttaggg ataacagggt aatctgctag tgtcgaggtt tgca                    44

SEQ ID NO: 827          moltype = DNA  length = 49
FEATURE                 Location/Qualifiers
misc_feature            1..49
                        note = Synthetic oligonucleotide
```

```
source                  1..49
                        mol_type = other DNA
                        organism = synthetic construct
SEQUENCE: 827
ccccttaggg ataacagggt aatcgtggag aaagtgctaa acaagaaaa             49

SEQ ID NO: 828          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 828
ccccttaggg ataacagggt aatcctccag agtctatgct caactgaa              48

SEQ ID NO: 829          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 829
ccccttaggg ataacagggt aatcatggcc ataagttgaa atttgcgt              48

SEQ ID NO: 830          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 830
ccccttaggg ataacagggt aatcgggacc tcaggtgctg ctt                   43

SEQ ID NO: 831          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 831
ccccttaggg ataacagggt aatctgattc aatcttacat gcgacagcct            50

SEQ ID NO: 832          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 832
ccccttaggg ataacagggt aatcagagaa gcctgtcagg accat                 45

SEQ ID NO: 833          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 833
ccccttaggg ataacagggt aatctcaccg tctacttctc ttgtgtg               47

SEQ ID NO: 834          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 834
ccccttaggg ataacagggt aatcccacat gcaaatgaac gacactgac             49

SEQ ID NO: 835          moltype = DNA  length = 46
FEATURE                 Location/Qualifiers
misc_feature            1..46
```

```
                        note = Synthetic oligonucleotide
source                  1..46
                        mol_type = other DNA
                        organism = synthetic construct
SEQUENCE: 835
cccccttaggg ataacagggt aatcgcagca atttggtccc ccatgg              46

SEQ ID NO: 836          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 836
ccccttaggg ataacagggt aatctcagac cgtgactcag tatgttg              47

SEQ ID NO: 837          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 837
ccccttaggg ataacagggt aatcaggccc ctgtctctac catcc                45

SEQ ID NO: 838          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 838
ccccttaggg ataacagggt aatcgtggag aaggcagcct cccaa                45

SEQ ID NO: 839          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 839
ccccttaggg ataacagggt aatctgcctg gagtggtgtc tggt                 44

SEQ ID NO: 840          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 840
ccccttaggg ataacagggt aatcacagac ctcagagccc agtcc                45

SEQ ID NO: 841          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 841
ccccttaggg ataacagggt aatcgcacac agccaacaag atgactca             48

SEQ ID NO: 842          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 842
ccccttaggg ataacagggt aatccccctg tttttacctc aaccttaggg           50

SEQ ID NO: 843          moltype = DNA  length = 43
FEATURE                 Location/Qualifiers
```

```
misc_feature           1..43
                       note = Synthetic oligonucleotide
source                 1..43
                       mol_type = other DNA
                       organism = synthetic construct
SEQUENCE: 843
ccccttaggg ataacagggt aatctcactg ctgcccccac aag                 43

SEQ ID NO: 844         moltype = DNA  length = 42
FEATURE                Location/Qualifiers
misc_feature           1..42
                       note = Synthetic oligonucleotide
source                 1..42
                       mol_type = other DNA
                       organism = synthetic construct
SEQUENCE: 844
ccccttaggg ataacagggt aatcggccag gccggagtca gg                  42

SEQ ID NO: 845         moltype = DNA  length = 49
FEATURE                Location/Qualifiers
misc_feature           1..49
                       note = Synthetic oligonucleotide
source                 1..49
                       mol_type = other DNA
                       organism = synthetic construct
SEQUENCE: 845
ccccttaggg ataacagggt aatcttggaa tggcaatccg ttggaaatg           49

SEQ ID NO: 846         moltype = DNA  length = 50
FEATURE                Location/Qualifiers
misc_feature           1..50
                       note = Synthetic oligonucleotide
source                 1..50
                       mol_type = other DNA
                       organism = synthetic construct
SEQUENCE: 846
ccccttaggg ataacagggt aatctggaac tgtgggcata agcatatgtc          50

SEQ ID NO: 847         moltype = DNA  length = 45
FEATURE                Location/Qualifiers
misc_feature           1..45
                       note = Synthetic oligonucleotide
source                 1..45
                       mol_type = other DNA
                       organism = synthetic construct
SEQUENCE: 847
ccccttaggg ataacagggt aatcacaggt ttcaggcgga gtgga               45

SEQ ID NO: 848         moltype = DNA  length = 50
FEATURE                Location/Qualifiers
misc_feature           1..50
                       note = Synthetic oligonucleotide
source                 1..50
                       mol_type = other DNA
                       organism = synthetic construct
SEQUENCE: 848
ccccttaggg ataacagggt aatcaggagg aattaaccct gtgaacatcg          50

SEQ ID NO: 849         moltype = DNA  length = 49
FEATURE                Location/Qualifiers
misc_feature           1..49
                       note = Synthetic oligonucleotide
source                 1..49
                       mol_type = other DNA
                       organism = synthetic construct
SEQUENCE: 849
ccccttaggg ataacagggt aatctttcac aagaacggta ctggccaat           49

SEQ ID NO: 850         moltype = DNA  length = 50
FEATURE                Location/Qualifiers
misc_feature           1..50
                       note = Synthetic oligonucleotide
source                 1..50
                       mol_type = other DNA
                       organism = synthetic construct
SEQUENCE: 850
ccccttaggg ataacagggt aatcataaga ggtgaactag caagcagagc          50

SEQ ID NO: 851         moltype = DNA  length = 49
```

```
FEATURE                 Location/Qualifiers
misc_feature            1..49
                        note = Synthetic oligonucleotide
source                  1..49
                        mol_type = other DNA
                        organism = synthetic construct
SEQUENCE: 851
ccccttaggg ataacagggt aatcagagtg taagctcacc ctacagtct              49

SEQ ID NO: 852          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 852
ccccttaggg ataacagggt aatcgacagc aagtccagac taaggca                47

SEQ ID NO: 853          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 853
ccccttaggg ataacagggt aatcgaggta gggttcttcg tgttggc                47

SEQ ID NO: 854          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 854
ccccttaggg ataacagggt aatccctaag tggagttgac ctgtacaagg             50

SEQ ID NO: 855          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 855
ccccttaggg ataacagggt aatccttcag ccactccctt atgaggtag              49

SEQ ID NO: 856          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 856
ccccttaggg ataacagggt aatcacacca ggctacaagt ctcctga                47

SEQ ID NO: 857          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 857
ccccttaggg ataacagggt aatcccctgc tcctgtctgc ctgatta                47

SEQ ID NO: 858          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 858
ccccttaggg ataacagggt aatcaaggct tgttcaccct gaggag                 46
```

```
SEQ ID NO: 859          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 859
ccccttaggg ataacagggt aatcggaaag ctaaaagatt tgcgttgact            50

SEQ ID NO: 860          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 860
ccccttaggg ataacagggt aatctccttc cacggagttc actgagt               47

SEQ ID NO: 861          moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 861
ccccttaggg ataacagggt aatcagcttt ggcccctagg attctg                46

SEQ ID NO: 862          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 862
ccccttaggg ataacagggt aatcctctgg gtgcggggga act                   43

SEQ ID NO: 863          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 863
ccccttaggg ataacagggt aatctccagt gatctagtaa ctccgtggt             49

SEQ ID NO: 864          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 864
ccccttaggg ataacagggt aatcccttca gaaactagtt agccctgt              48

SEQ ID NO: 865          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 865
ccccttaggg ataacagggt aatcatggtc caaggtcagc tggcggaca             49

SEQ ID NO: 866          moltype = DNA  length = 44
FEATURE                 Location/Qualifiers
misc_feature            1..44
                        note = Synthetic oligonucleotide
source                  1..44
                        mol_type = other DNA
                        organism = synthetic construct
SEQUENCE: 866
ccccttaggg ataacagggt aatcaggacc caccacggat tcct                  44
```

```
SEQ ID NO: 867          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 867
ccccttaggg ataacagggt aatcactgcc tcctccttag tcgat                  45

SEQ ID NO: 868          moltype = DNA  length = 48
FEATURE                 Location/Qualifiers
misc_feature            1..48
                        note = Synthetic oligonucleotide
source                  1..48
                        mol_type = other DNA
                        organism = synthetic construct
SEQUENCE: 868
ccccttaggg ataacagggt aatcgctgta gacagattgg cctcagtt               48

SEQ ID NO: 869          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 869
ccccttaggg ataacagggt aatcccaagg tatgggggct aaccatt                47

SEQ ID NO: 870          moltype = DNA  length = 50
FEATURE                 Location/Qualifiers
misc_feature            1..50
                        note = Synthetic oligonucleotide
source                  1..50
                        mol_type = other DNA
                        organism = synthetic construct
SEQUENCE: 870
ccccttaggg ataacagggt aatcttctgg aaattcgtcg aaggatggtc             50

SEQ ID NO: 871          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 871
ccccttaggg ataacagggt aatcagctgt gctcttccgt ttcagtg                47

SEQ ID NO: 872          moltype = DNA  length = 47
FEATURE                 Location/Qualifiers
misc_feature            1..47
                        note = Synthetic oligonucleotide
source                  1..47
                        mol_type = other DNA
                        organism = synthetic construct
SEQUENCE: 872
ccccttaggg ataacagggt aatcccacga ggcgtattca tctgcat                47

SEQ ID NO: 873          moltype = DNA  length = 49
FEATURE                 Location/Qualifiers
misc_feature            1..49
                        note = Synthetic oligonucleotide
source                  1..49
                        mol_type = other DNA
                        organism = synthetic construct
SEQUENCE: 873
ccccttaggg ataacagggt aatcaatgga accacactac atcaagtta              49

SEQ ID NO: 874          moltype = DNA  length = 45
FEATURE                 Location/Qualifiers
misc_feature            1..45
                        note = Synthetic oligonucleotide
source                  1..45
                        mol_type = other DNA
                        organism = synthetic construct
SEQUENCE: 874
```

```
ccccttaggg ataacagggt aatccctgac cctgccgtgt accag                45

SEQ ID NO: 875          moltype = DNA  length = 43
FEATURE                 Location/Qualifiers
misc_feature            1..43
                        note = Synthetic oligonucleotide
source                  1..43
                        mol_type = other DNA
                        organism = synthetic construct
SEQUENCE: 875
ccccttaggg ataacagggt aatccctgcg aaggcaccaa agc                  43

SEQ ID NO: 876          moltype = DNA  length = 56
FEATURE                 Location/Qualifiers
misc_feature            1..56
                        note = Synthetic oligonucleotide
source                  1..56
                        mol_type = other DNA
                        organism = synthetic construct
SEQUENCE: 876
gtgactggag ttcagacgtg tgctcttccg atctggctca gggtcgaagg ctcact    56

SEQ ID NO: 877          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 877
gtgactggag ttcagacgtg tgctcttccg atcttcaaac catcggggga aaaatgacaa  60

SEQ ID NO: 878          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 878
gtgactggag ttcagacgtg tgctcttccg atctgtagat ggggccggaa agtagaaaag  60

SEQ ID NO: 879          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 879
gtgactggag ttcagacgtg tgctcttccg atctcccagc tccaagtcca tctgg     55

SEQ ID NO: 880          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 880
gtgactggag ttcagacgtg tgctcttccg atctgctacc aagccccacc ct        52

SEQ ID NO: 881          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 881
gtgactggag ttcagacgtg tgctcttccg atctcaccct atacccacca tactcacgtt  60

SEQ ID NO: 882          moltype = DNA  length = 60
FEATURE                 Location/Qualifiers
misc_feature            1..60
                        note = Synthetic oligonucleotide
source                  1..60
                        mol_type = other DNA
                        organism = synthetic construct
```

SEQUENCE: 882
gtgactggag ttcagacgtg tgctcttccg atctagggaa ggggcaactt ttcaaaatct 60

SEQ ID NO: 883 moltype = DNA length = 60
FEATURE Location/Qualifiers
misc_feature 1..60
note = Synthetic oligonucleotide
source 1..60
mol_type = other DNA
organism = synthetic construct
SEQUENCE: 883
gtgactggag ttcagacgtg tgctcttccg atctgcacca agcttttgtg atgctccaac 60

SEQ ID NO: 884 moltype = DNA length = 58
FEATURE Location/Qualifiers
misc_feature 1..58
note = Synthetic oligonucleotide
source 1..58
mol_type = other DNA
organism = synthetic construct
SEQUENCE: 884
gtgactggag ttcagacgtg tgctcttccg atctcacctg caggaaacgg ttgcgttc 58

SEQ ID NO: 885 moltype = DNA length = 54
FEATURE Location/Qualifiers
misc_feature 1..54
note = Synthetic oligonucleotide
source 1..54
mol_type = other DNA
organism = synthetic construct
SEQUENCE: 885
gtgactggag ttcagacgtg tgctcttccg atctgctggg ccgcctgatc tacc 54

SEQ ID NO: 886 moltype = DNA length = 54
FEATURE Location/Qualifiers
misc_feature 1..54
note = Synthetic oligonucleotide
source 1..54
mol_type = other DNA
organism = synthetic construct
SEQUENCE: 886
gtgactggag ttcagacgtg tgctcttccg atctgccagt cactgcagct ctct 54

SEQ ID NO: 887 moltype = DNA length = 58
FEATURE Location/Qualifiers
misc_feature 1..58
note = Synthetic oligonucleotide
source 1..58
mol_type = other DNA
organism = synthetic construct
SEQUENCE: 887
gtgactggag ttcagacgtg tgctcttccg atctacatgt ccaccgttca gacacagc 58

SEQ ID NO: 888 moltype = DNA length = 58
FEATURE Location/Qualifiers
misc_feature 1..58
note = Synthetic oligonucleotide
source 1..58
mol_type = other DNA
organism = synthetic construct
SEQUENCE: 888
gtgactggag ttcagacgtg tgctcttccg atctgggagg ctggtactac tgggcatc 58

SEQ ID NO: 889 moltype = DNA length = 59
FEATURE Location/Qualifiers
misc_feature 1..59
note = Synthetic oligonucleotide
source 1..59
mol_type = other DNA
organism = synthetic construct
SEQUENCE: 889
gtgactggag ttcagacgtg tgctcttccg atctagacac tgcttccctg gtaatggac 59

SEQ ID NO: 890 moltype = DNA length = 54
FEATURE Location/Qualifiers
misc_feature 1..54
note = Synthetic oligonucleotide
source 1..54
mol_type = other DNA

```
                         organism = synthetic construct
SEQUENCE: 890
gtgactggag ttcagacgtg tgctcttccg atctcctgcc agggtgcaag aact        54

SEQ ID NO: 891           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 891
gtgactggag ttcagacgtg tgctcttccg atctccatga atgttgtggc gcattttcat  60

SEQ ID NO: 892           moltype = DNA  length = 54
FEATURE                  Location/Qualifiers
misc_feature             1..54
                         note = Synthetic oligonucleotide
source                   1..54
                         mol_type = other DNA
                         organism = synthetic construct
SEQUENCE: 892
gtgactggag ttcagacgtg tgctcttccg atcttgctgt gggctccttt gctt        54

SEQ ID NO: 893           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 893
gtgactggag ttcagacgtg tgctcttccg atctcaaagg acctacatgt ggctccaatt  60

SEQ ID NO: 894           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 894
gtgactggag ttcagacgtg tgctcttccg atctgcgaag gatcaggaga gtactattag  60

SEQ ID NO: 895           moltype = DNA  length = 54
FEATURE                  Location/Qualifiers
misc_feature             1..54
                         note = Synthetic oligonucleotide
source                   1..54
                         mol_type = other DNA
                         organism = synthetic construct
SEQUENCE: 895
gtgactggag ttcagacgtg tgctcttccg atctaggggt gggagagtgc tact        54

SEQ ID NO: 896           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 896
gtgactggag ttcagacgtg tgctcttccg atcttgtatg ttggttatgc gggaagagac  60

SEQ ID NO: 897           moltype = DNA  length = 60
FEATURE                  Location/Qualifiers
misc_feature             1..60
                         note = Synthetic oligonucleotide
source                   1..60
                         mol_type = other DNA
                         organism = synthetic construct
SEQUENCE: 897
gtgactggag ttcagacgtg tgctcttccg atcttggatt tccaaagaga agccctagtc  60

SEQ ID NO: 898           moltype = DNA  length = 57
FEATURE                  Location/Qualifiers
misc_feature             1..57
                         note = Synthetic oligonucleotide
source                   1..57
```

```
                        mol_type = other DNA
                        organism = synthetic construct
SEQUENCE: 898
gtgactggag ttcagacgtg tgctcttccg atctacggat gagacttcag tgagtac     57

SEQ ID NO: 899          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 899
gtgactggag ttcagacgtg tgctcttccg atcttgcttc agatcccgtg acatcagtgt  60

SEQ ID NO: 900          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 900
gtgactggag ttcagacgtg tgctcttccg atctagtggg gacttgctgc tggtatctac  60

SEQ ID NO: 901          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 901
gtgactggag ttcagacgtg tgctcttccg atctgctaca ttcaggtaac atgtttctgc  60

SEQ ID NO: 902          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 902
gtgactggag ttcagacgtg tgctcttccg atctgccaaa tcctcccagg tgca        54

SEQ ID NO: 903          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 903
gtgactggag ttcagacgtg tgctcttccg atctggccac aacttaggtg agagtgacga  60

SEQ ID NO: 904          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 904
gtgactggag ttcagacgtg tgctcttccg atctcctctg aactaagtgg gagtttggc   59

SEQ ID NO: 905          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 905
gtgactggag ttcagacgtg tgctcttccg atcttgccat ttctctaatc aaggggtgtg  60

SEQ ID NO: 906          moltype = DNA  length = 60
FEATURE                 Location/Qualifiers
misc_feature            1..60
                        note = Synthetic oligonucleotide
```

```
source                  1..60
                        mol_type = other DNA
                        organism = synthetic construct
SEQUENCE: 906
gtgactggag ttcagacgtg tgctcttccg atcttcccag tcttgcttta tactgtgcct  60

SEQ ID NO: 907          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 907
gtgactggag ttcagacgtg tgctcttccg atctctgggc tcgttggtta ccctattcct  60

SEQ ID NO: 908          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 908
gtgactggag ttcagacgtg tgctcttccg atctgaggag ctaccagggc ccta        54

SEQ ID NO: 909          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 909
gtgactggag ttcagacgtg tgctcttccg atctacctca tcatttctca ggcgaaagg   59

SEQ ID NO: 910          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 910
gtgactggag ttcagacgtg tgctcttccg atctgcatga ttgtgtgacc gaatgcctca  60

SEQ ID NO: 911          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 911
gtgactggag ttcagacgtg tgctcttccg atctggtttg caccatagaa agctgag     57

SEQ ID NO: 912          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 912
gtgactggag ttcagacgtg tgctcttccg atctggtaaa ccagaactat ctttctctcc  60

SEQ ID NO: 913          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 913
gtgactggag ttcagacgtg tgctcttccg atctgaactt gaaatgctta cagccagaat  60

SEQ ID NO: 914          moltype = DNA  length = 60
FEATURE                 Location/Qualifiers
misc_feature            1..60
```

```
                        note = Synthetic oligonucleotide
source                  1..60
                        mol_type = other DNA
                        organism = synthetic construct
SEQUENCE: 914
gtgactggag ttcagacgtg tgctcttccg atctccataa gttgaaattt gcgtttcggt  60

SEQ ID NO: 915          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 915
gtgactggag ttcagacgtg tgctcttccg atctcctcag gtgctgcttc ctcaa       55

SEQ ID NO: 916          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 916
gtgactggag ttcagacgtg tgctcttccg atctcatgcg acagcctgat ccgtttct    58

SEQ ID NO: 917          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 917
gtgactggag ttcagacgtg tgctcttccg atctgcctgt caggaccata caaatcttac  60

SEQ ID NO: 918          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 918
gtgactggag ttcagacgtg tgctcttccg atctttctct tgtgtgatcc agagttgaca  60

SEQ ID NO: 919          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 919
gtgactggag ttcagacgtg tgctcttccg atctaacgac actgacagaa aacactcacg  60

SEQ ID NO: 920          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 920
gtgactggag ttcagacgtg tgctcttccg atctagcaat ttggtccccc atggagagac  60

SEQ ID NO: 921          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 921
gtgactggag ttcagacgtg tgctcttccg atctaaaact tgactgttca ttgggttcaa  60

SEQ ID NO: 922          moltype = DNA  length = 60
FEATURE                 Location/Qualifiers
```

```
misc_feature            1..60
                        note = Synthetic oligonucleotide
source                  1..60
                        mol_type = other DNA
                        organism = synthetic construct
SEQUENCE: 922
gtgactggag ttcagacgtg tgctcttccg atctcccctg tctctaccat cctagacacc  60

SEQ ID NO: 923          moltype = DNA  length = 57
FEATURE                 Location/Qualifiers
misc_feature            1..57
                        note = Synthetic oligonucleotide
source                  1..57
                        mol_type = other DNA
                        organism = synthetic construct
SEQUENCE: 923
gtgactggag ttcagacgtg tgctcttccg atctagaagg cagcctccca aagcact     57

SEQ ID NO: 924          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 924
gtgactggag ttcagacgtg tgctcttccg atctgcctgg agtggtgtct ggtacaatga  60

SEQ ID NO: 925          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 925
gtgactggag ttcagacgtg tgctcttccg atctgtccct ggccttaaag aaatgacaga  60

SEQ ID NO: 926          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 926
gtgactggag ttcagacgtg tgctcttccg atctagcctt gattactgtt cccactagc   59

SEQ ID NO: 927          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 927
gtgactggag ttcagacgtg tgctcttccg atctgggctt ccttgctttg gttactgt    58

SEQ ID NO: 928          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 928
gtgactggag ttcagacgtg tgctcttccg atctcactgc tgcccccaca agcttaac    58

SEQ ID NO: 929          moltype = DNA  length = 52
FEATURE                 Location/Qualifiers
misc_feature            1..52
                        note = Synthetic oligonucleotide
source                  1..52
                        mol_type = other DNA
                        organism = synthetic construct
SEQUENCE: 929
gtgactggag ttcagacgtg tgctcttccg atctgccgga gtcaggggca tc          52

SEQ ID NO: 930          moltype = DNA  length = 60
```

```
FEATURE                 Location/Qualifiers
misc_feature            1..60
                        note = Synthetic oligonucleotide
source                  1..60
                        mol_type = other DNA
                        organism = synthetic construct
SEQUENCE: 930
gtgactggag ttcagacgtg tgctcttccg atctatggca atccgttgga aatgtcttct  60

SEQ ID NO: 931          moltype = DNA  length = 56
FEATURE                 Location/Qualifiers
misc_feature            1..56
                        note = Synthetic oligonucleotide
source                  1..56
                        mol_type = other DNA
                        organism = synthetic construct
SEQUENCE: 931
gtgactggag ttcagacgtg tgctcttccg atctcccata ccccactccc actact      56

SEQ ID NO: 932          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 932
gtgactggag ttcagacgtg tgctcttccg atctcaggtt tcaggcggag tggaagaagt  60

SEQ ID NO: 933          moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 933
gtgactggag ttcagacgtg tgctcttccg atctaaccct gtgaacatcg tgattccag   59

SEQ ID NO: 934          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 934
gtgactggag ttcagacgtg tgctcttccg atctcggtac tggccaatga aattttccca  60

SEQ ID NO: 935          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 935
gtgactggag ttcagacgtg tgctcttccg atctttggct ctctggattg ttcctctaaa  60

SEQ ID NO: 936          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 936
gtgactggag ttcagacgtg tgctcttccg atctcaccct acagtctatg ttccaggtca  60

SEQ ID NO: 937          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 937
gtgactggag ttcagacgtg tgctcttccg atctccagac taaggcaagc aactgtaaca  60
```

```
SEQ ID NO: 938          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 938
gtgactggag ttcagacgtg tgctcttccg atctcttcgt gttggccagg tgggt       55

SEQ ID NO: 939          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 939
gtgactggag ttcagacgtg tgctcttccg atcttgaagc tgagttacct gggagctc    58

SEQ ID NO: 940          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 940
gtgactggag ttcagacgtg tgctcttccg atctcttacg ggaaagcaag ttgactttgc  60

SEQ ID NO: 941          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 941
gtgactggag ttcagacgtg tgctcttccg atctacaaaa caaaaccctc cggatggtct  60

SEQ ID NO: 942          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 942
gtgactggag ttcagacgtg tgctcttccg atcttgctcc tgtctgcctg attacttact  60

SEQ ID NO: 943          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 943
gtgactggag ttcagacgtg tgctcttccg atctggtcat gcctccaacc tgca        54

SEQ ID NO: 944          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 944
gtgactggag ttcagacgtg tgctcttccg atctttgcgt tgacttaaat gaaagtgtcc  60

SEQ ID NO: 945          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 945
gtgactggag ttcagacgtg tgctcttccg atctactgtc gggagaaggc gtct        54
```

```
SEQ ID NO: 946          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 946
gtgactggag ttcagacgtg tgctcttccg atcttgatct gtttgtgaat ggctcagaca  60

SEQ ID NO: 947          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 947
gtgactggag ttcagacgtg tgctcttccg atctactctg ggtgcggggg aacttatttg  60

SEQ ID NO: 948          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 948
gtgactggag ttcagacgtg tgctcttccg atctccgtgg tggatttaac tcccctattg  60

SEQ ID NO: 949          moltype = DNA  length = 54
FEATURE                 Location/Qualifiers
misc_feature            1..54
                        note = Synthetic oligonucleotide
source                  1..54
                        mol_type = other DNA
                        organism = synthetic construct
SEQUENCE: 949
gtgactggag ttcagacgtg tgctcttccg atctagcatt ctgcctctga cagg        54

SEQ ID NO: 950          moltype = DNA  length = 55
FEATURE                 Location/Qualifiers
misc_feature            1..55
                        note = Synthetic oligonucleotide
source                  1..55
                        mol_type = other DNA
                        organism = synthetic construct
SEQUENCE: 950
gtgactggag ttcagacgtg tgctcttccg atcttccaag gtcagctggc ggaca       55

SEQ ID NO: 951          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 951
gtgactggag ttcagacgtg tgctcttccg atctacggat tcctgctgta ctggctaaag  60

SEQ ID NO: 952          moltype = DNA  length = 60
FEATURE                 Location/Qualifiers
misc_feature            1..60
                        note = Synthetic oligonucleotide
source                  1..60
                        mol_type = other DNA
                        organism = synthetic construct
SEQUENCE: 952
gtgactggag ttcagacgtg tgctcttccg atcttgcctc ctccttagtc gattcttacc  60

SEQ ID NO: 953          moltype = DNA  length = 58
FEATURE                 Location/Qualifiers
misc_feature            1..58
                        note = Synthetic oligonucleotide
source                  1..58
                        mol_type = other DNA
                        organism = synthetic construct
SEQUENCE: 953
```

```
gtgactggag ttcagacgtg tgctcttccg atctaacaag tgtccctggc aaatgtga    58

SEQ ID NO: 954         moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 954
gtgactggag ttcagacgtg tgctcttccg atctgggggc taaccattgg caattgaa    58

SEQ ID NO: 955         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 955
gtgactggag ttcagacgtg tgctcttccg atctttcgtc gaaggatggt ctctctgttg  60

SEQ ID NO: 956         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 956
gtgactggag ttcagacgtg tgctcttccg atcttgtgct cttccgtttc agtgtgaaaa  60

SEQ ID NO: 957         moltype = DNA  length = 59
FEATURE                Location/Qualifiers
misc_feature           1..59
                       note = Synthetic oligonucleotide
source                 1..59
                       mol_type = other DNA
                       organism = synthetic construct
SEQUENCE: 957
gtgactggag ttcagacgtg tgctcttccg atctatctgc atgcatgagt cctgacttc   59

SEQ ID NO: 958         moltype = DNA  length = 60
FEATURE                Location/Qualifiers
misc_feature           1..60
                       note = Synthetic oligonucleotide
source                 1..60
                       mol_type = other DNA
                       organism = synthetic construct
SEQUENCE: 958
gtgactggag ttcagacgtg tgctcttccg atctatcaag ttacatagaa atggggaggt  60

SEQ ID NO: 959         moltype = DNA  length = 58
FEATURE                Location/Qualifiers
misc_feature           1..58
                       note = Synthetic oligonucleotide
source                 1..58
                       mol_type = other DNA
                       organism = synthetic construct
SEQUENCE: 959
gtgactggag ttcagacgtg tgctcttccg atctcctgcc gtgtaccagc tgagagac    58

SEQ ID NO: 960         moltype = DNA  length = 56
FEATURE                Location/Qualifiers
misc_feature           1..56
                       note = Synthetic oligonucleotide
source                 1..56
                       mol_type = other DNA
                       organism = synthetic construct
SEQUENCE: 960
gtgactggag ttcagacgtg tgctcttccg atctgctgtt gttgaaggcg tttgca      56

SEQ ID NO: 961         moltype = DNA  length = 23
FEATURE                Location/Qualifiers
misc_feature           1..23
                       note = Synthetic oligonucleotide
source                 1..23
                       mol_type = other DNA
                       organism = synthetic construct
```

```
SEQUENCE: 961
gaccccctcc accccgcctc cgg                                          23

SEQ ID NO: 962          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 962
ctacccctcc accccgcctc cgg                                          23

SEQ ID NO: 963          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 963
attccccccc accccgcctc agg                                          23

SEQ ID NO: 964          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 964
gggcccctcc accccgcctc tgg                                          23

SEQ ID NO: 965          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 965
gacccccttc accccaccta tgg                                          23

SEQ ID NO: 966          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 966
taccccccac accccgcctc tgg                                          23

SEQ ID NO: 967          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 967
gcccccaccc accccgcctc tgg                                          23

SEQ ID NO: 968          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 968
tgcccccccc accccacctc tgg                                          23

SEQ ID NO: 969          moltype = DNA  length = 23
FEATURE                 Location/Qualifiers
misc_feature            1..23
                        note = Synthetic oligonucleotide
source                  1..23
                        mol_type = other DNA
```

```
                         organism = synthetic construct
SEQUENCE: 969
acaccccccc accccgcctc agg                                      23

SEQ ID NO: 970           moltype = DNA  length = 23
FEATURE                  Location/Qualifiers
misc_feature             1..23
                         note = Synthetic oligonucleotide
source                   1..23
                         mol_type = other DNA
                         organism = synthetic construct
SEQUENCE: 970
ctcccccccc tccccgcctc ggg                                      23

SEQ ID NO: 971           moltype = DNA  length = 23
FEATURE                  Location/Qualifiers
misc_feature             1..23
                         note = Synthetic oligonucleotide
source                   1..23
                         mol_type = other DNA
                         organism = synthetic construct
SEQUENCE: 971
tgcccctccc accccgcctc tgg                                      23

SEQ ID NO: 972           moltype = DNA  length = 23
FEATURE                  Location/Qualifiers
misc_feature             1..23
                         note = Synthetic oligonucleotide
source                   1..23
                         mol_type = other DNA
                         organism = synthetic construct
SEQUENCE: 972
cgccctcccc accccgcctc cgg                                      23

SEQ ID NO: 973           moltype = DNA  length = 23
FEATURE                  Location/Qualifiers
misc_feature             1..23
                         note = Synthetic oligonucleotide
source                   1..23
                         mol_type = other DNA
                         organism = synthetic construct
SEQUENCE: 973
agcccccccc accccgactc agg                                      23

SEQ ID NO: 974           moltype = DNA  length = 23
FEATURE                  Location/Qualifiers
misc_feature             1..23
                         note = Synthetic oligonucleotide
source                   1..23
                         mol_type = other DNA
                         organism = synthetic construct
SEQUENCE: 974
gccccccacc accccacctc ggg                                      23

SEQ ID NO: 975           moltype = DNA  length = 23
FEATURE                  Location/Qualifiers
misc_feature             1..23
                         note = Synthetic oligonucleotide
source                   1..23
                         mol_type = other DNA
                         organism = synthetic construct
SEQUENCE: 975
gacacacccc accccacctc agg                                      23

SEQ ID NO: 976           moltype = DNA  length = 23
FEATURE                  Location/Qualifiers
misc_feature             1..23
                         note = Synthetic oligonucleotide
source                   1..23
                         mol_type = other DNA
                         organism = synthetic construct
SEQUENCE: 976
ggccctctcc actccacctc agg                                      23

SEQ ID NO: 977           moltype = DNA  length = 23
FEATURE                  Location/Qualifiers
misc_feature             1..23
                         note = Synthetic oligonucleotide
source                   1..23
```

```
                        mol_type = other DNA
                        organism = synthetic construct
SEQUENCE: 977
cccccccccc cccccgcctc cgg                                             23

SEQ ID NO: 978          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 978
tcccccctca accccacctc agg                                             23

SEQ ID NO: 979          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 979
ctgccccccc accccgccac tgg                                             23

SEQ ID NO: 980          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 980
tgcccccccc accccgcccc cgg                                             23

SEQ ID NO: 981          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 981
gtcctccacc accccgcctc tgg                                             23

SEQ ID NO: 982          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 982
gccacccacc accccacctc agg                                             23

SEQ ID NO: 983          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 983
tacccccccc accccgccac agg                                             23

SEQ ID NO: 984          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 984
ctccccaccc accccgcctc agg                                             23

SEQ ID NO: 985          moltype = DNA  length = 23
FEATURE                 Location/Qualifiers
misc_feature            1..23
                        note = Synthetic oligonucleotide
```

```
source                  1..23
                        mol_type = other DNA
                        organism = synthetic construct
SEQUENCE: 985
caacccccc accccgcttc agg                                          23

SEQ ID NO: 986          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 986
gcttccctcc accccgcatc cgg                                         23

SEQ ID NO: 987          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 987
gtcactcccc accccgcctc tgg                                         23

SEQ ID NO: 988          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 988
atccccctcc accccacccc tgg                                         23

SEQ ID NO: 989          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 989
gacccccccc accccgcccc cgg                                         23

SEQ ID NO: 990          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 990
gccaccttcc accccacctc agg                                         23

SEQ ID NO: 991          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 991
cactcccccc accccgcccc agg                                         23

SEQ ID NO: 992          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 992
gacccctccc accccgactc cgg                                         23

SEQ ID NO: 993          moltype = DNA  length = 23
FEATURE                 Location/Qualifiers
misc_feature            1..23
```

```
                        note = Synthetic oligonucleotide
source                  1..23
                        mol_type = other DNA
                        organism = synthetic construct
SEQUENCE: 993
cccccccccc cccccgcctc agg                                           23

SEQ ID NO: 994          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 994
gcctctctgc accccgcctc agg                                           23

SEQ ID NO: 995          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 995
cccccccccc accccgcccc cgg                                           23

SEQ ID NO: 996          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 996
ctctcccccc accccgcctc tgg                                           23

SEQ ID NO: 997          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 997
ccccaccccc accccgcctc agg                                           23

SEQ ID NO: 998          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 998
gacccccccc accccacccc agg                                           23

SEQ ID NO: 999          moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 999
ccaccccccc accccgcccc agg                                           23

SEQ ID NO: 1000         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1000
aggccccccc gccccgcctc agg                                           23

SEQ ID NO: 1001         moltype = DNA  length = 23
FEATURE                 Location/Qualifiers
```

```
misc_feature          1..23
                      note = Synthetic oligonucleotide
source                1..23
                      mol_type = other DNA
                      organism = synthetic construct
SEQUENCE: 1001
cccccccccc cccccacccc cag                                          23

SEQ ID NO: 1002       moltype = DNA  length = 23
FEATURE               Location/Qualifiers
misc_feature          1..23
                      note = Synthetic oligonucleotide
source                1..23
                      mol_type = other DNA
                      organism = synthetic construct
SEQUENCE: 1002
gatcgactcc accccgcctc tgg                                          23

SEQ ID NO: 1003       moltype = DNA  length = 23
FEATURE               Location/Qualifiers
misc_feature          1..23
                      note = Synthetic oligonucleotide
source                1..23
                      mol_type = other DNA
                      organism = synthetic construct
SEQUENCE: 1003
agccaacccc accccgcctc tgg                                          23

SEQ ID NO: 1004       moltype = DNA  length = 23
FEATURE               Location/Qualifiers
misc_feature          1..23
                      note = Synthetic oligonucleotide
source                1..23
                      mol_type = other DNA
                      organism = synthetic construct
SEQUENCE: 1004
tccacccccc accccgcccc ggg                                          23

SEQ ID NO: 1005       moltype = DNA  length = 23
FEATURE               Location/Qualifiers
misc_feature          1..23
                      note = Synthetic oligonucleotide
source                1..23
                      mol_type = other DNA
                      organism = synthetic construct
SEQUENCE: 1005
cacccccgc accccgcccc agg                                           23

SEQ ID NO: 1006       moltype = DNA  length = 23
FEATURE               Location/Qualifiers
misc_feature          1..23
                      note = Synthetic oligonucleotide
source                1..23
                      mol_type = other DNA
                      organism = synthetic construct
SEQUENCE: 1006
cctcccccac accccgcatc cgg                                          23

SEQ ID NO: 1007       moltype = DNA  length = 23
FEATURE               Location/Qualifiers
misc_feature          1..23
                      note = Synthetic oligonucleotide
source                1..23
                      mol_type = other DNA
                      organism = synthetic construct
SEQUENCE: 1007
ggcagcctcc accacgcctc cgg                                          23

SEQ ID NO: 1008       moltype = DNA  length = 23
FEATURE               Location/Qualifiers
misc_feature          1..23
                      note = Synthetic oligonucleotide
source                1..23
                      mol_type = other DNA
                      organism = synthetic construct
SEQUENCE: 1008
catccccccc accccacccc ggg                                          23

SEQ ID NO: 1009       moltype = DNA  length = 23
```

```
FEATURE                 Location/Qualifiers
misc_feature            1..23
                        note = Synthetic oligonucleotide
source                  1..23
                        mol_type = other DNA
                        organism = synthetic construct
SEQUENCE: 1009
ccaccccccc accccgcccc tgg                                           23

SEQ ID NO: 1010         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1010
aggcccccac accccgcctc agg                                           23

SEQ ID NO: 1011         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1011
gtaccccacc accccgcccc agg                                           23

SEQ ID NO: 1012         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1012
catacccccc accccgcccc ggg                                           23

SEQ ID NO: 1013         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1013
ccgcccctcc accccgccac tgg                                           23

SEQ ID NO: 1014         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1014
agtagccccc accccgcctc ggg                                           23

SEQ ID NO: 1015         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1015
accccccccc cccccgcccc cgg                                           23

SEQ ID NO: 1016         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1016
gccccgctcc tccccgcctc cgg                                           23
```

```
SEQ ID NO: 1017        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1017
ccacccctcc accctgcttc ggg                                          23

SEQ ID NO: 1018        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1018
catttcccct accccgcccc tgg                                          23

SEQ ID NO: 1019        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1019
aacacgcccc accccgcccc agg                                          23

SEQ ID NO: 1020        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1020
gagccactgt gcccagccta ggg                                          23

SEQ ID NO: 1021        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1021
cactccccac cccccacccc cag                                          23

SEQ ID NO: 1022        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1022
ccctcccccc accccacaac agg                                          23

SEQ ID NO: 1023        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1023
gtccctttcc accctgcctc tgg                                          23

SEQ ID NO: 1024        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1024
gagctccccc accccgcccc ggg                                          23
```

```
SEQ ID NO: 1025        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1025
aacacccgcc cccccacccc cgg                                          23

SEQ ID NO: 1026        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1026
gattccctgg accacatctc tgg                                          23

SEQ ID NO: 1027        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1027
gagccaccaa acccagcctc agg                                          23

SEQ ID NO: 1028        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1028
gaatcccagg agcccgcctc gag                                          23

SEQ ID NO: 1029        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1029
ggcccccttt cccacatctc tgg                                          23

SEQ ID NO: 1030        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1030
ctcccccagc cccccacctc ccg                                          23

SEQ ID NO: 1031        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1031
cattctcgac accccgcccc cgg                                          23

SEQ ID NO: 1032        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1032
```

```
tactccttca cccccacccc agg                                         23

SEQ ID NO: 1033        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1033
cacactctca acctcacttc tag                                         23

SEQ ID NO: 1034        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1034
tccatcctca gccccacctc tcg                                         23

SEQ ID NO: 1035        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1035
aacccattcc accctgcctc agg                                         23

SEQ ID NO: 1036        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1036
gccaccccccc accctgcctc cgg                                        23

SEQ ID NO: 1037        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1037
caccaggtct gccccgcatc agg                                         23

SEQ ID NO: 1038        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1038
aatcctctca cctcagcctc cgg                                         23

SEQ ID NO: 1039        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1039
gtgccactcc accccaccct ggg                                         23

SEQ ID NO: 1040        moltype = DNA  length = 23
FEATURE                Location/Qualifiers
misc_feature           1..23
                       note = Synthetic oligonucleotide
source                 1..23
                       mol_type = other DNA
                       organism = synthetic construct
```

```
SEQUENCE: 1040
ccccccggcc cccccacccc agg                                          23

SEQ ID NO: 1041        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1041
caccccccgc cccccgcccc cgg                                          23

SEQ ID NO: 1042        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1042
ctcaccataa actccgcctc ccg                                          23

SEQ ID NO: 1043        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1043
gagccactgc acccagcctc aag                                          23

SEQ ID NO: 1044        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1044
gagccaccac aaccagcctc gag                                          23

SEQ ID NO: 1045        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1045
gtttcccttc ttcccgcccc agg                                          23

SEQ ID NO: 1046        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1046
cccccacccc cccccacccc cag                                          23

SEQ ID NO: 1047        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1047
atcctcccac accccacatc aga                                          23

SEQ ID NO: 1048        moltype = DNA  length = 23
FEATURE                Location/Qualifiers
misc_feature           1..23
                       note = Synthetic oligonucleotide
source                 1..23
                       mol_type = other DNA
```

```
                       organism = synthetic construct
SEQUENCE: 1048
caccgcgccc agccagcttc tgg                                            23

SEQ ID NO: 1049        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1049
gagccacctc acccagccta aag                                            23

SEQ ID NO: 1050        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1050
gagccaccac acccagccta aag                                            23

SEQ ID NO: 1051        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1051
gagccactgc gcccagcccc agg                                            23

SEQ ID NO: 1052        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1052
gaaccagacc tccccatctc cag                                            23

SEQ ID NO: 1053        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1053
gagccactgc acctggcctc agg                                            23

SEQ ID NO: 1054        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1054
gcacaccacc cccccgccac cgg                                            23

SEQ ID NO: 1055        moltype = DNA  length = 91
FEATURE                Location/Qualifiers
misc_feature           1..91
                       note = Synthetic oligonucleotide
source                 1..91
                       mol_type = other DNA
                       organism = synthetic construct
SEQUENCE: 1055
tgtgaaaact aagagagagc tccacccctc tgtgccctcc tcctgtcctg agtcggggtg  60
gggggggctg gccttggagg gggcgtcccc t                                   91

SEQ ID NO: 1056        moltype = DNA  length = 100
FEATURE                Location/Qualifiers
misc_feature           1..100
                       note = Synthetic polynucleotide
```

```
source                  1..100
                        mol_type = other DNA
                        organism = synthetic construct
SEQUENCE: 1056
ggccacgtcg cccgtgtatg agatggcagc ctccaccacg cctccggcac ttcctgccgc  60
ctccatgccc agcagcatgt tgggcaagta gttgagggag                         100

SEQ ID NO: 1057         moltype = AA  length = 33
FEATURE                 Location/Qualifiers
REGION                  1..33
                        note = Synthetic polypeptide
source                  1..33
                        mol_type = protein
                        organism = synthetic construct
SEQUENCE: 1057
AVDGTYSIAA EVVGGASGAA EMGLLMNPLY NLS                                33

SEQ ID NO: 1058         moltype = DNA  length = 88
FEATURE                 Location/Qualifiers
misc_feature            1..88
                        note = Synthetic oligonucleotide
source                  1..88
                        mol_type = other DNA
                        organism = synthetic construct
SEQUENCE: 1058
ccacccacca ccccacctca ggcaaatgcc cagcccctgc ctcgcctcca gcctcctttc  60
cacaacccag catccagtca ctccagtc                                      88

SEQ ID NO: 1059         moltype = DNA  length = 46
FEATURE                 Location/Qualifiers
misc_feature            1..46
                        note = Synthetic oligonucleotide
source                  1..46
                        mol_type = other DNA
                        organism = synthetic construct
SEQUENCE: 1059
gccccgggtt tcaagtgatt ttcatacttc agcctcctga gtagct                  46

SEQ ID NO: 1060         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1060
agccccagca agagcacaag agg                                           23

SEQ ID NO: 1061         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1061
atcaccccca agagcacaag ggg                                           23

SEQ ID NO: 1062         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1062
agccccagtg agagcacaag agg                                           23

SEQ ID NO: 1063         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1063
agttccagca acagcacaaa agg                                           23

SEQ ID NO: 1064         moltype = DNA  length = 23
```

-continued

```
FEATURE                Location/Qualifiers
misc_feature           1..23
                       note = Synthetic oligonucleotide
source                 1..23
                       mol_type = other DNA
                       organism = synthetic construct
SEQUENCE: 1064
aactccagcg agagcacaag agg                                          23

SEQ ID NO: 1065        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1065
agccccagta agagcacaag agg                                          23

SEQ ID NO: 1066        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1066
aacacaagca agagcacgag agg                                          23

SEQ ID NO: 1067        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1067
agccccagca agagcacgag agg                                          23

SEQ ID NO: 1068        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1068
agcctaagaa agaacacaag agg                                          23

SEQ ID NO: 1069        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1069
agccccagct aaagcaaaag agg                                          23

SEQ ID NO: 1070        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1070
tgccccagct aaaacacaag tgg                                          23

SEQ ID NO: 1071        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1071
aaaccaaaca aggacacaag aga                                          23
```

```
SEQ ID NO: 1072        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1072
aatcccagtg agagcacaag agg                                         23

SEQ ID NO: 1073        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1073
acccctagct acagcacaag agg                                         23

SEQ ID NO: 1074        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1074
tgcagcagca agagcacagg cgg                                         23

SEQ ID NO: 1075        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1075
cacaagagca agagcacaag agg                                         23

SEQ ID NO: 1076        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1076
gctctcagca agaccacaag tgg                                         23

SEQ ID NO: 1077        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1077
tgccccaaga acaacaaaaa aag                                         23

SEQ ID NO: 1078        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1078
tgcctcagtc aaagcacagc agg                                         23

SEQ ID NO: 1079        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1079
aaaaccaaca acagtacaaa agg                                         23
```

```
SEQ ID NO: 1080        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1080
cactccagcc tgggcaaaag agg                                          23

SEQ ID NO: 1081        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1081
attctgagga agaaaacaag ggg                                          23

SEQ ID NO: 1082        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1082
tccccctacc agagcacata cag                                          23

SEQ ID NO: 1083        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1083
aggcaaatca aaaccacaat gag                                          23

SEQ ID NO: 1084        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1084
aaaacaagaa agaacaaaag aga                                          23

SEQ ID NO: 1085        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1085
cttgccccac agggcagtaa cgg                                          23

SEQ ID NO: 1086        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1086
cttggcctgc agggcagtta tgg                                          23

SEQ ID NO: 1087        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1087
```

```
tctaccccac atggcagtaa tgg                                          23

SEQ ID NO: 1088        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1088
actgagcctc agggcagtaa tgg                                          23

SEQ ID NO: 1089        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1089
cctgccccac agggcaatta tgg                                          23

SEQ ID NO: 1090        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1090
cctctcccac agggcagtaa agg                                          23

SEQ ID NO: 1091        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1091
gctgccccac agggcagcaa agg                                          23

SEQ ID NO: 1092        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1092
cctccaatac agggcagtaa agg                                          23

SEQ ID NO: 1093        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1093
cctgtcccac agggcaggaa ggg                                          23

SEQ ID NO: 1094        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1094
ctggcaccac agagcagaaa ggg                                          23

SEQ ID NO: 1095        moltype = DNA  length = 23
FEATURE                Location/Qualifiers
misc_feature           1..23
                       note = Synthetic oligonucleotide
source                 1..23
                       mol_type = other DNA
                       organism = synthetic construct
```

```
SEQUENCE: 1095
catgctccac agagcagcaa agg                                          23

SEQ ID NO: 1096        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1096
gggctgcccc agggcagtaa tgg                                          23

SEQ ID NO: 1097        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1097
cttgctgcac aggacaataa agg                                          23

SEQ ID NO: 1098        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1098
ctcgcccctc agggcagtag tgg                                          23

SEQ ID NO: 1099        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1099
gttggccctc agggcagaaa tgg                                          23

SEQ ID NO: 1100        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1100
gaggcgccac agggcagtaa tgg                                          23

SEQ ID NO: 1101        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1101
gctgtgtcat agggcagtaa cgg                                          23

SEQ ID NO: 1102        moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 1102
ctttcttcac agggtagtaa tgg                                          23

SEQ ID NO: 1103        moltype = DNA  length = 23
FEATURE                Location/Qualifiers
misc_feature           1..23
                       note = Synthetic oligonucleotide
source                 1..23
                       mol_type = other DNA
```

```
                         organism = synthetic construct
SEQUENCE: 1103
tgccccagac agggcagtaa ggg                                          23

SEQ ID NO: 1104          moltype = DNA  length = 23
FEATURE                  Location/Qualifiers
misc_feature             1..23
                         note = Synthetic oligonucleotide
source                   1..23
                         mol_type = other DNA
                         organism = synthetic construct
SEQUENCE: 1104
cttgcactac aagtcagtaa tgg                                          23

SEQ ID NO: 1105          moltype = DNA  length = 23
FEATURE                  Location/Qualifiers
misc_feature             1..23
                         note = Synthetic oligonucleotide
source                   1..23
                         mol_type = other DNA
                         organism = synthetic construct
SEQUENCE: 1105
atttcctcac agggcagaaa agg                                          23

SEQ ID NO: 1106          moltype = DNA  length = 23
FEATURE                  Location/Qualifiers
misc_feature             1..23
                         note = Synthetic oligonucleotide
source                   1..23
                         mol_type = other DNA
                         organism = synthetic construct
SEQUENCE: 1106
tcacccccac aggccagtaa agg                                          23

SEQ ID NO: 1107          moltype = DNA  length = 23
FEATURE                  Location/Qualifiers
misc_feature             1..23
                         note = Synthetic oligonucleotide
source                   1..23
                         mol_type = other DNA
                         organism = synthetic construct
SEQUENCE: 1107
gtcatgtcac agggcagtag tgg                                          23

SEQ ID NO: 1108          moltype = DNA  length = 23
FEATURE                  Location/Qualifiers
misc_feature             1..23
                         note = Synthetic oligonucleotide
source                   1..23
                         mol_type = other DNA
                         organism = synthetic construct
SEQUENCE: 1108
ggccctgccc agggcagtaa tgg                                          23

SEQ ID NO: 1109          moltype = DNA  length = 23
FEATURE                  Location/Qualifiers
misc_feature             1..23
                         note = Synthetic oligonucleotide
source                   1..23
                         mol_type = other DNA
                         organism = synthetic construct
SEQUENCE: 1109
cttaatacac agggaaggaa tgg                                          23

SEQ ID NO: 1110          moltype = DNA  length = 23
FEATURE                  Location/Qualifiers
misc_feature             1..23
                         note = Synthetic oligonucleotide
source                   1..23
                         mol_type = other DNA
                         organism = synthetic construct
SEQUENCE: 1110
cttcaagagc aacagtgctg tgg                                          23

SEQ ID NO: 1111          moltype = DNA  length = 23
FEATURE                  Location/Qualifiers
misc_feature             1..23
                         note = Synthetic oligonucleotide
source                   1..23
```

```
                        mol_type = other DNA
                        organism = synthetic construct
SEQUENCE: 1111
gagagacagc aacagtgcta tgg                                          23

SEQ ID NO: 1112         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1112
agcaaggagc aacagtgatg tgg                                          23

SEQ ID NO: 1113         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1113
agcaaacatc aacagtgctg agg                                          23

SEQ ID NO: 1114         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1114
taggaagagc aacagggctg tgg                                          23

SEQ ID NO: 1115         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1115
catgaagggc aacagagctg agg                                          23

SEQ ID NO: 1116         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1116
cactctaagc aacagtgctg ggg                                          23

SEQ ID NO: 1117         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1117
tgcgaggagc aacagtgctt ggg                                          23

SEQ ID NO: 1118         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1118
gtctctaggc aacagtgctg agg                                          23

SEQ ID NO: 1119         moltype = DNA  length = 23
FEATURE                 Location/Qualifiers
misc_feature            1..23
                        note = Synthetic oligonucleotide
```

```
source                  1..23
                        mol_type = other DNA
                        organism = synthetic construct
SEQUENCE: 1119
gggcagcagc tacagtgctg agg                                          23

SEQ ID NO: 1120         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1120
gggcggtgct acaactgggc tgg                                          23

SEQ ID NO: 1121         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1121
gggtggttct acaaccaggc tgg                                          23

SEQ ID NO: 1122         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1122
gggcggtgct acaactgggc tgg                                          23

SEQ ID NO: 1123         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1123
gggaggtgcc acatcagggc cgg                                          23

SEQ ID NO: 1124         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1124
gggcagtgat ccaactgtgc agg                                          23

SEQ ID NO: 1125         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1125
agctggggct acatctgggc tgg                                          23

SEQ ID NO: 1126         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1126
gctgggtgct acaacagggc agg                                          23

SEQ ID NO: 1127         moltype = DNA  length = 23
FEATURE                 Location/Qualifiers
misc_feature            1..23
```

```
                        note = Synthetic oligonucleotide
source                  1..23
                        mol_type = other DNA
                        organism = synthetic construct
SEQUENCE: 1127
ctgtggtgca acaactgggc tgg                                              23

SEQ ID NO: 1128         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1128
gggaggaggt acaactggga ggg                                              23

SEQ ID NO: 1129         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1129
cagtgtggct acaactgcgc agg                                              23

SEQ ID NO: 1130         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1130
ctggtcagct acaactggcc tgg                                              23

SEQ ID NO: 1131         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1131
ggtgtaaaat caacacccta agg                                              23

SEQ ID NO: 1132         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1132
gctggaaaaa aaacacccta ggg                                              23

SEQ ID NO: 1133         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1133
gaggtaaaac caacacctta agg                                              23

SEQ ID NO: 1134         moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 1134
tggctgaaat caacacccca ggg                                              23

SEQ ID NO: 1135         moltype = DNA  length = 23
FEATURE                 Location/Qualifiers
```

```
misc_feature         1..23
                     note = Synthetic oligonucleotide
source               1..23
                     mol_type = other DNA
                     organism = synthetic construct
SEQUENCE: 1135
tgacaccaat caacacctta agg                                    23

SEQ ID NO: 1136      moltype = DNA  length = 23
FEATURE              Location/Qualifiers
misc_feature         1..23
                     note = Synthetic oligonucleotide
source               1..23
                     mol_type = other DNA
                     organism = synthetic construct
SEQUENCE: 1136
tctgatccat caacacccta tgg                                    23
```